United States Patent
Toyazaki et al.

(10) Patent No.: US 10,883,125 B2
(45) Date of Patent: Jan. 5, 2021

(54) METHOD FOR PRODUCING ALDEHYDE

(71) Applicant: AJINOMOTO CO., INC., Tokyo (JP)

(72) Inventors: Miku Toyazaki, Kanagawa (JP); Keita Fukui, Kanagawa (JP)

(73) Assignee: AJINOMOTO CO., INC., Tokyo (JP)

(*) Notice: Subject to any disclaimer, the term of this patent is extended or adjusted under 35 U.S.C. 154(b) by 0 days.

(21) Appl. No.: 16/392,837

(22) Filed: Apr. 24, 2019

(65) Prior Publication Data

US 2019/0249207 A1    Aug. 15, 2019

Related U.S. Application Data

(63) Continuation of application No. PCT/JP2017/038875, filed on Oct. 27, 2017.

(30) Foreign Application Priority Data

| Oct. 27, 2016 | (JP) | 2016-211103 |
| Oct. 27, 2016 | (JP) | 2016-211106 |
| Oct. 27, 2016 | (JP) | 2016-211107 |
| Feb. 9, 2017 | (JP) | 2017-022265 |
| Feb. 9, 2017 | (JP) | 2017-022314 |
| Feb. 9, 2017 | (JP) | 2017-022330 |

(51) Int. Cl.
    *C12P 7/22*       (2006.01)
    *C12N 9/02*       (2006.01)
    *C12P 7/24*       (2006.01)
    *C12N 9/12*       (2006.01)

(52) U.S. Cl.
CPC .............. *C12P 7/24* (2013.01); *C12N 9/0008* (2013.01); *C12N 9/1205* (2013.01); *C12Y 102/07005* (2013.01)

(58) Field of Classification Search
CPC ..................................... C12N 9/02; C12P 7/24
See application file for complete search history.

(56) References Cited

U.S. PATENT DOCUMENTS

| 5,795,759 | A | 8/1998 | Rosazza et al. |
| 6,372,461 | B1 | 4/2002 | Frost |
| 2004/0180400 | A1 | 9/2004 | Rosazza et al. |
| 2015/0267227 | A1 | 9/2015 | Lindberg Moller et al. |

FOREIGN PATENT DOCUMENTS

| JP | 2015-535181 A | 12/2015 |
| WO | WO2004/111254 A1 | 12/2004 |
| WO | WO2013/022881 A1 | 2/2013 |
| WO | WO2015/009558 A1 | 1/2015 |
| WO | WO2017/073701 A2 | 5/2017 |

OTHER PUBLICATIONS

Kaur, B., et al., "Biotechnological and Molecular Approaches for Vanillin Production: a Review," Appl. Biochem. Biotechnol. 2013;169:1353-1372.
International Search Report and Written Opinion for PCT Patent App. No. PCT/JP2017/038875 (dated Jan. 30, 2018).

*Primary Examiner* — Maryam Monshipouri
(74) *Attorney, Agent, or Firm* — Cermak Nakajima & McGowan LLP; Shelly Guest Cermak

(57) ABSTRACT

A method is described for producing an objective substance, for example, an aldehyde such as vanillin. The objective substance is produced from a carbon source or a precursor of the objective substance by using a microorganism having an ability to produce the objective substance, wherein the microorganism has been modified to have a specific carboxylic acid reductase (CAR) gene, such as a *Gordonia* CAR gene, *Novosphingobium* CAR gene, or *Coccomyxa* CAR gene.

13 Claims, No Drawings
Specification includes a Sequence Listing.

SEQUENCE LISTING

<160> NUMBER OF SEQ ID NOS: 85

<210> SEQ ID NO 1
<211> LENGTH: 1071
<212> TYPE: DNA
<213> ORGANISM: Escherichia coli

<400> SEQUENCE: 1

```
atgcaaaaag acgcgctgaa taacgtacat attaccgacg aacaggtttt aatgactccg      60
gaacaactga aggccgcttt tccattgagc ctgcaacaag aagcccagat tgctgactcg     120
cgtaaaagca tttcagatat tatcgccggg cgcgatcctc gtctgctggt agtatgtggt     180
ccttgttcca ttcatgatcc ggaaactgct ctggaatatg ctcgtcgatt taaagccctt     240
gccgcagagg tcagcgatag cctctatctg gtaatgcgcg tctattttga aaacccccgt     300
accactgtcg gctggaaagg gttaattaac gatccccata tggatggctc ttttgatgta     360
gaagccgggc tgcagatcgc gcgtaaattg ctgcttgagc tggtgaatat gggactgcca     420
ctggcgacgg aagcgttaga tccgaatagc ccgcaatacc tgggcgatct gtttagctgg     480
tcagcaattg gtgctcgtac aacggaatcg caaactcacc gtgaaatggc ctccgggctt     540
tccatgccgg ttggttttaa aacggcacc gacggcagtc tggcaacagc aattaacgct     600
atgcgcgccg ccgcccagcc gcaccgtttt gttggcatta accaggcagg caggttgcg      660
ttgctacaaa ctcaggggaa tccggacggc catgtgatcc tgcgcggtgg taaagcgccg     720
aactatagcc ctgcggatgt tgcgcaatgt gaaaaagaga tggaacaggc gggactgcgc     780
ccgtctctga tggtagattg cagccacggt aattccaata agattatcg ccgtcagcct     840
gcggtggcag aatccgtggt tgctcaaatc aaagatggca atcgctcaat tattggtctg     900
atgatcgaaa gtaatatcca cgagggcaat cagtcttccg agcaaccgcg cagtgaaatg     960
aaatacggtg tatccgtaac cgatgcctgc attagctggg aaatgaccga tgccttgctg    1020
cgtgaaattc atcaggatct gaacgggcag ctgacggctc gcgtggctta a              1071
```

<210> SEQ ID NO 2
<211> LENGTH: 356
<212> TYPE: PRT
<213> ORGANISM: Escherichia coli

<400> SEQUENCE: 2

```
Met Gln Lys Asp Ala Leu Asn Asn Val His Ile Thr Asp Glu Gln Val
1               5                   10                  15

Leu Met Thr Pro Glu Gln Leu Lys Ala Ala Phe Pro Leu Ser Leu Gln
            20                  25                  30

Gln Glu Ala Gln Ile Ala Asp Ser Arg Lys Ser Ile Ser Asp Ile Ile
        35                  40                  45

Ala Gly Arg Asp Pro Arg Leu Leu Val Val Cys Gly Pro Cys Ser Ile
    50                  55                  60

His Asp Pro Glu Thr Ala Leu Glu Tyr Ala Arg Arg Phe Lys Ala Leu
65                  70                  75                  80

Ala Ala Glu Val Ser Asp Ser Leu Tyr Leu Val Met Arg Val Tyr Phe
                85                  90                  95

Glu Lys Pro Arg Thr Thr Val Gly Trp Lys Gly Leu Ile Asn Asp Pro
            100                 105                 110

His Met Asp Gly Ser Phe Asp Val Glu Ala Gly Leu Gln Ile Ala Arg
        115                 120                 125

Lys Leu Leu Leu Glu Leu Val Asn Met Gly Leu Pro Leu Ala Thr Glu
```

```
                130                   135                   140
Ala Leu Asp Pro Asn Ser Pro Gln Tyr Leu Gly Asp Leu Phe Ser Trp
145                 150                 155                 160

Ser Ala Ile Gly Ala Arg Thr Thr Glu Ser Gln Thr His Arg Glu Met
                165                 170                 175

Ala Ser Gly Leu Ser Met Pro Val Gly Phe Lys Asn Gly Thr Asp Gly
            180                 185                 190

Ser Leu Ala Thr Ala Ile Asn Ala Met Arg Ala Ala Gln Pro His
        195                 200                 205

Arg Phe Val Gly Ile Asn Gln Ala Gly Gln Val Ala Leu Leu Gln Thr
    210                 215                 220

Gln Gly Asn Pro Asp Gly His Val Ile Leu Arg Gly Gly Lys Ala Pro
225                 230                 235                 240

Asn Tyr Ser Pro Ala Asp Val Ala Gln Cys Glu Lys Glu Met Glu Gln
                245                 250                 255

Ala Gly Leu Arg Pro Ser Leu Met Val Asp Cys Ser His Gly Asn Ser
            260                 265                 270

Asn Lys Asp Tyr Arg Arg Gln Pro Ala Val Ala Glu Ser Val Val Ala
        275                 280                 285

Gln Ile Lys Asp Gly Asn Arg Ser Ile Ile Gly Leu Met Ile Glu Ser
    290                 295                 300

Asn Ile His Glu Gly Asn Gln Ser Ser Glu Gln Pro Arg Ser Glu Met
305                 310                 315                 320

Lys Tyr Gly Val Ser Val Thr Asp Ala Cys Ile Ser Trp Glu Met Thr
                325                 330                 335

Asp Ala Leu Leu Arg Glu Ile His Gln Asp Leu Asn Gly Gln Leu Thr
            340                 345                 350

Ala Arg Val Ala
        355

<210> SEQ ID NO 3
<211> LENGTH: 1089
<212> TYPE: DNA
<213> ORGANISM: Escherichia coli

<400> SEQUENCE: 3
atggagagga ttgtcgttac tctcggggaa cgtagttacc caattaccat cgcatctggt      60
ttgtttaatg aaccagcttc attcttaccg ctgaaatcgg gcgagcaggt catgttggtc     120
accaacgaaa ccctggctcc tctgtatctc gataaggtcc gcggcgtact tgaacaggcg     180
ggtgttaacg tcgatagcgt tatcctccct gacggcgagc agtataaaag cctggctgta     240
ctcgataccg tctttacggc gttgttacaa aaaccgcatg gtcgcgatac tacgctggtg     300
gcgcttggcg gcggcgtagt gggcgatctg accggcttcg cggcggcgag ttatcagcgc     360
ggtgtccgtt tcattcaagt cccgacgacg ttactgtcgc aggtcgattc ctccgttggc     420
ggcaaaactg cggtcaacca tcccctcggt aaaaacatga ttggcgcgtt ctaccaacct     480
gcttcagtgg tggtggatct cgactgtctg aaaacgcttc cccgcgtgaa gttagcgtcg     540
gggctggcag aagtcatcaa ataccggcat tattcttgacg gtgcgttttt taactggctg     600
gaagagaatc tggatgcgtt gttgcgtctg gacggtccgg caatggcgta ctgtattcgc     660
cgttgttgtg aactgaaggc agaagttgtc gccgccgacg agcgcgaaac cgggttacgt     720
gctttactga atctgggaca caccttggt catgccattg aagctgaaat ggggtatggc     780
aattggttac atggtgaagc ggtcgctgcg ggtatggtga tggcggcgcg gacgtcggaa     840
```

```
cgtctcgggc agtttagttc tgccgaaacg cagcgtatta taaccctgct caagcgggct    900
gggttaccgg tcaatgggcc gcgcgaaatg tccgcgcagg cgtatttacc gcatatgctg    960
cgtgacaaga aagtccttgc gggagagatg cgcttaattc ttccgttggc aattggtaag   1020
agtgaagttc gcagcggcgt ttcgcacgag cttgttctta acgccattgc cgattgtcaa   1080
tcagcgtaa                                                            1089
```

<210> SEQ ID NO 4
<211> LENGTH: 362
<212> TYPE: PRT
<213> ORGANISM: Escherichia coli

<400> SEQUENCE: 4

```
Met Glu Arg Ile Val Val Thr Leu Gly Glu Arg Ser Tyr Pro Ile Thr
 1               5                  10                  15

Ile Ala Ser Gly Leu Phe Asn Glu Pro Ala Ser Phe Leu Pro Leu Lys
            20                  25                  30

Ser Gly Glu Gln Val Met Leu Val Thr Asn Glu Thr Leu Ala Pro Leu
        35                  40                  45

Tyr Leu Asp Lys Val Arg Gly Val Leu Glu Gln Ala Gly Val Asn Val
 50                  55                  60

Asp Ser Val Ile Leu Pro Asp Gly Glu Gln Tyr Lys Ser Leu Ala Val
 65                  70                  75                  80

Leu Asp Thr Val Phe Thr Ala Leu Leu Gln Lys Pro His Gly Arg Asp
                85                  90                  95

Thr Thr Leu Val Ala Leu Gly Gly Gly Val Val Gly Asp Leu Thr Gly
            100                 105                 110

Phe Ala Ala Ser Tyr Gln Arg Gly Val Arg Phe Ile Gln Val Pro
        115                 120                 125

Thr Thr Leu Leu Ser Gln Val Asp Ser Ser Val Gly Gly Lys Thr Ala
130                 135                 140

Val Asn His Pro Leu Gly Lys Asn Met Ile Gly Ala Phe Tyr Gln Pro
145                 150                 155                 160

Ala Ser Val Val Val Asp Leu Asp Cys Leu Lys Thr Leu Pro Pro Arg
                165                 170                 175

Glu Leu Ala Ser Gly Leu Ala Glu Val Ile Lys Tyr Gly Ile Ile Leu
            180                 185                 190

Asp Gly Ala Phe Phe Asn Trp Leu Glu Glu Asn Leu Asp Ala Leu Leu
        195                 200                 205

Arg Leu Asp Gly Pro Ala Met Ala Tyr Cys Ile Arg Arg Cys Cys Glu
210                 215                 220

Leu Lys Ala Glu Val Val Ala Asp Glu Arg Glu Thr Gly Leu Arg
225                 230                 235                 240

Ala Leu Leu Asn Leu Gly His Thr Phe Gly His Ala Ile Glu Ala Glu
                245                 250                 255

Met Gly Tyr Gly Asn Trp Leu His Gly Glu Ala Val Ala Ala Gly Met
            260                 265                 270

Val Met Ala Ala Arg Thr Ser Glu Arg Leu Gly Gln Phe Ser Ser Ala
        275                 280                 285

Glu Thr Gln Arg Ile Ile Thr Leu Leu Lys Arg Ala Gly Leu Pro Val
    290                 295                 300

Asn Gly Pro Arg Glu Met Ser Ala Gln Ala Tyr Leu Pro His Met Leu
305                 310                 315                 320
```

Arg Asp Lys Lys Val Leu Ala Gly Glu Met Arg Leu Ile Leu Pro Leu
            325                 330                 335

Ala Ile Gly Lys Ser Glu Val Arg Ser Gly Val Ser His Glu Leu Val
            340                 345                 350

Leu Asn Ala Ile Ala Asp Cys Gln Ser Ala
            355                 360

<210> SEQ ID NO 5
<211> LENGTH: 759
<212> TYPE: DNA
<213> ORGANISM: Escherichia coli

<400> SEQUENCE: 5

```
atgaaaaccg taactgtaaa agatctcgtc attggtacgg gcgcacctaa aatcatcgtc      60
tcgctgatgg cgaaagatat cgccagcgtg aaatccgaag ctctcgccta tcgtgaagcg     120
gactttgata ttctggaatg gcgtgtggac cactatgccg acctctccaa tgtggagtct     180
gtcatggcgg cagcaaaaat tctccgtgag accatgccag aaaaaccgct gctgtttacc     240
ttccgcagtg ccaaagaagg cggcgagcag gcgatttcca ccgaggctta tattgcactc     300
aatcgtgcag ccatcgacag cggcctggtt gatatgatcg atctggagtt atttaccggt     360
gatgatcagg ttaaagaaac cgtcgcctac gcccacgcgc atgatgtgaa agtagtcatg     420
tccaaccatg acttccataa aacgccggaa gccgaagaaa tcattgcccg tctgcgcaaa     480
atgcaatcct tcgacgccga tattcctaag attgcgctga tgccgcaaag taccagcgat     540
gtgctgacgt tgcttgccgc gaccctggag atgcaggagc agtatgccga tcgtccaatt     600
atcacgatgt cgatggcaaa aactggcgta atttctcgtc tggctggtga agtatttggc     660
tcggcggcaa cttttggtgc ggtaaaaaaa gcgtctgcgc agggcaaat ctcggtaaat      720 gatttgcgca cggtattaac tattttacac caggcataa                           759
```

<210> SEQ ID NO 6
<211> LENGTH: 252
<212> TYPE: PRT
<213> ORGANISM: Escherichia coli

<400> SEQUENCE: 6

Met Lys Thr Val Thr Val Lys Asp Leu Val Ile Gly Thr Gly Ala Pro
1               5                   10                  15

Lys Ile Ile Val Ser Leu Met Ala Lys Asp Ile Ala Ser Val Lys Ser
            20                  25                  30

Glu Ala Leu Ala Tyr Arg Glu Ala Asp Phe Asp Ile Leu Glu Trp Arg
        35                  40                  45

Val Asp His Tyr Ala Asp Leu Ser Asn Val Glu Ser Val Met Ala Ala
    50                  55                  60

Ala Lys Ile Leu Arg Glu Thr Met Pro Glu Lys Pro Leu Leu Phe Thr
65                  70                  75                  80

Phe Arg Ser Ala Lys Glu Gly Gly Glu Gln Ala Ile Ser Thr Glu Ala
                85                  90                  95

Tyr Ile Ala Leu Asn Arg Ala Ala Ile Asp Ser Gly Leu Val Asp Met
            100                 105                 110

Ile Asp Leu Glu Leu Phe Thr Gly Asp Asp Gln Val Lys Glu Thr Val
        115                 120                 125

Ala Tyr Ala His Ala His Asp Val Lys Val Val Met Ser Asn His Asp
    130                 135                 140

Phe His Lys Thr Pro Glu Ala Glu Glu Ile Ile Ala Arg Leu Arg Lys

```
              145                 150                 155                 160
Met Gln Ser Phe Asp Ala Asp Ile Pro Lys Ile Ala Leu Met Pro Gln
                        165                 170                 175

Ser Thr Ser Asp Val Leu Thr Leu Leu Ala Ala Thr Leu Glu Met Gln
                180                 185                 190

Glu Gln Tyr Ala Asp Arg Pro Ile Ile Thr Met Ser Met Ala Lys Thr
            195                 200                 205

Gly Val Ile Ser Arg Leu Ala Gly Glu Val Phe Gly Ser Ala Ala Thr
        210                 215                 220

Phe Gly Ala Val Lys Lys Ala Ser Ala Pro Gly Gln Ile Ser Val Asn
225                 230                 235                 240

Asp Leu Arg Thr Val Leu Thr Ile Leu His Gln Ala
                245                 250

<210> SEQ ID NO 7
<211> LENGTH: 843
<212> TYPE: DNA
<213> ORGANISM: Bacillus thuringiensis

<400> SEQUENCE: 7
atgaaatatt cgctatgtac catttcattt cgtcatcaat taatttcatt tactgatatt    60
gttcaatttg catatgaaaa cggttttgaa ggaattgaat tatgggggac gcatgcacaa   120
aatttgtaca tgcaagaacg tgaaacgaca gaacgagaat tgaattttct aaaggataaa   180
aacttagaaa ttacgatgat aagtgattac ttagatatat cattatcagc agattttgaa   240
aaaacgatag agaaagtga acaacttgta gtactagcta attggtttaa tacgaataaa   300
attcgcacgt ttgctgggca aaagggagc aaggacttct cggaacaaga gagaaaagag   360
tatgtgaagc gaatacgtaa gatttgtgat gtgtttgctc agaacaatat gtatgtgctg   420
ttagaaacac atcccaatac actaacggac acattgcctt ctactataga gttattagaa   480
gaagtaaacc atccgaattt aaaaataaat cttgattttc ttcatatatg ggagtctggc   540
gcagatccaa tagacagttt ccatcgatta aagccgtgga cactacatta ccatttaag   600 aatatatctt cagcggatta tttgcatgtg tttgaaccta ataatgtata tgctgcagca   660
ggaagtcgta taggtatggt tccgttattt gaaggtattg taaattatga tgagattatt   720
caggaagtga aaatacgga tctttttgct tccttagaat ggtttggaca taattccaaaa   780 gagatattaa agaagaaat gaaagtatta ataaatagaa aattagaagt agtaacttcg   840
taa                                                                 843

<210> SEQ ID NO 8
<211> LENGTH: 280
<212> TYPE: PRT
<213> ORGANISM: Bacillus thuringiensis

<400> SEQUENCE: 8

Met Lys Tyr Ser Leu Cys Thr Ile Ser Phe Arg His Gln Leu Ile Ser
1               5                   10                  15

Phe Thr Asp Ile Val Gln Phe Ala Tyr Glu Asn Gly Phe Glu Gly Ile
            20                  25                  30

Glu Leu Trp Gly Thr His Ala Gln Asn Leu Tyr Met Gln Glu Arg Glu
        35                  40                  45

Thr Thr Glu Arg Glu Leu Asn Phe Leu Lys Asp Lys Asn Leu Glu Ile
    50                  55                  60

Thr Met Ile Ser Asp Tyr Leu Asp Ile Ser Leu Ser Ala Asp Phe Glu
```

|  |  |  |  |  | 65 |  |  |  |  | 70 |  |  |  |  | 75 |  |  |  |  | 80 |
|---|---|---|---|---|---|---|---|---|---|---|---|---|---|---|---|---|---|---|---|---|

Lys Thr Ile Glu Lys Ser Glu Gln Leu Val Val Leu Ala Asn Trp Phe
                    85                  90                  95

Asn Thr Asn Lys Ile Arg Thr Phe Ala Gly Gln Lys Gly Ser Lys Asp
                100                 105                 110

Phe Ser Glu Gln Glu Arg Lys Glu Tyr Val Lys Arg Ile Arg Lys Ile
            115                 120                 125

Cys Asp Val Phe Ala Gln Asn Asn Met Tyr Val Leu Leu Glu Thr His
        130                 135                 140

Pro Asn Thr Leu Thr Asp Thr Leu Pro Ser Thr Ile Glu Leu Leu Glu
145                 150                 155                 160

Glu Val Asn His Pro Asn Leu Lys Ile Asn Leu Asp Phe Leu His Ile
                165                 170                 175

Trp Glu Ser Gly Ala Asp Pro Ile Asp Ser Phe His Arg Leu Lys Pro
            180                 185                 190

Trp Thr Leu His Tyr His Phe Lys Asn Ile Ser Ser Ala Asp Tyr Leu
        195                 200                 205

His Val Phe Glu Pro Asn Asn Val Tyr Ala Ala Gly Ser Arg Ile
        210                 215                 220

Gly Met Val Pro Leu Phe Glu Gly Ile Val Asn Tyr Asp Glu Ile Ile
225                 230                 235                 240

Gln Glu Val Arg Asn Thr Asp Leu Phe Ala Ser Leu Glu Trp Phe Gly
                245                 250                 255

His Asn Ser Lys Glu Ile Leu Lys Glu Glu Met Lys Val Leu Ile Asn
            260                 265                 270

Arg Lys Leu Glu Val Val Thr Ser
        275                 280

<210> SEQ ID NO 9
<211> LENGTH: 1542
<212> TYPE: DNA
<213> ORGANISM: Escherichia coli

<400> SEQUENCE: 9
atgcgtctgg aagtcttttg tgaagaccga ctcggtctga cccgcgaatt actcgatcta     60
ctcgtgctaa gaggcattga tttacgcggt attgagattg atcccattgg gcgaatctac    120
ctcaattttg ctgaactgga gtttgagagt ttcagcagtc tgatggccga atacgccgt     180 attgcgggtg ttaccgatgt gcgtactgtc ccgtggatgc cttccgaacg tgagcatctg    240
gcgttgagcg cgttactgga ggcgttgcct gaacctgtgc tctctgtcga tatgaaaagc    300
aaagtggata tggcgaaccc ggcgagctgt cagcttttg ggcaaaaatt ggatcgcctg    360
cgcaaccata ccgccgcaca attgattaac ggctttaatt ttttacgttg gctggaaagc    420
gaaccgcaag attcgcataa cgagcatgtc gttattaatg gcagaatttt cctgatggag    480
attacgcctg tttatcttca ggatgaaaat gatcaacacg tcctgaccgg tgcggtggtg    540
atgttgcgat caacgattcg tatgggccgc cagttgcaaa atgtcgccgc ccaggacgtc    600
agcgccttca gtcaaattgt cgccgtcagc ccgaaaatga agcatgttgt cgaacaggcg    660
cagaaactgg cgatgctaag cgcgccgctg ctgattacgg gtgacacagg tacaggtaaa    720
gatctctttg cctacgcctg ccatcaggca agccccagag cgggcaaacc ttacctggcg    780
ctgaactgtg cgtctatacc ggaagatgcg gtcgagagtg aactgtttgg tcatgctccg    840
gaagggaaga aggattcttt tgagcaggcg aacggtggtt cggtgctgtt ggatgaaata    900

-continued

```
ggggaaatgt caccacggat gcaggcgaaa ttactgcgtt tccttaatga tggcactttc    960
cgtcgggttg gcgaagacca tgaggtgcat gtcgatgtgc gggtgatttg cgctacgcag   1020
aagaatctgg tcgaactggt gcaaaaaggc atgttccgtg aagatctcta ttatcgtctg   1080
aacgtgttga cgctcaatct gccgccgcta cgtgactgtc cgcaggacat catgccgtta   1140
actgagctgt tcgtcgcccg ctttgccgac gagcagggcg tgccgcgtcc gaaactggcc   1200
gctgacctga atactgtact tacgcgttat gcgtggccgg gaaatgtgcg gcagttaaag   1260
aacgctatct atcgcgcact gacacaactg gacggttatg agctgcgtcc acaggatatt   1320
ttgttgccgg attatgacgc cgcaacggta gccgtgggcg aagatgcgat ggaaggttcg   1380
ctggacgaaa tcaccagccg ttttgaacgc tcggtattaa cccagcttta tcgcaattat   1440
cccagcacgc gcaaactggc aaaacgtctc ggcgtttcac ataccgcgat tgccaataag   1500
ttgcgggaat atggtctgag tcagaagaag aacgaagagt aa                      1542
```

```
<210> SEQ ID NO 10
<211> LENGTH: 513
<212> TYPE: PRT
<213> ORGANISM: Escherichia coli

<400> SEQUENCE: 10
```

Met Arg Leu Glu Val Phe Cys Glu Asp Arg Leu Gly Leu Thr Arg Glu
1               5                   10                  15

Leu Leu Asp Leu Val Leu Arg Gly Ile Asp Leu Arg Gly Ile Glu
            20                  25                  30

Ile Asp Pro Ile Gly Arg Ile Tyr Leu Asn Phe Ala Glu Leu Glu Phe
        35                  40                  45

Glu Ser Phe Ser Ser Leu Met Ala Glu Ile Arg Arg Ile Ala Gly Val
    50                  55                  60

Thr Asp Val Arg Thr Val Pro Trp Met Pro Ser Glu Arg Glu His Leu
65                  70                  75                  80

Ala Leu Ser Ala Leu Leu Glu Ala Leu Pro Glu Pro Val Leu Ser Val
                85                  90                  95

Asp Met Lys Ser Lys Val Asp Met Ala Asn Pro Ala Ser Cys Gln Leu
            100                 105                 110

Phe Gly Gln Lys Leu Asp Arg Leu Arg Asn His Thr Ala Ala Gln Leu
        115                 120                 125

Ile Asn Gly Phe Asn Phe Leu Arg Trp Leu Glu Ser Glu Pro Gln Asp
    130                 135                 140

Ser His Asn Glu His Val Val Ile Asn Gly Gln Asn Phe Leu Met Glu
145                 150                 155                 160

Ile Thr Pro Val Tyr Leu Gln Asp Glu Asn Asp Gln His Val Leu Thr
                165                 170                 175

Gly Ala Val Val Met Leu Arg Ser Thr Ile Arg Met Gly Arg Gln Leu
            180                 185                 190

Gln Asn Val Ala Ala Gln Asp Val Ser Ala Phe Ser Gln Ile Val Ala
        195                 200                 205

Val Ser Pro Lys Met Lys His Val Val Glu Gln Ala Gln Lys Leu Ala
    210                 215                 220

Met Leu Ser Ala Pro Leu Leu Ile Thr Gly Asp Thr Gly Thr Gly Lys
225                 230                 235                 240

Asp Leu Phe Ala Tyr Ala Cys His Gln Ala Ser Pro Arg Ala Gly Lys
                245                 250                 255

Pro Tyr Leu Ala Leu Asn Cys Ala Ser Ile Pro Glu Asp Ala Val Glu

```
            260                 265                 270
Ser Glu Leu Phe Gly His Ala Pro Glu Gly Lys Lys Gly Phe Phe Glu
        275                 280                 285
Gln Ala Asn Gly Gly Ser Val Leu Leu Asp Glu Ile Gly Glu Met Ser
    290                 295                 300
Pro Arg Met Gln Ala Lys Leu Leu Arg Phe Leu Asn Asp Gly Thr Phe
305                 310                 315                 320
Arg Arg Val Gly Glu Asp His Glu Val His Val Asp Val Arg Val Ile
                325                 330                 335
Cys Ala Thr Gln Lys Asn Leu Val Glu Leu Val Gln Lys Gly Met Phe
            340                 345                 350
Arg Glu Asp Leu Tyr Tyr Arg Leu Asn Val Leu Thr Leu Asn Leu Pro
        355                 360                 365
Pro Leu Arg Asp Cys Pro Gln Asp Ile Met Pro Leu Thr Glu Leu Phe
    370                 375                 380
Val Ala Arg Phe Ala Asp Glu Gln Gly Val Pro Arg Pro Lys Leu Ala
385                 390                 395                 400
Ala Asp Leu Asn Thr Val Leu Thr Arg Tyr Ala Trp Pro Gly Asn Val
                405                 410                 415
Arg Gln Leu Lys Asn Ala Ile Tyr Arg Ala Leu Thr Gln Leu Asp Gly
            420                 425                 430
Tyr Glu Leu Arg Pro Gln Asp Ile Leu Leu Pro Asp Tyr Asp Ala Ala
        435                 440                 445
Thr Val Ala Val Gly Glu Asp Ala Met Glu Gly Ser Leu Asp Glu Ile
    450                 455                 460
Thr Ser Arg Phe Glu Arg Ser Val Leu Thr Gln Leu Tyr Arg Asn Tyr
465                 470                 475                 480
Pro Ser Thr Arg Lys Leu Ala Lys Arg Leu Gly Val Ser His Thr Ala
                485                 490                 495
Ile Ala Asn Lys Leu Arg Glu Tyr Gly Leu Ser Gln Lys Lys Asn Glu
            500                 505                 510
Glu

<210> SEQ ID NO 11
<211> LENGTH: 2304
<212> TYPE: DNA
<213> ORGANISM: Homo sapiens

<400> SEQUENCE: 11
cggcctgcgt ccgccaccgg aagcgccctc ctaatccccg cagcgccacc gccattgccg      60
ccatcgtcgt ggggcttctg gggcagctag ggctgcccgc cgcgctgcct gcgccggacc     120
ggggcgggtc cagtcccggg cgggccgtcg cgggagagaa ataacatctg ctttgctgcc     180
gagctcagag gagaccccag accccctcccg cagccagagg gctggagcct gctcagaggt     240
gctttgaaga tgccggaggc cccgcctctg ctgttggcag ctgtgttgct ggcctggtg      300 ctgctggtgg tgctgctgct gcttctgagg cactggggct ggggcctgtg ccttatcggc     360
tggaacgagt tcatcctgca gcccatccac aacctgctca tgggtgacac caaggagcag     420
cgcatcctga accacgtgct gcagcatgcg gagcccggga cgcacagag cgtgctggag      480 gccattgaca cctactgcga gcagaaggag tgggccatga cgtgggcga caagaaggc      540 aagatcgtgg acgccgtgat tcaggagcac cagccctccg tgctgctgga ctgggggcc     600 tactgtggct actcagctgt gcgcatggcc cgcctgctgt caccaggggc gaggctcatc     660
```

-continued

| | |
|---|---|
| accatcgaga tcaaccccga ctgtgccgcc atcacccagc ggatggtgga tttcgctggc | 720 |
| gtgaaggaca aggtcaccct tgtggttgga gcgtcccagg acatcatccc ccagctgaag | 780 |
| aagaagtatg atgtggacac actggacatg gtcttcctcg accactggaa ggaccggtac | 840 |
| ctgccggaca cgcttctctt ggaggaatgt ggcctgctgc ggaaggggac agtgctactg | 900 |
| gctgacaacg tgatctgccc aggtgcgcca gacttcctag cacacgtgcg cgggagcagc | 960 |
| tgctttgagt gcacacacta ccaatcgttc ctggaataca gggaggtggt ggacggcctg | 1020 |
| gagaaggcca tctacaaggg cccaggcagc gaagcagggc cctgactgcc ccccggccc | 1080 |
| ccctctcggg ctctctcacc cagcctgta ctgaaggtgc cagacgtgct cctgctgacc | 1140 |
| ttctgcggct ccgggctgtg tcctaaatgc aaagcacacc tcggccgagg cctgcgccct | 1200 |
| gacatgctaa cctctctgaa ctgcaacact ggattgttct tttttaagac tcaatcatga | 1260 |
| cttctttact aacactggct agctatatta tcttatatac taatatcatg ttttaaaaat | 1320 |
| ataaaataga aattaagaat ctaaatattt agatataact cgacttagta catccttctc | 1380 |
| aactgccatt cccctgctgc ccttgacttg ggcaccaaac attcaaagct ccccttgacg | 1440 |
| gacgctaacg ctaagggcgg ggcccctagc tggctgggtt ctgggtggca cgcctggccc | 1500 |
| actggcctcc cagccacagt ggtgcagagg tcagccctcc tgcagctagg caggggcac | 1560 |
| ctgttagccc catggggacg actgccggcc tgggaaacga agaggagtca gccagcattc | 1620 |
| acacctttct gaccaagcag gcgctgggga caggtggacc ccgcagcagc accagccct | 1680 |
| ctgggcccca tgtggcacag agtggaagca tctccttccc tactcccac tgggccttgc | 1740 |
| ttacagaaga ggcaatggct cagaccagct cccgcatccc tgtagttgcc tccctggccc | 1800 |
| atgagtgagg atgcagtgct ggtttctgcc cacctacacc tagagctgtc cccatctcct | 1860 |
| ccaagggtc agactgctag ccacctcaga ggctccaagg gcccagttcc caggcccagg | 1920 |
| acaggaatca accctgtgct agctgagttc acctgcaccg agaccagccc ctagccaaga | 1980 |
| ttctactcct gggctcaagg cctggctagc ccccagccag cccactccta tggatagaca | 2040 |
| gaccagtgag cccaagtgga caagtttggg gccacccagg accagaaac agagcctctg | 2100 |
| caggacacag cagatgggca cctgggacca cctccaccca gggccctgcc ccagacgcgc | 2160 |
| agaggcccga cacaagggag aagccagcca cttgtgccag acctgagtgg cagaaagcaa | 2220 |
| aaagttcctt tgctgcttta atttttaaat tttcttacaa aaatttaggt gtttaccaat | 2280 |
| agtcttattt tggcttattt ttaa | 2304 |

<210> SEQ ID NO 12
<211> LENGTH: 2262
<212> TYPE: DNA
<213> ORGANISM: Homo sapiens

<400> SEQUENCE: 12

| | |
|---|---|
| ctcccacggg aggagcaaga acacagaaca gaggggcaa acagctcca ccaggagtca | 60 |
| ggagtgaatc ccctctggga acgaggcact aggaagaaga acttccagcc caggagaaat | 120 |
| aacatctgct ttgctgccga gctcagagga gaccccagac ccctcccgca gccagagggc | 180 |
| tggagcctgc tcagaggtgc tttgaagatg ccggaggccc cgcctctgct gttggcagct | 240 |
| gtgttgctgg gcctggtgct gctggtggtg ctgctgctgc ttctgaggca ctgggctgg | 300 |
| ggcctgtgcc ttatcggctg gaacgagttc atcctgcagc ccatccacaa cctgctcatg | 360 |
| ggtgacacca aggagcagcg catcctgaac cacgtgctgc agcatgcgga gccccgggaac | 420 |
| gcacagagcg tgctggaggc cattgacacc tactgcgagc agaaggagtg ggccatgaac | 480 |

```
gtgggcgaca agaaaggcaa gatcgtggac gccgtgattc aggagcacca gccctccgtg    540
ctgctggagc tggggggccta ctgtggctac tcagctgtgc gcatggcccg cctgctgtca    600 ccagggggcga ggctcatcac catcgagatc aaccccgact gtgccgccat cacccagcgg    660
atggtggatt tcgctggcgt gaaggacaag gtcaccctttg tggttggagc gtcccaggac    720
atcatccccc agctgaagaa gaagtatgat gtggacacac tggacatggt cttcctcgac    780
cactggaagg accggtacct gccggacacg cttctcttgg aggaatgtgg cctgctgcgg    840
aaggggacag tgctactggc tgacaacgtg atctgcccag gtgcgccaga cttcctagca    900
cacgtgcgcg ggagcagctg ctttgagtgc acacactacc aatcgttcct ggaatacagg    960
gaggtggtgg acggcctgga aaggccatc tacaagggcc caggcagcga agcagggccc    1020
tgactgcccc cccggccccc ctctcgggct ctctcaccca gcctggtact gaaggtgcca    1080
gacgtgctcc tgctgacctt ctgcggctcc gggctgtgtc ctaaatgcaa agcacacctc    1140
ggccgaggcc tgcgccctga catgctaacc tctctgaact gcaacactgg attgttcttt    1200
tttaagactc aatcatgact tctttactaa cactggctag ctatattatc ttatatacta    1260
atatcatgtt ttaaaaatat aaaatagaaa ttaagaatct aaatatttag atataactcg    1320
acttagtaca tccttctcaa ctgccattcc cctgctgccc ttgacttggg caccaaacat    1380
tcaaagctcc ccttgacgga cgctaacgct aagggcgggg cccctagctg gctgggttct    1440
gggtggcacg cctggcccac tggcctccca gccacagtgg tgcagaggtc agccctcctg    1500
cagctaggcc aggggcacct gttagcccca tggggacgac tgccggcctg ggaaacgaag    1560
aggagtcagc cagcattcac acctttctga ccaagcaggc gctggggaca ggtggacccc    1620
gcagcagcac cagcccctct gggccccatg tggcacagag tggaagcatc tccttccccta   1680 ctccccactg ggccttgctt acagaagagg caatggctca gaccagctcc cgcatccctg    1740
tagttgcctc cctggcccat gagtgaggat gcagtgctgg tttctgccca cctacaccta    1800
gagctgtccc catctcctcc aagggggtcag actgctagcc acctcagagg ctccaagggc    1860
ccagttccca ggcccaggac aggaatcaac cctgtgctag ctgagttcac ctgcaccgag    1920
accagcccct agccaagatt ctactcctgg gctcaaggc tggctagccc ccagccagcc    1980
cactcctatg gatagacaga ccagtgagcc caagtggaca gtttggggc cacccaggga    2040 ccagaaacag agcctctgca ggacacagca gatgggcacc tgggaccacc tccacccagg    2100
gccctgcccc agacgcgcag aggcccgaca caagggagaa gccagccact tgtgccagac    2160
ctgagtggca gaaagcaaaa agttcctttg ctgctttaat ttttaaattt tcttacaaaa    2220
atttaggtgt ttaccaatag tcttatttttg gcttattttt aa                      2262
```

<210> SEQ ID NO 13
<211> LENGTH: 2279
<212> TYPE: DNA
<213> ORGANISM: Homo sapiens

<400> SEQUENCE: 13

```
tggagataac acggatcgct gtgtacactg tgtgctccgg ttgttgcatc cgagggttga     60
tcggatggtg gttcccatcc agatccaagt cctggcccct gatcacagag aaacacagct    120
ggacattaaa gtgaaataac atctgctttg ctgccgagct cagaggagac cccagacccc    180
tcccgcagcc agagggctgg agcctgctca gaggtgctttt gaagatgccg gaggccccgc    240
ctctgctgtt ggcagctgtg ttgctgggcc tggtgctgct ggtggtgctg ctgctgcttc    300
```

```
tgaggcactg gggctggggc ctgtgcctta tcggctggaa cgagttcatc ctgcagccca    360
tccacaacct gctcatgggt gacaccaagg agcagcgcat cctgaaccac gtgctgcagc    420
atgcggagcc cgggaacgca cagagcgtgc tggaggccat tgacacctac tgcgagcaga    480
aggagtgggc catgaacgtg ggcgacaaga aaggcaagat cgtggacgcc gtgattcagg    540
agcaccagcc ctccgtgctg ctggagctgg gggcctactg tggctactca gctgtgcgca    600
tggcccgcct gctgtcacca ggggcgaggc tcatcaccat cgagatcaac ccgactgtg    660 ccgccatcac ccagcggatg gtggatttcg ctggcgtgaa ggacaaggtc acccttgtgg    720
ttggagcgtc ccaggacatc atccccagc tgaagaagaa gtatgatgtg acacactgg    780 acatggtctt cctcgaccac tggaaggacc ggtacctgcc ggacacgctt ctcttggagg    840
aatgtggcct gctgcggaag gggacagtgc tactggctga acgtgatc tgcccaggtg    900 cgccagactt cctagcacac gtgcgcggga gcagctgctt tgagtgcaca cactaccaat    960
cgttcctgga atacagggag gtggtggacg cctggagaa ggccatctac aagggcccag    1020
gcagcgaagc agggccctga ctgccccccc ggccccctc tcgggctctc tcacccagcc    1080
tggtactgaa ggtgccagac gtgctcctgc tgaccttctg cggctccggg ctgtgtccta    1140
aatgcaaagc acacctcggc cgaggcctgc gccctgacat gctaacctct ctgaactgca    1200
acactggatt gttctttttt aagactcaat catgacttct ttactaacac tggctagcta    1260
tattatctta tatactaata tcatgtttta aaaatataaa atagaaatta gaatctaaa    1320 tatttagata taactcgact tagtacatcc ttctcaactg ccattcccct gctgcccttg    1380
acttgggcac caaacattca aagctcccct tgacggacgc taacgctaag ggcggggccc    1440
ctagctggct gggttctggg tggcacgcct ggcccactgg cctcccagcc acagtggtgc    1500
agaggtcagc cctcctgcag ctaggccagg ggcacctgtt agcccatgg ggacgactgc    1560 cggcctggga aacgaagagg agtcagccag cattcacacc tttctgacca gcaggcgct    1620 ggggacaggt ggacccccgca gcagcaccag ccctctggg ccccatgtgg cacagagtgg    1680
aagcatctcc ttccctactc cccactgggc cttgcttaca aagaggcaa tggctcagac    1740 cagctcccgc atccctgtag ttgcctccct ggcccatgag tgaggatgca gtgctggttt    1800
ctgcccacct acacctagag ctgtccccat ctcctccaag gggtcagact gctagccacc    1860
tcagaggctc caagggccca gttcccaggc ccaggacagg aatcaaccct gtgctagctg    1920
agttcacctg caccgagacc agcccctagc caagattcta ctcctgggct caaggcctgg    1980
ctagccccca gccagcccac tcctatggat agacagacca gtgagcccaa gtggacaagt    2040
ttggggccac ccagggacca gaaacagagc ctctgcagga cacagcagat gggcacctgg    2100
gaccacctcc acccagggcc ctgccccaga gcgcagagg cccgacacaa gggagaagcc    2160
agccacttgt gccagacctg agtggcagaa agcaaaaagt tcctttgctg ctttaatttt    2220
taaattttct tacaaaaatt taggtgttta ccaatagtct tatttggct tatttttaa    2279
```

<210> SEQ ID NO 14
<211> LENGTH: 2035
<212> TYPE: DNA
<213> ORGANISM: Homo sapiens

<400> SEQUENCE: 14

```
gctgttggca gctgtgttgc tgggcctggt gctgctggtg gtgctgctgc tgcttctgag     60 gcactgggc tggggcctgt gccttatcgg ctggaacgag ttcatcctgc agcccatcca    120
caacctgctc atgggtgaca ccaaggagca gcgcatcctg aaccacgtgc tgcagcatgc    180
```

-continued

```
ggagcccggg aacgcacaga gcgtgctgga ggccattgac acctactgcg agcagaagga    240
gtgggccatg aacgtgggcg acaagaaagg caagatcgtg gacgccgtga ttcaggagca    300
ccagccctcc gtgctgctgg agctgggggc ctactgtggc tactcagctg tgcgcatggc    360
ccgcctgctg tcaccagggg cgaggctcat caccatcaga atcaaccccg actgtgccgc    420
catcacccag cggatggtgg atttcgctgg cgtgaaggac aaggtcaccc ttgtggttgg    480
agcgtcccag gacatcatcc cccagctgaa gaagaagtat gatgtggaca cactggacat    540
ggtcttcctc gaccactgga aggaccggta cctgccggac acgcttctct ggaggaatg    600 tggcctgctg cggaagggga cagtgctact ggctgacaac gtgatctgcc aggtgcgcc    660 agacttccta gcacacgtgc gcgggagcag ctgctttgag tgcacacact accaatcgtt    720
cctggaatac agggaggtgg tggacggcct ggagaaggcc atctacaagg cccaggcag    780 cgaagcaggg ccctgactgc cccccggcc cccctctcgg gctctctcac ccagcctggt    840
actgaaggtg ccagacgtgc tcctgctgac cttctgcggc tccgggctgt gtcctaaatg    900
caaagcacac ctcggccgag gcctgcgccc tgacatgcta acctctctga actgcaacac    960
tggattgttc tttttaaga ctcaatcatg acttctttac taacactggc tagctatatt   1020
atcttatata ctaatatcat gttttaaaaa tataaaatag aaattaagaa tctaaatatt   1080
tagatataac tcgacttagt acatccttct caactgccat tccctgctg cccttgactt   1140 gggcaccaaa cattcaaagc tccccttgac ggacgctaac gctaagggcg ggcccctag   1200 ctggctgggt tctgggtggc acgcctggcc cactggcctc ccagccacag tggtgcagag   1260
gtcagccctc ctgcagctag gccaggggca cctgttagcc ccatggggac gactgccggc   1320
ctgggaaacg aagaggagtc agccagcatt cacacctttc tgaccaagca ggcgctgggg   1380
acaggtggac cccgcagcag caccagcccc tctgggcccc atgtggcaca gagtggaagc   1440
atctccttcc ctactcccca ctgggccttg cttacagaag aggcaatggc tcagaccagc   1500
tcccgcatcc ctgtagttgc ctccctggcc catgagtgag gatgcagtgc tggtttctgc   1560
ccacctacac ctagagctgt ccccatctcc tccaagggt cagactgcta gccacctcag   1620
aggctccaag ggcccagttc ccaggcccag gacaggaatc aaccctgtgc tagctgagtt   1680
cacctgcacc gagaccagcc cctagccaag attctactcc tgggctcaag gcctggctag   1740
cccccagcca gcccactcct atggatagac agaccagtga gcccaagtgg acaagtttgg   1800
ggccacccag ggaccagaaa cagagcctct gcaggacaca gcagatgggc acctgggacc   1860
acctccaccc agggccctgc cccagacgcg cagaggcccg acacaaggga gaagccagcc   1920
acttgtgcca gacctgagtg gcagaaagca aaagttcct ttgctgcttt aattttaaa    1980 ttttcttaca aaaatttagg tgtttaccaa tagtcttatt ttggcttatt tttaa          2035
```

<210> SEQ ID NO 15
<211> LENGTH: 271
<212> TYPE: PRT
<213> ORGANISM: Homo sapiens

<400> SEQUENCE: 15

```
Met Pro Glu Ala Pro Pro Leu Leu Leu Ala Ala Val Leu Leu Gly Leu
1               5                   10                  15

Val Leu Leu Val Val Leu Leu Leu Leu Arg His Trp Gly Trp Gly
            20                  25                  30

Leu Cys Leu Ile Gly Trp Asn Glu Phe Ile Leu Gln Pro Ile His Asn
        35                  40                  45
```

Leu Leu Met Gly Asp Thr Lys Glu Gln Arg Ile Leu Asn His Val Leu
            50                  55                  60

Gln His Ala Glu Pro Gly Asn Ala Gln Ser Val Leu Glu Ala Ile Asp
65                  70                  75                  80

Thr Tyr Cys Glu Gln Lys Glu Trp Ala Met Asn Val Gly Asp Lys Lys
                85                  90                  95

Gly Lys Ile Val Asp Ala Val Ile Gln Glu His Gln Pro Ser Val Leu
            100                 105                 110

Leu Glu Leu Gly Ala Tyr Cys Gly Tyr Ser Ala Val Arg Met Ala Arg
        115                 120                 125

Leu Leu Ser Pro Gly Ala Arg Leu Ile Thr Ile Glu Ile Asn Pro Asp
    130                 135                 140

Cys Ala Ala Ile Thr Gln Arg Met Val Asp Phe Ala Gly Val Lys Asp
145                 150                 155                 160

Lys Val Thr Leu Val Val Gly Ala Ser Gln Asp Ile Ile Pro Gln Leu
                165                 170                 175

Lys Lys Lys Tyr Asp Val Asp Thr Leu Asp Met Val Phe Leu Asp His
            180                 185                 190

Trp Lys Asp Arg Tyr Leu Pro Asp Thr Leu Leu Leu Glu Glu Cys Gly
        195                 200                 205

Leu Leu Arg Lys Gly Thr Val Leu Leu Ala Asp Asn Val Ile Cys Pro
    210                 215                 220

Gly Ala Pro Asp Phe Leu Ala His Val Arg Gly Ser Ser Cys Phe Glu
225                 230                 235                 240

Cys Thr His Tyr Gln Ser Phe Leu Glu Tyr Arg Glu Val Val Asp Gly
                245                 250                 255

Leu Glu Lys Ala Ile Tyr Lys Gly Pro Gly Ser Glu Ala Gly Pro
            260                 265                 270

<210> SEQ ID NO 16
<211> LENGTH: 221
<212> TYPE: PRT
<213> ORGANISM: Homo sapiens

<400> SEQUENCE: 16

Met Gly Asp Thr Lys Glu Gln Arg Ile Leu Asn His Val Leu Gln His
1               5                   10                  15

Ala Glu Pro Gly Asn Ala Gln Ser Val Leu Glu Ala Ile Asp Thr Tyr
            20                  25                  30

Cys Glu Gln Lys Glu Trp Ala Met Asn Val Gly Asp Lys Lys Gly Lys
        35                  40                  45

Ile Val Asp Ala Val Ile Gln Glu His Gln Pro Ser Val Leu Leu Glu
    50                  55                  60

Leu Gly Ala Tyr Cys Gly Tyr Ser Ala Val Arg Met Ala Arg Leu Leu
65                  70                  75                  80

Ser Pro Gly Ala Arg Leu Ile Thr Ile Glu Ile Asn Pro Asp Cys Ala
                85                  90                  95

Ala Ile Thr Gln Arg Met Val Asp Phe Ala Gly Val Lys Asp Lys Val
            100                 105                 110

Thr Leu Val Val Gly Ala Ser Gln Asp Ile Ile Pro Gln Leu Lys Lys
        115                 120                 125

Lys Tyr Asp Val Asp Thr Leu Asp Met Val Phe Leu Asp His Trp Lys
    130                 135                 140

Asp Arg Tyr Leu Pro Asp Thr Leu Leu Leu Glu Glu Cys Gly Leu Leu

```
                145                 150                 155                 160
Arg Lys Gly Thr Val Leu Leu Ala Asp Asn Val Ile Cys Pro Gly Ala
                    165                 170                 175
Pro Asp Phe Leu Ala His Val Arg Gly Ser Ser Cys Phe Glu Cys Thr
            180                 185                 190
His Tyr Gln Ser Phe Leu Glu Tyr Arg Glu Val Val Asp Gly Leu Glu
                195                 200                 205
Lys Ala Ile Tyr Lys Gly Pro Gly Ser Glu Ala Gly Pro
        210                 215                 220

<210> SEQ ID NO 17
<211> LENGTH: 3387
<212> TYPE: DNA
<213> ORGANISM: Gordonia effusa

<400> SEQUENCE: 17
```

| | | | | | |
|---|---|---|---|---|---|
| atgtctgacc | agcccaacgc | gcttccgtct | gccatcgagc | cgctgaaccc | cgatcctcaa | 60 |
| gcgacagagc | agatctcgca | ctgtgcgacg | attgccgaac | ttgtccgggt | tctcgccgag | 120 |
| agctacggtg | atcgcccgc | gctgggttgg | cgaaacaata | gtgatccctc | gtcctggcat | 180 |
| tcgatgactt | accgagatct | cgctgagcgg | gcggattcca | tggcgcgact | tctccattcg | 240 |
| acacttggcg | tcgccgagaa | cgaccgggtg | gcgacggtgg | gcttcactag | cgcggagtac | 300 |
| accatcgcct | cgcttgccgt | cggcacgctc | ggcgcgatgg | aggtaccact | gcaaaacgcc | 360 |
| gggtccgtcg | acgtctgggc | cgcaatcctc | accgaaaccg | actgtgtgag | cgcggttgtc | 420 |
| gcggccgatc | aactgccttc | gatcgctcgg | ctggccgaat | cgggcaccta | caccggcctg | 480 |
| cgacatgtgc | tggtcttcga | catcggctcg | cgcgacggaa | ccacgctcga | tgacgcggca | 540 |
| cgacgactgg | tcgctgcggg | cacccaggtg | catctccgcc | agcccggcgc | cgagccgacg | 600 |
| acaccgccgg | ctccactgcc | ccagatcacg | gccaaccccg | accgcgtcgc | cctcctcatc | 660 |
| tacacctccg | gtagcaccgg | agcccccaaa | ggcgccatgt | acaccgaaac | cgcggtgacc | 720 |
| cggttattcc | aatcgggact | cagcggcttg | gggcgcgcca | ccgacggtca | cggctggatc | 780 |
| accctgaact | tcatgccgat | gagccacgtg | atgggacgca | gcactctgtg | caaaccctg | 840 |
| ggaaatggtg | caccgcgta | cttcaccccg | cgcgccgacc | tcgccgagtt | gctcaccgac | 900 |
| ctcgcagcgg | tccagccgac | cgacctgcaa | ttcgtaccgc | gcatctggga | catgctgtac | 960 |
| caggagtacg | tccgcctcac | cgatcaggac | gtcagtgaac | aagacgccct | cacccgtatg | 1020 |
| cgcgaacact | atttcggtac | ccggactgcc | accgccatca | ccggttccgc | accgatctcc | 1080 |
| gatgaggttc | ggcgtttcgt | cgaagcgatg | ctgccggttc | cactcatcga | aggctatgga | 1140 |
| agtaccgagg | ccgccggcgt | ctccatcgac | ggccgcatcc | agcgaccgcc | ggtggtggat | 1200 |
| tacaagcttc | tcgacgttcc | tgaactcggc | tacctgagca | ccgatcggcc | gcaccgcgc | 1260 |
| ggcgaactgc | tcgtcaagac | cgaccatatc | ttccgggggt | actacaaccg | tcccgacctc | 1320 |
| acctcatcgg | tcttcgacga | ccagggctac | taccggacgg | gcgacatcgt | cgccgagacc | 1380 |
| ggcccagacc | aaatcgagta | tgtcgaccgc | cggaacaacg | tgatgaagct | ttcgcagggt | 1440 |
| gagttcgtcg | cgatcgccca | catcgaggcg | gtactgacca | ccccgccgat | ccagcaactg | 1500 |
| tacgtctacg | gcaacagcgc | gcggccctat | ctgctcgcgg | tcgtcgtgcc | caccccgag | 1560 |
| ttacgcgaac | gacacgccga | cgacaacgag | ctgcgacgag | aagtactgac | ggcactgcgc | 1620 |
| tctcatggcg | aacgtaatgg | ccttgcggcc | gtagagattc | cgcgcgatgt | gattgtcgaa | 1680 |
| cgcacgccgt | tcagcctgga | gaacggtctt | cttaccggca | tccgaaaact | cgcgcgccca | 1740 |

-continued

```
caactcaaag agcgctacgg cgctcggctg gaggccctct acgccgagct ggccgatagc    1800
cgtatcacca ggctgcgcga cgtcaaagcc gttgccgcac aacgctcaac ggtgacaacg    1860
gtcatcgacg tggtcacagc gatactcgac ctcgccgacg gggaggtcac ggccgcggca    1920
catttcaccg acctcggcgg agattccctc accgccgtca cggtcgggaa cgaactccgc    1980
gacatcttcg acgccgaagt accggtcggc gtcttgacca gcccgtcatc gacgctggcc    2040
gacatagcca acatatcga cgggcgcaca agcgaggccc ggccaaccgc ggaatcggtc    2100
cacggcaccg gaaccaccct tcgggcagcg gacctcactc tcgacaaatt cctcgacgag    2160
gagaccttgc gcgctgcgtc cgacgtgacg tcggctgcga ccgacgtacg gaccgtattc    2220
atcaccggcg caaccggatt cctcggtcgc tatctgacac tcgactggtt gcgtcggatg    2280
gcaaaagtcg gcggcacggt gatctgcctc gttcgaggtg cggacgatga tgccgcccgg    2340
gcgcgcctag acgcggcatt cgactccagc gatctatggt cggagtacca gcgactggcc    2400
aaagaccacc ttcgggttct cgccggcgac aaggactcgg atcacctcgc gctcacccca    2460
gacgtatggg atgaattggc aaagtccgtc gacctcatca tcgatcccgc ggcgctggtc    2520
aaccatgtgt tgccatatcg agaactattc ggacccaacg tatctggcac tgctgagctg    2580
atcagactcg cggtgacgac cacccgtaag ccatacgtgt atatctcaac ggtcggtgta    2640
ggcgaccagg tcgcgccggg atctttcacc gaggaccccg acatccgcga gatgagctcg    2700
gtacgcgaga ttaacgacac ttacgccaac ggatatggca acagcaaatg ggccggcgaa    2760
gtattgctcg cgcaggcgca cgaacgattt gagttaccgg tcagcgtctt cgctgcgac    2820
atgatcgtcg ccgatgatca caccatcggg cagctgaacc tacctgacat gttcacgcgg    2880
ctactgatga gcgtgctcgc caccggcttg gcacctcgct ctttctatca actcgccacc    2940
gacggatcgg cacaggaggc ccacttcgat gctctgccgg tcgatttcct cgccgaagcg    3000
atcaacaccc tgtgggttaa ggacggagcc cgcaccttca cgcgatgaa cccgcacgcc    3060
gacggcatcg gattcgatca gtacattcgc tggctgatcg acagcggcga gcagatcagc    3120
cttgtagaca actatgacga ttggtatcgg cgattcggtg cggccctcgc cgatctgccg    3180
gaaaagcagc gacgcggatc gttgattccg ttgctgcaca actatgttca cccgatgacg    3240
ccgcacaatc gcggtatggc gtcggcggac cgattccacg acgcggtccg aaccgctggc    3300
gtcgggcagt cgtccgacat cccgcatatc acgccacaga tcatcgagaa ctacgcccgc    3360
agcctccgcg gtctcggggt gatctga                                         3387
```

<210> SEQ ID NO 18
<211> LENGTH: 1128
<212> TYPE: PRT
<213> ORGANISM: Gordonia effusa

<400> SEQUENCE: 18

```
Met Ser Asp Gln Pro Asn Ala Leu Pro Ser Ala Ile Glu Pro Leu Asn
 1               5                  10                  15

Pro Asp Pro Gln Ala Thr Glu Gln Ile Ser His Cys Ala Thr Ile Ala
            20                  25                  30

Glu Leu Val Arg Val Leu Ala Glu Ser Tyr Gly Asp Arg Pro Ala Leu
        35                  40                  45

Gly Trp Arg Asn Asn Ser Asp Pro Ser Ser Trp His Ser Met Thr Tyr
    50                  55                  60

Arg Asp Leu Ala Glu Arg Ala Asp Ser Met Ala Arg Leu Leu His Ser
65                  70                  75                  80
```

```
Thr Leu Gly Val Ala Glu Asn Asp Arg Val Ala Thr Val Gly Phe Thr
                    85                  90                  95

Ser Ala Glu Tyr Thr Ile Ala Ser Leu Ala Val Gly Thr Leu Gly Ala
                100                 105                 110

Met Glu Val Pro Leu Gln Asn Ala Gly Ser Val Asp Val Trp Ala Ala
                115                 120                 125

Ile Leu Thr Glu Thr Asp Cys Val Ser Ala Val Ala Ala Asp Gln
            130                 135                 140

Leu Pro Ser Ile Ala Arg Leu Ala Glu Ser Gly Thr Tyr Thr Gly Leu
145                 150                 155                 160

Arg His Val Leu Val Phe Asp Ile Gly Ser Arg Asp Gly Thr Thr Leu
                165                 170                 175

Asp Asp Ala Ala Arg Arg Leu Val Ala Ala Gly Thr Gln Val His Leu
                180                 185                 190

Arg Gln Pro Gly Ala Glu Pro Thr Thr Pro Ala Pro Leu Pro Gln
            195                 200                 205

Ile Thr Ala Asn Pro Asp Arg Val Ala Leu Leu Ile Tyr Thr Ser Gly
            210                 215                 220

Ser Thr Gly Ala Pro Lys Gly Ala Met Tyr Thr Glu Thr Ala Val Thr
225                 230                 235                 240

Arg Leu Phe Gln Ser Gly Leu Ser Gly Leu Gly Arg Ala Thr Asp Gly
                245                 250                 255

His Gly Trp Ile Thr Leu Asn Phe Met Pro Met Ser His Val Met Gly
                260                 265                 270

Arg Ser Thr Leu Trp Gln Thr Leu Gly Asn Gly Gly Thr Ala Tyr Phe
            275                 280                 285

Thr Pro Arg Ala Asp Leu Ala Glu Leu Leu Thr Asp Leu Ala Ala Val
            290                 295                 300

Gln Pro Thr Asp Leu Gln Phe Val Pro Arg Ile Trp Asp Met Leu Tyr
305                 310                 315                 320

Gln Glu Tyr Val Arg Leu Thr Asp Gln Asp Val Ser Glu Gln Asp Ala
                325                 330                 335

Leu Thr Arg Met Arg Glu His Tyr Phe Gly Thr Arg Thr Ala Thr Ala
            340                 345                 350

Ile Thr Gly Ser Ala Pro Ile Ser Asp Glu Val Arg Arg Phe Val Glu
            355                 360                 365

Ala Met Leu Pro Val Pro Leu Ile Glu Gly Tyr Gly Ser Thr Glu Ala
            370                 375                 380

Ala Gly Val Ser Ile Asp Gly Arg Ile Gln Arg Pro Pro Val Val Asp
385                 390                 395                 400

Tyr Lys Leu Leu Asp Val Pro Glu Leu Gly Tyr Leu Ser Thr Asp Arg
                405                 410                 415

Pro His Pro Arg Gly Glu Leu Leu Val Lys Thr Asp His Ile Phe Ala
            420                 425                 430

Gly Tyr Tyr Asn Arg Pro Asp Leu Thr Ser Ser Val Phe Asp Asp Gln
            435                 440                 445

Gly Tyr Tyr Arg Thr Gly Asp Ile Val Ala Glu Thr Gly Pro Asp Gln
            450                 455                 460

Ile Glu Tyr Val Asp Arg Arg Asn Asn Val Met Lys Leu Ser Gln Gly
465                 470                 475                 480

Glu Phe Val Ala Ile Ala His Ile Glu Ala Val Leu Thr Thr Pro Pro
                485                 490                 495
```

```
Ile Gln Gln Leu Tyr Val Tyr Gly Asn Ser Ala Arg Pro Tyr Leu Leu
                500                 505                 510

Ala Val Val Pro Thr Pro Glu Leu Arg Glu Arg His Ala Asp Asp
            515                 520                 525

Asn Glu Leu Arg Arg Glu Val Leu Thr Ala Leu Arg Ser His Gly Glu
    530                 535                 540

Arg Asn Gly Leu Ala Ala Val Glu Ile Pro Arg Asp Val Ile Val Glu
545                 550                 555                 560

Arg Thr Pro Phe Ser Leu Glu Asn Gly Leu Leu Thr Gly Ile Arg Lys
                565                 570                 575

Leu Ala Arg Pro Gln Leu Lys Glu Arg Tyr Gly Ala Arg Leu Glu Ala
                580                 585                 590

Leu Tyr Ala Glu Leu Ala Asp Ser Arg Ile Thr Arg Leu Arg Asp Val
            595                 600                 605

Lys Ala Val Ala Ala Gln Arg Ser Thr Val Thr Val Ile Asp Val
            610                 615                 620

Val Thr Ala Ile Leu Asp Leu Ala Asp Gly Glu Val Thr Ala Ala Ala
625                 630                 635                 640

His Phe Thr Asp Leu Gly Gly Asp Ser Leu Thr Ala Val Thr Val Gly
                645                 650                 655

Asn Glu Leu Arg Asp Ile Phe Asp Ala Glu Val Pro Val Gly Val Leu
            660                 665                 670

Thr Ser Pro Ser Ser Thr Leu Ala Asp Ile Ala Glu His Ile Asp Gly
                675                 680                 685

Arg His Ser Glu Ala Arg Pro Thr Ala Glu Ser Val His Gly Thr Gly
            690                 695                 700

Thr Thr Leu Arg Ala Ala Asp Leu Thr Leu Asp Lys Phe Leu Asp Glu
705                 710                 715                 720

Glu Thr Leu Arg Ala Ala Ser Asp Val Thr Ser Ala Ala Thr Asp Val
                725                 730                 735

Arg Thr Val Phe Ile Thr Gly Ala Thr Gly Phe Leu Gly Arg Tyr Leu
            740                 745                 750

Thr Leu Asp Trp Leu Arg Arg Met Ala Lys Val Gly Gly Thr Val Ile
            755                 760                 765

Cys Leu Val Arg Gly Ala Asp Asp Ala Ala Arg Ala Arg Leu Asp
            770                 775                 780

Ala Ala Phe Asp Ser Ser Asp Leu Trp Ser Glu Tyr Gln Arg Leu Ala
785                 790                 795                 800

Lys Asp His Leu Arg Val Leu Ala Gly Asp Lys Asp Ser Asp His Leu
                805                 810                 815

Ala Leu Thr Pro Asp Val Trp Asp Glu Leu Ala Lys Ser Val Asp Leu
                820                 825                 830

Ile Ile Asp Pro Ala Ala Leu Val Asn His Val Leu Pro Tyr Arg Glu
            835                 840                 845

Leu Phe Gly Pro Asn Val Ser Gly Thr Ala Glu Leu Ile Arg Leu Ala
    850                 855                 860

Val Thr Thr Thr Arg Lys Pro Tyr Val Tyr Ile Ser Thr Val Gly Val
865                 870                 875                 880

Gly Asp Gln Val Ala Pro Gly Ser Phe Thr Glu Asp Pro Asp Ile Arg
                885                 890                 895

Glu Met Ser Ser Val Arg Glu Ile Asn Asp Thr Tyr Ala Asn Gly Tyr
                900                 905                 910

Gly Asn Ser Lys Trp Ala Gly Glu Val Leu Leu Ala Gln Ala His Glu
```

```
                915                 920                 925
Arg Phe Glu Leu Pro Val Ser Val Phe Arg Cys Asp Met Ile Val Ala
    930                 935                 940

Asp Asp His Thr Ile Gly Gln Leu Asn Leu Pro Asp Met Phe Thr Arg
945                 950                 955                 960

Leu Leu Met Ser Val Leu Ala Thr Gly Leu Ala Pro Arg Ser Phe Tyr
                965                 970                 975

Gln Leu Ala Thr Asp Gly Ser Ala Gln Glu Ala His Phe Asp Ala Leu
            980                 985                 990

Pro Val Asp Phe Leu Ala Glu Ala Ile Asn Thr Leu Trp Val Lys Asp
        995                 1000                1005

Gly Ala Arg Thr Phe Asn Ala Met Asn Pro His Ala Asp Gly Ile
    1010                1015                1020

Gly Phe Asp Gln Tyr Ile Arg Trp Leu Ile Asp Ser Gly Glu Gln
    1025                1030                1035

Ile Ser Leu Val Asp Asn Tyr Asp Asp Trp Tyr Arg Arg Phe Gly
    1040                1045                1050

Ala Ala Leu Ala Asp Leu Pro Glu Lys Gln Arg Arg Gly Ser Leu
    1055                1060                1065

Ile Pro Leu Leu His Asn Tyr Val His Pro Met Thr Pro His Asn
    1070                1075                1080

Arg Gly Met Ala Ser Ala Asp Arg Phe His Asp Ala Val Arg Thr
    1085                1090                1095

Ala Gly Val Gly Gln Ser Ser Asp Ile Pro His Ile Thr Pro Gln
    1100                1105                1110

Ile Ile Glu Asn Tyr Ala Arg Ser Leu Arg Gly Leu Gly Val Ile
    1115                1120                1125

<210> SEQ ID NO 19
<211> LENGTH: 4636
<212> TYPE: DNA
<213> ORGANISM: Artificial Sequence
<220> FEATURE:
<223> OTHER INFORMATION: Nucleotide sequence of DNA fragment containing
      CAR gene of Nocardia brasiliensis (codon-optimized) and entD gene
      of Escherichia coli

<400> SEQUENCE: 19
ccaagcttgc atgccagatc gtttagatcc gaaggaaaac gtcgaaaagc aatttgcttt      60
tcgacgcccc accccgcgcg ttttagcgtg tcagtagacg cgtagggtaa gtggggtagc     120
ggcttgttag atatcttgaa atcggctttc aacagcattg atttcgatgt atttagctgg     180
ccgtttgaga cgcgatgtcc acagggtagc tggtagtttg aaaatcaacg ccgttgccct     240
taggattcag taactggcac attttgtaat gcgctagatc tgtgtgccca gtcttccagg     300
ctgcttatca cagtgaaagc aaaaccaatt cgtggctgcg aaagtcgtag ccaccacgaa     360
gtccaggagg acatacaatg caactgaca gcaggagcga ccgtctacgt aggcggatag      420
ctcagctatt tgcagaagat gaacaggtta aggcagcagt tccggatcag gaagttgttg     480
aagcaattcg tgcacctggt ctgcgtctgg ctcagattat ggcaaccgtg atggaacgtt     540
acgcagatcc tcctgcagtt gggcagcgtg caagcgaacc ggttaccgaa gcgggcgta     600 ccacctttcg tctgttaccg gagtttgaaa ccctgaccta tcgtgaactg tgggcacgtg     660
tgcgtgcagt tgcagcagca tggcatgggg acgcagagag gcccttacgt gcaggagact     720
ttgtcgctct gctggggttt gcaggtattg actatggtac cttagactta gcaaatattc     780
```

```
acctgggttt agttaccgtt ccgctgcaaa gcggtgcaac tgcaccgcaa ctggcagcaa        840
ttctggcaga aaccacccct cgtgttctgg cagcaactcc tgatcacctg gacattgcag        900
tagagctact gaccggaggg gcaagcccgg agcgtctggt tgtctttgac tatcgtcctg        960
cagatgatga ccatcgtgca gcattagaaa gcgcacgtag gcgtctaagc gatgcaggtt       1020
cggcagttgt tgttgaaacc ttagatgcag tccgtgcacg cggtagcgag ctaccggcag       1080
caccgctgtt tgtccctgca gcagatgaag atccgctggc tctgttaatt tacaccagcg       1140
gtagcaccgg gaccccaaa ggtgcaatgt ataccgagag gctgaatcgt actacgtggc       1200
tgagcggtgc aaagggtgtt ggtttaacct taggttatat gccgatgtcg cacatagcag       1260
gacgtgcatc atttgcaggg gttctggcac gcggtggtac cgtttatttt accgcacgca       1320
gcgacatgag caccctgttt gaggacctgg cactggttcg tccgaccgaa atgttttttg       1380
ttccgcgtgt ttgtgacatg attttcaac gttaccaggc agagctgagc cggcgtgcac       1440
ctgcagcagc agcaagcccg gagttagaac aggagctgaa aaccgagctg cgtctaagcg       1500
cagtcggaga tcgtctatta ggggcaattg caggtagcgc accgctgagc gcagaaatgc       1560
gtgaatttat ggaaagcctg ctggacctgg agctgcatga cggttatggt agcaccgaag       1620
cagggattgg tgtcctgcaa gataacattg ttcagaggcc gccggttatt gactataaat       1680
tagttgatgt tccggagcta ggttattttc gtacggatca gccgcaccct cgtggggaac       1740
tactgctaaa gaccgaggga atgataccgg gttattttcg tcgtcctgaa gttaccgcag       1800
aaatttttga cgaagatggg ttttacagga ccggggatat tgttgcagag ttagagccgg       1860
accgtctgat ttaccttgat cgtcgtaata acgttctgaa gctggcacag ggtgaatttg       1920
ttaccgttgc acacctggag gcagttttg caacctcgcc gctgattcgt cagatttaca       1980 tttacgtaa tagcgaacgt agctttctgc tggcagttat tgttcctacc gcagatgcac       2040
tggcagatgg ggttaccgat gcactgaata ccgcactgac cgagagccta aggcagttag       2100
caaaggaggc aggactgcaa agctacgaac tgccgcgtga atttctggtt gagaccgagc       2160
cgtttaccgt agaaaatggg ctgttaagcg ggattgcaaa gctgctacgt cctaaattaa       2220
aagaacatta cggtgaaagg ttagaacagc tgtatcgtga cattgaggca aatcgtaatg       2280
atgaactgat tgagctgcgt cgtaccgcag cagaactgcc ggttttagag accgtaaccc       2340
gtgctgctag gagcatgtta gggctggcag caagcgaact acgtccggat gcacacttta       2400
ccgacttagg tggggactcg ctgagcgcac tgagcttcag caccctgctg caggatatgt       2460
tagaagttga agttccggtt ggggttattg ttagccctgc aaatagctta gcagacctgg       2520
caaagtatat tgaggcagag cgtcacagcg gagttcgtcg tccgagcctg attagcgttc       2580
atgggcctgg taccgaaatt agggcagcag acttaaccct ggataaattt attgacgaac       2640
gtaccttagc tgcagcaaag gcagtcccgg cagcaccggc acaggcacag accgtactgt       2700
taaccggagc aaatggttac ctgggtcgtt ttctgtgtct ggagtggctg cagaggctgg       2760
atcagaccgg ggggaccctg gtttgtattg ttcgtgggac cgatgcagca gcagcacgca       2820
aacgtctgga cgcagttttt gacagcgggg accggagct gttagatcat taccgtaaac       2880
tggcagcaga acatttagaa gttttagcag gtgacattgg tgatccgaac ttaggtctgg       2940
atgaggcaac ttggcagcgt ttagcagcaa ccgtcgatct gattgttcat cctgcagcat       3000
tagttaatca cgttctgccg tatagccagc tgtttggacc gaacgttgtt ggtaccgcag       3060
aaattattcg tctggcaatt accgaacgta ggaaacctgt tacctatctg agcaccgttg       3120
cagttgcagc tcaggttgac ccggcaggtt ttgacgaaga acgtgacatt cgtgaaatga       3180
```

```
gcgcagttcg tagcattgac gcaggatatg caaatgggta tggtaatagc aaatgggcag    3240
gtgaagttct gctgcgtgaa gcacacgatc tgtgtggact gccggttgca gttttcgta     3300 gcgatatgat tctggcacat agcaagtatg ttgggcagtt aaatgttcct gacgttttta    3360
cccgtttaat tctgagcctg gcattaaccg ggattgctcc gtacagcttt tacggaaccg    3420
atagcgcagg acagcgtagg cgtgcacatt cgacgggct gcctgcagac tttgttgcag     3480
aagcaattac caccttaggt gcaagggcag aaagcggatt tcacacctat gatgtttgga    3540
atccgtatga tgatggtatt agcctggatg agtttgttga ttggttaggt gactttggtg    3600
ttccgattca gcgtattgac gactatgatg agtggtttcg taggtttgaa accgcaattc    3660
gtgcactgcc tgagaaacag cgtgacgcta gcctgctacc gctgctggat gctcatcgtc    3720
gtcccctgcg tgcagttcgt gggagcctgc tacctgcaaa aaattttcaa gcagcagttc    3780
agagcgcacg cattggtcct gaccaggata ttccgcacct aagcccgcag ctaattgaca    3840
aatatgttac cgatctgcgt catttaggtc tgttataaag gaggacatac aatggtcgat    3900
atgaaaacta cgcataccct cctccccttt gccggacata cgctgcattt tgttgagttc    3960
gatccggcga ttttgtga gcaggattta ctctggctgc cgcactacgc acaactgcaa    4020
cacgctggac gtaaacgtaa aacagagcat ttagccggac ggatcgctgc tgtttatgct    4080
ttgcgggaat atggctataa atgtgtgccc gcaatcggcg agctacgcca acctgtctgg    4140
cctgcggagg tatacggcag tattagccac tgtgggacta cggcattagc cgtggtatct    4200
cgtcaaccga ttggcattga tatagaagaa atttttctg tacaaaccgc aagagaattg    4260
acagacaaca ttattacacc agcggaacac gagcgactcg cagactgcgg tttagccttt    4320
tctctggcgc tgacactggc attttccgcc aaagagagcg catttaaggc aagtgagatc    4380
caaactgatg caggttttct ggactatcag ataattagct ggaataaaca gcaggtcatc    4440
attcatcgtg agaatgagat gtttgctgtg cactggcaga taaagaaaa gatagtcata    4500 acgctgtgcc aacacgatta attgacaaca tctggtacga ttcgcccgca gccatcactg    4560
accacgggcg aaagtgtaaa gcaggtgcct taccatcctg acctgacaac cggatatgcg    4620
ggatccccgg gtaccg                                                    4636

<210> SEQ ID NO 20
<211> LENGTH: 4522
<212> TYPE: DNA
<213> ORGANISM: Artificial Sequence
<220> FEATURE:
<223> OTHER INFORMATION: Nucleotide sequence of DNA fragment containing
      CAR gene of Gordonia effusa (codon-optimized) and entD gene of
      Escherichia coli

<400> SEQUENCE: 20
ccaagcttgc atgccagatc gtttagatcc gaaggaaaac gtcgaaaagc aatttgcttt      60
tcgacgcccc accccgcgcg ttttagcgtg tcagtagacg cgtagggtaa gtggggtagc     120
ggcttgttag atatcttgaa atcggctttc aacagcattg atttcgatgt atttagctgg     180
ccgtttgaga cgcgatgtcc acagggtagc tggtagtttg aaaatcaacg ccgttgccct     240
taggattcag taactggcac attttgtaat gcgctagatc tgtgtgccca gtcttccagg     300
ctgcttatca cagtgaaagc aaaaccaatt cgtggctgcg aaagtcgtag ccaccacgaa     360
gtccaggagg acatacaatg agcgatcagc cgaatgcact gccgagcgca attgaaccgc     420
tgaatccgga tccgcaggca accgagcaga ttagccattg tgcaaccatt gcagaactgg     480
```

```
ttcgtgttct ggcagaaagc tatggtgatc gtccggcact gggttggcgt aataatagcg      540
atccgagcag ctggcatagc atgacctatc gtgatctggc cgaacgtgca gatagcatgg      600
cacgtctgct gcatagcacc ctgggtgttg cagaaaatga tcgtgttgca accgttggtt      660
ttaccagcgc agaatatacc attgcaagcc tggcagttgg tacactgggt gcaatggaag      720
ttccgctgca gaatgcaggt agcgttgatg tttgggcagc aattctgacc gaaaccgatt      780
gtgttagcgc agttgttgca gcagatcagc tgccgagcat tgcccgtctg gcggaaagcg      840
gcacctatac cggtctgcgt catgttctgg tttttgatat tggtagccgt gatggcacca      900
ccctggatga tgcagcacgt cgtctggttg ccgcaggcac ccaggttcat ctgcgtcagc      960
ctggtgcaga accgaccacc cctccggcac cgctgccgca gattaccgca aacccggatc     1020
gtgtggcact gctgatttat accagcggta gcacaggtgc accgaaaggt gcaatgtata     1080
ccgaaacagc agttacccgt ctgtttcaga gcggtctgag tggtctgggt cgtgcaaccg     1140
atggtcatgg ttggattacc ctgaacttta tgccgatgag ccatgttatg ggtcgtagta     1200
ccctgtggca gaccctgggt aatggtggca ccgcatattt tacaccgcgt gcagatctgg     1260
ctgaactgct gaccgatctg gcagccgttc agccgacgga tctgcagttt gttccgcgta     1320
tttgggatat gctgtatcaa gaatatgttc gtctgacaga tcaggatgtt agcgaacagg     1380
atgcactgac ccgtatgcgt gaacattatt tcggcacccg taccgcaacc gcaattaccg     1440
gtagcgcacc gattagtgat gaagttcgtc gttttgttga agcaatgctg ccggttccgc     1500
tgattgaagg ttatggtagc accgaagcag ccggtgttag cattgatggt cgtattcagc     1560
gtccgcctgt tgttgattat aaactgctgg atgtgccgga actgggttat ctgagcaccg     1620
atcgtccgca tccgcgtggt gagctgctgg ttaaaaccga tcatatttt gccggttatt     1680 acaatcgtcc ggatctgacc agcagcgttt ttgatgatca gggttattat cgtaccggtg     1740
atattgttgc cgaaaccggt ccggatcaga ttgaatatgt tgatcgtcgt aacaacgtga     1800
tgaaactgag ccagggtgaa tttgttgcaa ttgcccatat tgaagcagtt ctgaccaccc     1860
caccgattca gcagctgtat gtttatggta atagcgcacg tccgtatctg ctggccgttg     1920
ttgttccgac accggaactg cgtgaacgtc atgcagatga taatgaactg cgtcgtgaag     1980
ttctgacagc actgcgtagc catggtgaac gtaatggtct ggcagcagtt gaaattccgc     2040
gtgatgttat tgttaacgt accccgttta gcctggaaaa tggtctgctg acaggtattc     2100
gtaaactggc acgtccgcag ctgaaagaac gttatggtgc acgtctggaa gcactgtatg     2160
ccgaactggc cgatagccgt attacacgtc tgcgtgatgt gaaagcagtt gcagcccagc     2220
gtagcaccgt taccaccgtt attgatgttg ttaccgcaat tctggatctg gcggatggtg     2280
aagttaccgc agcagcacat tttacagatc tgggtggtga tagcctgacc gcagttaccg     2340
ttggtaacga actgcgcgat attttgatg ccgaagttcc ggttggtgtg ctgaccagcc     2400
cgagcagtac cctggcagat attgcggaac atattgatgg ccgtcatagc gaagcacgtc     2460
cgaccgcaga aagcgttcat ggcaccggta caaccctgcg tgcagccgat ctgaccctgg     2520
ataaatttct ggatgaagaa acactgcgtg ccgcaagtga tgttaccagt gcagccaccg     2580
atgttcgtac cgtgttttatt accggtgcaa ccggttttct gggtcgctac ctgacactgg     2640
attggctgcg tcgtatggca aaagttggtg gtacagttat ttgtctggtg cgtggtgccg     2700
atgatgacgc agcccgtgcg cgtctggatg cagcatttga tagcagcgat ctgtggtctg     2760
aatatcagcg tctggcaaaa gatcatctgc gcgtgctggc aggcgataaa gatagcgatc     2820
atctggcact gacaccggat gtgtgggatg aactggcaaa aagcgttgat ctgattattg     2880
```

```
atccggcagc actggttaat catgtactgc cgtatcgcga actgtttggt ccgaatgtta    2940
gcggcaccgc agaactgatc cgtctggcag ttaccaccac ccgtaaaccg tatgtgtata    3000
tttcaaccgt gggtgttggt gatcaggttg ctccgggtag ctttaccgaa gatcctgata    3060
ttcgtgaaat gagcagcgtg cgtgaaatca atgataccta tgcaaatggt tacggcaata    3120
gcaaatgggc aggcgaagtt ctgctggcac aggcacatga acgttttgaa ctgccggtta    3180 gcgttttttcg ttgtgatatg attgttgcgg atgatcatac cattggtcag ctgaatctgc    3240
cggatatgtt tactcgcctg ctgatgagcg ttctggcaac aggtctggca ccgcgtagct    3300
tttatcagct ggcgaccgat ggtagtgcac aagaggcaca ttttgatgcg ctgccggtgg    3360
atttcctggc cgaagcaatt aatacactgt gggttaaaga tggtgcccgt acctttaatg    3420
caatgaatcc gcatgccgat ggtattggtt ttgatcagta tattcgttgg ctgattgata    3480
gcggtgaaca aattagcctg gtggataatt atgatgattg gtatcgtcgc tttggtgccg    3540
cactggcgga tctgcctgaa aaacagcgtc gtggtagcct gattccgctg ctgcacaatt    3600
atgttcatcc gatgacaccg cataatcgtg gtatggcaag cgcagatcgt tttcatgatg    3660
cagttcgtac agcaggcgtt ggtcagagca gcgatattcc gcatattacc cctcagatta    3720
ttgaaaatta tgcacgtagc ctgcgtggcc tgggtgtgat ttaaaggagg acatacaatg    3780
gtcgatatga aaactacgca tacctccctc ccctttgccg acatacgct gcattttgtt    3840 gagttcgatc cggcgaattt tgtgagcag gatttactct ggctgccgca ctacgcacaa    3900
ctgcaacacg ctggacgtaa acgtaaaaca gagcatttag ccggacggat cgctgctgtt    3960
tatgctttgc gggaatatgg ctataaatgt gtgcccgcaa tcggcgagct acgccaacct    4020
gtctggcctg cggaggtata cggcagtatt agccactgtg ggactacggc attagccgtg    4080
gtatctcgtc aaccgattgg cattgatata gaagaaattt tttctgtaca aaccgcaaga    4140
gaattgacag acaacattat tacaccagcg gaacacgagc gactcgcaga ctgcggttta    4200
gccttttctc tggcgctgac actggcattt tccgccaaag agagcgcatt taaggcaagt    4260
gagatccaaa ctgatgcagg ttttctggac tatcagataa ttagctggaa taaacagcag    4320
gtcatcattc atcgtgagaa tgagatgttt gctgtgcact ggcagataaa agaaaagata    4380
gtcataacgc tgtgccaaca cgattaattg acaacatctg gtacgattcg cccgcagcca    4440
tcactgacca cgggcgaaag tgtaaagcag gtgccttacc atcctgacct gacaaccgga    4500
tatgcgggat ccccgggtac cg                                             4522
```

<210> SEQ ID NO 21  
<211> LENGTH: 621  
<212> TYPE: DNA  
<213> ORGANISM: Escherichia coli

<400> SEQUENCE: 21

```
atgaaaacta cgcataccct cctccccttt gccggacata cgctgcattt tgttgagttc      60
gatccggcga atttttgtga gcaggattta ctctggctgc cgcactacgc acaactgcaa     120
cacgctggac gtaaacgtaa aacagagcat ttagccggac ggatcgctgc tgtttatgct     180
ttgcgggaat atggctataa atgtgtgccc gcaatcggcg agctacgcca acctgtctgg     240
cctgcggagg tatacggcag tattagccac tgtgggacta cggcattagc cgtggtatct     300
cgtcaaccga ttggcattga tatagaagaa attttttctg tacaaaccgc aagagaattg     360
acagacaaca ttattacacc agcggaacac gagcgactcg cagactgcgg tttagccttt     420
```

-continued

```
tctctggcgc tgacactggc attttccgcc aaagagagcg catttaaggc aagtgagatc    480
caaactgatg caggttttct ggactatcag ataattagct ggaataaaca gcaggtcatc    540
attcatcgtg agaatgagat gtttgctgtg cactggcaga taaagaaaa gatagtcata    600 acgctgtgcc aacacgatta a                                              621
```

<210> SEQ ID NO 22
<211> LENGTH: 206
<212> TYPE: PRT
<213> ORGANISM: Escherichia coli

<400> SEQUENCE: 22

```
Met Lys Thr Thr His Thr Ser Leu Pro Phe Ala Gly His Thr Leu His
1               5                   10                  15

Phe Val Glu Phe Asp Pro Ala Asn Phe Cys Glu Gln Asp Leu Leu Trp
            20                  25                  30

Leu Pro His Tyr Ala Gln Leu Gln His Ala Gly Arg Lys Arg Lys Thr
        35                  40                  45

Glu His Leu Ala Gly Arg Ile Ala Ala Val Tyr Ala Leu Arg Glu Tyr
    50                  55                  60

Gly Tyr Lys Cys Val Pro Ala Ile Gly Glu Leu Arg Gln Pro Val Trp
65                  70                  75                  80

Pro Ala Glu Val Tyr Gly Ser Ile Ser His Cys Gly Thr Thr Ala Leu
                85                  90                  95

Ala Val Val Ser Arg Gln Pro Ile Gly Ile Asp Ile Glu Glu Ile Phe
            100                 105                 110

Ser Val Gln Thr Ala Arg Glu Leu Thr Asp Asn Ile Ile Thr Pro Ala
        115                 120                 125

Glu His Glu Arg Leu Ala Asp Cys Gly Leu Ala Phe Ser Leu Ala Leu
    130                 135                 140

Thr Leu Ala Phe Ser Ala Lys Glu Ser Ala Phe Lys Ala Ser Glu Ile
145                 150                 155                 160

Gln Thr Asp Ala Gly Phe Leu Asp Tyr Gln Ile Ile Ser Trp Asn Lys
                165                 170                 175

Gln Gln Val Ile Ile His Arg Glu Asn Glu Met Phe Ala Val His Trp
            180                 185                 190

Gln Ile Lys Glu Lys Ile Val Ile Thr Leu Cys Gln His Asp
        195                 200                 205
```

<210> SEQ ID NO 23
<211> LENGTH: 654
<212> TYPE: DNA
<213> ORGANISM: Corynebacterium glutamicum

<400> SEQUENCE: 23

```
atgctggatg agtctttgtt tccaaattcg gcaaagtttt ctttcattaa aactggcgat    60
gctgttaatt tagaccattt ccatcagttg catccgttgg aaaaggcact ggtagcgcac   120
tcggttgata ttagaaaagc agagtttgga gatgccaggt ggtgtgcaca tcaggcactc   180
caagctttgg gacgagatag cggtgatccc attttgcgtg gggaacgagg aatgccattg   240
tggccttctt cggtgtctgg ttcattgacc cacactgacg gattccgagc tgctgttgtg   300
gcgccacgat tgttggtgcg ttctatggga ttggatgccg aacctgcgga ccgttgccc   360 aaggatgttt tgggttcaat cgctcgggtg ggggagattc ctcaacttaa gcgcttggag   420
gaacaaggtg tgcactgcgc ggatcgcctg ctgttttgtg ccaaggaagc aacatacaaa   480
```

```
gcgtggttcc cgctgacgca taggtggctt ggttttgaac aagctgagat cgacttgcgt      540
gatgatggca cttttgtgtc ctatttgctg gttcgaccaa ctccagtgcc gtttatttca      600
ggtaaatggg tactgcgtga tggttatgtc atagctgcga ctgcagtgac ttga            654
```

<210> SEQ ID NO 24
<211> LENGTH: 217
<212> TYPE: PRT
<213> ORGANISM: Corynebacterium glutamicum

<400> SEQUENCE: 24

```
Met Leu Asp Glu Ser Leu Phe Pro Asn Ser Ala Lys Phe Ser Phe Ile
1               5                   10                  15

Lys Thr Gly Asp Ala Val Asn Leu Asp His Phe His Gln Leu His Pro
            20                  25                  30

Leu Glu Lys Ala Leu Val Ala His Ser Val Asp Ile Arg Lys Ala Glu
        35                  40                  45

Phe Gly Asp Ala Arg Trp Cys Ala His Gln Ala Leu Gln Ala Leu Gly
    50                  55                  60

Arg Asp Ser Gly Asp Pro Ile Leu Arg Gly Glu Arg Gly Met Pro Leu
65                  70                  75                  80

Trp Pro Ser Ser Val Ser Gly Ser Leu Thr His Thr Asp Gly Phe Arg
                85                  90                  95

Ala Ala Val Val Ala Pro Arg Leu Leu Val Arg Ser Met Gly Leu Asp
            100                 105                 110

Ala Glu Pro Ala Glu Pro Leu Pro Lys Asp Val Leu Gly Ser Ile Ala
        115                 120                 125

Arg Val Gly Glu Ile Pro Gln Leu Lys Arg Leu Glu Glu Gln Gly Val
    130                 135                 140

His Cys Ala Asp Arg Leu Leu Phe Cys Ala Lys Glu Ala Thr Tyr Lys
145                 150                 155                 160

Ala Trp Phe Pro Leu Thr His Arg Trp Leu Gly Phe Glu Gln Ala Glu
                165                 170                 175

Ile Asp Leu Arg Asp Asp Gly Thr Phe Val Ser Tyr Leu Leu Val Arg
            180                 185                 190

Pro Thr Pro Val Pro Phe Ile Ser Gly Lys Trp Val Leu Arg Asp Gly
        195                 200                 205

Tyr Val Ile Ala Ala Thr Ala Val Thr
    210                 215
```

<210> SEQ ID NO 25
<211> LENGTH: 1428
<212> TYPE: DNA
<213> ORGANISM: Corynebacterium glutamicum

<400> SEQUENCE: 25

```
atgcgcctgc gtgtctcgag tagtctcctc cccttcctcg tccccaacct cgaccattac      60
ggtcgccctc tcctaaagga gcctggcatg gatatccgcc aaacaattaa cgacacagca     120
atgtcgagat atcagtggtt cattgtattt atcgcagtgc tgctcaacgc actggacggc     180
tttgatgtcc tcgccatgtc ttttactgcg aatgcagtga ccgaagaatt tggactgagt     240
ggcagccagc ttggtgtgct gctgagttcc gcgctgttcg gcatgaccgc tggatctttg     300
ctgttcggtc cgatcggtga ccgtttcggc gtaagaatg cctgatgat cgcgctgctg       360 ttcaacgtgg tgggattggt attgtccgcc accgcgcagt ccgcaggcca gttgggcgtg     420
tggcgtttga tcactggtat cggcatcggc ggaatcctcg cctgcatcac agtggtgatc     480
```

```
agtgagttct ccaacaacaa aaaccgcggc atggccatgt ccatctacgc tgctggttac      540
ggcatcggcg cgtccttggg cggattcggc gcagcgcagc tcatcccaac atttggatgg      600
cgctccgtgt tcgcagccgg tgcgatcgca actggtatcg ccaccatcgc tactttcttc      660
ttcctgccag aatccgttga ttggctgagc actcgccgcc ctgcgggcgc tcgcgacaag      720
atcaattaca ttgcgcgccg cctgggcaaa gtcggtacct tgagcttcc aggcgaacaa       780 agcttgtcga cgaaaaaagc cggtctccaa tcgtatgcag tgctcgttaa caaagagaac      840
cgtggaacca gcatcaagct gtgggttgcg ttcggcatcg tgatgttcgg cttctacttc      900
gccaacactt ggaccccgaa gctgctcgtg aaaccggaa tgtcagaaca gcagggcatc      960
atcggtggtt tgatgttgtc catgggtgga gcattcggtt ccctgctcta cggtttcctc     1020
accaccaagt tcagctcccg aaacacactg atgaccttca tggtgctgtc cggcctgacg     1080
ctgatcctgt tcatttcctc cacctctgtt ccatccatcg cgtttgccag cggcgttgtc     1140
gtgggcatgc tgatcaatgg ttgtgtggct ggtctgtaca ccctgtcccc acagctgtac     1200
tccgctgaag tacgcaccac tggtgtgggc gctgcgattg gtatgggtcg tgtcggtgcg     1260
atttccgcgc cactgctggt gggtagcctg ctggattctg gctggtcccc aacgcagctg     1320
tatgttggtg tggcagtgat tgttattgcc ggtgcaaccg cattgattgg gatgcgcact     1380
caggcagtag ccgtcgaaaa gcagcctgaa gccctagcga ccaaatag                  1428
```

<210> SEQ ID NO 26
<211> LENGTH: 475
<212> TYPE: PRT
<213> ORGANISM: Corynebacterium glutamicum

<400> SEQUENCE: 26

```
Met Arg Leu Arg Val Ser Ser Leu Leu Pro Phe Leu Val Pro Asn
1               5                   10                  15

Leu Asp His Tyr Gly Arg Pro Leu Leu Lys Glu Pro Gly Met Asp Ile
            20                  25                  30

Arg Gln Thr Ile Asn Asp Thr Ala Met Ser Arg Tyr Gln Trp Phe Ile
        35                  40                  45

Val Phe Ile Ala Val Leu Leu Asn Ala Leu Asp Gly Phe Asp Val Leu
    50                  55                  60

Ala Met Ser Phe Thr Ala Asn Ala Val Thr Glu Glu Phe Gly Leu Ser
65                  70                  75                  80

Gly Ser Gln Leu Gly Val Leu Ser Ser Ala Leu Phe Gly Met Thr
                85                  90                  95

Ala Gly Ser Leu Leu Phe Gly Pro Ile Gly Asp Arg Phe Gly Arg Lys
            100                 105                 110

Asn Ala Leu Met Ile Ala Leu Leu Phe Asn Val Gly Leu Val Leu
            115                 120                 125

Ser Ala Thr Ala Gln Ser Ala Gly Gln Leu Gly Val Trp Arg Leu Ile
        130                 135                 140

Thr Gly Ile Gly Ile Gly Gly Ile Leu Ala Cys Ile Thr Val Val Ile
145                 150                 155                 160

Ser Glu Phe Ser Asn Asn Lys Asn Arg Gly Met Ala Met Ser Ile Tyr
                165                 170                 175

Ala Ala Gly Tyr Gly Ile Gly Ala Ser Leu Gly Gly Phe Gly Ala Ala
            180                 185                 190

Gln Leu Ile Pro Thr Phe Gly Trp Arg Ser Val Phe Ala Ala Gly Ala
        195                 200                 205
```

```
Ile Ala Thr Gly Ile Ala Thr Ile Ala Thr Phe Phe Phe Leu Pro Glu
    210                 215                 220
Ser Val Asp Trp Leu Ser Thr Arg Arg Pro Ala Gly Ala Arg Asp Lys
225                 230                 235                 240
Ile Asn Tyr Ile Ala Arg Arg Leu Gly Lys Val Gly Thr Phe Glu Leu
            245                 250                 255
Pro Gly Glu Gln Ser Leu Ser Thr Lys Lys Ala Gly Leu Gln Ser Tyr
            260                 265                 270
Ala Val Leu Val Asn Lys Glu Asn Arg Gly Thr Ser Ile Lys Leu Trp
        275                 280                 285
Val Ala Phe Gly Ile Val Met Phe Gly Phe Tyr Phe Ala Asn Thr Trp
    290                 295                 300
Thr Pro Lys Leu Leu Val Glu Thr Gly Met Ser Glu Gln Gln Gly Ile
305                 310                 315                 320
Ile Gly Gly Leu Met Leu Ser Met Gly Gly Ala Phe Gly Ser Leu Leu
            325                 330                 335
Tyr Gly Phe Leu Thr Thr Lys Phe Ser Ser Arg Asn Thr Leu Met Thr
            340                 345                 350
Phe Met Val Leu Ser Gly Leu Thr Leu Ile Leu Phe Ile Ser Ser Thr
        355                 360                 365
Ser Val Pro Ser Ile Ala Phe Ala Ser Gly Val Val Gly Met Leu
    370                 375                 380
Ile Asn Gly Cys Val Ala Gly Leu Tyr Thr Leu Ser Pro Gln Leu Tyr
385                 390                 395                 400
Ser Ala Glu Val Arg Thr Thr Gly Val Gly Ala Ala Ile Gly Met Gly
            405                 410                 415
Arg Val Gly Ala Ile Ser Ala Pro Leu Leu Val Gly Ser Leu Leu Asp
        420                 425                 430
Ser Gly Trp Ser Pro Thr Gln Leu Tyr Val Gly Val Ala Val Ile Val
    435                 440                 445
Ile Ala Gly Ala Thr Ala Leu Ile Gly Met Arg Thr Gln Ala Val Ala
    450                 455                 460
Val Glu Lys Gln Pro Glu Ala Leu Ala Thr Lys
465                 470                 475

<210> SEQ ID NO 27
<211> LENGTH: 1296
<212> TYPE: DNA
<213> ORGANISM: Corynebacterium glutamicum

<400> SEQUENCE: 27
gtgtcaacga ccaccccaac ccgcgcaacc aaaagtgtcg gaacagttct cgcactcctg      60
tggttcgcaa ttgtcctcga cggctttgac ctagtcgtcc tgggcgcaac aatcccgtcc     120
atgctggagg atcccgcgtg ggatctcact gctggacagg ccacacagat ttccaccatc     180
ggcctcgtcg gcatgaccat cggcgcactg accattggtt tcttaactga ccgtctgggt     240
cgacgccgcg tcatgctgtt ctctgtggca gtgttttctg tattcaccct cctgctggca     300
ttcaccacca acgtccagct cttcagcctg tggcgtttcc tcgcaggtgt tggccttggt     360
ggagcactcc ccaccgcaat tgccatggtg accgagtttc gccccggcac caaagcgggc     420
tctgcatcaa ctaccttgat gaccggatac cacgtcgggg cagtagcaac cgctttcctt     480
ggtctcttcc ttatcgacgg ctttggttgg cactccatgt tcatcgcagg cgctgtgcca     540
ggactactcc tgctgccact gctgtatttc ttccttccag aatccccgca gtacctcaaa     600
```

```
atctccggca agttggatga ggcgcaggca gttgcagcat cttatggact ttccctggat    660
gatgatcttg atcgcgaaca cgaagaagaa cttggcgagt cctcctcact ttcctccctg    720
ttcaagccct cgttccgccg caacaccctg gcgatttggg gcacctcatt catgggactc    780
ctcctggtct acggcctgaa acatggctgc cacaaatca tgcgccaagc agactacgac     840
atgggtaact ccctgggctt cctcatggtt cttaacatcg gcgcagtgat cggcctttat    900
attgcagggc gaattgccga taagaactcc cctcgcaaaa cagcactcgt atggttcgtg    960
ttctctgcat ttttcctcgc actacttgct gtccggatgc cactgatcgg tctgtatggc    1020
atcgtgctgc tcaccggcat ctttgtgttc agctcccagg tactcatcta cgccttcgtt    1080
ggtgagaatc accctgccaa gatgcgtgca actgccatgg gattctccgc aggaattggt    1140
cgcctcggcg cgatctcggg tccgttgctg ggcggcctgc ttgtcagtgc caaccttgct    1200
tacccatggg gcttcttcgc cttcgctggc gttggactgc tgggcgcgct gatttctcc     1260
gcatcgaaga ctctgaggca tcgcgagaac gcttag                              1296
```

<210> SEQ ID NO 28
<211> LENGTH: 431
<212> TYPE: PRT
<213> ORGANISM: Corynebacterium glutamicum

<400> SEQUENCE: 28

```
Met Ser Thr Thr Thr Pro Thr Arg Ala Thr Lys Ser Val Gly Thr Val
1               5                   10                  15

Leu Ala Leu Leu Trp Phe Ala Ile Val Leu Asp Gly Phe Asp Leu Val
            20                  25                  30

Val Leu Gly Ala Thr Ile Pro Ser Met Leu Glu Asp Pro Ala Trp Asp
        35                  40                  45

Leu Thr Ala Gly Gln Ala Thr Gln Ile Ser Thr Ile Gly Leu Val Gly
    50                  55                  60

Met Thr Ile Gly Ala Leu Thr Ile Gly Phe Leu Thr Asp Arg Leu Gly
65                  70                  75                  80

Arg Arg Arg Val Met Leu Phe Ser Val Ala Val Phe Ser Val Phe Thr
                85                  90                  95

Leu Leu Leu Ala Phe Thr Thr Asn Val Gln Leu Phe Ser Leu Trp Arg
            100                 105                 110

Phe Leu Ala Gly Val Gly Leu Gly Gly Ala Leu Pro Thr Ala Ile Ala
        115                 120                 125

Met Val Thr Glu Phe Arg Pro Gly Thr Lys Ala Gly Ser Ala Ser Thr
    130                 135                 140

Thr Leu Met Thr Gly Tyr His Val Gly Ala Val Ala Thr Ala Phe Leu
145                 150                 155                 160

Gly Leu Phe Leu Ile Asp Gly Phe Gly Trp His Ser Met Phe Ile Ala
                165                 170                 175

Gly Ala Val Pro Gly Leu Leu Leu Pro Leu Leu Tyr Phe Leu
            180                 185                 190

Pro Glu Ser Pro Gln Tyr Leu Lys Ile Ser Gly Lys Leu Asp Glu Ala
        195                 200                 205

Gln Ala Val Ala Ala Ser Tyr Gly Leu Ser Leu Asp Asp Leu Asp
    210                 215                 220

Arg Glu His Glu Glu Leu Gly Glu Ser Ser Ser Leu Ser Ser Leu
225                 230                 235                 240

Phe Lys Pro Ser Phe Arg Arg Asn Thr Leu Ala Ile Trp Gly Thr Ser
```

```
            245                 250                 255
Phe Met Gly Leu Leu Val Tyr Gly Leu Asn Thr Trp Leu Pro Gln
            260                 265                 270

Ile Met Arg Gln Ala Asp Tyr Asp Met Gly Asn Ser Leu Gly Phe Leu
        275                 280                 285

Met Val Leu Asn Ile Gly Ala Val Ile Gly Leu Tyr Ile Ala Gly Arg
    290                 295                 300

Ile Ala Asp Lys Asn Ser Pro Arg Lys Thr Ala Leu Val Trp Phe Val
305                 310                 315                 320

Phe Ser Ala Phe Phe Leu Ala Leu Leu Ala Val Arg Met Pro Leu Ile
            325                 330                 335

Gly Leu Tyr Gly Ile Val Leu Leu Thr Gly Ile Phe Val Phe Ser Ser
            340                 345                 350

Gln Val Leu Ile Tyr Ala Phe Val Gly Glu Asn His Pro Ala Lys Met
            355                 360                 365

Arg Ala Thr Ala Met Gly Phe Ser Ala Gly Ile Gly Arg Leu Gly Ala
        370                 375                 380

Ile Ser Gly Pro Leu Leu Gly Gly Leu Leu Val Ser Ala Asn Leu Ala
385                 390                 395                 400

Tyr Pro Trp Gly Phe Phe Ala Phe Ala Gly Val Gly Leu Leu Gly Ala
            405                 410                 415

Leu Ile Phe Ser Ala Ser Lys Thr Leu Arg His Arg Glu Asn Ala
            420                 425                 430

<210> SEQ ID NO 29
<211> LENGTH: 1131
<212> TYPE: DNA
<213> ORGANISM: Corynebacterium glutamicum

<400> SEQUENCE: 29
atgacactgt ccgaacgcaa gctcaccacc accgccaaga ttcttcccca cccactcaac      60
gcctggtacg tcgccgcttg ggattatgaa gtcacatcta aaaagcccat ggccaggaca     120
atcgccaaca aaccactcgc tttgtaccgc accaaagatg ccgagccgt tgcccttgca      180 gacgcctgct ggcaccgcct cgcaccgcta tccaaggaa aactcgtggg cacagacgga     240
atccaatgcc cttatcacgg cttggagtac aactccgcgg ccgctgcat gaaaatgccc      300 gcgcaggaaa ccctcaaccc gtcagcagcc gtcaactcct accccgtggt ggaagcccac     360
cgctttgtgt gggtgtggct gggcgatccc acattggcag atcccaccca gtacccgat      420 atgcaccaga tgagccaccc cgaatgggca ggcgatggac gcaccatctc cgctgactgc     480
aactaccaat tagtgctgga caacttgatg gacctcaccc acgaagaatt cgtgcactcc     540
tccagcatcg gccaagacga acttagtgaa tcagagttcg tggtcaccca cactgaagat     600
tccgtgacgg tcacccgctg gatgcatgac atagatgcac caccgttttg gcaaaagaac     660
atgaatgata agttcccagg atttgaaggc aaggtggatc gttggcagat catccactac     720 tactacccctt ccaccatctg cattgatgtt ggtgtagcaa aggctggaac cggcgcgcag     780
gaaggcgacc gcagccaggg cgttaatggg tatgtaatga acaccattac cccagattca     840
gatcgttcct ctcattactt ctgggcattc atgcgcaact accgcctgga agccaaaacc     900
atcaccaccc agctcgcgcga cggtgtatcc ggtgtattca agaagacga agacatgctg     960 accgctcagc aagatgccat cgacgccaac accgactatg agttttacag cctcaacatt    1020
gatgccggtg gcatgtgggt gcgccgaatc ctcgaggaag cactctccaa ggaaggccga    1080
```

```
ctggatatcc ccaccacatt cccccgcgca acaccgaagc cggaggcata a            1131
```

<210> SEQ ID NO 30
<211> LENGTH: 376
<212> TYPE: PRT
<213> ORGANISM: Corynebacterium glutamicum

<400> SEQUENCE: 30

| Met | Thr | Leu | Ser | Glu | Arg | Lys | Leu | Thr | Thr | Thr | Ala | Lys | Ile | Leu | Pro |
|---|---|---|---|---|---|---|---|---|---|---|---|---|---|---|---|
| 1 | | | | 5 | | | | | 10 | | | | | 15 | |

| His | Pro | Leu | Asn | Ala | Trp | Tyr | Val | Ala | Ala | Trp | Asp | Tyr | Glu | Val | Thr |
| | | | 20 | | | | 25 | | | | 30 | | | | |

| Ser | Lys | Lys | Pro | Met | Ala | Arg | Thr | Ile | Ala | Asn | Lys | Pro | Leu | Ala | Leu |
| | 35 | | | | 40 | | | | 45 | | | | | | |

| Tyr | Arg | Thr | Lys | Asp | Gly | Arg | Ala | Val | Ala | Leu | Ala | Asp | Ala | Cys | Trp |
| 50 | | | | 55 | | | | | 60 | | | | | | |

| His | Arg | Leu | Ala | Pro | Leu | Ser | Lys | Gly | Lys | Leu | Val | Gly | Thr | Asp | Gly |
| 65 | | | | 70 | | | | 75 | | | | | | 80 | |

| Ile | Gln | Cys | Pro | Tyr | His | Gly | Leu | Glu | Tyr | Asn | Ser | Ala | Gly | Arg | Cys |
| | | | | 85 | | | | 90 | | | | | 95 | | |

| Met | Lys | Met | Pro | Ala | Gln | Glu | Thr | Leu | Asn | Pro | Ser | Ala | Ala | Val | Asn |
| | | | 100 | | | | | 105 | | | | | 110 | | |

| Ser | Tyr | Pro | Val | Val | Glu | Ala | His | Arg | Phe | Val | Trp | Val | Trp | Leu | Gly |
| | | 115 | | | | | 120 | | | | | 125 | | | |

| Asp | Pro | Thr | Leu | Ala | Asp | Pro | Thr | Gln | Val | Pro | Asp | Met | His | Gln | Met |
| 130 | | | | | 135 | | | | | 140 | | | | | |

| Ser | His | Pro | Glu | Trp | Ala | Gly | Asp | Gly | Arg | Thr | Ile | Ser | Ala | Asp | Cys |
| 145 | | | | | 150 | | | | | 155 | | | | | 160 |

| Asn | Tyr | Gln | Leu | Val | Leu | Asp | Asn | Leu | Met | Asp | Leu | Thr | His | Glu | Glu |
| | | | | 165 | | | | | 170 | | | | | 175 | |

| Phe | Val | His | Ser | Ser | Ser | Ile | Gly | Gln | Asp | Glu | Leu | Ser | Glu | Ser | Glu |
| | | | | 180 | | | | | 185 | | | | | 190 | |

| Phe | Val | Val | Thr | His | Thr | Glu | Asp | Ser | Val | Thr | Val | Thr | Arg | Trp | Met |
| | | 195 | | | | | 200 | | | | | 205 | | | |

| His | Asp | Ile | Asp | Ala | Pro | Pro | Phe | Trp | Gln | Lys | Asn | Met | Asn | Asp | Lys |
| 210 | | | | | 215 | | | | | 220 | | | | | |

| Phe | Pro | Gly | Phe | Glu | Gly | Lys | Val | Asp | Arg | Trp | Gln | Ile | Ile | His | Tyr |
| 225 | | | | | 230 | | | | | 235 | | | | | 240 |

| Tyr | Tyr | Pro | Ser | Thr | Ile | Cys | Ile | Asp | Val | Gly | Val | Ala | Lys | Ala | Gly |
| | | | | 245 | | | | | 250 | | | | | 255 | |

| Thr | Gly | Ala | Gln | Glu | Gly | Asp | Arg | Ser | Gln | Gly | Val | Asn | Gly | Tyr | Val |
| | | | 260 | | | | | 265 | | | | | 270 | | |

| Met | Asn | Thr | Ile | Thr | Pro | Asp | Ser | Asp | Arg | Ser | Ser | His | Tyr | Phe | Trp |
| | | 275 | | | | | 280 | | | | | 285 | | | |

| Ala | Phe | Met | Arg | Asn | Tyr | Arg | Leu | Glu | Ser | Gln | Thr | Ile | Thr | Thr | Gln |
| | 290 | | | | | 295 | | | | | 300 | | | | |

| Leu | Arg | Asp | Gly | Val | Ser | Gly | Val | Phe | Lys | Glu | Asp | Glu | Asp | Met | Leu |
| 305 | | | | | 310 | | | | | 315 | | | | | 320 |

| Thr | Ala | Gln | Gln | Asp | Ala | Ile | Asp | Ala | Asn | Thr | Asp | Tyr | Glu | Phe | Tyr |
| | | | | 325 | | | | | 330 | | | | | 335 | |

| Ser | Leu | Asn | Ile | Asp | Ala | Gly | Gly | Met | Trp | Val | Arg | Arg | Ile | Leu | Glu |
| | | | 340 | | | | | 345 | | | | | 350 | | |

| Glu | Ala | Leu | Ser | Lys | Glu | Gly | Arg | Leu | Asp | Ile | Pro | Thr | Thr | Phe | Pro |
| | | | 355 | | | | | 360 | | | | | 365 | | |

Arg Ala Thr Pro Lys Pro Glu Ala
        370             375

<210> SEQ ID NO 31
<211> LENGTH: 978
<212> TYPE: DNA
<213> ORGANISM: Corynebacterium glutamicum

<400> SEQUENCE: 31
atgaactcgc aatggcaaga tgcacatgtt gtttccagcg aaatcatcgc tgcagacatt      60
cgacgaatag aactatcccc gaaatttgcg attccagtaa acccggcga acatctcaag      120 atcatggtgc ccctaaaaac tggacaggaa aagagatcgt actccatcgt tgacgctcgt      180
cacgacggtt cgactctcgc cctgagcgta ctcaaaacca gaaactcccg tggaggatct      240
gagttcatgc atacgcttcg agctggagac acagttactg tctccaggcc gtctcaggat      300
tttcctctcc gcgtgggtgc gcctgagtat gtacttgttg ccggcggaat tggaatcaca      360
gcgatccgtt caatggcatc tttattaaag aaattgggag caaactaccg cattcatttc      420
gcagcacgca gccttgatgc catggcttac aaagatgagc tcgtggcaga acacggcgac      480
aagctgcacc tgcatctaga ttctgaaggc accaccatcg atgtcccagc attgatcgaa      540
accttaaacc cccacactga gctttatatg tgcggcccca tccgcttgat ggatgccatc      600
cggcgcgcat ggaacacccg cggacttgac cccaccaatc tgcgtttcga acgtttgga      660 aacagtggat ggttctcccc agaggttttc cacatccaag taccagagct ggggcttcac      720
gccacagtca acaaggatga aagcatgctg gaggctttgc aaaaggctgg ggcgaatatg      780
atgtttgatt gtcgaaaagg cgaatgtggt ttgtgccagg ttcgcgttct agaagtcgat      840
ggccaggttg atcaccgcga tgtgttcttc tctgatcgtc aaaaagaatc cgacgcaaag      900
gcatgcgcct gcgtgtctcg agtagtctcc tcccttcct cgtccccaac ctcgaccatt      960
acggtcgccc tctcctaa                                                   978

<210> SEQ ID NO 32
<211> LENGTH: 325
<212> TYPE: PRT
<213> ORGANISM: Corynebacterium glutamicum

<400> SEQUENCE: 32

Met Asn Ser Gln Trp Gln Asp Ala His Val Val Ser Glu Ile Ile
1               5                  10                  15

Ala Ala Asp Ile Arg Arg Ile Glu Leu Ser Pro Lys Phe Ala Ile Pro
                20                  25                  30

Val Lys Pro Gly Glu His Leu Lys Ile Met Val Pro Leu Lys Thr Gly
            35                  40                  45

Gln Glu Lys Arg Ser Tyr Ser Ile Val Asp Ala Arg His Asp Gly Ser
        50                  55                  60

Thr Leu Ala Leu Ser Val Leu Lys Thr Arg Asn Ser Arg Gly Gly Ser
65                  70                  75                  80

Glu Phe Met His Thr Leu Arg Ala Gly Asp Thr Val Thr Val Ser Arg
                85                  90                  95

Pro Ser Gln Asp Phe Pro Leu Arg Val Gly Ala Pro Glu Tyr Val Leu
            100                 105                 110

Val Ala Gly Gly Ile Gly Ile Thr Ala Ile Arg Ser Met Ala Ser Leu
        115                 120                 125

Leu Lys Lys Leu Gly Ala Asn Tyr Arg Ile His Phe Ala Ala Arg Ser
    130                 135                 140

```
Leu Asp Ala Met Ala Tyr Lys Asp Glu Leu Val Ala Glu His Gly Asp
145                 150                 155                 160

Lys Leu His Leu His Leu Asp Ser Glu Gly Thr Thr Ile Asp Val Pro
            165                 170                 175

Ala Leu Ile Glu Thr Leu Asn Pro His Thr Glu Leu Tyr Met Cys Gly
        180                 185                 190

Pro Ile Arg Leu Met Asp Ala Ile Arg Arg Ala Trp Asn Thr Arg Gly
    195                 200                 205

Leu Asp Pro Thr Asn Leu Arg Phe Glu Thr Phe Gly Asn Ser Gly Trp
210                 215                 220

Phe Ser Pro Glu Val Phe His Ile Gln Val Pro Glu Leu Gly Leu His
225                 230                 235                 240

Ala Thr Val Asn Lys Asp Glu Ser Met Leu Glu Ala Leu Gln Lys Ala
            245                 250                 255

Gly Ala Asn Met Met Phe Asp Cys Arg Lys Gly Glu Cys Gly Leu Cys
        260                 265                 270

Gln Val Arg Val Leu Glu Val Asp Gly Gln Val Asp His Arg Asp Val
    275                 280                 285

Phe Phe Ser Asp Arg Gln Lys Glu Ser Asp Ala Lys Ala Cys Ala Cys
290                 295                 300

Val Ser Arg Val Val Ser Ser Pro Ser Ser Pro Thr Ser Thr Ile
305                 310                 315                 320

Thr Val Ala Leu Ser
            325

<210> SEQ ID NO 33
<211> LENGTH: 615
<212> TYPE: DNA
<213> ORGANISM: Corynebacterium glutamicum

<400> SEQUENCE: 33
atgattgata cagggaagaa cggcgagttc cgctacgagc agtcgaatat catcgatcag      60
aacgaagccg agttcggcat cactccttca cagaccgtgg gcccttacgt ccacatcggt     120
ttgacccttg aaggtgcgga gcatctcgtg gagccaggtt cggaaggcgc ggtgtccttt     180
actgtttccg caactgatgg caacggcgac cccatcgcgg atgccatgtt tgaactgtgg     240
caggccgatc cagagggcat ccacaactct gatttggatc aaaccgcac agcaccagca     300 accgcagatg gcttccgcgg gcttggtcgc gcgatggcaa acgcgcaggg tgaggcaacg     360
ttcaccactt tggttccggg agcattcgca gatgaggcac acacttcaa ggttggtgtg     420 ttcgcccgtg gcatgctgga gcgtctgtac actcgcgcat acctgccaga cgccgatttg     480
agcaccgacc cagttttggc tgtggtccca gctgatcgac gtgacctcct ggtggctcaa     540
aagaccgatg atggattccg cttcgacatc actgtccagg ctgaagacaa tgaaacccca     600 tttttggac tctaa                                                        615

<210> SEQ ID NO 34
<211> LENGTH: 204
<212> TYPE: PRT
<213> ORGANISM: Corynebacterium glutamicum

<400> SEQUENCE: 34

Met Ile Asp Thr Gly Lys Asn Gly Glu Phe Arg Tyr Glu Gln Ser Asn
1               5                   10                  15

Ile Ile Asp Gln Asn Glu Ala Glu Phe Gly Ile Thr Pro Ser Gln Thr
```

```
              20                  25                  30
Val Gly Pro Tyr Val His Ile Gly Leu Thr Leu Glu Gly Ala Glu His
             35                  40                  45

Leu Val Glu Pro Gly Ser Glu Gly Ala Val Ser Phe Thr Val Ser Ala
         50                  55                  60

Thr Asp Gly Asn Gly Asp Pro Ile Ala Asp Ala Met Phe Glu Leu Trp
 65                  70                  75                  80

Gln Ala Asp Pro Glu Gly Ile His Asn Ser Asp Leu Asp Pro Asn Arg
                 85                  90                  95

Thr Ala Pro Ala Thr Ala Asp Gly Phe Arg Gly Leu Gly Arg Ala Met
             100                 105                 110

Ala Asn Ala Gln Gly Glu Ala Thr Phe Thr Thr Leu Val Pro Gly Ala
         115                 120                 125

Phe Ala Asp Glu Ala Pro His Phe Lys Val Gly Val Phe Ala Arg Gly
     130                 135                 140

Met Leu Glu Arg Leu Tyr Thr Arg Ala Tyr Leu Pro Asp Ala Asp Leu
145                 150                 155                 160

Ser Thr Asp Pro Val Leu Ala Val Val Pro Ala Asp Arg Arg Asp Leu
                 165                 170                 175

Leu Val Ala Gln Lys Thr Asp Asp Gly Phe Arg Phe Asp Ile Thr Val
             180                 185                 190

Gln Ala Glu Asp Asn Glu Thr Pro Phe Phe Gly Leu
         195                 200

<210> SEQ ID NO 35
<211> LENGTH: 693
<212> TYPE: DNA
<213> ORGANISM: Corynebacterium glutamicum

<400> SEQUENCE: 35
atggacatcc cacacttcgc cccgacggga ggcgaatact ccccactgca cttcccggag      60
taccggacca ccatcaagcg caacccaagc aacgatctca tcatggttcc tagtcgcctc    120
ggcgagtcca cgggacctgt cttcggcgac cgcgacttgg agacatcga caacgacatg     180 accaaggtga acggtggcga ggctatcggc cagcgcatct tcgttcacgg ccgtgtcctc    240
ggtttcgatg caagccagt tccgcacacc ttggtcgagg cgtggcaggc aaacgccgca     300
ggccgttacc gccacaagaa tgactcctgg ccagcgccac tggatccaca cttcaacggt    360
gttgcacgta ctctcaccga caaggacggc cagtaccact tctggaccgt tatgccaggt    420
aattacccct tggggtaacca ccacaacgca tggcgcccgg cgcacattca cttctcgctc    480
tatggtcgtc agtttacgga gcgtctggtc acccagatgt acttcccgaa cgatccattg    540
ttcttccagg atccgatcta caacgcggtg ccaaagggtg cacgtgagcg catgatcgca    600
acgttcgact atgacgagac ccgtgaaaac ttcgcgcttg gttacaagtt cgacatcgtc    660
cttcgtggcc gcaacgccac cccatttgag taa                                693

<210> SEQ ID NO 36
<211> LENGTH: 230
<212> TYPE: PRT
<213> ORGANISM: Corynebacterium glutamicum

<400> SEQUENCE: 36

Met Asp Ile Pro His Phe Ala Pro Thr Gly Gly Glu Tyr Ser Pro Leu
 1               5                  10                  15

His Phe Pro Glu Tyr Arg Thr Thr Ile Lys Arg Asn Pro Ser Asn Asp
```

```
                   20                  25                  30
Leu Ile Met Val Pro Ser Arg Leu Gly Glu Ser Thr Gly Pro Val Phe
             35                  40                  45

Gly Asp Arg Asp Leu Gly Asp Ile Asp Asn Asp Met Thr Lys Val Asn
         50                  55                  60

Gly Gly Glu Ala Ile Gly Gln Arg Ile Phe Val His Gly Arg Val Leu
65                  70                  75                  80

Gly Phe Asp Gly Lys Pro Val Pro His Thr Leu Val Glu Ala Trp Gln
                 85                  90                  95

Ala Asn Ala Ala Gly Arg Tyr Arg His Lys Asn Asp Ser Trp Pro Ala
            100                 105                 110

Pro Leu Asp Pro His Phe Asn Gly Val Ala Arg Thr Leu Thr Asp Lys
        115                 120                 125

Asp Gly Gln Tyr His Phe Trp Thr Val Met Pro Gly Asn Tyr Pro Trp
    130                 135                 140

Gly Asn His His Asn Ala Trp Arg Pro Ala His Ile His Phe Ser Leu
145                 150                 155                 160

Tyr Gly Arg Gln Phe Thr Glu Arg Leu Val Thr Gln Met Tyr Phe Pro
                165                 170                 175

Asn Asp Pro Leu Phe Phe Gln Asp Pro Ile Tyr Asn Ala Val Pro Lys
            180                 185                 190

Gly Ala Arg Glu Arg Met Ile Ala Thr Phe Asp Tyr Asp Glu Thr Arg
        195                 200                 205

Glu Asn Phe Ala Leu Gly Tyr Lys Phe Asp Ile Val Leu Arg Gly Arg
    210                 215                 220

Asn Ala Thr Pro Phe Glu
225                 230

<210> SEQ ID NO 37
<211> LENGTH: 1164
<212> TYPE: DNA
<213> ORGANISM: Escherichia coli

<400> SEQUENCE: 37
atgaacaact taatctgca caccccaacc cgcattctgt tggtaaagg cgcaatcgct        60 ggtttacgcg aacaaattcc tcacgatgct cgcgtattga ttacctacgg cggcggcagc    120
gtgaaaaaaa ccggcgttct cgatcaagtt ctggatgccc tgaaaggcat ggacgtgctg    180
gaatttggcg gtattgagcc aaacccggct tatgaaacgc tgatgaacgc cgtgaaactg    240
gttcgcgaac agaaagtgac tttcctgctg gcggttggcg cgggttctgt actggacggc    300 accaaatttta tcgccgcagc ggctaactat ccggaaaata tcgatccgtg gcacattctg    360
caaacgggcg gtaaagagat taaaagcgcc atcccgatgg gctgtgtgct gacgctgcca    420
gcaaccggtt cagaatccaa cgcaggcgcg gtgatctccc gtaaaccac aggcgacaag    480 caggcgttcc attctgccca tgttcagccg gtatttgccg tgctcgatcc ggtttatacc    540
tacaccctgc cgccgcgtca ggtggctaac ggcgtagtgg acgcctttgt acacaccgtg    600
gaacagtatg ttaccaaacc ggttgatgcc aaaattcagg accgtttcgc agaaggcatt    660
ttgctgacgc taatcgaaga tggtccgaaa gccctgaaag agccagaaaa ctacgatgtg    720
cgcgccaacg tcatgtgggc ggcgactcag gcgctgaacg gtttgattgg cgctggcgta    780
ccgcaggact gggcaacgca tatgctgggc acgaactga ctgcgatgca cggtctggat    840
cacgcgcaaa cactggctat cgtcctgcct gcactgtgga atgaaaaacg cgataccaag    900
```

```
cgcgctaagc tgctgcaata tgctgaacgc gtctggaaca tcactgaagg ttccgatgat       960
gagcgtattg acgccgcgat tgccgcaacc cgcaatttct ttgagcaatt aggcgtgccg      1020
acccacctct ccgactacgg tctggacggc agctccatcc cggctttgct gaaaaaactg      1080
gaagagcacg gcatgaccca actgggcgaa atcatgaca ttacgttgga tgtcagccgc      1140
cgtatatacg aagccgcccg ctaa                                             1164
```

<210> SEQ ID NO 38
<211> LENGTH: 387
<212> TYPE: PRT
<213> ORGANISM: Escherichia coli

<400> SEQUENCE: 38

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln

```
                325                 330                 335
Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385

<210> SEQ ID NO 39
<211> LENGTH: 1062
<212> TYPE: DNA
<213> ORGANISM: Corynebacterium glutamicum

<400> SEQUENCE: 39
atgagcatcc aagtaaaagc actccagaaa accggccccg aagcaccttt cgaggtcaaa      60
atcattgagc gtcgtgagcc tcgcgctgac gacgtagtta tcgacatcaa agctgccggc     120
atctgccaca gcgatatcca caccatccgc aacgaatggg gcgaggcaca cttcccgctc     180
accgtcggcc acgaaatcgc aggcgttgtc tctgcggttg gctccgatgt aaccaagtgg     240
aaagtcggcg accgcgttgg cgtcggctgc ctagttaact cctgcggcga atgtgaacag     300
tgtgtcgcgg gatttgaaaa caactgcctt cgcggaaacg tcggaaccta caactccgac     360
gacgtcgacg gcaccatcac gcaaggtggc tacgccgaaa aggtagtggt caacgaacgt     420
ttcctctgca gcatcccaga ggaactcgac ttcgatgtcg cagcaccact gctgtgcgca     480
ggcatcacca cctactcccc gatcgctcgc tggaacgtta agaaggcga caaagtagca     540 gtcatgggcc tcggcgggct cggccacatg ggtgtccaaa tcgccgcagc caagggcgct     600
gacgttaccg ttctgtcccg ttccctgcgc aaggctgaac ttgccaagga actcggcgca     660
gctcgcacgc ttgcgacttc tgatgaggat ttcttcaccg aacacgccgg tgaattcgac     720
ttcatcctca acaccattag cgcatccatc ccagtcgaca gtacctgag ccttctcaag     780 ccacacggtg tcatggctgt tgtcggtctg ccaccagaga agcagccact gagcttcggt     840
gcgctcatcg gcggcggaaa agtcctcacc ggatccaaca ttggcggcat ccctgaaacc     900
caggaaatgc tcgacttctg tgcaaaaacac ggcctcggcg cgatgatcga aactgtcggc     960
gtcaacgatg ttgatgcagc ctacgaccgc gttgttgccg gcgacgttca gttccgcgtt    1020
gtcattgata ctgcttcgtt tgcagaggta gaggcggttt ag                        1062

<210> SEQ ID NO 40
<211> LENGTH: 353
<212> TYPE: PRT
<213> ORGANISM: Corynebacterium glutamicum

<400> SEQUENCE: 40

Met Ser Ile Gln Val Lys Ala Leu Gln Lys Thr Gly Pro Glu Ala Pro
1               5                   10                  15

Phe Glu Val Lys Ile Ile Glu Arg Arg Glu Pro Arg Ala Asp Asp Val
            20                  25                  30

Val Ile Asp Ile Lys Ala Ala Gly Ile Cys His Ser Asp Ile His Thr
        35                  40                  45

Ile Arg Asn Glu Trp Gly Glu Ala His Phe Pro Leu Thr Val Gly His
    50                  55                  60

Glu Ile Ala Gly Val Val Ser Ala Val Gly Ser Asp Val Thr Lys Trp
```

```
            65                  70                  75                  80
Lys Val Gly Asp Arg Val Gly Val Gly Cys Leu Val Asn Ser Cys Gly
                85                  90                  95
Glu Cys Glu Gln Cys Val Ala Gly Phe Glu Asn Asn Cys Leu Arg Gly
            100                 105                 110
Asn Val Gly Thr Tyr Asn Ser Asp Val Asp Gly Thr Ile Thr Gln
            115                 120                 125
Gly Gly Tyr Ala Glu Lys Val Val Asn Glu Arg Phe Leu Cys Ser
130                 135                 140
Ile Pro Glu Glu Leu Asp Phe Asp Val Ala Ala Pro Leu Leu Cys Ala
145                 150                 155                 160
Gly Ile Thr Thr Tyr Ser Pro Ile Ala Arg Trp Asn Val Lys Glu Gly
                165                 170                 175
Asp Lys Val Ala Val Met Gly Leu Gly Gly Leu Gly His Met Gly Val
            180                 185                 190
Gln Ile Ala Ala Ala Lys Gly Ala Asp Val Thr Val Leu Ser Arg Ser
            195                 200                 205
Leu Arg Lys Ala Glu Leu Ala Lys Glu Leu Gly Ala Ala Arg Thr Leu
            210                 215                 220
Ala Thr Ser Asp Glu Asp Phe Phe Thr Glu His Ala Gly Glu Phe Asp
225                 230                 235                 240
Phe Ile Leu Asn Thr Ile Ser Ala Ser Ile Pro Val Asp Lys Tyr Leu
                245                 250                 255
Ser Leu Leu Lys Pro His Gly Val Met Ala Val Val Gly Leu Pro Pro
            260                 265                 270
Glu Lys Gln Pro Leu Ser Phe Gly Ala Leu Ile Gly Gly Gly Lys Val
            275                 280                 285
Leu Thr Gly Ser Asn Ile Gly Gly Ile Pro Glu Thr Gln Glu Met Leu
            290                 295                 300
Asp Phe Cys Ala Lys His Gly Leu Gly Ala Met Ile Glu Thr Val Gly
305                 310                 315                 320
Val Asn Asp Val Asp Ala Ala Tyr Arg Val Val Ala Gly Asp Val
                325                 330                 335
Gln Phe Arg Val Val Ile Asp Thr Ala Ser Phe Ala Glu Val Glu Ala
            340                 345                 350
Val

<210> SEQ ID NO 41
<211> LENGTH: 1113
<212> TYPE: DNA
<213> ORGANISM: Corynebacterium glutamicum

<400> SEQUENCE: 41
gtgtccatga gcactgtcgt gcctggaatt gtcgccctgt ccaaggggc accggtagaa      60
aaagtaaacg ttgttgtccc tgatccaggt gctaacgatg tcatcgtcaa gattcaggcc     120
tgcggtgtgt gccacaccga cttggcctac cgcgatggcg atatttcaga tgagttccct     180
tacctcctcg gccacgaggc agcaggtatt gttgaggagg taggcgagtc cgtcacccac     240
gttgaggtcg gcgatttcgt catcttgaac tggcgtgcag tgtgcggcga gtgccgtgca     300
tgtaagaagg gcgagccaaa gtactgcttt aacacccaca acgcatctaa gaagatgacc     360
ctggaagacg gcaccgagct gtccccagca ctgggtattg gcgcgttctt ggaaaagacc     420
ctggtccacg aaggccagtg caccaaggtt aaccctgagg aagatccagc agcagctggc     480
```

```
cttctgggtt gcggcatcat ggcaggtctt ggtgctgcgg taaacaccgg tgatattaag    540
cgcggcgagt ccgtggcagt cttcggcctt ggtggcgtgg gcatggcagc tattgctggc    600
gccaagattg ctggtgcatc gaagattatt gctgttgata tcgatgagaa gaagttggag    660
tgggcgaagg aattcggcgc aacccacacc attaattcct ctggtcttgg tggcgagggt    720
gatgcctctg aggtcgtggc aaaggttcgt gagctcactg atggtttcgg tactgacgtc    780
tccatcgatg cggtaggcat catgccgacc tggcagcagg cgttttactc ccgtgatcat    840
gcaggccgca tggtgatggt gggcgttcca aacctgacgt ctcgcgtaga tgttcctgcg    900
attgattttt acggtcgcgg tggctctgtg cgccctgcat ggtacggcga ctgcctgcct    960
gagcgtgatt tcccaactta tgtggatctg cacctgcagg tcgtttccc gctggataag    1020 tttgtttctg agcgtattgg tcttgatgat gttgaagagg ctttcaacac catgaaggct    1080
ggcgacgtgc tgcgttctgt ggtggagatc taa                                1113
```

<210> SEQ ID NO 42
<211> LENGTH: 370
<212> TYPE: PRT
<213> ORGANISM: Corynebacterium glutamicum

<400> SEQUENCE: 42

```
Met Ser Met Ser Thr Val Val Pro Gly Ile Val Ala Leu Ser Lys Gly
1               5                   10                  15

Ala Pro Val Glu Lys Val Asn Val Val Pro Asp Pro Gly Ala Asn
            20                  25                  30

Asp Val Ile Val Lys Ile Gln Ala Cys Gly Val Cys His Thr Asp Leu
        35                  40                  45

Ala Tyr Arg Asp Gly Asp Ile Ser Asp Glu Phe Pro Tyr Leu Leu Gly
    50                  55                  60

His Glu Ala Ala Gly Ile Val Glu Glu Val Gly Ser Val Thr His
65                  70                  75                  80

Val Glu Val Gly Asp Phe Val Ile Leu Asn Trp Arg Ala Val Cys Gly
                85                  90                  95

Glu Cys Arg Ala Cys Lys Lys Gly Glu Pro Lys Tyr Cys Phe Asn Thr
            100                 105                 110

His Asn Ala Ser Lys Lys Met Thr Leu Glu Asp Gly Thr Glu Leu Ser
        115                 120                 125

Pro Ala Leu Gly Ile Gly Ala Phe Leu Glu Lys Thr Leu Val His Glu
    130                 135                 140

Gly Gln Cys Thr Lys Val Asn Pro Glu Glu Asp Pro Ala Ala Ala Gly
145                 150                 155                 160

Leu Leu Gly Cys Gly Ile Met Ala Gly Leu Gly Ala Ala Val Asn Thr
                165                 170                 175

Gly Asp Ile Lys Arg Gly Glu Ser Val Ala Val Phe Gly Leu Gly Gly
            180                 185                 190

Val Gly Met Ala Ala Ile Ala Gly Ala Lys Ile Ala Gly Ala Ser Lys
        195                 200                 205

Ile Ile Ala Val Asp Ile Asp Glu Lys Lys Leu Glu Trp Ala Lys Glu
    210                 215                 220

Phe Gly Ala Thr His Thr Ile Asn Ser Ser Gly Leu Gly Gly Glu Gly
225                 230                 235                 240

Asp Ala Ser Glu Val Val Ala Lys Val Arg Glu Leu Thr Asp Gly Phe
                245                 250                 255

Gly Thr Asp Val Ser Ile Asp Ala Val Gly Ile Met Pro Thr Trp Gln
```

```
            260                 265                 270
Gln Ala Phe Tyr Ser Arg Asp His Ala Gly Arg Met Val Met Val Gly
            275                 280                 285

Val Pro Asn Leu Thr Ser Arg Val Asp Val Pro Ala Ile Asp Phe Tyr
            290                 295                 300

Gly Arg Gly Gly Ser Val Arg Pro Ala Trp Tyr Gly Asp Cys Leu Pro
305                 310                 315                 320

Glu Arg Asp Phe Pro Thr Tyr Val Asp Leu His Leu Gln Gly Arg Phe
                325                 330                 335

Pro Leu Asp Lys Phe Val Ser Glu Arg Ile Gly Leu Asp Asp Val Glu
            340                 345                 350

Glu Ala Phe Asn Thr Met Lys Ala Gly Asp Val Leu Arg Ser Val Val
            355                 360                 365

Glu Ile
    370

<210> SEQ ID NO 43
<211> LENGTH: 1047
<212> TYPE: DNA
<213> ORGANISM: Corynebacterium glutamicum

<400> SEQUENCE: 43
gtgagtttta tgaccactgc tgcacccaa gaatttaccg ctgctgttgt tgaaaaattc     60
ggtcatgacg tgaccgtgaa ggatattgac cttccaaagc cagggccaca ccaggcattg    120
gtgaaggtac tcacctccgg catctgccac accgacctcc acgccttgga gggcgattgg    180
ccagtaaagc cggaaccacc attcgtacca ggacacgaag gtgtaggtga agttgttgag    240
ctcggaccag gtgaacacga tgtgaaggtc ggcgatattg tcggcaatgc gtggctctgg    300
tcagcgtgcg gcacctgcga atactgcatc acaggcaggg aaactcagtg taacgaagct    360
gagtacggtg gctacaccca aaatggatcc ttcggccagt acatgctggt ggatacccga    420
tacgccgctc gcatcccaga cggcgtggac tacctcgaag cagcgccaat tctgtgtgca    480
ggcgtgactg tctacaaggc actcaaagtc tctgaaaccc gcccgggcca attcatggtg    540
atctccggtg tcggcggact tggccacatc gcagtccaat acgcagcggc gatgggcatg    600
cgtgtcattg cggtagatat tgccgaggac aagctggaac ttgcccgtaa gcacggtgcg    660
gaatttaccg tgaatgcgcg taatgaagat ccaggcgaag ctgtacagaa gtacaccaac    720
ggtggcgcac acggcgtgct tgtgactgca gttcacgagg cagcattcgg ccaggcactg    780
gatatggctc gacgtgcagg aacaattgtg ttcaacggtc tgccaccggg agagttccca    840
gcatccgtgt tcaacatcgt attcaagggc ctgaccatcc gtggatccct cgtgggaacc    900
cgccaagact tggccgaagc gctcgatttc tttgcacgcg actaatcaa gccaaccgtg    960
agtgagtgct ccctcgatga ggtcaatgga gttcttgacc gcatgcgaaa cggcaagatc   1020
gatggtcgtg tggcgattcg tttctaa                                       1047

<210> SEQ ID NO 44
<211> LENGTH: 348
<212> TYPE: PRT
<213> ORGANISM: Corynebacterium glutamicum

<400> SEQUENCE: 44

Met Ser Phe Met Thr Thr Ala Ala Pro Gln Glu Phe Thr Ala Ala Val
1               5                   10                  15

Val Glu Lys Phe Gly His Asp Val Thr Val Lys Asp Ile Asp Leu Pro
```

```
                    20                  25                  30
Lys Pro Gly Pro His Gln Ala Leu Val Lys Val Leu Thr Ser Gly Ile
                35                  40                  45

Cys His Thr Asp Leu His Ala Leu Glu Gly Asp Trp Pro Val Lys Pro
            50                  55                  60

Glu Pro Pro Phe Val Pro Gly His Glu Gly Val Gly Glu Val Val Glu
65                  70                  75                  80

Leu Gly Pro Gly Glu His Asp Val Lys Val Gly Asp Ile Val Gly Asn
                85                  90                  95

Ala Trp Leu Trp Ser Ala Cys Gly Thr Cys Glu Tyr Cys Ile Thr Gly
                100                 105                 110

Arg Glu Thr Gln Cys Asn Glu Ala Glu Tyr Gly Gly Tyr Thr Gln Asn
            115                 120                 125

Gly Ser Phe Gly Gln Tyr Met Leu Val Asp Thr Arg Tyr Ala Ala Arg
            130                 135                 140

Ile Pro Asp Gly Val Asp Tyr Leu Glu Ala Ala Pro Ile Leu Cys Ala
145                 150                 155                 160

Gly Val Thr Val Tyr Lys Ala Leu Lys Val Ser Glu Thr Arg Pro Gly
                165                 170                 175

Gln Phe Met Val Ile Ser Gly Val Gly Leu Gly His Ile Ala Val
                180                 185                 190

Gln Tyr Ala Ala Ala Met Gly Met Arg Val Ile Ala Val Asp Ile Ala
            195                 200                 205

Glu Asp Lys Leu Glu Leu Ala Arg Lys His Gly Ala Glu Phe Thr Val
210                 215                 220

Asn Ala Arg Asn Glu Asp Pro Gly Glu Ala Val Gln Lys Tyr Thr Asn
225                 230                 235                 240

Gly Gly Ala His Gly Val Leu Val Thr Ala Val His Glu Ala Ala Phe
                245                 250                 255

Gly Gln Ala Leu Asp Met Ala Arg Arg Ala Gly Thr Ile Val Phe Asn
            260                 265                 270

Gly Leu Pro Pro Gly Glu Phe Pro Ala Ser Val Phe Asn Ile Val Phe
            275                 280                 285

Lys Gly Leu Thr Ile Arg Gly Ser Leu Val Gly Thr Arg Gln Asp Leu
            290                 295                 300

Ala Glu Ala Leu Asp Phe Phe Ala Arg Gly Leu Ile Lys Pro Thr Val
305                 310                 315                 320

Ser Glu Cys Ser Leu Asp Glu Val Asn Gly Val Leu Asp Arg Met Arg
                325                 330                 335

Asn Gly Lys Ile Asp Gly Arg Val Ala Ile Arg Phe
                340                 345

<210> SEQ ID NO 45
<211> LENGTH: 1020
<212> TYPE: DNA
<213> ORGANISM: Corynebacterium glutamicum

<400> SEQUENCE: 45
atgcccaaat acattgccat gcaggtatcc gaatccggtg caccgttagc cgcgaatctc      60
gtgcaacctg ctccgttgaa atcgagggaa gtccgcgtgg aaatcgctgc tagtggtgtg     120
tgccatgcag atattggcac ggcagcagca tcggggaagc acactgtttt tcctgttacc     180
cctggtcatg agattgcagg aaccatcgcg gaaattggtg aaaacgtatc tcggtggacg     240
gttggtgatc gcgttgcaat cggttggttt ggtggcaatt gcggtgactg cgctttttgt     300
```

-continued

```
cgtgcaggtg atcctgtgca ttgcagagag cggaagattc ctggcgtttc ttatgcgggt    360
ggttgggcac agaatattgt tgttccagcg gaggctcttg ctgcgattcc agatggcatg    420
gacttttacg aggccgcccc gatgggctgc gcaggtgtga caacattcaa tgcgttgcga    480
aacctgaagc tggatcccgg tgcggctgtc gcggtctttg gaatcggcgg tttagtgcgc    540
ctagctattc agtttgctgc gaaaatgggt tatcgaacca tcaccatcgc ccgcggttta    600
gagcgtgagg agctagctag caacttggc gccaaccact acatcgatag caatgatctg    660
caccctggcc aggcgttatt tgaacttggc ggggctgact tgatcttgtc tactgcgtcc    720
accacggagc ctctttcgga gttgtctacc ggtctttcta ttggcgggca gctaaccatt    780
atcggagttg atgggggaga tatcaccgtt tcggcagccc aattgatgat gaaccgtcag    840
atcatcacag gtcacctcac tggaagtgcg aatgacacgg aacagactat gaaatttgct    900
catctccatg gcgtgaaacc gcttattgaa cggatgcctc tcgatcaagc caacgaggct    960
attgcacgta tttcagctgg taaaccacgt ttccgtattg tcttggagcc gaattcataa   1020
```

<210> SEQ ID NO 46
<211> LENGTH: 339
<212> TYPE: PRT
<213> ORGANISM: Corynebacterium glutamicum
<400> SEQUENCE: 46

```
Met Pro Lys Tyr Ile Ala Met Gln Val Ser Glu Ser Gly Ala Pro Leu
1               5                  10                  15

Ala Ala Asn Leu Val Gln Pro Ala Pro Leu Lys Ser Arg Glu Val Arg
            20                  25                  30

Val Glu Ile Ala Ala Ser Gly Val Cys His Ala Asp Ile Gly Thr Ala
        35                  40                  45

Ala Ala Ser Gly Lys His Thr Val Phe Pro Val Thr Pro Gly His Glu
    50                  55                  60

Ile Ala Gly Thr Ile Ala Glu Ile Gly Glu Asn Val Ser Arg Trp Thr
65                  70                  75                  80

Val Gly Asp Arg Val Ala Ile Gly Trp Phe Gly Gly Asn Cys Gly Asp
                85                  90                  95

Cys Ala Phe Cys Arg Ala Gly Asp Pro Val His Cys Arg Glu Arg Lys
            100                 105                 110

Ile Pro Gly Val Ser Tyr Ala Gly Gly Trp Ala Gln Asn Ile Val Val
        115                 120                 125

Pro Ala Glu Ala Leu Ala Ala Ile Pro Asp Gly Met Asp Phe Tyr Glu
    130                 135                 140

Ala Ala Pro Met Gly Cys Ala Gly Val Thr Thr Phe Asn Ala Leu Arg
145                 150                 155                 160

Asn Leu Lys Leu Asp Pro Gly Ala Ala Val Ala Val Phe Gly Ile Gly
                165                 170                 175

Gly Leu Val Arg Leu Ala Ile Gln Phe Ala Ala Lys Met Gly Tyr Arg
            180                 185                 190

Thr Ile Thr Ile Ala Arg Gly Leu Glu Arg Glu Glu Leu Ala Arg Gln
        195                 200                 205

Leu Gly Ala Asn His Tyr Ile Asp Ser Asn Asp Leu His Pro Gly Gln
    210                 215                 220

Ala Leu Phe Glu Leu Gly Gly Ala Asp Leu Ile Leu Ser Thr Ala Ser
225                 230                 235                 240

Thr Thr Glu Pro Leu Ser Glu Leu Ser Thr Gly Leu Ser Ile Gly Gly
```

```
                 245                 250                 255
Gln Leu Thr Ile Ile Gly Val Asp Gly Gly Asp Ile Thr Val Ser Ala
            260                 265                 270

Ala Gln Leu Met Met Asn Arg Gln Ile Ile Thr Gly His Leu Thr Gly
        275                 280                 285

Ser Ala Asn Asp Thr Glu Gln Thr Met Lys Phe Ala His Leu His Gly
    290                 295                 300

Val Lys Pro Leu Ile Glu Arg Met Pro Leu Asp Gln Ala Asn Glu Ala
305                 310                 315                 320

Ile Ala Arg Ile Ser Ala Gly Lys Pro Arg Phe Arg Ile Val Leu Glu
                325                 330                 335

Pro Asn Ser

<210> SEQ ID NO 47
<211> LENGTH: 879
<212> TYPE: DNA
<213> ORGANISM: Corynebacterium glutamicum

<400> SEQUENCE: 47
atgcaaaccc ttgctgctat tgttcgtgcc acgaagcaac cttttgagat caccaccatt      60
gatctggatg caccacgacc agatgaagtt caaatccgtg ttattgctgc cggagtgcgc     120
cacactgacg caattgttcg tgatcagatt tacccaactt tcttcccgc agttttcggc      180 cacgaaggcg ccggagtagt tgtcgccgtg ggttctgcag tcacctcggt gaaaccagat     240
gacaaggtag tgctgggatt caactcttgt ggccagtgct tgaagtgttt gggcggtaag     300
cctgcgtact gtgagaaatt ctatgaccgc aacttcgcat gcacccgcga tgccgggcac     360
actactttgt ttacccgtgc aacaaaagag caggcagagg ccatcatcga caccttgat     420 gatgttttct acgatgcgga tgcgggtttc ctggcatacc cagcaactcc cccagaggct     480 tcggagtaa gcgtgttggt tgtcgcggct ggtacctctg atctccccca agcaaaggaa      540
gcactacaca ctgcctccta cttggggcgc tccacctcac tgattgttga ttttggagtg     600
gctggcatcc accgcctgct ttcatacgaa gaagaactcc gcgctgcggg cgtgctcatc     660
gttgccgctg gaatggatgg tgcgctaccc ggagttgtcg caggcttagt gtccgcacct     720
gtcgtcgcac tgccaacctc cgtgggatac ggcgcaggtg ctggaggaat cgcaccactt     780
ctgaccatgc ttaacgcctg cgcgccggga gttgagtgg tcaacattga taacggctat     840
ggagcaggac acctggctgc gcagattgcg gcgaggtaa                             879

<210> SEQ ID NO 48
<211> LENGTH: 292
<212> TYPE: PRT
<213> ORGANISM: Corynebacterium glutamicum

<400> SEQUENCE: 48

Met Gln Thr Leu Ala Ala Ile Val Arg Ala Thr Lys Gln Pro Phe Glu
1               5                   10                  15

Ile Thr Thr Ile Asp Leu Asp Ala Pro Arg Pro Asp Glu Val Gln Ile
            20                  25                  30

Arg Val Ile Ala Ala Gly Val Arg His Thr Asp Ala Ile Val Arg Asp
        35                  40                  45

Gln Ile Tyr Pro Thr Phe Leu Pro Ala Val Phe Gly His Glu Gly Ala
    50                  55                  60

Gly Val Val Val Ala Val Gly Ser Ala Val Thr Ser Val Lys Pro Asp
65                  70                  75                  80
```

```
Asp Lys Val Val Leu Gly Phe Asn Ser Cys Gly Gln Cys Leu Lys Cys
                85                  90                  95

Leu Gly Gly Lys Pro Ala Tyr Cys Glu Lys Phe Tyr Asp Arg Asn Phe
            100                 105                 110

Ala Cys Thr Arg Asp Ala Gly His Thr Thr Leu Phe Thr Arg Ala Thr
        115                 120                 125

Lys Glu Gln Ala Glu Ala Ile Ile Asp Thr Leu Asp Asp Val Phe Tyr
    130                 135                 140

Asp Ala Asp Ala Gly Phe Leu Ala Tyr Pro Ala Thr Pro Pro Glu Ala
145                 150                 155                 160

Ser Gly Val Ser Val Leu Val Val Ala Ala Gly Thr Ser Asp Leu Pro
                165                 170                 175

Gln Ala Lys Glu Ala Leu His Thr Ala Ser Tyr Leu Gly Arg Ser Thr
            180                 185                 190

Ser Leu Ile Val Asp Phe Gly Val Ala Gly Ile His Arg Leu Leu Ser
                195                 200                 205

Tyr Glu Glu Glu Leu Arg Ala Ala Gly Val Leu Ile Val Ala Ala Gly
        210                 215                 220

Met Asp Gly Ala Leu Pro Gly Val Ala Gly Leu Val Ser Ala Pro
225                 230                 235                 240

Val Val Ala Leu Pro Thr Ser Val Gly Tyr Gly Ala Gly Ala Gly Gly
                245                 250                 255

Ile Ala Pro Leu Leu Thr Met Leu Asn Ala Cys Ala Pro Gly Val Gly
            260                 265                 270

Val Val Asn Ile Asp Asn Gly Tyr Gly Ala Gly His Leu Ala Ala Gln
                275                 280                 285

Ile Ala Ala Arg
    290

<210> SEQ ID NO 49
<211> LENGTH: 819
<212> TYPE: DNA
<213> ORGANISM: Escherichia coli

<400> SEQUENCE: 49
atggaaacct atgctgtttt tggtaatccg atagcccaca gcaaatcgcc attcattcat      60
cagcaatttg ctcagcaact gaatattgaa catccctatg ggcgcgtgtt ggcacccatc     120
aatgatttca tcaacacact gaacgctttc tttagtgctg gtggtaaagg tgcgaatgtg     180
acggtgcctt ttaaagaaga ggcttttgcc agagcggatg agcttactga acgggcagcg     240
ttggctggtg ctgttaatac cctcatgcgg ttagaagatg gacgcctgct gggtgacaat     300
accgatggtg taggcttgtt aagcgatctg gaacgtctgt cttttatccg ccctggttta     360
cgtattctgc ttatcggcgc tggtggagca tctcgcggcg tactactgcc actccttcc     420
ctggactgtg cggtgacaat aactaatcgg acggtatccc gcgcggaaga gttggctaaa     480
ttgtttgcgc acactggcag tattcaggcg ttgagtatgg acgaactgga aggtcatgag     540
tttgatctca ttattaatgc aacatccagt ggcatcagtg gtgatattcc ggcgatcccg     600
tcatcgctca ttcatccagg catttattgc tatgacatgt ctatcagaa ggaaaaaact     660
ccttttctgg catggtgtga gcagcgaggc tcaaagcgta atgctgatgg tttaggaatg     720
ctggtggcac aggcggctca tgcctttctt ctctggcacg tgttctgcc tgacgtagaa     780
ccagttataa agcaattgca ggaggaattg tccgcgtga                           819
```

-continued

<210> SEQ ID NO 50
<211> LENGTH: 272
<212> TYPE: PRT
<213> ORGANISM: Escherichia coli

<400> SEQUENCE: 50

Met Glu Thr Tyr Ala Val Phe Gly Asn Pro Ile Ala His Ser Lys Ser
1               5                   10                  15

Pro Phe Ile His Gln Gln Phe Ala Gln Gln Leu Asn Ile Glu His Pro
            20                  25                  30

Tyr Gly Arg Val Leu Ala Pro Ile Asn Asp Phe Ile Asn Thr Leu Asn
        35                  40                  45

Ala Phe Phe Ser Ala Gly Gly Lys Gly Ala Asn Val Thr Val Pro Phe
    50                  55                  60

Lys Glu Glu Ala Phe Ala Arg Ala Asp Glu Leu Thr Glu Arg Ala Ala
65                  70                  75                  80

Leu Ala Gly Ala Val Asn Thr Leu Met Arg Leu Glu Asp Gly Arg Leu
                85                  90                  95

Leu Gly Asp Asn Thr Asp Gly Val Gly Leu Leu Ser Asp Leu Glu Arg
            100                 105                 110

Leu Ser Phe Ile Arg Pro Gly Leu Arg Ile Leu Leu Ile Gly Ala Gly
        115                 120                 125

Gly Ala Ser Arg Gly Val Leu Leu Pro Leu Leu Ser Leu Asp Cys Ala
    130                 135                 140

Val Thr Ile Thr Asn Arg Thr Val Ser Arg Ala Glu Glu Leu Ala Lys
145                 150                 155                 160

Leu Phe Ala His Thr Gly Ser Ile Gln Ala Leu Ser Met Asp Glu Leu
                165                 170                 175

Glu Gly His Glu Phe Asp Leu Ile Ile Asn Ala Thr Ser Ser Gly Ile
            180                 185                 190

Ser Gly Asp Ile Pro Ala Ile Pro Ser Ser Leu Ile His Pro Gly Ile
        195                 200                 205

Tyr Cys Tyr Asp Met Phe Tyr Gln Lys Gly Lys Thr Pro Phe Leu Ala
    210                 215                 220

Trp Cys Glu Gln Arg Gly Ser Lys Arg Asn Ala Asp Gly Leu Gly Met
225                 230                 235                 240

Leu Val Ala Gln Ala Ala His Ala Phe Leu Leu Trp His Gly Val Leu
                245                 250                 255

Pro Asp Val Glu Pro Val Ile Lys Gln Leu Gln Glu Glu Leu Ser Ala
            260                 265                 270

<210> SEQ ID NO 51
<211> LENGTH: 35
<212> TYPE: DNA
<213> ORGANISM: Artificial Sequence
<220> FEATURE:
<223> OTHER INFORMATION: primer

<400> SEQUENCE: 51
cggtacccgg ggatccttac ttccgcgtat ccaac                      35

<210> SEQ ID NO 52
<211> LENGTH: 41
<212> TYPE: DNA
<213> ORGANISM: Artificial Sequence
<220> FEATURE:
<223> OTHER INFORMATION: primer -continued

<400> SEQUENCE: 52
ctaggaatcg cggccggtga actcctaaag aactatataa c         41

<210> SEQ ID NO 53
<211> LENGTH: 20
<212> TYPE: DNA
<213> ORGANISM: Artificial Sequence
<220> FEATURE:
<223> OTHER INFORMATION: primer

<400> SEQUENCE: 53
ggccgcgatt cctagcatgc         20

<210> SEQ ID NO 54
<211> LENGTH: 35
<212> TYPE: DNA
<213> ORGANISM: Artificial Sequence
<220> FEATURE:
<223> OTHER INFORMATION: primer

<400> SEQUENCE: 54
ccaagcttgc atgccagtca tcatcaacgg tgccg         35

<210> SEQ ID NO 55
<211> LENGTH: 21
<212> TYPE: DNA
<213> ORGANISM: Artificial Sequence
<220> FEATURE:
<223> OTHER INFORMATION: primer

<400> SEQUENCE: 55
atctccgcag aagacgtact g         21

<210> SEQ ID NO 56
<211> LENGTH: 20
<212> TYPE: DNA
<213> ORGANISM: Artificial Sequence
<220> FEATURE:
<223> OTHER INFORMATION: primer

<400> SEQUENCE: 56
tccgatcatg tatgacctcc         20

<210> SEQ ID NO 57
<211> LENGTH: 36
<212> TYPE: DNA
<213> ORGANISM: Artificial Sequence
<220> FEATURE:
<223> OTHER INFORMATION: primer

<400> SEQUENCE: 57
cggtacccgg ggatcggcat agtgcttcca acgctc         36

<210> SEQ ID NO 58
<211> LENGTH: 36
<212> TYPE: DNA
<213> ORGANISM: Artificial Sequence
<220> FEATURE:
<223> OTHER INFORMATION: primer

<400> SEQUENCE: 58
tagctccact caagattcct cgatattacc tacagg         36

<210> SEQ ID NO 59
<211> LENGTH: 20

```
<212> TYPE: DNA
<213> ORGANISM: Artificial Sequence
<220> FEATURE:
<223> OTHER INFORMATION: primer

<400> SEQUENCE: 59
tcttgagtgg agctagggcc                                              20

<210> SEQ ID NO 60
<211> LENGTH: 37
<212> TYPE: DNA
<213> ORGANISM: Artificial Sequence
<220> FEATURE:
<223> OTHER INFORMATION: primer

<400> SEQUENCE: 60
ccaagcttgc atgcccatat agagcccagg agctctc                           37

<210> SEQ ID NO 61
<211> LENGTH: 23
<212> TYPE: DNA
<213> ORGANISM: Artificial Sequence
<220> FEATURE:
<223> OTHER INFORMATION: primer

<400> SEQUENCE: 61
cgccgcaaag tccaaataga aag                                          23

<210> SEQ ID NO 62
<211> LENGTH: 20
<212> TYPE: DNA
<213> ORGANISM: Artificial Sequence
<220> FEATURE:
<223> OTHER INFORMATION: primer

<400> SEQUENCE: 62
ggattcttcc tgaactcagc                                              20

<210> SEQ ID NO 63
<211> LENGTH: 36
<212> TYPE: DNA
<213> ORGANISM: Artificial Sequence
<220> FEATURE:
<223> OTHER INFORMATION: primer

<400> SEQUENCE: 63
cggtacccgg ggatcgggct cgtcctgaaa ttgcac                            36

<210> SEQ ID NO 64
<211> LENGTH: 35
<212> TYPE: DNA
<213> ORGANISM: Artificial Sequence
<220> FEATURE:
<223> OTHER INFORMATION: primer

<400> SEQUENCE: 64
tccgtcgtga gccatgttgt gcccacgaga ctacc                             35

<210> SEQ ID NO 65
<211> LENGTH: 20
<212> TYPE: DNA
<213> ORGANISM: Artificial Sequence
<220> FEATURE:
<223> OTHER INFORMATION: primer

<400> SEQUENCE: 65
```
atggctcacg acggattgcg                                              20

<210> SEQ ID NO 66
<211> LENGTH: 36
<212> TYPE: DNA
<213> ORGANISM: Artificial Sequence
<220> FEATURE:
<223> OTHER INFORMATION: primer

<400> SEQUENCE: 66
ccaagcttgc atgcccggtt gcagccttca taaacg                            36

<210> SEQ ID NO 67
<211> LENGTH: 21
<212> TYPE: DNA
<213> ORGANISM: Artificial Sequence
<220> FEATURE:
<223> OTHER INFORMATION: primer

<400> SEQUENCE: 67
agaccaatga gtacccaacc g                                            21

<210> SEQ ID NO 68
<211> LENGTH: 20
<212> TYPE: DNA
<213> ORGANISM: Artificial Sequence
<220> FEATURE:
<223> OTHER INFORMATION: primer

<400> SEQUENCE: 68
tcagcgtctg gctcagctac                                              20

<210> SEQ ID NO 69
<211> LENGTH: 36
<212> TYPE: DNA
<213> ORGANISM: Artificial Sequence
<220> FEATURE:
<223> OTHER INFORMATION: primer

<400> SEQUENCE: 69
cggtacccgg ggatcaaccc cagctcaaat aacacc                            36

<210> SEQ ID NO 70
<211> LENGTH: 37
<212> TYPE: DNA
<213> ORGANISM: Artificial Sequence
<220> FEATURE:
<223> OTHER INFORMATION: primer

<400> SEQUENCE: 70
tttcaacaca atccgtcctt ctcgcttgga ttacttg                           37

<210> SEQ ID NO 71
<211> LENGTH: 23
<212> TYPE: DNA
<213> ORGANISM: Artificial Sequence
<220> FEATURE:
<223> OTHER INFORMATION: primer

<400> SEQUENCE: 71
cggattgtgt tgaaattgct ctg                                          23

<210> SEQ ID NO 72
<211> LENGTH: 35
<212> TYPE: DNA
<213> ORGANISM: Artificial Sequence

```
<220> FEATURE:
<223> OTHER INFORMATION: primer

<400> SEQUENCE: 72
ccaagcttgc atgcctcacc acgggaatct tcagg                                35

<210> SEQ ID NO 73
<211> LENGTH: 20
<212> TYPE: DNA
<213> ORGANISM: Artificial Sequence
<220> FEATURE:
<223> OTHER INFORMATION: primer

<400> SEQUENCE: 73
ccggactggg gtgtgttttg                                                 20

<210> SEQ ID NO 74
<211> LENGTH: 20
<212> TYPE: DNA
<213> ORGANISM: Artificial Sequence
<220> FEATURE:
<223> OTHER INFORMATION: primer

<400> SEQUENCE: 74
cccggaaaat acggtatagc                                                 20

<210> SEQ ID NO 75
<211> LENGTH: 47
<212> TYPE: DNA
<213> ORGANISM: Artificial Sequence
<220> FEATURE:
<223> OTHER INFORMATION: primer

<400> SEQUENCE: 75
ccaagcttgc atgccaggag gattataatg cgcctgcgtg tctcgag                   47

<210> SEQ ID NO 76
<211> LENGTH: 34
<212> TYPE: DNA
<213> ORGANISM: Artificial Sequence
<220> FEATURE:
<223> OTHER INFORMATION: primer

<400> SEQUENCE: 76
cggtacccgg ggatccaact acgcggcgac gtac                                 34

<210> SEQ ID NO 77
<211> LENGTH: 3387
<212> TYPE: DNA
<213> ORGANISM: Gordonia effusa

<400> SEQUENCE: 77
atgagcgatc agccgaatgc actgccgagc gcaattgaac cgctgaatcc ggatccgcag      60
gcaaccgagc agattagcca ttgtgcaacc attgcagaac tggttcgtgt tctggcagaa     120
agctatggtg atcgtccggc actgggttgg cgtaataata gcgatccgag cagctggcat     180
agcatgacct atcgtgatct ggccgaacgt gcagatagca tggcacgtct gctgcatagc     240
accctgggtg ttgcagaaaa tgatcgtgtt gcaaccgttg gttttaccag cgcagaatat     300
accattgcaa gcctggcagt tggtacactg ggtgcaatgg aagttccgct gcagaatgca     360
ggtagcgttg atgtttgggc agcaattctg accgaaaccg attgtgttag cgcagttgtt     420
gcagcagatc agctgccgag cattgcccgt ctggcggaaa gcggcaccta taccggtctg     480
```

```
cgtcatgttc tggtttttga tattggtagc cgtgatggca ccaccctgga tgatgcagca    540
cgtcgtctgg ttgccgcagg cacccaggtt catctgcgtc agcctggtgc agaaccgacc    600 accccctccgg caccgctgcc gcagattacc gcaaacccgg atcgtgtggc actgctgatt    660
tataccagcg gtagcacagg tgcaccgaaa ggtgcaatgt ataccgaaac agcagttacc    720
cgtctgtttc agagcggtct gagtggtctg ggtcgtgcaa ccgatggtca tggttggatt    780
accctgaact ttatgccgat gagccatgtt atgggtcgta gtaccctgtg cagaccctg     840 ggtaatggtg gcaccgcata ttttacaccg cgtgcagatc tggctgaact gctgaccgat    900
ctggcagccg ttcagccgac ggatctgcag tttgttccgc gtatttggga tatgctgtat    960
caagaatatg ttcgtctgac agatcaggat gttagcgaac aggatgcact gacccgtatg   1020
cgtgaacatt atttcggcac ccgtaccgca accgcaatta ccggtagcgc accgattagt   1080
gatgaagttc gtcgttttgt tgaagcaatg ctgccggttc cgctgattga aggttatggt   1140
agcaccgaag cagccggtgt tagcattgat ggtcgtattc agcgtccgcc tgttgttgat   1200
tataaactgc tggatgtgcc ggaactgggt tatctgagca ccgatcgtcc gcatccgcgt   1260
ggtgagctgc tggttaaaac cgatcatatt tttgccggtt attacaatcg tccggatctg   1320
accagcagcg ttttttgatga tcagggttat tatcgtaccg gtgatattgt tgccgaaacc   1380
ggtccggatc agattgaata tgttgatcgt cgtaacaacg tgatgaaact gagccagggt   1440
gaatttgttg caattgccca tattgaagca gttctgacca ccccaccgat tcagcagctg   1500
tatgtttatg gtaatagcgc acgtccgtat ctgctggccg ttgttgttcc gacaccggaa   1560
ctgcgtgaac gtcatgcaga tgataatgaa ctgcgtcgtg aagttctgac agcactgcgt   1620
agccatggtg aacgtaatgg tctggcagca gttgaaattc gcgtgatgt tattgttgaa    1680 cgtacccccgt ttagcctgga aaatggtctg ctgacaggta ttcgtaaact ggcacgtccg   1740
cagctgaaag aacgttatgg tgcacgtctg gaagcactgt atgccgaact ggccgatagc   1800
cgtattacac gtctgcgtga tgtgaaagca gttgcagccc agcgtagcac cgttaccacc   1860
gttattgatg ttgttaccgc aattctggat ctggcggatg gtgaagttac cgcagcagca   1920
cattttacag atctgggtgg tgatagcctg accgcagtta ccgttggtaa cgaactgcgc   1980 gatattttg atgccgaagt tccggttggt gtgctgacca gcccgagcag taccctggca   2040
gatattgcgg aacatattga tggccgtcat agcgaagcac gtccgaccgc agaaagcgtt   2100
catggcaccg gtacaaccct gcgtgcagcc gatctgaccc tggataaatt tctggatgaa   2160
gaaacactgc gtgccgcaag tgatgttacc agtcagcca ccgatgttcg taccgtgttt    2220
attaccggtg caaccggttt tctgggtcgc tacctgacac tggattggct gcgtcgtatg   2280
gcaaaagttg gtggtacagt tatttgtctg gtgcgtggtg ccgatgatga cgcagcccgt   2340
gcgcgtctgg atgcagcatt tgatagcagc gatctgtggt ctgaatatca gcgtctggca   2400
aaagatcatc tgcgcgtgct ggcaggcgat aaagatagcg atcatctggc actgacaccg   2460
gatgtgtggg atgaactggc aaaaagcgtt gatctgatta ttgatccggc agcactggtt   2520
aatcatgtac tgccgtatcg cgaactgttt ggtccgaatg ttagcggcac cgcagaactg   2580
atccgtctgg cagttaccac cacccgtaaa ccgtatgtgt atatttcaac cgtgggtgtt   2640
ggtgatcagg ttgctccggg tagctttacc gaagatcctg atattcgtga atgagcagc    2700 gtgcgtgaaa tcaatgatac ctatgcaaat ggttacggca atagcaaatg gcaggcgaa    2760 gttctgctgg cacaggcaca tgaacgtttt gaactgccgg ttagcgtttt tcgttgtgat   2820
atgattgttg cggatgatca taccattggt cagctgaatc tgccggatat gtttactcgc   2880
```

```
ctgctgatga gcgttctggc aacaggtctg gcaccgcgta gcttttatca gctggcgacc    2940
gatggtagtg cacaagaggc acattttgat gcgctgccgg tggatttcct ggccgaagca    3000
attaatacac tgtgggttaa agatggtgcc cgtaccttta atgcaatgaa tccgcatgcc    3060
gatggtattg gttttgatca gtatattcgt tggctgattg atagcggtga acaaattagc    3120
ctggtggata attatgatga ttggtatcgt cgctttggtg ccgcactggc ggatctgcct    3180
gaaaaacagc gtcgtggtag cctgattccg ctgctgcaca attatgttca tccgatgaca    3240
ccgcataatc gtggtatggc aagcgcagat cgttttcatg atgcagttcg tacagcaggc    3300
gttggtcaga gcagcgatat tccgcatatt accccctcaga ttattgaaaa ttatgcacgt    3360
agcctgcgtg gcctgggtgt gatttaa                                       3387

<210> SEQ ID NO 78
<211> LENGTH: 3408
<212> TYPE: DNA
<213> ORGANISM: Novosphingobium malaysiense

<400> SEQUENCE: 78
atggatgccg agagcggagt catgccgagc gatcccgatg tggttgcctt cgtccgccgg     60
ccggacacgt gccttagcgc gatgatcgag aaagcgctcg attcctatgc cgggcgcgat    120
gcattagcct ggcgccccac gcgttcaggc gtgttgagcg ataccttcga agtcatgacc    180
tacaaggacc tggcaaggcg cgtccgctcc gtggcgacgg cgctcgccaa agaccccgat    240
ctgggtctga agccggcga cccgatcggg atcatggcct tgccaacgt cgacttcgtc     300 accctcaatc tcgcgctggg cctctgcggt ggcgttatcg cgccgctgca gacctccgcc    360
agcatggaag cactgaccgg gctggtcagg gaactggcag cgccctgcct cgccgcatcg    420
ctcgaacatc tcgaagcgat caccacgctc gccatcgcaa gcgaaaaaac gcgcgcaatc    480
cttatcttcg accacgatgg cctcgacgaa gatgcccggg ccgcgatcgc cgccgcccag    540
caacgcctag acgcggaaaa gcccggctgc ctgatcctgc cgttttccga agtgatcgca    600
cgcggcgaaa gctgccgcc gctcgatccc ttcgttccgg cgccgggcga ggaccccttg    660
gctctgatct attacacctc gggcagcacc ggcacaccaa agggcgttat gtacacgcag    720
aagctggtga gctgggcta ttcgatagcc cgcgaccatg ccccgatcgt cctgcactat    780
cagccgctca accactcctt cgggatgtcc ttcatcgcca tggccctcgc cagcggcggc    840
acgtcctact ttaccgccaa gagcgacctg tcgacgctgc tgagcgacat gaagatggtc    900
cgcccgacga ccatggctct cgtcccgcgc atatcggaaa tgctgttcca gcgtttccat    960
gccgactacg ccgacgagat cgcacgcgac gaggatgccg caatggcgcg gttccgcgaa   1020
gacgttctcg gggggcggat gaccgacatc gtcaccgggg ccgcacctac ttcgccggaa   1080
cttcgcgact tcatcgagaa gatgaccggt ctcacactga tggaagggta cggctgcacc   1140
gaagcaggcg gctcgatcac cttcaacgac cgggtgatgc cccgcccgt gctcgaatac   1200 cgcctgatcg acgtgcccga gctcggctat ttcactaccg atacgcccca tccgcgcggc   1260
gagctcatcc tcaagagcga tgcgatgttc gccgggtact cgcgcgtcc ggacctcacg   1320 gcaaaggcct tcgacgacga ggggttctac cataccggcg acattatggc cgagatcgaa   1380
cccgaccacc tcgtctacct cgaccgcacc aacaacgtga tgaagctgtc gcagggcgaa   1440
ttcgtaccgg tcgcgttgct ggaatcgctc tatgcgggcg tgatccggt gatccgccag   1500 atctatctct atggcaattc gacgcgggct ttcctgctcg gcgtggccgt gcccaacatg   1560
```

-continued

```
gatgccctgc ccgagggaat cggtgatgag gaaatcaagg cccgcatgct ccaggctctg   1620
gaacgcatcg ccagggccaa cgaacgccat tcctacgaag tcccgcgcga cctgattata   1680
gagcatgagc cgttctctcc cgaaaacggc ctgcttgcgg gcgtcggcaa gtacatgcgc   1740
cccgccttca aggcgcgata cggagagcag ctcgaagcgc tctatgaaga aatcgctcgc   1800
agtcaggacc gcgagctgca ggaattgcgc agaaccggcc gcaccttccc agttctcgaa   1860
accgtgtgcc gggcggccgg cgccgtactg ggcggcaaga ccgttgccct tccgagaca    1920 ggctccttcg cgtcgtcggg tggggattcg ctttcagcac tgtccctctc gctgcttttg   1980
gaggacatct acgaactgcc cgtcgaagtc agcgcgatcc tccatccctc gggcacgtac   2040
gggctgcttg ccgcggaaat cgaggagaag ctgggcggcg gtgcgaagcg acgcgacgcc   2100
gtggccgttc atggcgcgga cctcaccgtg ctcaaggcgg ccgacctgac gctcgacaag   2160
ttcatagacg ccgagatcct tggcgccgcc accggcctgc ccgcgccgcc cgacgctgaa   2220
ccagaggtgg tgcttctcac cggtgtcacc ggcttcctag gccgtttcat gtgcctggaa   2280
tggctgcgtc ggctggagcg caacggcaag ggcaaggtgt ctgcgtggc gcgcggtgcc    2340 gatgacgacg atgcccgccg ccgcgtcctg gcaggctttg aaggcggtga tggcgcactg   2400
gcggcggaag tggcccggct gggcgaaggc cggctggccg tcttcgcagg cgatcttgcc   2460
gcaccccggc tgggtctcac cgcgacatgc tggcaggcgc tgtgcgacca ggtggacctc   2520
attgctcacc ctggcgcctt cgtgaaccac aagctgccct accgcagct gttcggagcc    2580 aacacagcag gcacggccga actgatcgcg ctggctctca ccacgcgcaa gaagcgcttc   2640
gcccatgtct ctaccatcgc cacgacatac aacgatggtc atcgcgcgga tgaaaacggc   2700
tacatcgaca gcgccattcc cgaatggcat gtaagcgacg cctacgccga cggctatggg   2760
tcgtccaaat gggccgcaga agtgctgctg gccagagcca atgagcaata tggcctaccc   2820
gtttcggtct accgttcgaa catgatcatg gcacccggcg agttctccgg tcagctcaat   2880
gtgcccgata tcttcactcg cctgctgctg agcctggcgc tgacccggct ggccccgcc    2940 agcttctatt cgggcgattc cgcgcgggcc cattacgaag gcctgccggt cgatttcctg   3000
gcccgcgcca tcgtgaccat tgccgaagac aaccgcgcgg ggttccatac cttccacacg   3060
atcaacccgc acgatgacgg gatctcgacc gacactttcg tcgactggat cggtgaagcg   3120
ggcattccga tcgaacggat cgcggactac gacgaatggg tcacgcgttt cgggacggcc   3180
ctgcgcgccc tgcctgaaaa gcagcggcaa gcctcgatcc tgccgttgat ggacgcgtac   3240
aagcacccgt ccccggcgat ccccgacttc cgcgatcagg cacctaactt ccgcaggcg    3300 gttgccgaat cgcaagtgaa cggagacggc gcgatccctc atctcacgcc ggcattgatt   3360
gctcggtatc tggaggacct gaaggccacc ggcctgctca cctcctga                3408
```

<210> SEQ ID NO 79
<211> LENGTH: 1135
<212> TYPE: PRT
<213> ORGANISM: Novosphingobium malaysiense

<400> SEQUENCE: 79

Met Asp Ala Glu Ser Gly Val Met Pro Ser Asp Pro Asp Val Val Ala
1               5                   10                  15

Phe Val Arg Arg Pro Asp Thr Cys Leu Ser Ala Met Ile Glu Lys Ala
            20                  25                  30

Leu Asp Ser Tyr Ala Gly Arg Asp Ala Leu Ala Trp Arg Pro Thr Arg
        35                  40                  45

```
Ser Gly Val Leu Ser Asp Thr Phe Glu Val Met Thr Tyr Lys Asp Leu
    50              55                  60

Ala Arg Arg Val Arg Ser Val Ala Thr Ala Leu Ala Lys Asp Pro Asp
65              70                  75                  80

Leu Gly Leu Lys Ala Gly Asp Pro Ile Gly Ile Met Ala Phe Ala Asn
                85                  90                  95

Val Asp Phe Val Thr Leu Asn Leu Ala Leu Gly Leu Cys Gly Gly Val
                100                 105                 110

Ile Ala Pro Leu Gln Thr Ser Ala Ser Met Glu Ala Leu Thr Gly Leu
                115                 120                 125

Val Arg Glu Leu Ala Ala Pro Cys Leu Ala Ala Ser Leu Glu His Leu
130                 135                 140

Glu Ala Ile Thr Thr Leu Ala Ile Ala Ser Glu Lys Thr Arg Ala Ile
145                 150                 155                 160

Leu Ile Phe Asp His Asp Gly Leu Asp Glu Asp Ala Arg Ala Ala Ile
                165                 170                 175

Ala Ala Ala Gln Gln Arg Leu Asp Ala Glu Lys Pro Gly Cys Leu Ile
                180                 185                 190

Leu Pro Phe Ser Glu Val Ile Ala Arg Gly Glu Lys Leu Pro Pro Leu
                195                 200                 205

Asp Pro Phe Val Pro Ala Pro Gly Glu Asp Pro Leu Ala Leu Ile Tyr
210                 215                 220

Tyr Thr Ser Gly Ser Thr Gly Thr Pro Lys Gly Val Met Tyr Thr Gln
225                 230                 235                 240

Lys Leu Val Lys Leu Gly Tyr Ser Ile Ala Arg Asp His Ala Pro Ile
                245                 250                 255

Val Leu His Tyr Gln Pro Leu Asn His Ser Phe Gly Met Ser Phe Ile
                260                 265                 270

Ala Met Ala Leu Ala Ser Gly Gly Thr Ser Tyr Phe Thr Ala Lys Ser
            275                 280                 285

Asp Leu Ser Thr Leu Leu Ser Asp Met Lys Met Val Arg Pro Thr Thr
            290                 295                 300

Met Ala Leu Val Pro Arg Ile Ser Glu Met Leu Phe Gln Arg Phe His
305                 310                 315                 320

Ala Asp Tyr Ala Asp Glu Ile Ala Arg Asp Glu Asp Ala Ala Met Ala
                325                 330                 335

Arg Phe Arg Glu Asp Val Leu Gly Gly Arg Met Thr Asp Ile Val Thr
                340                 345                 350

Gly Ala Ala Pro Thr Ser Pro Glu Leu Arg Asp Phe Ile Glu Lys Met
                355                 360                 365

Thr Gly Leu Thr Leu Met Glu Gly Tyr Gly Cys Thr Glu Ala Gly Gly
370                 375                 380

Ser Ile Thr Phe Asn Asp Arg Val Met Arg Pro Pro Val Leu Glu Tyr
385                 390                 395                 400

Arg Leu Ile Asp Val Pro Glu Leu Gly Tyr Phe Thr Thr Asp Thr Pro
                405                 410                 415

His Pro Arg Gly Glu Leu Ile Leu Lys Ser Asp Ala Met Phe Ala Gly
                420                 425                 430

Tyr Phe Ala Arg Pro Asp Leu Thr Ala Lys Ala Phe Asp Asp Glu Gly
                435                 440                 445

Phe Tyr His Thr Gly Asp Ile Met Ala Glu Ile Glu Pro Asp His Leu
            450                 455                 460

Val Tyr Leu Asp Arg Thr Asn Asn Val Met Lys Leu Ser Gln Gly Glu
```

-continued

```
        465                 470                 475                 480
    Phe Val Pro Val Ala Leu Leu Glu Ser Leu Tyr Ala Gly Gly Asp Pro
                        485                 490                 495
    Val Ile Arg Gln Ile Tyr Leu Tyr Gly Asn Ser Thr Arg Ala Phe Leu
                        500                 505                 510
    Leu Gly Val Ala Val Pro Asn Met Asp Ala Leu Pro Glu Gly Ile Gly
                        515                 520                 525
    Asp Glu Glu Ile Lys Ala Arg Met Leu Gln Ala Leu Glu Arg Ile Ala
                        530                 535                 540
    Arg Ala Asn Glu Arg His Ser Tyr Glu Val Pro Arg Asp Leu Ile Ile
    545                 550                 555                 560
    Glu His Glu Pro Phe Ser Pro Glu Asn Gly Leu Leu Ala Gly Val Gly
                        565                 570                 575
    Lys Tyr Met Arg Pro Ala Phe Lys Ala Arg Tyr Gly Glu Gln Leu Glu
                        580                 585                 590
    Ala Leu Tyr Glu Glu Ile Ala Arg Ser Gln Asp Arg Glu Leu Gln Glu
                        595                 600                 605
    Leu Arg Arg Thr Gly Arg Thr Phe Pro Val Leu Glu Thr Val Cys Arg
                        610                 615                 620
    Ala Ala Gly Ala Val Leu Gly Gly Lys Thr Val Ala Leu Ser Glu Thr
    625                 630                 635                 640
    Gly Ser Phe Ala Ser Ser Gly Gly Asp Ser Leu Ser Ala Leu Ser Leu
                        645                 650                 655
    Ser Leu Leu Leu Glu Asp Ile Tyr Glu Leu Pro Val Glu Val Ser Ala
                        660                 665                 670
    Ile Leu His Pro Ser Gly Thr Tyr Gly Leu Leu Ala Ala Glu Ile Glu
                        675                 680                 685
    Glu Lys Leu Gly Gly Gly Ala Lys Arg Arg Asp Ala Val Ala Val His
                        690                 695                 700
    Gly Ala Asp Leu Thr Val Leu Lys Ala Ala Asp Leu Thr Leu Asp Lys
    705                 710                 715                 720
    Phe Ile Asp Ala Glu Ile Leu Gly Ala Ala Thr Gly Leu Pro Ala Pro
                        725                 730                 735
    Pro Asp Ala Glu Pro Glu Val Val Leu Leu Thr Gly Val Thr Gly Phe
                        740                 745                 750
    Leu Gly Arg Phe Met Cys Leu Glu Trp Leu Arg Arg Leu Glu Arg Asn
                        755                 760                 765
    Gly Lys Gly Lys Val Val Cys Val Ala Arg Gly Ala Asp Asp Asp
                        770                 775                 780
    Ala Arg Arg Arg Val Leu Ala Gly Phe Glu Gly Asp Gly Ala Leu
    785                 790                 795                 800
    Ala Ala Glu Val Ala Arg Leu Gly Glu Gly Arg Leu Ala Val Phe Ala
                        805                 810                 815
    Gly Asp Leu Ala Ala Pro Arg Leu Gly Leu Thr Ala Thr Cys Trp Gln
                        820                 825                 830
    Ala Leu Cys Asp Gln Val Asp Leu Ile Ala His Pro Gly Ala Phe Val
                        835                 840                 845
    Asn His Lys Leu Pro Tyr Arg Gln Leu Phe Gly Ala Asn Thr Ala Gly
                        850                 855                 860
    Thr Ala Glu Leu Ile Ala Leu Ala Leu Thr Thr Arg Lys Lys Arg Phe
    865                 870                 875                 880
    Ala His Val Ser Thr Ile Ala Thr Thr Tyr Asn Asp Gly His Arg Ala
                        885                 890                 895
```

```
Asp Glu Asn Gly Tyr Ile Asp Ser Ala Ile Pro Glu Trp His Val Ser
                900                 905                 910

Asp Ala Tyr Ala Asp Gly Tyr Gly Ser Ser Lys Trp Ala Ala Glu Val
            915                 920                 925

Leu Leu Ala Arg Ala Asn Glu Gln Tyr Gly Leu Pro Val Ser Val Tyr
930                 935                 940

Arg Ser Asn Met Ile Met Ala Pro Gly Glu Phe Ser Gly Gln Leu Asn
945                 950                 955                 960

Val Pro Asp Ile Phe Thr Arg Leu Leu Leu Ser Leu Ala Leu Thr Arg
                965                 970                 975

Leu Ala Pro Ala Ser Phe Tyr Ser Gly Asp Ser Ala Arg Ala His Tyr
            980                 985                 990

Glu Gly Leu Pro Val Asp Phe Leu Ala Arg Ala Ile Val Thr Ile Ala
        995                 1000                1005

Glu Asp Asn Arg Ala Gly Phe His Thr Phe His Thr Ile Asn Pro
    1010                1015                1020

His Asp Asp Gly Ile Ser Thr Asp Thr Phe Val Asp Trp Ile Gly
    1025                1030                1035

Glu Ala Gly Ile Pro Ile Glu Arg Ile Ala Asp Tyr Asp Glu Trp
    1040                1045                1050

Val Thr Arg Phe Gly Thr Ala Leu Arg Ala Leu Pro Glu Lys Gln
    1055                1060                1065

Arg Gln Ala Ser Ile Leu Pro Leu Met Asp Ala Tyr Lys His Pro
    1070                1075                1080

Ser Pro Ala Ile Pro Asp Phe Arg Asp Gln Ala Pro Asn Phe Arg
    1085                1090                1095

Gln Ala Val Ala Glu Ser Gln Val Asn Gly Asp Gly Ala Ile Pro
    1100                1105                1110

His Leu Thr Pro Ala Leu Ile Ala Arg Tyr Leu Glu Asp Leu Lys
    1115                1120                1125

Ala Thr Gly Leu Leu Thr Ser
    1130                1135

<210> SEQ ID NO 80
<211> LENGTH: 4543
<212> TYPE: DNA
<213> ORGANISM: Artificial Sequence
<220> FEATURE:
<223> OTHER INFORMATION: Nucleotide sequence of DNA fragment containing
      ACAR gene of Novosphingobium malaysiense (codon-optimized) and
      entD gene of Escherichia coli

<400> SEQUENCE: 80
ccaagcttgc atgccagatc gtttagatcc gaaggaaaac gtcgaaaagc aatttgcttt    60
tcgacgcccc accccgcgcg ttttagcgtg tcagtagacg cgtagggtaa gtggggtagc   120
ggcttgttag atatcttgaa atcggctttc aacagcattg atttcgatgt atttagctgg   180
ccgtttgaga cgcgatgtcc acagggtagc tggtagtttg aaaatcaacg ccgttgccct   240
taggattcag taactggcac attttgtaat gcgctagatc tgtgtgccca gtcttccagg   300
ctgcttatca cagtgaaagc aaaaccaatt cgtggctgcg aaagtcgtag ccaccacgaa   360
gtccaggagg acatacaatg gatgcagaaa gcggtgttat gccgagcgat ccggatgttg   420
ttgcatttgt tcgtcgtccg gatacctgtc tgagcgcaat gattgaaaaa gcactggata   480
gctatgcagg tcgtgatgca ctggcatggc gtccgacccg tagcggtgtt ctgagcgata   540
```

```
cctttgaagt tatgacctat aaagatctgg cacgtcgtgt tcgtagcgtt gcaaccgcac    600
tggcaaaaga tcctgatctg ggtctgaaag ccggtgatcc gattggtatt atggcatttg    660
ccaatgttga tttcgttacc ctgaatctgg cactgggtct gtgtggtggt gttattgcac    720
cgctgcagac cagcgcaagc atggaagcac tgaccggtct ggttcgtgaa ctggcagcac    780
cgtgtctggc agcaagcctg gaacatctgg aagcaattac caccctggca attgcaagcg    840
aaaaaacccg tgcaattctg atctttgatc atgatggtct ggatgaagat gcacgtgccg    900
caattgcagc agcacagcag cgtctggatg ccgaaaaacc gggttgtctg attctgccgt    960
ttagcgaagt tattgcccgt ggtgaaaaac tgcctccgct ggatccgttt gttccggcac   1020
cgggtgaaga tccgctggca ctgatctatt ataccagcgg tagcaccggc accccgaaag   1080
gtgttatgta tacccagaaa ctggttaaac tgggttatag cattgcacgt gatcatgcac   1140
cgattgttct gcattatcag ccgctgaatc atagctttgg tatgagcttt attgcaatgg   1200
cactggcgag cggtggcacc agctatttta ccgcaaaaag cgatctgagc accctgctga   1260
gtgatatgaa aatggttcgt ccgaccacca tggccctggt tccgcgtatt agcgaaatgc   1320
tgtttcagcg ttttcatgca gattatgcag atgaaattgc gcgtgatgag gatgcagcca   1380
tggcacgttt tcgtgaagat gttctgggtg tcgtatgac cgatattgtt accggtgcag   1440
caccgaccag tccggaactg cgtgattta ttgaaaaaat gacaggtctg accctgatgg   1500
aaggttatgg ttgtaccgaa gccggtggta gcattacctt taatgatcgt gttatgcgtc   1560
cgcctgttct ggaatatcgt ctgattgatg ttcctgaact gggatatttt accaccgata   1620
caccgcatcc gcgtggtgaa ctgattctga aaagtgatgc aatgtttgcc ggttattttg   1680
cacgtccgga tctgaccgca aaagcatttg atgatgaagg ctttatcac accggtgata   1740 ttatggccga aattgaaccg gatcatctgg tttatctgga tcgtaccaat aacgtgatga   1800
aactgagcca gggtgaattt gtgccggttg cactgctgga aagcctgtat gccggtggtg   1860
atccggtgat tcgtcagatt tatctgtatg gtaatagcac ccgtgccttt ctgctgggtg   1920
ttgcagttcc gaatatggat gcactgccgg aaggtattgg tgatgaagaa attaaagcac   1980
gtatgctgca ggcactggaa cgtattgcac gcgcaaatga acgtcatagt tatgaagttc   2040
cgcgtgatct gattattgaa cacgaaccgt ttagtccgga aaatggtctg ctggcaggcg   2100
ttggcaaata tatgcgtcct gcatttaaag cccgttatgg tgagcagctg aagccctgt   2160 acgaagaaat tgcacgtagc caggatcgcg aactgcaaga actgcgtcgt accggtcgta   2220
cctttccggt tctggaaacc gtttgtcgtg cagccggtgc agtgctgggt ggcaaaaccg   2280
ttgcactgag cgaaaccggt agctttgcaa gcagtggtgg tgatagcctg agcgcactga   2340
gcctgagcct gctgctggaa gatatttatg aactgccggt tgaagttagc gcaatcctgc   2400
atccgagcgg cacctacggc ctgctggctg cagaaattga agaaaaactg ggtggtggtg   2460
caaaacgccg tgatgcagtt gccgttcatg gtgcagatct gacagttctg aaagcagccg   2520
atctgacact ggataaattc attgatgcgg aaattctggg tgcagcaacc ggtctgcctg   2580
cccctcctga tgccgaaccg gaagttgttc tgctgaccgg tgttacaggt tttctgggtc   2640
gttttatgtg tctggaatgg ctgcgtcgtc tggaacgcaa tggtaaaggt aaagttgttt   2700
gtgttgcacg tggtgccgat gatgatgacg cacgtcgtcg cgttctggca ggttttgaag   2760
gtggtgatgg tgccctggca gccgaagttg cacgtctggg tgaaggtcgt ctggccgttt   2820 ttgcggggtga tctggcagcc cctcgtctgg gcctgaccgc cacatgttgg caggccctgt   2880
gtgatcaggt ggatctgatt gcacatccgg gtgccttgt taatcataaa ctgccgtatc   2940
```

```
gtcagctgtt tggtgcaaat accgcaggca ccgcagaact gattgccctg gccctgacca   3000
cccgtaaaaa acgctttgca catgttagca ccattgccac cacctataat gatggtcatc   3060
gtgcggatga aaacggctat attgatagcg ccatcccgga atggcatgtt agtgatgcat   3120
atgccgatgg ttatggtagc tcaaaatggg cagcggaagt gctgctggca cgtgcgaatg   3180
aacagtatgg tctgccggtg agcgtttatc gtagcaatat gattatggca cctggtgaat   3240
ttagcggtca gctgaatgtt ccggatatct ttacccgtct gctgctgagc ctggcgctga   3300
cccgtctggc accggcaagc ttttatagcg tgatagcgc acgtgcacat tatgaaggcc   3360
tgccggtgga ttttctggct cgtgccattg tgaccattgc cgaagataat cgtgcaggtt   3420
ttcatacctt tcacaccatt aatccgcatg atgatggtat tagcacagat acatttgtgg   3480
attggattgg tgaagcaggt attccgattg aacgcattgc ggattatgat gaatgggtta   3540
cccgttttgg caccgcactg cgtgccctgc cggaaaaaca gcgtcaggca agcattctgc   3600
cgctgatgga tgcatataaa catccgagtc cggcaattcc ggattttcgc gatcaggcac   3660
cgaattttcg tcaggcagtt gcggaaagcc aggttaatgg tgatggcgca attccgcatc   3720
tgacaccggc actgattgcg cgttatctgg aagatctgaa agcgacaggc ctgctgacca   3780
gctaaaggag gacatacaat ggtcgatatg aaaactacgc atacctccct ccccttttgcc   3840
ggacatacgc tgcattttgt tgagttcgat ccggcgaatt tttgtgagca ggatttactc   3900
tggctgccgc actacgcaca actgcaacac gctggacgta aacgtaaaac agagcattta   3960
gccggacgga tcgctgctgt ttatgctttg cgggaatatg gctataaatg tgtgcccgca   4020
atcggcgagc tacgccaacc tgtctggcct gcggaggtat acggcagtat tagccactgt   4080
gggactacgg cattagccgt ggtatctcgt caaccgattg gcattgatat agaagaaatt   4140
ttttctgtac aaaccgcaag agaattgaca gacaacatta ttacaccagc ggaacacgag   4200
cgactcgcag actgcggttt agccttttct ctggcgctga cactggcatt ttccgccaaa   4260
gagagcgcat ttaaggcaag tgagatccaa actgatgcag gttttctgga ctatcagata   4320
attagctgga ataaacagca ggtcatcatt catcgtgaga atgagatgtt tgctgtgcac   4380
tggcagataa aagaaaagat agtcataacg ctgtgccaac acgattaatt gacaacatct   4440
ggtacgattc gcccgcagcc atcactgacc acgggcgaaa gtgtaaagca ggtgccttac   4500
catcctgacc tgacaaccgg atatgcggga tccccgggta ccg   4543

<210> SEQ ID NO 81
<211> LENGTH: 3408
<212> TYPE: DNA
<213> ORGANISM: Novosphingobium malaysiense

<400> SEQUENCE: 81
atggatgcag aaagcggtgt tatgccgagc gatccggatg ttgttgcatt tgttcgtcgt     60
ccggatacct gtctgagcgc aatgattgaa aaagcactgg atagctatgc aggtcgtgat    120
gcactggcat ggcgtccgac ccgtagcggt gttctgagcg ataccttgta agttatgacc    180
tataaagatc tggcacgtcg tgttcgtagc gttcaaccg cactggcaaa agatcctgat    240
ctgggtctga agccggtga tccgattggt attatggcat ttgccaatgt tgatttcgtt    300
accctgaatc tggcactggg tctgtgtggt ggtgttattg caccgctgca gaccagcgca    360
agcatggaag cactgaccgg tctggttcgt gaactggcag caccgtgtct ggcagcaagc    420
ctggaacatc tggaagcaat taccaccctg gcaattgcaa gcgaaaaaac ccgtgcaatt    480
```

```
ctgatctttg atcatgatgg tctggatgaa gatgcacgtg ccgcaattgc agcagcacag      540
cagcgtctgg atgccgaaaa accgggttgt ctgattctgc cgtttagcga agttattgcc      600
cgtggtgaaa aactgcctcc gctggatccg tttgttccgg caccgggtga agatccgctg      660
gcactgatct attataccag cggtagcacc ggcaccccga aaggtgttat gtatacccag      720
aaactggtta aactgggtta tagcattgca cgtgatcatg caccgattgt tctgcattat      780
cagccgctga atcatagctt tggtatgagc tttattgcaa tggcactggc gagcggtggc      840
accagctatt ttaccgcaaa aagcgatctg agcaccctgc tgagtgatat gaaaatggtt      900
cgtccgacca ccatggccct ggttccgcgt attagcgaaa tgctgtttca gcgttttcat      960
gcagattatg cagatgaaat tgcgcgtgat gaggatgcag ccatggcacg ttttcgtgaa     1020
gatgttctgg gtggtcgtat gaccgatatt gttaccggtg cagcaccgac cagtccggaa     1080
ctgcgtgatt ttattgaaaa aatgacaggt ctgaccctga tggaaggtta tggttgtacc     1140
gaagccggtg gtagcattac ctttaatgat cgtgttatgc gtccgcctgt tctggaatat     1200
cgtctgattg atgttcctga actgggtatt tttaccaccg atacaccgca tccgcgtggt     1260
gaactgattc tgaaaagtga tgcaatgttt gccggttatt ttgcacgtcc ggatctgacc     1320
gcaaaagcat tgatgatga aggctttat cacaccggtg atattatggc cgaaattgaa     1380
ccggatcatc tggtttatct ggatcgtacc aataacgtga tgaaactgag ccagggtgaa     1440
tttgtgccgg ttgcactgct ggaaagcctg tatgccggtg tgatccggt gattcgtcag     1500 atttatctgt atggtaatag cacccgtgcc tttctgctgg tgttgcagt tccgaatatg     1560 gatgcactgc cggaaggtat tggtgatgaa gaaattaaag cacgtatgct gcaggcactg     1620
gaacgtattg cacgcgcaaa tgaacgtcat agttatgaag ttccgcgtga tctgattatt     1680
gaaacgaaac cgtttagtcc ggaaaatggt ctgctggcag cgttggcaa atatatgcgt     1740 cctgcattta aagcccgtta tggtgagcag ctggaagccc tgtacgaaga aattgcacgt     1800
agccaggatc gcgaactgca agaactgcgt cgtaccggtc gtaccttcc ggttctggaa     1860 accgtttgtc gtgcagccgg tgcagtgctg gtggcaaaaa ccgttgcact gagcgaaacc     1920
ggtagctttg caagcagtgg tggtgatagc ctgagcgcac tgagcctgag cctgctgctg     1980
gaagatattt atgaactgcc ggttgaagtt agcgcaatcc tgcatccgag cggcacctac     2040
ggcctgctgg ctgcagaaat tgaagaaaaa ctgggtggtg gtgcaaaacg ccgtgatgca     2100
gttgccgttc atggtgcaga tctgacagtt ctgaaagcag ccgatctgac actggataaa     2160
ttcattgatg cggaaattct gggtgcagca accggtctgc ctgcccctcc tgatgccgaa     2220
ccggaagttg ttctgctgac cggtgttaca ggttttctgg gtcgttttat gtgtctggaa     2280
tggctgcgtc gtctggaacg caatggtaaa ggtaaagttg tttgtgttgc acgtggtgcc     2340
gatgatgatg acgcacgtcg tcgcgttctg cagggttttg aaggtggtga tggtgccctg     2400
gcagccgaag ttgcacgtct gggtgaaggt cgtctggccg tttttgcggg tgatctggca     2460
gcccctcgtc tgggcctgac cgccacatgt tggcaggccc tgtgtgatca ggtggatctg     2520
attgcacatc cgggtgcctt tgttaatcat aaactgccgt atcgtcagct gtttggtgca     2580
aataccgcag gcaccgcaga actgattgcc ctggccctga ccacccgtaa aaaacgcttt     2640
gcacatgtta gcaccattgc caccacctat aatgatggtc atcgtgcgga tgaaaacggc     2700
tatattgata gcgccatccc ggaatggcat gttagtgatg catatgccga tggttatggt     2760
agctcaaaat gggcagcgga agtgctgctg cacgtgcga atgaacagta tggtctgccg     2820
gtgagcgttt atcgtagcaa tatgattatg gcacctggtg aatttagcgg tcagctgaat     2880
```

| | |
|---|---|
| gttccggata tctttacccg tctgctgctg agcctggcgc tgacccgtct ggcaccggca | 2940 |
| agctttata gcggtgatag cgcacgtgca cattatgaag gcctgccggt ggattttctg | 3000 |
| gctcgtgcca ttgtgaccat tgccgaagat aatcgtgcag gttttcatac ctttcacacc | 3060 |
| attaatccgc atgatgatgg tattagcaca gatacatttg tggattggat tggtgaagca | 3120 |
| ggtattccga ttgaacgcat tgcggattat gatgaatggg ttacccgttt tggcaccgca | 3180 |
| ctgcgtgccc tgccggaaaa acagcgtcag gcaagcattc tgccgctgat ggatgcatat | 3240 |
| aaacatccga gtccggcaat tccggatttt cgcgatcagg caccgaattt tcgtcaggca | 3300 |
| gttgcgaaaa gccaggttaa tggtgatggc gcaattccgc atctgacacc ggcactgatt | 3360 |
| gcgcgttatc tggaagatct gaaagcgaca ggcctgctga ccagctaa | 3408 |

<210> SEQ ID NO 82
<211> LENGTH: 3582
<212> TYPE: DNA
<213> ORGANISM: Coccomyxa subellipsoidea

<400> SEQUENCE: 82

| | |
|---|---|
| atgacagaga acggaggact acctcaggtc aatggaggcg ccccccagta ctgggagatg | 60 |
| tccaacggcc agaaccagac taacaatgtc attcagaaga ggcttgcccg cgctcgcgaa | 120 |
| gtcatcaagc aagaccccca gctgcaggcg ccaagtttg acaggaaatc acttcaacgg | 180 |
| atcacggatg cggggaacac cagcattgag attattgcgg ccatgttcaa ggagtatgcg | 240 |
| tcgcgcgatc tattcggcgc ctgcacaccg ggagagtcca ccttccacac tgtgacttat | 300 |
| ggagcagtct gggagcgcat tcaggcgctg gtggcgggct ggacagcgct gggattcgtg | 360 |
| gctccggggg actttgtggg gatctctggg tttgccagcg tggactgggt ggtgtctgat | 420 |
| ctggcgacgc tgcatgctgg gggggtcatg gtcccctgc cacaaacat cctggcagag | 480 |
| gacgtgcgcg caatcattga cgaggctgaa gtgcgttgcc tcatggtcag cgctgaggag | 540 |
| cttgcggcca ttgcaccggt catcggcggc tgcgcgagcg tgaaggccgt cattgtcatg | 600 |
| gacagttcca cggacgccgt gacatcctcg ggagcctacg cggagatgca ggccaacctg | 660 |
| ccggcaggcg caaagctgac caccatcgac gaagttttgg cggcaggccg cgcaaccggc | 720 |
| aagcagcccg cactggtgat ccccggcagg gatgggcggc ccgcggaccc cttagtaaac | 780 |
| ctcatgtaca cctcgggcag ctctgggcgt cccaaggggg ccgagtaccc cgagcacctc | 840 |
| atctttgact tcctcaagaa ctcgatgccc acagatgcgc cggagctgcc gaccatcata | 900 |
| atgggcttcc ttcctttaaa ccatttgatg ggaagattta ctctgctcaa gtgcctgctc | 960 |
| accggaggcc agaactggtt tgtgcgctcg accgacatgt cgaccttctt cgatgacctg | 1020 |
| gcgacgatcc gtcccacgga ggcgatgttc cctccgcgga ttatgaacat gctgcacgac | 1080 |
| agattcgtgg agcagctcga ccgcctgccg ccagccccca gcgaggccga gcgcgcgcag | 1140 |
| caacgccagg acctgatcaa cgcttcagg gaagtggact gggtggccg cctcttcacc | 1200 |
| ggctcctttg gcagcgcgcc agcgtcccca gatgtgatcc aatggctgga ggaggtcctc | 1260 |
| ggcttcccc cagtgaatgg ctacggctcc acagagggcg gcatgatcat gctcgacaac | 1320 |
| aagatccagc atagttatgt gccggcgtac aagctggtag atgtgccaga gctgggctac | 1380 |
| accacaaagg acaagcccct ccccgcggga gaactgcgca tcaagacccg gcgcatgatc | 1440 |
| ccgggctact acaaacatcc tgaggcaaca gcggatctgt ttgacgagga gggcttcctg | 1500 |
| aagactgggg atgtggtgga gcagcgcgat gcagacacct tcatctggct ggaccgcgtc | 1560 |

| | | | | |
|---|---|---|---|---|
| aagaacatca | tcaagctctc | acagggtgag | tacgtgagcg | tgtcgcggct | ggaggagatc | 1620 |
| tatgtgggca | actccaagct | catccaccag | atgtacatct | acgggaactc | cctccgtgcc | 1680 |
| tacctggtcg | ccgtcgtcgt | gccccacatc | gagaacggag | cgtgtgcgga | tgcgggcaag | 1740 |
| ctgagggcgg | cgctgcggac | agagctggat | gacgtggcgc | gacgcaaggc | actacagggg | 1800 |
| tatgagatcc | cgcgcgagtt | catagtggag | atgcgcccct | tctccaagga | caatcacctg | 1860 |
| ctcactgact | ccgccaagcc | cgcccgcggc | cagctcaaga | gaggtacca | ggcggagctg | 1920 |
| gagggccttt | acacggccct | ggaggagcgt | ctgcgcgaga | gactgcgcgc | catgaaggag | 1980 |
| ggcaaggatg | catctgtgca | ggaccgtatc | aagcaggcgc | tggaggttac | tctgggactg | 2040 |
| gcggaggagg | acatggcgga | cgtggcttcg | cgcagcttcg | cgcagctggg | cggtgactcg | 2100 |
| ctggcggcga | tccagtttgc | gcgctacgtg | ggcgagcttt | cgcgcgtcaa | cctgccggtg | 2160 |
| tcctttgtgc | tggaccactc | ccactccctc | caggccatcg | ccgaccgcgt | ccacgaactc | 2220 |
| gtcagcggcg | acgcgagcgc | agggatcacg | ttcgagtcga | tccacggcag | cgatggcgtg | 2280 |
| aacatcaagg | cagccgacct | gaagctggac | cggttcctat | cagaagctga | cacggccgcg | 2340 |
| gccgccgcgg | ccgccccggc | ctccgagctg | ccggcgcggc | cgacacacgt | gctgctgacc | 2400 |
| ggcgccaacg | gcttcctcgg | ccgcttcctg | ctgctggacc | tgctgcagcg | cggttctgac | 2460 |
| aagaatggag | ccgtgtggt | ggctatagtg | cgcggcagca | gcgatgagaa | ggcggctgag | 2520 |
| cggctgcgcg | ccggttttga | cagcggtgac | gcgaccctgc | tgcagcgcta | tgacccctc | 2580 |
| agcaagcatc | tgaccgtcta | tcaggcgac | ctggcgaagc | cgcagctggg | cctgagccag | 2640 |
| gggtgtatg | agtcgctgtg | cgctgagctg | acaccatcg | tgcacaacgg | cgcgctggtc | 2700 |
| aaccacgctt | actcctatga | gcagctcttt | gagcccaatg | tgctcggcag | cgtggaggtg | 2760 |
| atgcggatgg | ctctggcaaa | gcgcagaaag | gcgctgacat | tcatctccag | tgtgggagtg | 2820 |
| gtgggaggcc | tggaccaccc | acagccggtg | actgaggctg | aggacggtcc | aactctgtgt | 2880 |
| gatgtgcacc | cggggcgacgg | cggctacgcc | atcgggtacg | gctgcagcaa | gtgggcggtg | 2940 |
| gaggtgcttc | tcaaggagct | gcaccagcgc | tggggtgttc | ccgtcaaggt | cttccgctgc | 3000 |
| ggcatgatcc | tgtcgcacac | cagctacttg | gccagatca | acccaaccga | cttcttcacg | 3060 |
| cggctgctgt | gcggcattgc | ctacacgggg | atcgccccgc | agtccttcta | caccctgccc | 3120 |
| cacgccccg | aggagcactt | tgacggcatg | cccatcgact | tcgtgtccgg | cgtgatctct | 3180 |
| gccacaacgg | cggccgagcg | cagcggcttc | gacacgtacc | atgtggtcaa | tccccactgg | 3240 |
| agcgacggcg | tatccctcga | ccgcatcgtc | gactgggcgg | agagcgccgg | ctacccggtt | 3300 |
| aatcgcatcg | cgccatatga | gcagtggtac | gcgcagttca | aggcagcgct | ggaggctctt | 3360 |
| gaccacacgc | ggcagcagca | gtcgccgctg | cccatcatct | accaatggga | gcgcccggca | 3420 |
| tccggcacca | gcggcacgaa | gtacgatgcc | acgcagctgc | gcaagagggc | ggccgcatac | 3480 |
| acacagtgga | aggacgtgcc | ccatctggac | gaggcgttca | tccaccagaa | catgcgccac | 3540 |
| ctcaccaccc | tgcgcctcat | cacccctccc | ggcaaggcct | ga | | 3582 |

<210> SEQ ID NO 83
<211> LENGTH: 1193
<212> TYPE: PRT
<213> ORGANISM: Coccomyxa subellipsoidea

<400> SEQUENCE: 83

Met Thr Glu Asn Gly Gly Leu Pro Gln Val Asn Gly Gly Pro Gln
1               5                   10                  15

-continued

```
Tyr Trp Glu Met Ser Asn Gly Gln Asn Gln Thr Asn Asn Val Ile Gln
             20                  25                  30

Lys Arg Leu Ala Arg Ala Arg Glu Val Ile Lys Gln Asp Pro Gln Leu
         35                  40                  45

Gln Ala Ala Lys Phe Asp Arg Lys Ser Leu Gln Arg Ile Thr Asp Ala
     50                  55                  60

Gly Asn Thr Ser Ile Glu Ile Ile Ala Ala Met Phe Lys Glu Tyr Ala
 65                  70                  75                  80

Ser Arg Asp Leu Phe Gly Ala Cys Thr Pro Gly Glu Ser Thr Phe His
                 85                  90                  95

Thr Val Thr Tyr Gly Ala Val Trp Glu Arg Ile Gln Ala Leu Val Ala
            100                 105                 110

Gly Trp Thr Ala Leu Gly Phe Val Ala Pro Gly Asp Phe Val Gly Ile
        115                 120                 125

Ser Gly Phe Ala Ser Val Asp Trp Val Val Ser Asp Leu Ala Thr Leu
    130                 135                 140

His Ala Gly Gly Val Met Val Pro Leu Pro Thr Asn Ile Leu Ala Glu
145                 150                 155                 160

Asp Val Arg Ala Ile Ile Asp Glu Ala Glu Val Arg Cys Leu Met Val
                165                 170                 175

Ser Ala Glu Glu Leu Ala Ala Ile Ala Pro Val Ile Gly Gly Cys Ala
            180                 185                 190

Ser Val Lys Ala Val Ile Val Met Asp Ser Ser Thr Asp Ala Val Thr
        195                 200                 205

Ser Ser Gly Ala Tyr Ala Glu Met Gln Ala Asn Leu Pro Ala Gly Ala
    210                 215                 220

Lys Leu Thr Thr Ile Asp Glu Val Leu Ala Ala Gly Arg Ala Thr Gly
225                 230                 235                 240

Lys Gln Pro Ala Leu Val Ile Pro Gly Arg Asp Gly Arg Pro Ala Asp
                245                 250                 255

Pro Leu Val Asn Leu Met Tyr Thr Ser Gly Ser Ser Gly Arg Pro Lys
            260                 265                 270

Gly Ala Glu Tyr Pro Glu His Leu Ile Phe Asp Phe Leu Lys Asn Ser
        275                 280                 285

Met Pro Thr Asp Ala Pro Glu Leu Pro Thr Ile Ile Met Gly Phe Leu
    290                 295                 300

Pro Leu Asn His Leu Met Gly Arg Phe Thr Leu Leu Lys Cys Leu Leu
305                 310                 315                 320

Thr Gly Gly Gln Asn Trp Phe Val Arg Ser Thr Asp Met Ser Thr Phe
                325                 330                 335

Phe Asp Asp Leu Ala Thr Ile Arg Pro Thr Glu Ala Met Phe Pro Pro
            340                 345                 350

Arg Ile Met Asn Met Leu His Asp Arg Phe Val Glu Gln Leu Asp Arg
        355                 360                 365

Leu Pro Pro Ala Pro Ser Glu Ala Glu Arg Ala Gln Gln Arg Gln Asp
    370                 375                 380

Leu Ile Lys Arg Phe Arg Glu Val Asp Leu Gly Gly Arg Leu Phe Thr
385                 390                 395                 400

Gly Ser Phe Gly Ser Ala Pro Ala Ser Pro Asp Val Ile Gln Trp Leu
                405                 410                 415

Glu Glu Val Leu Gly Phe Pro Pro Val Asn Gly Tyr Gly Ser Thr Glu
            420                 425                 430

Gly Gly Met Ile Met Leu Asp Asn Lys Ile Gln His Ser Tyr Val Pro
```

```
                435                 440                 445
Ala Tyr Lys Leu Val Asp Val Pro Glu Leu Gly Tyr Thr Thr Lys Asp
450                 455                 460

Lys Pro Phe Pro Arg Gly Glu Leu Arg Ile Lys Thr Arg Arg Met Ile
465                 470                 475                 480

Pro Gly Tyr Tyr Lys His Pro Glu Ala Thr Ala Asp Leu Phe Asp Glu
                485                 490                 495

Glu Gly Phe Leu Lys Thr Gly Asp Val Val Glu Gln Arg Asp Ala Asp
                500                 505                 510

Thr Phe Ile Trp Leu Asp Arg Val Lys Asn Ile Ile Lys Leu Ser Gln
                515                 520                 525

Gly Glu Tyr Val Ser Val Ser Arg Leu Glu Glu Ile Tyr Val Gly Asn
                530                 535                 540

Ser Lys Leu Ile His Gln Met Tyr Ile Tyr Gly Asn Ser Leu Arg Ala
545                 550                 555                 560

Tyr Leu Val Ala Val Val Pro His Ile Glu Asn Gly Ala Cys Ala
                565                 570                 575

Asp Ala Gly Lys Leu Arg Ala Ala Leu Arg Thr Glu Leu Asp Asp Val
                580                 585                 590

Ala Arg Arg Lys Ala Leu Gln Gly Tyr Glu Ile Pro Arg Glu Phe Ile
                595                 600                 605

Val Glu Met Arg Pro Phe Ser Lys Asp Asn His Leu Leu Thr Asp Ser
610                 615                 620

Ala Lys Pro Ala Arg Gly Gln Leu Lys Lys Arg Tyr Gln Ala Glu Leu
625                 630                 635                 640

Glu Gly Leu Tyr Thr Ala Leu Glu Glu Arg Leu Arg Glu Arg Leu Arg
                645                 650                 655

Ala Met Lys Glu Gly Lys Asp Ala Ser Val Gln Asp Arg Ile Lys Gln
                660                 665                 670

Ala Leu Glu Val Thr Leu Gly Leu Ala Glu Glu Asp Met Ala Asp Val
                675                 680                 685

Ala Ser Arg Ser Phe Ala Gln Leu Gly Gly Asp Ser Leu Ala Ala Ile
                690                 695                 700

Gln Phe Ala Arg Tyr Val Gly Glu Leu Cys Gly Val Asn Leu Pro Val
705                 710                 715                 720

Ser Phe Val Leu Asp His Ser His Ser Leu Gln Ala Ile Ala Asp Arg
                725                 730                 735

Val His Glu Leu Val Ser Gly Asp Ala Ser Ala Gly Ile Thr Phe Glu
                740                 745                 750

Ser Ile His Gly Ser Asp Gly Val Asn Ile Lys Ala Ala Asp Leu Lys
                755                 760                 765

Leu Asp Arg Phe Leu Ser Glu Ala Asp Thr Ala Ala Ala Ala Ala
                770                 775                 780

Ala Pro Ala Ser Glu Leu Pro Ala Arg Pro Thr His Val Leu Leu Thr
785                 790                 795                 800

Gly Ala Asn Gly Phe Leu Gly Arg Phe Leu Leu Asp Leu Leu Gln
                805                 810                 815

Arg Gly Ser Asp Lys Asn Gly Arg Val Val Ala Ile Val Arg Gly
                820                 825                 830

Ser Ser Asp Glu Lys Ala Ala Glu Arg Leu Arg Ala Gly Phe Asp Ser
                835                 840                 845

Gly Asp Ala Thr Leu Leu Gln Arg Tyr Asp Thr Leu Ser Lys His Leu
850                 855                 860
```

Thr Val Tyr Ala Gly Asp Leu Ala Lys Pro Gln Leu Gly Leu Ser Gln
865                 870                 875                 880

Gly Val Tyr Glu Ser Leu Cys Ala Glu Leu Asp Thr Ile Val His Asn
                885                 890                 895

Gly Ala Leu Val Asn His Ala Tyr Ser Tyr Glu Gln Leu Phe Glu Pro
            900                 905                 910

Asn Val Leu Gly Ser Val Glu Val Met Arg Met Ala Leu Ala Lys Arg
        915                 920                 925

Arg Lys Ala Leu Thr Phe Ile Ser Ser Val Gly Val Gly Gly Leu
930                 935                 940

Asp His Pro Gln Pro Val Thr Glu Ala Glu Asp Gly Pro Thr Leu Cys
945                 950                 955                 960

Asp Val His Pro Gly Asp Gly Gly Tyr Ala Ile Gly Tyr Gly Cys Ser
                965                 970                 975

Lys Trp Ala Val Glu Val Leu Leu Lys Glu Leu His Gln Arg Trp Gly
            980                 985                 990

Val Pro Val Lys Val Phe Arg Cys Gly Met Ile Leu Ser His Thr Ser
        995                 1000                1005

Tyr Leu Gly Gln Ile Asn Pro Thr Asp Phe Phe Thr Arg Leu Leu
    1010                1015                1020

Cys Gly Ile Ala Tyr Thr Gly Ile Ala Pro Gln Ser Phe Tyr Thr
    1025                1030                1035

Leu Pro His Gly Pro Glu Glu His Phe Asp Gly Met Pro Ile Asp
    1040                1045                1050

Phe Val Ser Gly Val Ile Ser Ala Thr Thr Ala Ala Glu Arg Ser
    1055                1060                1065

Gly Phe Asp Thr Tyr His Val Val Asn Pro His Trp Ser Asp Gly
    1070                1075                1080

Val Ser Leu Asp Arg Ile Val Asp Trp Ala Glu Ser Ala Gly Tyr
    1085                1090                1095

Pro Val Asn Arg Ile Ala Pro Tyr Glu Gln Trp Tyr Ala Gln Phe
    1100                1105                1110

Lys Ala Ala Leu Glu Ala Leu Asp His Thr Arg Gln Gln Gln Ser
    1115                1120                1125

Pro Leu Pro Ile Ile Tyr Gln Trp Glu Arg Pro Ala Ser Gly Thr
    1130                1135                1140

Ser Gly Thr Lys Tyr Asp Ala Thr Gln Leu Arg Lys Arg Ala Ala
    1145                1150                1155

Ala Tyr Thr Gln Trp Lys Asp Val Pro His Leu Asp Glu Ala Phe
    1160                1165                1170

Ile His Gln Asn Met Arg His Leu Thr Thr Leu Arg Leu Ile Thr
    1175                1180                1185

Pro Pro Gly Lys Ala
    1190

<210> SEQ ID NO 84
<211> LENGTH: 4717
<212> TYPE: DNA
<213> ORGANISM: Artificial Sequence
<220> FEATURE:
<223> OTHER INFORMATION: Nucleotide sequence of DNA fragment containing
      ACAR gene of Coccomyxa subellipsoidea (codon-optimized) and entD
      gene of Escherichia coli

<400> SEQUENCE: 84

```
ccaagcttgc atgccagatc gtttagatcc gaaggaaaac gtcgaaaagc aatttgcttt    60
tcgacgcccc accccgcgcg ttttagcgtg tcagtagacg cgtagggtaa gtggggtagc   120
ggcttgttag atatcttgaa atcggctttc aacagcattg atttcgatgt atttagctgg   180
ccgtttgaga cgcgatgtcc acagggtagc tggtagtttg aaaatcaacg ccgttgccct   240
taggattcag taactggcac attttgtaat gcgctagatc tgtgtgccca gtcttccagg   300
ctgcttatca cagtgaaagc aaaaccaatt cgtggctgcg aaagtcgtag ccaccacgaa   360
gtccaggagg acatacaatg accgaaaatg tggtctgcc gcaggttaat ggtggtggtc    420
cgcagtattg ggaaatgagc aatggtcaga atcagaccaa taacgtgatt cagaaacgtc   480
tggcacgtgc gcgtgaagtt attaaacagg atccgcagct gcaggcagca aaatttgatc   540
gtaaaagcct gcagcgtatt accgatgcag gtaataccag cattgaaatt attgcagcca   600
tgtttaaaga atacgcaagc cgtgacctgt ttggtgcatg tacaccgggt gaaagcacct   660
ttcataccgt tacctatggt gcagtttggg aacgtattca ggcactggtt gcaggttgga   720
ccgcactggg ttttgttgct ccgggtgatt ttgttggtat tagcggtttt gcaagcgttg   780
attgggttgt tagcgatctg caaccctgc atgccggtgg tgttatggtt ccgctgccga    840
ccaatattct ggccgaagat gttcgtgcaa ttattgatga agccgaagtt cgttgtctga   900
tggttagcgc agaagaactg gcagcaattg caccggttat tggtggttgt gccagcgtta   960
aagcagttat tgttatggat agcagcaccg atgccgttac cagcagcggt gcatatgccg  1020
aaatgcaggc caatctgcct gccggtgcaa aactgaccac catcgatgaa gttctggcag  1080
caggtcgtgc aaccggtaaa cagcctgccc tggttattcc gggtcgtgat ggtcgtccgg  1140
cagatccgct ggttaatctg atgtatacca gcggtagcag cggtcgtccg aaaggtgcag  1200
aatatccgga acatctgatt tttgatttc tgaaaaatag catgccgacc gatgcaccgg   1260
aactgccgac gattattatg ggttttctgc cgctgaatca tctgatgggt cgttttaccc  1320
tgctgaaatg tctgctgacc ggtggccaga attggtttgt tcgtagcacc gatatgagca  1380
cctttttga tgatctggcg accattcgtc cgaccgaagc aatgtttccg cctcgtatta   1440
tgaatatgct gcatgatcgt tttgtggaac agctggatcg tctgcctccg gcaccgagcg  1500
aagcagaacg tgcacagcag cgtcaggatc tgattaaacg ttttcgtgaa gttgatctgg  1560
gtggtcgtct gtttacaggt agctttggta gcgcaccggc aagtccggat gttattcagt  1620
ggctggaaga agtgctgggt tttccgcctg ttaatggtta tggtagtacc gaaggtggta  1680
tgattatgct ggacaacaaa attcagcaca gctatgttcc agcctataaa ctggttgatg  1740
tgccggaact gggttatacc accaaagata accgtttcc gcgtggtgaa ctgcgtatta   1800
aaacccgtcg tatgattccg ggttattaca acatcctga gcaaccgca gacctgttcg    1860
atgaagaagg tttcctgaaa accggtgatg ttgttgaaca gcgtgatgca gatacctta   1920
tttggctgga tcgcgtgaaa acattatca aactgagcca gggtgaatat gttagcgtta   1980
gccgtctgga agaaattat gtgggtaaca gcaaactgat tcaccagatg tatatctatg   2040
gtaatagcct gcgtgcatat ctggttgccg ttgttgttcc gcatattgaa aatggcgcat  2100
gtgcagatgc cggtaaactg cgtgcagcac tgcgtaccga actggatgat gttgcacgtc  2160
gtaaagcact gcagggttat gaaattcctc gtgaatttat tgttgagatg cgtccgttta  2220
gcaaagataa tcatctgctg acagatagcc aaaaccggc acgtggtcag ctgaaaaaac  2280
gttatcagga gaactggaa ggtctgtata cggcactgga gaacgtctg cgtgaacggc    2340
tgcgtgcaat gaaagaaggt aaagacgcaa gcgttcagga tcgtatcaaa caggccctgg  2400
```

```
aagttaccct gggtctggcg aagaggata tggcagatgt tgcaagccgt agctttgcac    2460
agctgggtgg tgatagcctg gcagccattc agtttgcacg ttatgttggc gaactgtgtg    2520
gtgttaatct gccggttagc tttgttctgg atcatagcca tagtctgcag gcaattgcag    2580
atcgtgtgca tgaactggtt agcggtgatg cctcagcagg cattacccttt gaaagcattc    2640
atggtagtga tggcgttaac attaaagcag cagatctgaa actggatcgt tttctgagcg    2700
aagccgatac cgcagcagca gccgctgcag caccggcatc agaactgcct gcacgtccga    2760
cccatgttct gctgactggc gcaaatggtt ttctgggtcg ctttctgctg ctggatctgc    2820
tgcagcgtgg tagcgataaa aatggcggtc gtgttgttgc aattgttcgt ggtagcagtg    2880
atgaaaaagc agccgaacgc ctgcgtgcgg ttttgatag tggtgatgcc accctgctgc    2940
aacgttatga taccctgagc aaacatctga ccgtttatgc cggtgatctg gccaaaccgc    3000
agctgggtct gagtcagggt gtttatgaaa gcctgtgtgc agagctggat accattgttc    3060
ataatggtgc actggtgaac catgcctata gctatgagca gctgtttgaa ccgaatgttc    3120
tgggtagcgt tgaagttatg cgtatggcac tggcaaaacg ccgtaaagcc ctgacccttta    3180
ttagcagcgt tggtgttgtg ggtggcctgg atcatccgca gccggttacc gaagcggaag    3240
atggtccgac cctgtgtgat gttcatcctg gtgatggtgg ttatgcaatt ggttatggct    3300
gtagcaaatg ggcagttgaa gtgctgctga aagaactgca tcagcgttgg ggtgttccgg    3360
ttaaagtttt tcgttgcggt atgattctgt cccataccag ctatctgggt cagattaatc    3420
cgacagattt tttcacccgt ctgctgtgtg gtattgcata tacaggtatt gcaccgcaga    3480
gcttttatac cctgccgcat ggtccggaag aacattttga tggtatgccg attgattttg    3540
tgagcggtgt tattagcgca accacagccg cagaacgtag cggctttgat acctatcatg    3600
ttgttaatcc gcattggagt gatggtgtga gcctggatcg tattgtagat tgggcagaaa    3660
gtgcaggtta tccggttaat cgtatcgcac cgtacgaaca gtggtatgca cagtttaaag    3720
cagccctgga agcactggat cataccccgtc agcagcagtc accgctgccg attatctatc    3780
agtgggaacg tccggcaagc ggtacaagcg gcaccaaata tgatgcaaca cagctgcgta    3840
aacgtgcagc agcctatacc cagtggaaag atgtgccgca tctggatgaa gcatttattc    3900
atcagaatat gcgtcatctg accacccctgc gtctgattac ccctccgggt aaagcataaa    3960
ggaggacata caatggtcga tatgaaaact acgcatacct ccctcccctt tgccggacat    4020
acgctgcatt tgttgagtt cgatccggcg aattttgtg agcaggattt actctggctg    4080
ccgcactacg cacaactgca acacgctgga cgtaaacgta aaacagagca tttagccgga    4140
cggatcgctg ctgtttatgc tttgcgggaa tatggctata atgtgtgcc cgcaatcggc    4200
gagctacgcc aacctgtctg gcctgcgag gtatacggca gtattagcca ctgtgggact    4260
acggcattag ccgtggtatc tcgtcaaccg attggcattg atatagaaga aattttttct    4320
gtacaaaccg caagagaatt gacagacaac attattacac cagcgaaaca cgagcgactc    4380
gcagactgcg gtttagcctt ttctctggcg ctgacactgg cattttccgc caaagagagc    4440
gcatttaagg caagtgagat ccaaactgat gcaggttttc tggactatca gataattagc    4500
tggaataaac agcaggtcat cattcatcgt gagaatgaga tgtttgctgt gcactggcag    4560
ataaaagaaa agatagtcat aacgctgtgc caacacgatt aattgacaac atctggtacg    4620
attcgcccgc agccatcact gaccacgggc gaaagtgtaa agcaggtgcc ttaccatcct    4680
gacctgacaa ccggatatgc gggatccccg ggtaccg                              4717
```

<210> SEQ ID NO 85
<211> LENGTH: 3582
<212> TYPE: DNA
<213> ORGANISM: Coccomyxa subellipsoidea

<400> SEQUENCE: 85

| | | | | | |
|---|---|---|---|---|---|
| atgaccgaaa | atggtggtct | gccgcaggtt | aatggtggtg | gtccgcagta | ttgggaaatg | 60 |
| agcaatggtc | agaatcagac | caataacgtg | attcagaaac | gtctggcacg | tgcgcgtgaa | 120 |
| gttattaaac | aggatccgca | gctgcaggca | gcaaaatttg | atcgtaaaag | cctgcagcgt | 180 |
| attaccgatg | caggtaatac | cagcattgaa | attattgcag | ccatgtttaa | agaatacgca | 240 |
| agccgtgacc | tgtttggtgc | atgtacaccg | ggtgaaagca | cctttcatac | cgttacctat | 300 |
| ggtgcagttt | gggaacgtat | tcaggcactg | gttgcaggtt | ggaccgcact | gggttttgtt | 360 |
| gctccgggtg | attttgttgg | tattagcggt | tttgcaagcg | ttgattgggt | tgttagcgat | 420 |
| ctggcaaccc | tgcatgccgg | tggtgttatg | gttccgctgc | cgaccaatat | tctggccgaa | 480 |
| gatgttcgtg | caattattga | tgaagccgaa | gttcgttgtc | tgatggttag | cgcagaagaa | 540 |
| ctggcagcaa | ttgcaccggt | tattggtggt | tgtgccagcg | ttaaagcagt | tattgttatg | 600 |
| gatagcagca | ccgatgccgt | taccagcagc | ggtgcatatg | ccgaaatgca | ggccaatctg | 660 |
| cctgccggtg | caaaactgac | caccatcgat | gaagttctgg | cagcaggtcg | tgcaaccggt | 720 |
| aaacagcctg | ccctggttat | tccgggtcgt | gatggtcgtc | cggcagatcc | gctggttaat | 780 |
| ctgatgtata | ccagcggtag | cagcggtcgt | ccgaaaggtg | cagaatatcc | ggaacatctg | 840 |
| atttttgatt | ttctgaaaaa | tagcatgccg | accgatgcac | cggaactgcc | gacgattatt | 900 |
| atgggttttc | tgccgctgaa | tcatctgatg | ggtcgtttta | ccctgctgaa | atgtctgctg | 960 |
| accggtggcc | agaattggtt | tgttcgtagc | accgatatga | gcaccttttt | tgatgatctg | 1020 |
| gcgaccattc | gtccgaccga | agcaatgttt | ccgcctcgta | ttatgaatat | gctgcatgat | 1080 |
| cgttttgtgg | aacagctgga | tcgtctgcct | ccggcaccga | gcgaagcaga | acgtgcacag | 1140 |
| cagcgtcagg | atctgattaa | acgttttcgt | gaagttgatc | tgggtggtcg | tctgtttaca | 1200 |
| ggtagctttg | gtagcgcacc | ggcaagtccg | gatgttattc | agtggctgga | agaagtgctg | 1260 |
| ggttttccgc | ctgttaatgg | ttatggtagt | accgaaggtg | gtatgattat | gctggacaac | 1320 |
| aaaattcagc | acagctatgt | tccagcctat | aaactggttg | atgtgccgga | actgggttat | 1380 |
| accaccaaag | ataaaccgtt | tccgcgtggt | gaactgcgta | ttaaaacccg | tcgtatgatt | 1440 |
| ccgggttatt | acaaacatcc | tgaagcaacc | gcagacctgt | tcgatgaaga | aggtttcctg | 1500 |
| aaaaccggtg | atgttgttga | acagcgtgat | gcagatacct | ttatttggct | ggatcgcgtg | 1560 |
| aaaaacatta | tcaaactgag | ccagggtgaa | tatgttagcg | ttagccgtct | ggaagaaatt | 1620 |
| tatgtgggta | acagcaaact | gattcaccag | atgtatatct | atggtaatag | cctgcgtgca | 1680 |
| tatctggttg | ccgttgttgt | tccgcatatt | gaaaatggcg | catgtgcaga | tgccggtaaa | 1740 |
| ctgcgtgcag | cactgcgtac | cgaactggat | gatgttgcac | gtcgtaaagc | actgcagggt | 1800 |
| tatgaaattc | ctcgtgaatt | tattgttgag | atgcgtccgt | ttagcaaaga | taatcatctg | 1860 |
| ctgacagata | gcgcaaaacc | ggcacgtggt | cagctgaaaa | aacgttatca | ggcagaactg | 1920 |
| gaaggtctgt | ataccggcact | ggaagaacgt | ctgcgtgaac | ggctgcgtgc | aatgaaagaa | 1980 |
| ggtaaagacg | caagcgttca | ggatcgtatc | aaacaggccc | tggaagttac | cctgggtctg | 2040 |
| gcggaagagg | atatggcaga | tgttgcaagc | cgtagctttg | cacagctggg | tggtgatagc | 2100 |
| ctggcagcca | ttcagtttgc | acgttatgtt | ggcgaactgt | gtggtgttaa | tctgccggtt | 2160 |

```
agctttgttc tggatcatag ccatagtctg caggcaattg cagatcgtgt gcatgaactg    2220
gttagcggtg atgcctcagc aggcattacc tttgaaagca ttcatggtag tgatggcgtt    2280
aacattaaag cagcagatct gaaactggat cgttttctga gcgaagccga taccgcagca    2340
gcagccgctg cagcaccggc atcagaactg cctgcacgtc cgacccatgt tctgctgact    2400
ggcgcaaatg gtttctggg tcgctttctg ctgctggatc tgctgcagcg tggtagcgat    2460
aaaaatggcg gtcgtgttgt tgcaattgtt cgtggtagca gtgatgaaaa agcagccgaa    2520
cgcctgcgtg cgggttttga tagtggtgat gccaccctgc tgcaacgtta tgataccctg    2580
agcaaacatc tgaccgttta tgccggtgat ctggccaaac cgcagctggg tctgagtcag    2640
ggtgtttatg aaagcctgtg tgcagagctg gataccattg ttcataatgg tgcactggtg    2700
aaccatgcct atagctatga gcagctgttt gaaccgaatg ttctgggtag cgttgaagtt    2760
atgcgtatgg cactggcaaa acgccgtaaa gccctgacct ttattagcag cgttggtgtt    2820
gtgggtggcc tggatcatcc gcagccggtt accgaagcgg aagatggtcc gaccctgtgt    2880
gatgttcatc ctggtgatgg tggttatgca attggttatg gctgtagcaa atgggcagtt    2940
gaagtgctgc tgaaagaact gcatcagcgt tggggtgttc cggttaaagt ttttcgttgc    3000
ggtatgattc tgtcccatac cagctatctg ggtcagatta atccgacaga ttttttcacc    3060
cgtctgctgt gtggtattgc atatacaggt attgcaccgc agagcttttta taccctgccg    3120 catggtccgg aagaacattt tgatggtatg ccgattgatt ttgtgagcgg tgttattagc    3180
gcaaccacag ccgcagaacg tagcggcttt gatacctatc atgttgttaa tccgcattgg    3240
agtgatggtg tgagcctgga tcgtattgta gattgggcag aaagtgcagg ttatccggtt    3300
aatcgtatcg caccgtacga acagtggtat gcacagttta aagcagccct ggaagcactg    3360
gatcataccc gtcagcagca gtcaccgctg ccgattatct atcagtggga acgtccggca    3420
agcggtacaa gcggcaccaa atatgatgca acacagctgc gtaaacgtgc agcagcctat    3480
acccagtgga aagatgtgcc gcatctggat gaagcattta ttcatcagaa tatgcgtcat    3540
ctgaccaccc tgcgtctgat taccccctccg ggtaaagcat aa                      3582
```

METHOD FOR PRODUCING ALDEHYDE

This application is a Continuation of, and claims priority under 35 U.S.C. § 120 to, International Application No. PCT/JP2017/038875, filed Oct. 27, 2017, and claims priority therethrough under 35 U.S.C. § 119 to Japanese Patent Application No. 2016-211103, filed Oct. 27, 2016, Japanese Patent Application No. 2016-211106, filed Oct. 27, 2016, Japanese Patent Application No. 2016-211107, filed Oct. 27, 2016, Japanese Patent Application No. 2016-022265, filed Feb. 9, 2017, Japanese Patent Application No. 2017-022314, filed Feb. 9, 2017, and Japanese Patent Application No. 2017-022330, filed Feb. 9, 2017, the entireties of which are incorporated by reference herein. Also, the Sequence Listing filed electronically herewith is hereby incorporated by reference (File name: 2019-04-24T_US-569_Seq_List; File size: 179 KB; Date recorded: Apr. 24, 2019).

BACKGROUND

General Field

The present invention relates to a method for producing an objective substance, for example, an aldehyde such as vanillin, by using a microorganism.

Background Art

Vanillin is the major ingredient responsible for the smell of vanilla, and is used as an aromatic by being blended in foods, drinks, perfumes, and so forth. Vanillin is mainly produced by extraction from natural products or by chemical synthesis.

Bioengineering techniques have also been attempted to produce vanillin, such as by using various microorganisms with eugenol, isoeugenol, ferulic acid, glucose, vanillic acid, coconut husk, or the like as a raw material (Kaur B. and Chakraborty D., Biotechnological and molecular approaches for vanillin production: a review. Appl Biochem Biotechnol. 2013 February; 169(4):1353-72). Other bioengineering methods include a method of producing vanillin as a glycoside (WO2013/022881 and WO2004/111254), a method of producing vanillin from ferulic acid by using vanillin synthase (JP2015-535181), and a method of producing vanillic acid by fermentation of *Escherichia coli* and then enzymatically converting vanillic acid into vanillin (US6372461).

Vanillin can be produced via the intermediate protocatechuic acid. Specifically, protocatechuic acid can be converted to vanillic acid or protocatechualdehyde by the action of O-methyltransferase (OMT) or aldehyde oxidoreductase (carboxylic acid reductase; CAR), respectively; and vanillic acid or protocatechualdehyde can be converted to vanillin by the action of CAR or OMT, respectively. In addition, isovanillin can be produced as a by-product via the intermediate protocatechuic acid. Specifically, protocatechuic acid can be converted to isovanillic acid by the action of OMT; and isovanillic acid can be converted to isovanillin by the action of CAR.

SUMMARY

It is difficult to separate an aldehyde such as vanillin from another aldehyde such as protocatechualdehyde and isovanillin during the purification process. Hence, selective generation of vanillin can be useful for, for example, reducing the purification cost. However, a CAR suitable for selective generation of vanillin has not been previously reported.

It is an aspect of the present invention is to develop a novel technique for improving production of an objective substance, for example, an aldehyde such as vanillin, such as a novel technique useful for selective generation of the objective substance, and thereby provide a method for efficiently producing the objective substance.

It is described herein that an ability of a microorganism for producing an objective substance, for example, an aldehyde such as vanillin, could be significantly improved by using a microorganism that is able to express the carboxylic acid reductase (CAR) gene of *Gordonia effusa*, *Novosphingobium malaysiense*, or *Coccomyxa subellipsoidea*.

It is an aspect of the present invention to provide a method for producing an objective substance, the method comprising:
producing the objective substance by using a microorganism having an ability to produce the objective substance,
wherein the objective substance is an aldehyde,
wherein the microorganism has been modified to have an aldehyde oxidoreductase gene, and
wherein the aldehyde oxidoreductase gene encodes a protein selected from the group consisting of:
(a) a protein comprising the amino acid sequence of SEQ ID NO: 18, 79, or 83;
(b) a protein comprising the amino acid sequence of SEQ ID NO: 18, 79, or 83 but which includes substitution, deletion, insertion, and/or addition of 1 to 10 amino acid residues, and wherein said protein has aldehyde oxidoreductase activity;
(c) a protein comprising an amino acid sequence having an identity of 90% or higher to the amino acid sequence of SEQ ID NO: 18, 79, or 83, and wherein said protein has aldehyde oxidoreductase activity.

It is a further aspect of the invention to provide the method as described above, wherein said producing comprises:
cultivating the microorganism in a culture medium containing a carbon source to produce and accumulate the objective substance in the culture medium.

It is a further aspect of the invention to provide the method as described above, wherein said producing comprises:
converting a precursor of the objective substance into the objective substance by using the microorganism.

It is a further aspect of the invention to provide the method as described above, wherein said converting comprises:
cultivating the microorganism in a culture medium containing the precursor to produce and accumulate the objective substance in the culture medium.

It is a further aspect of the invention to provide the method as described above, wherein said converting comprises:
allowing cells of the microorganism to act on the precursor in a reaction mixture to produce and accumulate the objective substance in the reaction mixture.

It is a further aspect of the invention to provide the method as described above, wherein the cells are selected from the group consisting of:
cells present in a culture broth of the microorganism,
cells collected from the culture broth,
cells present in a processed product of the culture broth,
cells present in a processed product of the collected cells, and
a combination of these.

It is a further aspect of the invention to provide the method as described above, wherein the precursor is a substance selected from the group consisting of protocatechuic acid, vanillic acid, benzoic acid, L-phenylalanine, cinnamic acid, and combinations thereof.

It is a further aspect of the invention to provide the method as described above, the method further comprising collecting the objective substance from the culture medium or reaction mixture.

It is a further aspect of the invention to provide the method as described above, wherein the microorganism is a bacterium belonging to the family *Enterobacteriaceae*, a coryneform bacterium, or yeast.

It is a further aspect of the invention to provide the method as described above, wherein the microorganism is a bacterium belonging to the genus *Corynebacterium*.

It is a further aspect of the invention to provide the method as described above, wherein the microorganism is *Corynebacterium glutamicum*.

It is a further aspect of the invention to provide the method as described above, wherein the microorganism is a bacterium belonging to the genus *Escherichia*.

It is a further aspect of the invention to provide the method as described above, wherein the microorganism is *Escherichia coli*.

It is a further aspect of the invention to provide the method as described above, wherein the objective substance is an aromatic aldehyde.

It is a further aspect of the invention to provide the method as described above, wherein the objective substance is an aromatic aldehyde selected from the group consisting of vanillin, benzaldehyde, cinnamaldehyde, and combinations thereof.

It is a further aspect of the invention to provide the method as described above, wherein the microorganism has been further modified so that the activity of an enzyme that is involved in the biosynthesis of the objective substance is increased as compared with a non-modified strain.

It is a further aspect of the invention to provide the method as described above, wherein the enzyme that is involved in the biosynthesis of the objective substance is able to catalyze the conversion from a precursor of the objective substance into the objective substance.

It is a further aspect of the invention to provide the method as described above, wherein the enzyme that is involved in the biosynthesis of the objective substance is selected from the group consisting of 3-deoxy-D-arabino-heptulosonic acid 7-phosphate synthase, 3-dehydroquinate synthase, 3-dehydroquinate dehydratase, 3-dehydroshikimate dehydratase, O-methyltransferase, phenylalanine ammonia lyase, and combinations thereof.

It is a further aspect of the invention to provide the method as described above, wherein the microorganism has been further modified so that the activity of phosphopantetheinyl transferase is increased as compared with a non-modified strain.

It is a further aspect of the invention to provide the method as described above, wherein the microorganism has been further modified so that the activity of an uptake system of a substance other than the objective substance is increased as compared with a non-modified strain.

It is a further aspect of the invention to provide the method as described above, wherein the uptake system is selected from the group consisting of a vanillic acid uptake system, a protocatechuic acid uptake system, and combinations thereof.

It is a further aspect of the invention to provide the method as described above, wherein the microorganism has been further modified so that the activity of an enzyme that is involved in the production of a byproduct during the production of the objective substance is reduced as compared with a non-modified strain.

It is a further aspect of the invention to provide the method as described above, wherein the enzyme that is involved in the production of a byproduct during the production of the objective substance is selected from the group consisting of vanillate demethylase, protocatechuate 3,4-dioxygenase, alcohol dehydrogenase, shikimate dehydrogenase, and combinations thereof.

DETAILED DESCRIPTION OF THE PREFERRED EMBODIMENTS

Hereafter, the present invention will be explained in detail.

<1> Microorganism

The microorganism as described herein is a microorganism having an ability to produce an objective substance, which microorganism has been modified to have (i.e. to harbor) a specific carboxylic acid reductase (CAR) gene such as *Gordonia* CAR gene, *Novosphingobium* CAR gene, or *Coccomyxa* CAR gene. The ability to produce an objective substance can also be referred to as "objective substance-producing ability".

<1-1> Microorganism having objective substance-producing ability

The term "microorganism having an objective substance-producing ability" can refer to a microorganism that is able to produce an objective substance.

The term "microorganism having an objective substance-producing ability" can refer to a microorganism that is able to produce an objective substance by fermentation, if the microorganism is used in a fermentation method. That is, the term "microorganism having an objective substance-producing ability" may refer to a microorganism that is able to produce an objective substance from a carbon source. Specifically, the term "microorganism having an objective substance-producing ability" may refer to a microorganism that is able to, upon being cultured in a culture medium, such as a culture medium containing a carbon source, produce and accumulate the objective substance in the culture medium to such a degree that the objective substance can be collected therefrom.

Also, the term "microorganism having an objective substance-producing ability" can refer to a microorganism that is able to produce an objective substance by bioconversion, if the microorganism is used in a bioconversion method. That is, the term "microorganism having an objective substance-producing ability" may refer to a microorganism that is able to produce an objective substance from a precursor of the objective substance. Specifically, the term "microorganism having an objective substance-producing ability" may refer to a microorganism that is able to, upon being cultured in a culture medium containing a precursor of an objective substance, produce and accumulate the objective substance in the culture medium in such a degree that the objective substance can be collected therefrom. Also, specifically, the term "microorganism having an objective substance-producing ability" may refer to a microorganism that is able to, upon being allowed to act on a precursor of an objective substance in a reaction mixture, produce and accumulate the objective substance in the reaction mixture to such a degree that the objective substance can be collected from the reaction mixture.

The microorganism having an objective substance-producing ability may be a microorganism that is able to accumulate the objective substance in the culture medium or reaction mixture in an amount larger than that is obtained with a non-modified strain. A non-modified strain can also be referred to as a "strain of a non-modified microorganism" or a "non-modified microorganism". The term "non-modified strain" can refer to a control strain that has not been modified to have a specific CAR gene. Examples of the non-modified strain can include a strain having a CAR gene other than the specific CAR gene, such as the CAR gene of *Nocardia brasiliensis*, instead of the specific CAR gene. The microorganism having an objective substance-producing ability may be a microorganism that is able to accumulate the objective substance in the culture medium or reaction mixture in an amount of, for example, 0.01 g/L or more, 0.05 g/L or more, or 0.09 g/L or more.

The term "objective substance" can refer to an aldehyde. Examples of the aldehyde can include aromatic aldehydes. Examples of the aromatic aldehydes can include vanillin, benzaldehyde, and cinnamaldehyde. The microorganism may have an ability to produce only one kind of objective substance, or may have an ability to produce two or more kinds of objective substances. Also, the microorganism may have an ability to produce an objective substance from one kind of precursor of the objective substance or from two or more kinds of precursors of the objective substance.

A parent strain that is used to construct the microorganism as described herein is not particularly limited. Examples of the microorganism can include bacteria and yeast.

Examples of the bacteria can include bacteria belonging to the family *Enterobacteriaceae* and coryneform bacteria.

Examples of bacteria belonging to the family *Enterobacteriaceae* can include bacteria belonging to the genus *Escherichia*, *Enterobacter*, *Pantoea*, *Klebsiella*, *Serratia*, *Erwinia*, *Photorhabdus*, *Providencia*, *Salmonella*, *Morganella*, or the like. Specifically, bacteria classified into the family *Enterobacteriaceae* according to the taxonomy used in the NCBI (National Center for Biotechnology Information) database (ncbi.nlm.nih.gov/Taxonomy/Browser) can be used.

The *Escherichia* bacteria are not particularly limited, and examples thereof can include those classified into the genus *Escherichia* according to the taxonomy known to those skilled in the field of microbiology. Examples of the *Escherichia* bacteria can include, for example, those described in the work of Neidhardt et al. (Backmann B. J., 1996, Derivations and Genotypes of some mutant derivatives of *Escherichia coli* K-12, pp. 2460-2488, Table 1, In F. D. Neidhardt (ed.), *Escherichia coli* and *Salmonella* Cellular and Molecular Biology/Second Edition, American Society for Microbiology Press, Washington, D.C.). Examples of the *Escherichia* bacteria can include, for example, *Escherichia coli*. Specific examples of *Escherichia coli* can include, for example, *Escherichia coli* K-12 strains such as W3110 strain (ATCC 267325) and MG1655 strain (ATCC 47076); *Escherichia coli* K5 strain (ATCC 23506); *Escherichia coli* B strains such as BL21 (DE3) strain; and derivative strains thereof.

The *Enterobacter* bacteria are not particularly limited, and examples can include those classified into the genus *Enterobacter* according to the taxonomy known to those skilled in the field of microbiology. Examples the *Enterobacter* bacterium can include, for example, *Enterobacter agglomerans* and *Enterobacter aerogenes*. Specific examples of *Enterobacter agglomerans* can include, for example, the *Enterobacter agglomerans* ATCC 12287 strain. Specific examples of *Enterobacter aerogenes* can include, for example, the *Enterobacter aerogenes* ATCC 13048 strain, NBRC 12010 strain (Biotechnol. Bioeng., 2007, Mar. 27; 98(2):340-348), and AJ110637 strain (FERM BP-10955). Examples the *Enterobacter* bacteria can also include, for example, the strains described in European Patent Application Laid-open (EP-A) No. 0952221. In addition, *Enterobacter agglomerans* can also include some strains classified as *Pantoea agglomerans*.

The *Pantoea* bacteria are not particularly limited, and examples can include those classified into the genus *Pantoea* according to the taxonomy known to those skilled in the field of microbiology. Examples the *Pantoea* bacteria can include, for example, *Pantoea ananatis*, *Pantoea stewartii*, *Pantoea agglomerans*, and *Pantoea citrea*. Specific examples of *Pantoea ananatis* can include, for example, the *Pantoea ananatis* LMG20103 strain, AJ13355 strain (FERM BP-6614), AJ13356 strain (FERM BP-6615), AJ13601 strain (FERM BP-7207), SC17 strain (FERM BP-11091), SC17(0) strain (VKPM B-9246), and SC17sucA strain (FERM BP-8646). Some of *Enterobacter* bacteria and *Erwinia* bacteria were reclassified into the genus *Pantoea* (Int. J. Syst. Bacteriol., 39, 337-345 (1989); Int. J. Syst. Bacteriol., 43, 162-173 (1993)). For example, some strains of *Enterobacter agglomerans* were recently reclassified into *Pantoea agglomerans*, *Pantoea ananatis*, *Pantoea stewartii*, or the like on the basis of nucleotide sequence analysis of 16S rRNA etc. (Int. J. Syst. Bacteriol., 39, 337-345 (1989)). The *Pantoea* bacteria can include those reclassified into the genus *Pantoea* as described above.

Examples of the *Erwinia* bacteria can include *Erwinia amylovora* and *Erwinia carotovora*. Examples of the *Klebsiella* bacteria can include *Klebsiella planticola*.

Examples of coryneform bacteria can include bacteria belonging to the genus *Corynebacterium*, *Brevibacterium*, *Microbacterium*, or the like.

Specific examples of such coryneform bacteria can include the following species.

*Corynebacterium acetoacidophilum*
*Corynebacterium acetoglutamicum*
*Corynebacterium alkanolyticum*
*Corynebacterium callunae*
*Corynebacterium crenatum*
*Corynebacterium glutamicum*
*Corynebacterium lilium*
*Corynebacterium melassecola*
*Corynebacterium thermoaminogenes* (*Corynebacterium efficiens*)
*Corynebacterium herculis*
*Brevibacterium divaricatum* (*Corynebacterium glutamicum*)
*Brevibacterium flavum* (*Corynebacterium glutamicum*)
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Corynebacterium ammoniagenes* (*Corynebacterium stationis*)
*Brevibacterium album*
*Brevibacterium cerinum*
*Microbacterium ammoniaphilum*

Specific examples of the coryneform bacteria can include the following strains.

*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium crenatum* AS1.542
*Corynebacterium glutamicum* ATCC 13020, ATCC 13032, ATCC 13060, ATCC 13869, FERM BP-734
*Corynebacterium lilium* ATCC 15990
*Corynebacterium melassecola* ATCC 17965
*Corynebacterium efficiens* (*Corynebacterium thermoaminogenes*) AJ12340 (FERM BP-1539)
*Corynebacterium herculis* ATCC 13868
*Brevibacterium divaricatum* (*Corynebacterium glutamicum*) ATCC 14020
*Brevibacterium flavum* (*Corynebacterium glutamicum*) ATCC 13826, ATCC 14067, AJ12418 (FERM BP-2205)
*Brevibacterium immariophilum* ATCC 14068
*Brevibacterium lactofermentum* (*Corynebacterium glutamicum*) ATCC 13869
*Brevibacterium roseum* ATCC 13825
*Brevibacterium saccharolyticum* ATCC 14066
*Brevibacterium thiogenitalis* ATCC 19240
*Corynebacterium ammoniagenes* (*Corynebacterium stationis*) ATCC 6871, ATCC 6872
*Brevibacterium album* ATCC 15111
*Brevibacterium cerinum* ATCC 15112
*Microbacterium ammoniaphilum* ATCC 15354

The coryneform bacteria can include bacteria that had previously been classified into the genus *Brevibacterium*, but are presently united into the genus *Corynebacterium* (Int. J. Syst. Bacteriol., 41, 255 (1991)). Moreover, *Corynebacterium stationis* can include bacteria that had previously been classified as *Corynebacterium ammoniagenes*, but are presently re-classified into *Corynebacterium stationis* on the basis of nucleotide sequence analysis of 16S rRNA etc. (Int. J. Syst. Evol. Microbiol., 60, 874-879 (2010)).

The yeast may be budding yeast or may be fission yeast. The yeast may be haploid yeast or may be diploid or more polyploid yeast. Examples of the yeast can include yeast belonging to the genus *Saccharomyces* such as *Saccharomyces cerevisiae*, the genus *Pichia* (also referred to as the genus *Wickerhamomyces*) such as *Pichia ciferrii*, *Pichia sydowiorum*, and *Pichia pastoris*, the genus *Candida* such as *Candida utilis*, the genus *Hansenula* such as *Hansenula polymorpha*, and the genus *Schizosaccharomyces* such as *Schizosaccharomyces pombe*.

These strains are available from, for example, the American Type Culture Collection (Address: P.O. Box 1549, Manassas, Va. 20108, United States of America). That is, registration numbers are given to the respective strains, and the strains can be ordered by using these registration numbers (refer to atcc.org). The registration numbers of the strains are listed in the catalogue of the American Type Culture Collection. These strains can also be obtained from, for example, the depositories at which the strains were deposited.

The microorganism may inherently have an objective substance-producing ability, or may be modified so that it has an objective substance-producing ability. The microorganism having an objective substance-producing ability can be obtained by imparting an objective substance-producing ability to such a microorganism as described above, or enhancing an objective substance-producing ability of such a microorganism as described above.

Hereafter, specific examples of the method for imparting or enhancing an objective substance-producing ability will be explained. Such modifications as exemplified below for imparting or enhancing an objective substance-producing ability may be independently used, or may be used in an appropriate combination.

An objective substance can be generated by the action of an enzyme that is involved in the biosynthesis of the objective substance. Such an enzyme can also be referred to as "objective substance biosynthesis enzyme". Therefore, the microorganism may have an objective substance biosynthesis enzyme. In other words, the microorganism may have a gene encoding an objective substance biosynthesis enzyme. Such a gene can also be referred to as "objective substance biosynthesis gene". The microorganism may inherently have an objective substance biosynthesis gene, or may be introduced with an objective substance biosynthesis gene. The methods for introducing a gene are described herein.

Also, an objective substance-producing ability of a microorganism can be improved by increasing the activity of an objective substance biosynthesis enzyme. That is, examples of the method for imparting or enhancing an objective substance-producing ability can include a method of increasing the activity of an objective substance biosynthesis enzyme. That is, the microorganism may be modified so that the activity of an objective substance biosynthesis enzyme is increased. The activity of one kind of objective substance biosynthesis enzyme may be increased, or the activities of two or more kinds of objective substance biosynthesis enzymes may be increased. The method for increasing the activity of a protein (enzyme etc.) is described herein. The activity of a protein (enzyme etc.) can be increased by, for example, increasing the expression of a gene encoding the protein.

An objective substance can be generated from, for example, a carbon source and/or a precursor of the objective substance. Hence, examples of the objective substance biosynthesis enzyme can include, for example, enzymes that catalyze the conversion from the carbon source and/or the precursor into the objective substance. For example, 3-dehydroshikimic acid can be produced via a part of the shikimate pathway, which may include steps catalyzed by 3-deoxy-D-arabino-heptulosonic acid 7-phosphate synthase (DAHP synthase), 3-dehydroquinate synthase, and 3-dehydroquinate dehydratase; 3-dehydroshikimic acid can be converted to protocatechuic acid by the action of 3-dehydroshikimate dehydratase (DHSD); protocatechuic acid can be converted to vanillic acid or protocatechualdehyde by the action of O-methyltransferase (OMT) or aldehyde oxidoreductase (carboxylic acid reductase; CAR), respectively; and vanillic acid or protocatechualdehyde can be converted to vanillin by the action of CAR or OMT, respectively. Also, benzaldehyde and cinnamaldehyde can be generated from, for example, benzoic acid and cinnamic acid, respectively, by the action of CAR. That is, specific examples of the objective substance biosynthesis enzyme can include, for example, DAHP synthase, 3-dehydroquinate synthase, 3-dehydroquinate dehydratase, DHSD, OMT, and CAR. Particularly, use of the specific CAR may be effective for vanillin production via vanillic acid as an intermediate. Hence, vanillin production and related matters thereof are described on the premise that vanillin is generated partially or wholly via vanillic acid as an intermediate.

The term "3-deoxy-D-arabino-heptulosonic acid 7-phosphate synthase (DAHP synthase)" can refer to a protein that has the activity of catalyzing the reaction of converting D-erythrose 4-phosphate and phosphoenolpyruvic acid into 3-deoxy-D-arabino-heptulosonate 7-phosphate (DAHP) and phosphate (EC 2.5.1.54). A gene encoding DAHP synthase can also be referred to as "DAHP synthase gene". Examples of DAHP synthase can include AroF, AroG, and AroH proteins, which are encoded by aroF, aroG, and aroH genes, respectively. Among them, AroG may function as the major DAHP synthase. Examples of DAHP synthase such as AroF, AroG, and AroH proteins can include those of various organisms such as Enterobacteriaceae bacteria and coryneform bacteria. Specific examples of DAHP synthase can include AroF, AroG, and AroH proteins of E. coli. The nucleotide sequence of the aroG gene of the E. coli K-12 MG1655 strain is shown as SEQ ID NO: 1, and the amino acid sequence of the AroG protein encoded by this gene is shown as SEQ ID NO: 2.

The DAHP synthase activity can be measured by, for example, incubating the enzyme with substrates (i.e. D-erythrose 4-phosphate and phosphoenolpyruvic acid), and measuring the enzyme- and substrate-dependent generation of DAHP.

The term "3-dehydroquinate synthase" can refer to a protein that has the activity of catalyzing the reaction of dephosphorylating DAHP to generate 3-dehydroquinic acid (EC 4.2.3.4). A gene encoding 3-dehydroquinate synthase can also be referred to as "3-dehydroquinate synthase gene". Examples of 3-dehydroquinate synthase can include AroB protein, which is encoded by aroB gene. Examples of 3-dehydroquinate synthase such as AroB protein can include those of various organisms such as Enterobacteriaceae bacteria and coryneform bacteria. Specific examples of 3-dehydroquinate synthase can include AroB protein of E. coli. The nucleotide sequence of the aroB gene of the E. coli K-12 MG1655 strain is shown as SEQ ID NO: 3, and the amino acid sequence of the AroB protein encoded by this gene is shown as SEQ ID NO: 4.

The 3-dehydroquinate synthase activity can be measured by, for example, incubating the enzyme with a substrate (i.e. DAHP), and measuring the enzyme- and substrate-dependent generation of 3-dehydroquinic acid.

The term "3-dehydroquinate dehydratase" can refer to a protein that has the activity of catalyzing the reaction of dehydrating 3-dehydroquinic acid to generate 3-dehydroshikimic acid (EC 4.2.1.10). A gene encoding 3-dehydroquinate dehydratase can also be referred to as "3-dehydroquinate dehydratase gene". Examples of 3-dehydroquinate dehydratase can include AroD protein, which is encoded by aroD gene. Examples of 3-dehydroquinate dehydratase such as AroD protein can include those of various organisms such as Enterobacteriaceae bacteria and coryneform bacteria. Specific examples of 3-dehydroquinate dehydratase can include AroD protein of E. coli. The nucleotide sequence of the aroD gene of the E. coli K-12 MG1655 strain is shown as SEQ ID NO: 5, and the amino acid sequence of the AroD protein encoded by this gene is shown as SEQ ID NO: 6.

The 3-dehydroquinate dehydratase activity can be measured by, for example, incubating the enzyme with a substrate (i.e. 3-dehydroquinic acid), and measuring the enzyme- and substrate-dependent generation of 3-dehydroshikimic acid.

The term "3-dehydroshikimate dehydratase (DHSD)" can refer to a protein that has the activity of catalyzing the reaction of dehydrating 3-dehydroshikimic acid to generate protocatechuic acid (EC 4.2.1.118). A gene encoding DHSD can also be referred to as "DHSD gene". Examples of DHSD can include AsbF protein, which is encoded by asbF gene. Examples of DHSD such as AsbF protein can include those of various organisms such as Bacillus thuringiensis, Neurospora crassa, and Podospora pauciseta. The nucleotide sequence of the asbF gene of the Bacillus thuringiensis BMB171 strain is shown as SEQ ID NO: 7, and the amino acid sequence of the AsbF protein encoded by this gene is shown as SEQ ID NO: 8.

The DHSD activity can be measured by, for example, incubating the enzyme with a substrate (i.e. 3-dehydroshikimic acid), and measuring the enzyme- and substrate-dependent generation of protocatechuic acid.

The expression of a gene encoding an enzyme of shikimate pathway, such as DAHP synthase, 3-dehydroquinate synthase, and 3-dehydroquinate dehydratase, is repressed by a tyrosine repressor TyrR, which is encoded by tyrR gene. Therefore, the activity of an enzyme of shikimate pathway can also be increased by reducing the activity of the tyrosine repressor TyrR. The nucleotide sequence of the tyrR gene of the E. coli K-12 MG1655 strain is shown as SEQ ID NO: 9, and the amino acid sequence of the TyrR protein encoded by this gene is shown as SEQ ID NO: 10.

The term "O-methyltransferase (OMT)" can refer to a protein that has the activity of catalyzing the reaction of methylating protocatechuic acid in the presence of a methyl group donor to generate vanillic acid (i.e. methylation of hydroxyl group at the meta-position of protocatechuic acid, EC 2.1.1.68 etc.). This activity can also be referred to as "OMT activity". A gene encoding OMT can also be referred to as "OMT gene". OMT may also catalyze the reaction of methylating protocatechualdehyde in the presence of a methyl group donor to generate vanillin (i.e. methylation of hydroxyl group at the meta-position of protocatechualdehyde). OMT may generally use both protocatechuic acid and protocatechualdehyde as the substrate, but is not necessarily limited thereto. Examples of the methyl group donor can include S-adenosylmethionine (SAM). Examples of OMT can include OMTs of various organisms, such as OMT of Homo sapiens (Hs) (GenBank Accession No. NP_000745 and NP_009294), OMT of Arabidopsis thaliana (GenBank Accession Nos. NP_200227 and NP_009294), OMT of Fragaria x ananassa (GenBank Accession No. AAF28353), and other various OMTs of mammals, plants, and microorganisms exemplified in WO2013/022881A1. Four kinds of transcript variants and two kinds of OMT isoforms are known for the OMT gene of Homo sapiens. The nucleotide sequences of these four transcript variants (transcript variant 1-4, GenBank Accession No. NM_000754.3, NM_001135161.1, NM_001135162.1, and NM_007310.2) are shown as SEQ ID NOS: 11 to 14, the amino acid sequence of the longer OMT isoform (MB-COMT, GenBank Accession No. NP 000745.1) is shown as SEQ ID NO: 15, and the amino acid sequence of the shorter OMT isoform (S-COMT, GenBank Accession No. NP_009294.1) is shown as SEQ ID NO: 16. SEQ ID NO: 16 corresponds to SEQ ID NO: 15 of which the N-terminal 50 amino acid residues are truncated.

OMT may also catalyze the reaction of methylating protocatechuic acid and/or protocatechualdehyde to generate isovanillic acid and/or isovanillin (i.e. methylation of hydroxyl group at the para-position) as a side reaction. OMT may selectively catalyze the methylation of a hydroxyl group at the meta-position. The expression "selectively catalyzing the methylation of hydroxyl group at the meta-position" may mean that OMT selectively generates vanillic acid from protocatechuic acid and/or that OMT selectively generates vanillin from protocatechualdehyde. The expression "selectively generating vanillic acid from protocatechuic acid" may mean that OMT generates vanillic acid in an amount of, for example, 3 times or more, 5 times or more, 10 times or more, 15 times or more, 20 times or more, 25 times or more, or 30 times or more of that of isovanillic acid in terms of molar ratio, when OMT is allowed to act on protocatechuic acid. Also, the expression "selectively generating vanillic acid from protocatechualdehyde" may mean that OMT generates vanillin in an amount of, for example, 3 times or more, 5 times or more, 10 times or more, 15 times or more, 20 times or more, 25 times or more, or 30 times or more of that of isovanillin in terms of molar ratio, when OMT is allowed to act on protocatechualdehyde. Examples of OMT that selectively catalyzes the methylation of hydroxyl group at the meta-position can include OMT having a "specific mutation" described herein.

OMT having the "specific mutation" can also be referred to as "mutant OMT". A gene encoding a mutant OMT can also be referred to as "mutant OMT gene".

OMT not having the "specific mutation" can also be referred to as "wild-type OMT". A gene encoding a wild-type OMT can also be referred to as "wild-type OMT gene". The term "wild-type" is used for convenience to distinguish the "wild-type" OMT from the "mutant" OMT, and the "wild-type" OMT is not limited to those obtained as natural substances, and can include any OMT not having the "specific mutation". Examples of the wild-type OMT can include, for example, OMTs exemplified above. In addition, all conservative variants of OMTs exemplified above can be considered as wild-type OMTs, provided that such conservative variants do not have the "specific mutation".

Examples of the "specific mutation" can include the mutations contained in the mutant OMTs described in WO2013/022881A1. That is, examples of the "specific mutation" can include the mutation that the leucine residue at position 198 of the wild-type OMT (L198) is replaced with an amino acid residue showing a hydrophobic index (hydropathy index) lower than that of leucine residue, and the mutation that the glutamate residue at position 199 of the wild-type OMT (E199) is replaced with an amino acid residue having either a neutral or positive side-chain charge at pH 7.4. The mutant OMT may have either one or both of these mutations.

Examples of the "amino acid residue having a hydrophobic index (hydropathy index) lower than that of leucine residue" can include Ala, Arg, Asn, Asp, Cys, Glu, Gln, Gly, His, Lys, Met, Phe, Pro, Ser, Thr, Trp, and Tyr. As the "amino acid residue having a hydrophobic index (hydropathy index) lower than that of leucine residue", especially, an amino acid residue such as Ala, Arg, Asn, Asp, Glu, Gln, Gly, His, Lys, Met, Pro, Ser, Thr, Trp, and Tyr is preferred, and Tyr is more preferred.

The "amino acid residue having either a neutral or positive side-chain charge at pH 7.4" can include Ala, Arg, Asn, Cys, Gln, Gly, His, Ile, Leu, Lys, Met, Phe, Pro, Ser, Thr, Trp, Tyr, and Val. As the "amino acid residue having either a neutral or positive side-chain charge at pH 7.4", Ala or Gln is especially preferred.

The terms "L198" and "E199" in an arbitrary wild-type OMT can refer to "an amino acid residue corresponding to the leucine residue at position 198 of the amino acid sequence shown as SEQ ID NO: 16" and "an amino acid residue corresponding to the glutamate residue at position 199 of the amino acid sequence shown as SEQ ID NO: 16", respectively. The positions of these amino acid residues represent the relative positions, and the absolute positions thereof may shift due to deletion, insertion, addition, and so forth of amino acid residue(s). For example, if one amino acid residue is deleted or inserted at a position on the N-terminus side of position X in the amino acid sequence shown as SEQ ID NO: 16, the amino acid residue originally at position X is relocated at position X−1 or X+1, however, it is still regarded as the "amino acid residue corresponding to the amino acid residue at position X of the amino acid sequence shown as SEQ ID NO: 16". Furthermore, although "L198" and "E199" are usually leucine residue and glutamate residue, respectively, they may not be leucine residue and glutamate residue, respectively. That is, when "L198" and "E199" are not leucine residue and glutamate residue, respectively, the "specific mutation" can include a mutation in which those amino acid residues each are replaced with any of the aforementioned amino acid residues.

In the amino acid sequence of an arbitrary OMT, which amino acid residue is the amino acid residue corresponding to "L198" or "E199" can be determined by aligning the amino acid sequence of the arbitrary OMT and the amino acid sequence of SEQ ID NO: 16. The alignment can be performed by, for example, using known gene analysis software. Specific examples of such software can include DNASIS produced by Hitachi Solutions, GENETYX produced by Genetyx, and so forth (Elizabeth C. Tyler et al., Computers and Biomedical Research, 24 (1) 72-96, 1991; Barton G J et al., Journal of Molecular Biology, 198 (2), 327-37, 1987).

A mutant OMT gene can be obtained by, for example, modifying a wild-type OMT gene so that OMT encoded thereby has the "specific mutation". The wild-type OMT gene to be modified can be obtained by, for example, cloning from an organism having the wild-type OMT gene, or chemical synthesis. Furthermore, a mutant OMT gene can also be obtained without using a wild-type OMT gene. For example, a mutant OMT gene may be directly obtained by chemical synthesis. The obtained mutant OMT gene may be used as it is, or may be further modified before use.

Genes can be modified by using a known method. For example, an objective mutation can be introduced into a target site of DNA by the site-specific mutagenesis method. Examples of the site-specific mutagenesis method can include a method using PCR (Higuchi, R., 61, in PCR Technology, Erlich, H. A. Eds., Stockton Press (1989); Carter P., Meth. In Enzymol., 154, 382 (1987)), and a method of using a phage (Kramer, W. and Frits, H. J., Meth. in Enzymol., 154, 350 (1987); Kunkel, T. A. et al., Meth. in Enzymol., 154, 367 (1987)).

The activity of methylating hydroxyl group at the meta-position, such as the OMT activity, can be measured by, for example, incubating the enzyme with a substrate (i.e. protocatechuic acid or protocatechualdehyde) in the presence of SAM, and measuring the enzyme- and substrate-dependent generation of the corresponding product (i.e. vanillic acid or vanillin) (WO2013/022881A1). Furthermore, by measuring the generation of the corresponding by-product (i.e. isovanillic acid or isovanillin) under the same conditions, and comparing the generation of the by-product with the generation of the product, it can be determined whether OMT selectively generates the product.

Carboxylic acid reductase (CAR) is described below in "Introduction of specific carboxylic acid reductase gene".

CAR can be made into an active enzyme by phosphopantetheinylation (J. Biol. Chem., 2007, Vol. 282, No. 1, pp. 478-485). Therefore, CAR activity can also be increased by increasing the activity of an enzyme that catalyzes phosphopantetheinylation of a protein (also referred to as "phosphopantetheinylation enzyme"). That is, examples of the method for imparting or enhancing an objective substance-producing ability can include a method of increasing the activity of a phosphopantetheinylation enzyme. That is, the microorganism may be modified so that the activity of a phosphopantetheinylation enzyme is increased. Examples of the phosphopantetheinylation enzyme can include phosphopantetheinyl transferase (PPT).

The term "phosphopantetheinyl transferase (PPT)" can refer to a protein that has an activity of catalyzing the reaction of phosphopantetheinylating CAR in the presence of a phosphopantetheinyl group donor. This activity can also be referred to as "PPT activity". A gene encoding PPT can also be referred to as "PPT gene". Examples of the phosphopantetheinyl group donor can include coenzyme A (CoA). Examples of PPT can include EntD protein, which is encoded by entD gene. Examples of PPT such as EntD protein can include those of various organisms. Specific examples of PPT can include EntD protein of *E. coli*. The nucleotide sequence of the entD gene of the *E. coli* K-12 MG1655 strain is shown as SEQ ID NO: 21, and the amino acid sequence of the EntD protein encoded by this gene is shown as SEQ ID NO: 22. Specific examples of PPT can also include PPT of *Nocardia brasiliensis*, PPT of *Nocardia farcinica* IFM10152 (J. Biol. Chem., 2007, Vol. 282, No. 1, pp. 478-485), and PPT of *Corynebacterium glutamicum* (App. Env. Microbiol. 2009, Vol. 75, No. 9, p 2765-2774). The nucleotide sequence of the PPT gene of the *C. glutamicum* ATCC 13032 strain is shown as SEQ ID NO: 23, and the amino acid sequence of PPT encoded by this gene is shown as SEQ ID NO: 24.

The PPT activity can be measured on the basis of, for example, enhancement of the CAR activity observed when the enzyme is incubated with CAR in the presence of CoA (J. Biol. Chem., 2007, Vol. 282, No. 1, pp. 478-485).

Also, as described above, benzaldehyde and cinnamaldehyde can be generated from, for example, benzoic acid and cinnamic acid, respectively. That is, examples of the objective substance biosynthesis enzyme can also include, for example, benzoic acid biosynthesis enzymes and cinnamic acid biosynthesis enzymes. Specifically, cinnamic acid can be generated from, for example, L-phenylalanine, by the action of phenylalanine ammonia lyase (PAL; EC 4.3.1.24). That is, examples of cinnamic acid biosynthesis enzymes can include, for example, L-phenylalanine biosynthesis enzymes and PAL. Examples of the L-phenylalanine biosynthesis enzymes can include common biosynthesis enzymes of aromatic amino acids, such as 3-deoxy-D-arabinoheptulosonate-7-phosphate synthase (aroF, aroG, aroH), 3-dehydroquinate synthase (aroB), 3-dehydroquinate dehydratase (aroD), shikimate dehydrogenase (aroE), shikimate kinase (aroK, aroL), 5-enolpyruvylshikimate-3-phosphate synthase (aroA), and chorismate synthase (aroC); as well as chorismate mutase (pheA), prephenate dehydratase (pheA), and tyrosine amino transferase (tyrB). Chorismate mutase and prephenate dehydratase may be encoded by pheA gene as a bifunctional enzyme.

Examples of the method for imparting or enhancing an objective substance-producing ability can also include a method of increasing the activity of an uptake system of a substance other than an objective substance, such as a substance generated as an intermediate during production of an objective substance and a substance used as a precursor of an objective substance. That is, the microorganism may have been modified so that the activity of such an uptake system is increased. The term "uptake system of a substance" can refer to a protein having a function of incorporating the substance from the outside of a cell into the cell. This activity can also be referred to as "uptake activity of a substance". A gene encoding such an uptake system can also be referred to as "uptake system gene". Examples of such an uptake system can include a vanillic acid uptake system and a protocatechuic acid uptake system. Examples of the vanillic acid uptake system can include VanK protein, which is encoded by vanK gene (M. T. Chaudhry, et al., Microbiology, 2007, 153:857-865). The nucleotide sequence of the vanK gene (NCg12302) of the *C. glutamicum* ATCC 13869 strain is shown as SEQ ID NO: 25, and the amino acid sequence of the VanK protein encoded by this gene is shown as SEQ ID NO: 26. Examples of the protocatechuic acid uptake system gene can include PcaK protein, which is encoded by pcaK gene (M. T. Chaudhry, et al., Microbiology, 2007, 153:857-865). The nucleotide sequence of the pcaK gene (NCg11031) of the *C. glutamicum* ATCC 13869 strain is shown as SEQ ID NO: 27, and the amino acid sequence of the PcaK protein encoded by this gene is shown as SEQ ID NO: 28.

The uptake activity of a substance can be measured according to, for example, a known method (M. T. Chaudhry, et al., Microbiology, 2007. 153:857-865).

Examples of the method for imparting or enhancing an objective substance-producing ability further can include a method of reducing the activity of an enzyme that is involved in the by-production of a substance other than an objective substance. Such a substance other than an objective substance can also be referred to as "byproduct". Such an enzyme can also be referred to as "byproduct generation enzyme". Specifically, a byproduct generation enzyme can refer to an enzyme that is involved in the production of a byproduct during the production of the objective substance. Examples of the byproduct generation enzyme can include, for example, enzymes that are involved in the utilization of an objective substance, and enzymes that catalyze a reaction branching away from the biosynthetic pathway of an objective substance to generate a substance other than the objective substance. The method for reducing the activity of a protein (enzyme etc.) is described herein. The activity of a protein (enzyme etc.) can be reduced by, for example, disrupting a gene that encodes the protein. For example, it has been reported that, in coryneform bacteria, vanillin is metabolized in the order of vanillin → vanillic acid → protocatechuic acid, and utilized (Current Microbiology, 2005, Vol. 51, pp. 59-65). That is, specific examples of the byproduct generation enzyme can include an enzyme that catalyzes the conversion from vanillin into protocatechuic acid and enzymes that catalyze further metabolization of protocatechuic acid. Examples of such enzymes can include vanillate demethylase, protocatechuate 3,4-dioxygenase, and various enzymes that further decompose the reaction product of protocatechuate 3,4-dioxygenase to succinyl-CoA and acetyl-CoA (Appl. Microbiol. Biotechnol., 2012, Vol. 95, p 77-89). In addition, an aldehyde such as vanillin can be converted into the corresponding alcohol such as vanillyl alcohol by the action of alcohol dehydrogenase (Kunjapur A M. et al., J. Am. Chem. Soc., 2014, Vol. 136, p 11644-11654; Hansen E H. et al., App. Env. Microbiol., 2009, Vol. 75, p 2765-2774). That is, specific examples of the byproduct generation enzyme can also include alcohol dehydrogenase (ADH). In addition, 3-dehydroshikimic acid, which is an intermediate of the biosynthetic pathway of vanillic acid and vanillin, can also be converted into shikimic acid by the action of shikimate dehydrogenase. That is, specific examples of the byproduct generation enzyme for vanillin production can also include shikimate dehydrogenase.

The term "vanillate demethylase" can refer to a protein having an activity for catalyzing the reaction of demethylating vanillic acid to generate protocatechuic acid. This activity can also be referred to as "vanillate demethylase activity". A gene encoding vanillate demethylase can also be referred to as "vanillate demethylase gene". Examples of vanillate demethylase can include VanAB proteins, which are encoded by vanAB genes (Current Microbiology, 2005, Vol. 51, pp. 59-65). The vanA gene and vanB gene encode the subunit A and subunit B of vanillate demethylase, respectively. For reducing the vanillate demethylase activity, both the vanAB genes may be disrupted or the like, or only one of the two may be disrupted or the like. The nucleotide sequences of the vanAB genes of the C. glutamicum ATCC 13869 strain are shown as SEQ ID NOS: 29 and 31, and the amino acid sequences of the VanAB proteins encoded by these genes are shown as SEQ ID NOS: 30 and 6032, respectively. The vanAB genes usually constitute the vanABK operon together with the vanK gene. Therefore, in order to reduce the vanillate demethylase activity, the vanABK operon may be totally disrupted or the like (for example, deleted). In such a case, the vanK gene may be introduced to a host again. For example, when vanillic acid present outside cells is used, and the vanABK operon is totally disrupted or the like (for example, deleted), it is preferable to introduce the vanK gene anew.

The vanillate demethylase activity can be measured by, for example, incubating the enzyme with a substrate (i.e. vanillic acid), and measuring the enzyme- and substrate-dependent generation of protocatechuic acid (J Bacteriol, 2001, Vol. 183, p 3276-3281).

The term "protocatechuate 3,4-dioxygenase" can refer to a protein having an activity for catalyzing the reaction of oxidizing protocatechuic acid to generate beta-Carboxy-cis, cis-muconic acid. This activity can also be referred to as "protocatechuate 3,4-dioxygenase activity". A gene encoding protocatechuate 3,4-dioxygenase can also be referred to as "protocatechuate 3,4-dioxygenase gene". Examples of protocatechuate 3,4-dioxygenase can include PcaGH proteins, which are encoded by pcaGH genes (Appl. Microbiol. Biotechnol., 2012, Vol. 95, p 77-89). The pcaG gene and pcaH gene encode the alpha subunit and beta subunit of protocatechuate 3,4-dioxygenase, respectively. For reducing the protocatechuate 3,4-dioxygenase activity, both the pcaGH genes may be disrupted or the like, or only one of the two may be disrupted or the like. The nucleotide sequences of the pcaGH genes of the C. glutamicum ATCC 13032 strain are shown as SEQ ID NOS: 33 and 35, and the amino acid sequences of the PcaGH proteins encoded by these genes are shown as SEQ ID NOS: 34 and 36, respectively.

The protocatechuate 3,4-dioxygenase activity can be measured by, for example, incubating the enzyme with a substrate (i.e. protocatechuic acid), and measuring the enzyme- and substrate-dependent oxygen consumption (Meth. Enz., 1970, Vol. 17A, p 526-529).

The term "alcohol dehydrogenase (ADH)" can refer to a protein that has an activity for catalyzing the reaction of reducing an aldehyde in the presence of an electron donor to generate an alcohol (EC 1.1.1.1, EC 1.1.1.2, EC 1.1.1.71, etc.). This activity can also be referred to as "ADH activity". A gene encoding ADH is also referred to as "ADH gene". Examples of the aldehyde used as a substrate of ADH can include aldehydes exemplified as objective substances in the method as described herein, e.g. aromatic aldehydes such as vanillin, benzaldehyde, and cinnamaldehyde. That is, examples of combinations of the aldehyde and alcohol referred to in the definition of "ADH activity" can include a combination of an aromatic aldehyde and the corresponding aromatic alcohol, such as the combination of vanillin and vanillyl alcohol, the combination of benzaldehyde and benzyl alcohol, and the combination of cinnamaldehyde and cinnamyl alcohol. ADH that uses an aromatic aldehyde, vanillin, benzaldehyde, or cinnamaldehyde can also be referred to as "aromatic alcohol dehydrogenase", "vanillyl alcohol dehydrogenase", "benzyl alcohol dehydrogenase", or "cinnamyl alcohol dehydrogenase", respectively. Furthermore, the ADH activity wherein an aromatic aldehyde, vanillin, benzaldehyde, or cinnamaldehyde is used as a substrate can also be referred to as "aromatic alcohol dehydrogenase activity", "vanillyl alcohol dehydrogenase activity", "benzyl alcohol dehydrogenase activity", or "cinnamyl alcohol dehydrogenase activity", respectively. ADH may use one kind of alcohol, or may use two or more kinds of alcohols. Examples of the electron donor can include NADH and NADPH.

Examples of ADH can include YqhD protein, NCg10324 protein, NCg10313 protein, NCg12709 protein, NCg10219 protein, and NCg12382 protein, which are encoded by yqhD gene, NCg10324 gene, NCg10313 gene, NCg12709 gene, NCg10219 gene, and NCg12382 gene, respectively. The yqhD gene can be found in, for example, bacteria belonging to the family Enterobacteriaceae such as E. coli. The NCg10324 gene, NCg10313 gene, NCg12709 gene, NCg10219 gene, and NCg12382 gene can be found in, for example, coryneform bacteria such as C. glutamicum. The nucleotide sequence of the yqhD gene of the E. coli K-12 MG1655 strain is shown as SEQ ID NO: 37, and the amino acid sequence of the YqhD protein encoded by this gene is shown as SEQ ID NO: 38. The nucleotide sequences of the NCg10324 gene, NCg10313 gene, and NCg12709 gene of the C. glutamicum ATCC 13869 strain are shown as SEQ ID NOS: 39, 41, and 43, respectively, and the amino acid sequences of the proteins encoded by these genes are shown as SEQ ID NOS: 40, 42, and 44, respectively. The nucleotide sequences of the NCg10219 gene and NCg12382 gene of the C. glutamicum ATCC 13032 strain are shown as SEQ ID NOS: 45 and 47, respectively, and the amino acid sequences of the proteins encoded by these genes are shown as SEQ ID NOS: 46 and 48, respectively.

The activity of one kind of ADH may be reduced, or the activities of two or more kinds of ADHs may be reduced. For example, the activity or activities of one or more kinds of ADHs, e.g. all ADHs, such asNCg10324 protein, NCg12709 protein, and NCg10313 protein may be reduced. Also, at least the activity or activities of either one or both of NCg10324 protein and NCg12709 protein may be reduced. That is, for example, at least the activity of NCg10324 protein may be reduced, and the activity of NCg12709 protein may further be reduced. Alternatively, at least the activity of NCg12709 protein may be reduced, and the activity of NCg10324 protein may further be reduced. Combination of ADH and the objective substance is not particularly limited, so long as a reduction in the activity of ADH in a coryneform bacterium provides an increased production of the objective substance. For example, the activity of ADH that uses at least an aldehyde to be produced as an objective substance may be reduced. That is, for example, the activity of an aromatic alcohol dehydrogenase such as vanillyl alcohol dehydrogenase, benzyl alcohol dehydrogenase, and cinnamyl alcohol dehydrogenase may be reduced for production of an aromatic aldehyde such as vanillin, benzaldehyde, and cinnamaldehyde, respectively. Specifically, for example, when vanillin is produced, the activity of YqhD protein may be reduced. Also, specifically, for example, when vanillin is produced, the activity or activities of either one or both of NCg10324 protein and NCgl0313 protein may be reduced, or at least the activity of NCgl0324 protein may be reduced. Also, specifically, when benzaldehyde is produced, the activity or activities of either one or both of NCgl0324 protein and NCgl2709 protein may be reduced. Also, specifically, when cinnamaldehyde is produced, the activity or activities of either one or both of NCgl0324 protein and NCgl2709 protein may be reduced. YqhD protein may have the vanillyl alcohol dehydrogenase activity. NCgl0324 protein may have all of the vanillyl alcohol dehydrogenase activity, benzyl alcohol dehydrogenase activity, and cinnamyl alcohol dehydrogenase activity. NCgl2709 protein may have both the benzyl alcohol dehydrogenase activity and cinnamyl alcohol dehydrogenase activity.

The ADH activity can be measured by, for example, incubating the enzyme with a substrate (i.e. an aldehyde such as vanillin) in the presence of NADPH or NADH, and measuring the enzyme- and substrate-dependent oxidation of NADPH or NADH. It is sufficient that the ADH activity is detected under at least one appropriate condition, e.g. in the presence of an appropriate electron donor such as NADPH or NADH.

The term "shikimate dehydrogenase" can refer to a protein that has the activity of catalyzing the reaction of reducing 3-dehydroshikimic acid in the presence of an electron donor to generate shikimic acid (EC 1.1.1.25). This activity can also be referred to as "shikimate dehydrogenase activity". A gene encoding shikimate dehydrogenase can also be referred to as "shikimate dehydrogenase gene". Examples of the electron donor can include NADH and NADPH. Examples of shikimate dehydrogenase can include AroE protein, which is encoded by aroE gene. The nucleotide sequence of the aroE gene of the *E. coli* K-12 MG1655 strain is shown as SEQ ID NO: 49, and the amino acid sequence of the AroE protein encoded by this gene is shown as SEQ ID NO: 50.

The shikimate dehydrogenase activity can be measured by, for example, incubating the enzyme with a substrate (i.e. 3-dehydroshikimic acid) in the presence of NADPH or NADH, and measuring the enzyme- and substrate-dependent oxidation of NADPH or NADH.

The protein with a modified activity can be appropriately chosen depending on the type of biosynthesis pathway that produces the objective substance and on the types and activities of the proteins inherently possessed by the microorganism. For example, when vanillin is produced by the bioconversion method from protocatechuic acid, it may be preferable to increase the activity or activities of one or more kinds of proteins such as OMT, CAR, PPT, and the protocatechuic acid uptake system. Also, when vanillin is produced by the bioconversion method from vanillic acid, it may be preferable to enhance the activity or activities of one or more kinds of proteins such as CAR, PPT, and the vanillic acid uptake system. The microorganism as described herein has been modified to have a specific CAR gene, and thus at least CAR activity may be enhanced.

The genes and proteins used for breeding a microorganism having an objective substance-producing ability may have, for example, the above-exemplified or other known nucleotide sequences and amino acid sequences, respectively. Also, the genes and proteins used for breeding a microorganism having an objective substance-producing ability may be conservative variants of the genes and proteins exemplified above, such as genes and proteins having the above-exemplified or other known nucleotide sequences and amino acid sequences, respectively. Specifically, for example, the genes used for breeding a microorganism having an objective substance-producing ability may each be a gene encoding a protein having the amino acid sequence exemplified above or the amino acid sequence of a known protein, but including substitution, deletion, insertion, or addition of one or several some amino acid residues at one or several positions, so long as the original function thereof, i.e. enzymatic activity, transporter activity, etc., is maintained. As for conservative variants of genes and proteins, the descriptions concerning conservative variants of the CAR gene and CAR described later can be applied mutatis mutandis.

<1-2> Introduction of Specific Carboxylic Acid Reductase Gene

The microorganism as described herein has been modified to have a specific carboxylic acid reductase (CAR) gene. A microorganism having a CAR gene can also be referred to as "microorganism having CAR". By modifying a microorganism to have a specific CAR gene, an objective substance-producing ability of the microorganism can be improved, and that is, the production of an objective substance by using the microorganism can be increased. That is, an improved objective substance-producing ability and an increased production of an objective substance can be obtained for the microorganism, as compared with a non-modified strain. The increase in the production of an objective substance may be an increase in the absolute degree of production, such as absolute amount and absolute yield, of the objective substance, or may be in the relative degree of production, such as relative amount and relative yield, of the objective substance with respect to that of a by-product. Examples of the by-product can include, for example, protocatechualdehyde and isovanillin for vanillin production. It may be difficult to separate an aldehyde such as vanillin from another aldehyde such as protocatechualdehyde and isovanillin in purification process. Hence, the increase in the production of an objective substance such as vanillin may result in, for example, a reduction in a purification cost.

The microorganism can be obtained by modifying a microorganism having an objective substance-producing ability to have a specific CAR gene. The microorganism can also be obtained by modifying a microorganism to have a specific CAR gene, and then imparting an objective substance-producing ability to the microorganism or enhancing an objective substance-producing ability of the microorganism. In addition, the microorganism may be a microorganism that has acquired an objective substance-producing ability as a result of a modification for making the microorganism to have a specific CAR gene, or as a result of a combination of a modification for making the microorganism to have a specific CAR gene and other modification(s) for imparting or enhancing an objective substance-producing ability. The modifications for constructing the microorganism can be performed in an arbitrary order.

The term "aldehyde oxidoreductase (carboxylic acid reductase; CAR)" can refer to a protein that has an activity of catalyzing the reaction of reducing an carboxylic acid in the presence of an electron donor and ATP to generate a corresponding aldehyde (EC 1.2.99.6 etc.). This activity can also be referred to as "CAR activity". A gene encoding CAR can also be referred to as "CAR gene". There is employed CAR that uses at least a carboxylic acid corresponding to an aldehyde to be produced as an objective substance in the method as described herein. That is, examples of the aldehyde generated as a product of CAR can include aldehydes exemplified as objective substances in the method as described herein, e.g. aromatic aldehydes such as vanillin, benzaldehyde, and cinnamaldehyde. That is, examples of combinations of the carboxylic acid and the aldehyde referred to in the definition of "CAR activity" can include a combination of an aromatic carboxylic acid and the corresponding aromatic aldehyde, such as the combination of vanillic acid and vanillin, the combination of benzoic acid and benzaldehyde, and the combination of cinnamic acid and cinnamaldehyde. In other words, for example, the term "CAR activity" of CAR used for vanillin production can refer to an activity of catalyzing the reaction of reducing vanillic acid to generate vanillin. CAR that uses an aromatic carboxylic acid can also be referred to as "aromatic aldehyde oxidoreductase (aromatic carboxylic acid reductase; ACAR)". Furthermore, the CAR activity wherein an aromatic carboxylic acid is used as a substrate can also be referred to as "ACAR activity". The specific CAR may have ACAR activity. CAR may use one kind of carboxylic acid, or may use two or more kinds of carboxylic acids. Examples of the electron donor can include NADH and NADPH.

CAR may also catalyze the reaction of reducing protocatechuic acid and/or isovanillic acid in the presence of an electron donor and ATP to generate protocatechualdehyde and/or isovanillin. CAR may selectively catalyze the generation of vanillin. The expression "selectively catalyzing the generation of vanillin" may mean that CAR generates vanillin when CAR is allowed to act on vanillic acid, wherein vanillin is generated in an amount of, for example, in terms of molar ratio, 1.1 times or more, 1.2 times or more, 1.5 times or more, 2 times or more, 3 times or more, 4 times or more, 5 times or more, 10 times or more, 15 times or more, 20 times or more, 25 times or more, or 30 times or more of each or either one of the amount of protocatechualdehyde generated under the same conditions as vanillin generation except that the protocatechuic acid is used as the substrate and the amount of isovanillin generated under the same conditions as vanillin generation except that the isovanillic acid is used as the substrate.

The CAR activity can be measured by, for example, incubating the enzyme with a substrate (e.g. vanillic acid) in the presence of ATP and NADPH, and measuring the enzyme- and substrate-dependent oxidation of NADPH (modification of the method described in J. Biol. Chem., 2007, Vol. 282, No. 1, pp. 478-485). Furthermore, by measuring the generation of protocatechualdehyde or isovanillin under the same conditions except that the protocatechuic acid or isovanillic acid is used as the substrate, and comparing the generation of protocatechualdehyde or isovanillin with the generation of vanillin, it can be determined whether CAR selectively catalyzes the generation of vanillin. It is sufficient that the specific CAR has the CAR activity that is measured under at least one appropriate condition. Incidentally, it is also sufficient that all the other proteins referred to in this application have the respective activities that are each measured under at least one appropriate condition.

The term "specific CAR gene" can refer to a gene encoding a specific CAR. Examples of the specific CAR gene can include *Gordonia* CAR gene, *Novosphingobium* CAR gene, and *Coccomyxa* CAR gene. Examples of the specific CAR can include *Gordonia* CAR, *Novosphingobium* CAR, and *Coccomyxa* CAR. The term "*Gordonia* CAR gene" can refer to a gene encoding a *Gordonia* CAR. The term "*Gordonia* CAR" collectively can refer to CARs found in *Gordonia* bacteria and variations thereof within a specific range, such as conservative variants. The term "*Novosphingobium* CAR gene" can refer to a gene encoding a *Novosphingobium* CAR. The term "*Novosphingobium* CAR" collectively can refer to CARs found in *Novosphingobium* bacteria and variations thereof within a specific range, such as conservative variants. The term "*Coccomyxa* CAR gene" can refer to a gene encoding a *Coccomyxa* CAR. The term "*Coccomyxa* CAR" collectively can refer to CARs found in *Coccomyxa* algae and variations thereof within a specific range, such as conservative variants.

Examples of the *Gordonia* bacteria can include *Gordonia effusa*. That is, examples of the *Gordonia* CAR gene and the *Gordonia* CAR can include the CAR gene and CAR of *Gordonia effusa*, respectively. The nucleotide sequence of the CAR gene of *Gordonia effusa* is shown as SEQ ID NO: 17, and the amino acid sequence of CAR encoded by this gene is shown as SEQ ID NO: 18. Examples of the *Novosphingobium* bacteria can include *Novosphingobium malaysiense*. That is, examples of the *Novosphingobium* CAR gene and the *Novosphingobium* CAR can include the CAR gene and CAR of *Novosphingobium malaysiense*, respectively. The nucleotide sequence of the CAR gene of *Novosphingobium malaysiense* is shown as SEQ ID NO: 78, and the amino acid sequence of CAR encoded by this gene is shown as SEQ ID NO: 79. Examples of the *Coccomyxa* algae can include *Coccomyxa subelhpsoidea*. That is, examples of the *Coccomyxa* CAR gene and the *Coccomyxa* CAR can include the CAR gene and CAR of *Coccomyxa subelhpsoidea*, respectively. The nucleotide sequence of the CAR gene (cDNA) of *Coccomyxa subelhpsoidea* C-169 is shown as SEQ ID NO: 82, and the amino acid sequence of CAR encoded by this gene is shown as SEQ ID NO: 83. That is, the specific CAR gene may be, for example, a gene having the nucleotide sequence shown as SEQ ID NO: 17, 78, or 82. Also, the specific CAR may be, for example, a protein having the amino acid sequence shown as SEQ ID NO: 18, 79, or 83. The expression "a gene or protein has a nucleotide or amino acid sequence" can mean that a gene or protein includes the nucleotide or amino acid sequence unless otherwise stated, and can also include cases where a gene or protein includes only the nucleotide or amino acid sequence.

The specific CAR gene may be a variant of any of the CAR genes exemplified above (e.g. a gene having the nucleotide sequence shown as SEQ ID NO: 17, 78, or 82), so long as the original function thereof is maintained. Similarly, the specific CAR may be a variant of any of CARs exemplified above (e.g. a protein having the amino acid sequence shown as SEQ ID NO: 18, 79, or 83), so long as the original function thereof is maintained. A variant that maintains the original function thereof can also be referred to as "conservative variant". That is, examples of the specific CAR gene and the specific CAR further can include such conservative variants. Such conservative variants may be or may not be found in *Gordonia* bacteria, *Novosphingobium* bacteria, or *Coccomyxa* algae. Examples of the conservative variants can include, for example, homologues and artificially modified versions of the genes and proteins exemplified above.

The expression "the original function is maintained" can mean that a variant of gene or protein has a function (such as activity or property) corresponding to the function (such as activity or property) of the original gene or protein. The expression "the original function is maintained" in reference to a gene can mean that a variant of the gene encodes a protein that maintains the original function. That is, the expression "the original function is maintained" in reference to a CAR gene can mean that the variant of the gene encodes CAR. The expression "the original function is maintained" in reference to CAR can mean that the variant of the protein has CAR activity.

Hereafter, examples of the conservative variants will be explained.

Homologues of the specific CAR gene or homologues of the specific CAR can be easily obtained from public databases by, for example, BLAST search or FASTA search using any of the nucleotide sequences of the CAR genes exemplified above or any of the amino acid sequences of CARs exemplified above as a query sequence. Furthermore, homologues of the specific CAR gene can be obtained by, for example, PCR using a chromosome of an organism such as *Gordonia* bacteria, *Novosphingobium* bacteria, or *Coccomyxa* algae as the template, and oligonucleotides prepared on the basis of a nucleotide sequence of any of the nucleotide sequences of the CAR genes exemplified above as primers.

The specific CAR gene may be a gene encoding a protein having any of the aforementioned amino acid sequences (e.g. the amino acid sequence shown as SEQ ID NO: 18, 79, or 83) including substitution, deletion, insertion, and/or addition of one or several amino acid residues at one or several positions, so long as the original function is maintained. For example, the encoded protein may have an extended or deleted N-terminus and/or C-terminus. Although the number meant by the term "one or several" used above may differ depending on the positions of amino acid residues in the three-dimensional structure of the protein or the types of amino acid residues, specifically, it is, for example, 1 to 50, 1 to 40, 1 to 30, 1 to 20, 1 to 10, 1 to 5, or 1 to 3.

The aforementioned substitution, deletion, insertion, and/or addition of one or several amino acid residues are each a conservative mutation that maintains the original function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions can include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Furthermore, such substitution, deletion, insertion, addition, or the like of amino acid residues as mentioned above can include a naturally occurring mutation due to an individual difference, or a difference of species of the organism from which the gene is derived (mutant or variant).

Furthermore, the specific CAR gene may be a gene encoding a protein having an amino acid sequence having a homology of, for example, 50% or more, 65% or more, 80% or more, 90% or more, 95% or more, 97% or more, or 99% or more, to the total amino acid sequence of any of the aforementioned amino acid sequences, so long as the original function is maintained. In addition, in this specification, "homology" means "identity".

Furthermore, the specific CAR gene may be a gene, such as a DNA, that is able to hybridize under stringent conditions with a probe that can be prepared from any of the aforementioned nucleotide sequences (for example, the nucleotide sequence shown as SEQ ID NO: 17, 78, or 82), such as a sequence complementary to the whole sequence or a partial sequence of any of the aforementioned nucleotide sequences, so long as the original function is maintained. The "stringent conditions" can refer to conditions under which a so-called specific hybrid is formed, and a non-specific hybrid is not formed. Examples of the stringent conditions can include those under which highly homologous DNAs hybridize to each other, for example, DNAs not less than 50%, 65%, 80%, 90%, 95%, 97%, or 99% homologous, hybridize to each other, and DNAs less homologous than the above do not hybridize to each other, or conditions of washing of typical Southern hybridization, i.e., conditions of washing once, or 2 or 3 times, at a salt concentration and temperature corresponding to 1×SSC, 0.1% SDS at 60° C.; 0.1×SSC, 0.1% SDS at 60° C.; or 0.1×SSC, 0.1% SDS at 68° C.

The probe used for the aforementioned hybridization may be a part of a sequence that is complementary to the gene as described above. Such a probe can be prepared by PCR using oligonucleotides prepared on the basis of a known gene sequence as primers and a DNA fragment containing any of the aforementioned genes as a template. As the probe, for example, a DNA fragment having a length of about 300 bp can be used. When a DNA fragment having a length of about 300 bp is used as the probe, in particular, the washing conditions of the hybridization may be, for example, 50° C., 2×SSC and 0.1% SDS.

Furthermore, since properties concerning degeneracy of codons changes depending on the host, the specific CAR gene can include substitution of respective equivalent codons for arbitrary codons. That is, the specific CAR gene may be a variant of any of the CAR genes exemplified above due to the degeneracy of the genetic code. For example, the specific CAR gene may be a gene modified so that it has optimal codons according to codon frequencies in a host to be used. Examples of the codon-optimized specific CAR gene can include, for example, the CAR gene having the nucleotide sequence shown as SEQ ID NO: 77, 81, or 85, which has been codon-optimized for the codon usage of *E. coli*.

The percentage of the sequence identity between two sequences can be determined by, for example, using a mathematical algorithm. Non-limiting examples of such a mathematical algorithm can include the algorithm of Myers and Miller (1988) CABIOS 4:11-17, the local homology algorithm of Smith et al (1981) Adv. Appl. Math. 2:482, the homology alignment algorithm of Needleman and Wunsch (1970) J. Mol. Biol. 48:443-453, the method for searching homology of Pearson and Lipman (1988) Proc. Natl. Acad. Sci. 85:2444-2448, and a modified version of the algorithm of Karlin and Altschul (1990) Proc. Natl. Acad. Sci. USA 87:2264, such as that described in Karlin and Altschul (1993) Proc. Natl. Acad. Sci. USA 90:5873-5877.

By using a program based on such a mathematical algorithm, sequence comparison (i.e. alignment) for determining the sequence identity can be performed. The program can be appropriately executed by a computer. Examples of such a program can include, but not limited to, CLUSTAL of PC/Gene program (available from Intelligenetics, Mountain View, Calif.), ALIGN program (Version 2.0), and GAP, BESTFIT, BLAST, FASTA, and TFASTA of Wisconsin Genetics Software Package, Version 8 (available from Genetics Computer Group (GCG), 575 Science Drive, Madison, Wis., USA). Alignment using these programs can be performed by using, for example, initial parameters. The CLUSTAL program is well described in Higgins et al. (1988) Gene 73:237-244 (1988), Higgins et al. (1989) CABIOS 5:151-153, Corpet et al. (1988) Nucleic Acids Res. 16:10881-90, Huang et al. (1992) CABIOS 8:155-65, and Pearson et al. (1994) Meth. Mol. Biol. 24:307-331.

In order to obtain a nucleotide sequence homologous to a target nucleotide sequence, in particular, for example, BLAST nucleotide search can be performed by using BLASTN program with score of 100 and word length of 12. In order to obtain an amino acid sequence homologous to a target protein, in particular, for example, BLAST protein search can be performed by using BLASTX program with score of 50 and word length of 3. See ncbi.nlm.nih.gov for BLAST nucleotide search and BLAST protein search. In addition, Gapped BLAST (BLAST 2.0) can be used in order to obtain an alignment including gap(s) for the purpose of comparison. In addition, PSI-BLAST can be used in order to perform repetitive search for detecting distant relationships between sequences. See Altschul et al. (1997) Nucleic Acids Res. 25:3389 for Gapped BLAST and PSI-BLAST. When using BLAST, Gapped BLAST, or PSI-BLAST, initial parameters of each program (e.g. BLASTN for nucleotide sequences, and BLASTX for amino acid sequences) can be used. Alignment can also be manually performed.

The sequence identity between two sequences is calculated as the ratio of residues matching in the two sequences when aligning the two sequences so as to fit maximally with each other. The term "identity" between amino acid sequences may specifically mean an identity calculated by blastp with default scoring parameters (i.e. Matrix, BLOSUM62; Gap Costs, Existence=11, Extension=1; Compositional Adjustments, Conditional compositional score matrix adjustment), unless otherwise stated. The term "identity" between nucleotide sequences may specifically mean an identity calculated by blastn with default scoring parameters (i.e. Match/Mismatch Scores=1, −2; Gap Costs=Linear), unless otherwise stated.

The aforementioned descriptions concerning conservative variants of the genes and proteins can be applied mutatis mutandis to variants of arbitrary proteins such as objective substance biosynthesis enzymes and genes encoding them.

A microorganism can be modified to have a specific CAR gene by introducing the gene into the microorganism.

Methods for introducing a specific CAR gene into a microorganism are not particularly limited. It is sufficient that a specific CAR gene is operably harbored by the microorganism. The microorganism may have one copy of a specific CAR gene, or may have two or more copies of a specific CAR gene. The microorganism may have one kind of specific CAR gene, or may have two or more kinds of specific CAR genes. A specific CAR gene can be introduced into a microorganism by the same way as that for introduction of a gene described below in the "Methods for increasing activity of protein".

The microorganism may or may not have a CAR gene other than the specific CAR gene.

<1-3> Methods for Increasing Activity of Protein

Hereafter, the methods for increasing the activity of a protein, including methods for introduction of a gene, will be described.

The expression "the activity of a protein is increased" can mean that the activity of the protein is increased as compared with a non-modified strain. Specifically, the expression "the activity of a protein is increased" may mean that the activity of the protein per cell is increased as compared with that of a non-modified strain. The term "non-modified strain" can refer to a control strain that has not been modified so that the activity of an objective protein is increased. Examples of the non-modified strain can include a wild-type strain and parent strain. Specific examples of the non-modified strain can include the respective type strains of the species of microorganisms. Specific examples of the non-modified strain can also include strains exemplified above in relation to the description of microorganisms. That is, in an embodiment, the activity of a protein may be increased as compared with a type strain, i.e. the type strain of the species to which a microorganism belongs. In another embodiment, the activity of a protein may also be increased as compared with the *C. glutamicum* ATCC 13869 strain. In another embodiment, the activity of a protein may also be increased as compared with the *C. glutamicum* ATCC 13032 strain. In another embodiment, the activity of a protein may also be increased as compared with the *E. coli* K-12 MG1655 strain. The state that "the activity of a protein is increased" may also be expressed as "the activity of a protein is enhanced". More specifically, the expression "the activity of a protein is increased" may mean that the number of molecules of the protein per cell is increased, and/or the function of each molecule of the protein is increased as compared with those of a non-modified strain. That is, the term "activity" in the expression "the activity of a protein is increased" is not limited to the catalytic activity of the protein, but may also mean the transcription amount of a gene (i.e. the amount of mRNA) encoding the protein, or the translation amount of the protein (i.e. the amount of the protein). Furthermore, the state that "the activity of a protein is increased" can include not only a state that the activity of an objective protein is increased in a strain inherently having the activity of the objective protein, but also a state that the activity of an objective protein is imparted to a strain not inherently having the activity of the objective protein. Furthermore, so long as the activity of the protein is eventually increased, the activity of an objective protein inherently contained in a host may be attenuated and/or eliminated, and then an appropriate type of the objective protein may be imparted to the host.

The degree of the increase in the activity of a protein is not particularly limited, so long as the activity of the protein is increased as compared with a non-modified strain. The activity of the protein may be increased to, for example, 1.2 times or more, 1.5 times or more, 2 times or more, or 3 times or more of that of a non-modified strain. Furthermore, when the non-modified strain does not have the activity of the objective protein, it is sufficient that the protein is produced as a result of introduction of the gene encoding the protein, and for example, the protein may be produced to such an extent that the activity thereof can be measured.

The modification for increasing the activity of a protein can be attained by, for example, increasing the expression of a gene encoding the protein. The expression "the expression of a gene is increased" can mean that the expression of the gene is increased as compared with a non-modified strain such as a wild-type strain and parent strain. Specifically, the expression "the expression of a gene is increased" may mean that the expression amount of the gene per cell is increased as compared with that of a non-modified strain. More specifically, the expression "the expression of a gene is increased" may mean that the transcription amount of the gene (i.e. the amount of mRNA) is increased, and/or the translation amount of the gene (i.e. the amount of the protein expressed from the gene) is increased. The state that "the expression of a gene is increased" can also be referred to as "the expression of a gene is enhanced". The expression of a gene may be increased to, for example, 1.2 times or more, 1.5 times or more, 2 times or more, or 3 times or more of that of a non-modified strain. Furthermore, the state that "the expression of a gene is increased" can include not only a state that the expression amount of an objective gene is increased in a strain that inherently expresses the objective gene, but also a state that the gene is introduced into a strain that does not inherently express the objective gene, and expressed therein. That is, the phrase "the expression of a gene is increased" may also mean, for example, that an objective gene is introduced into a strain that does not possess the gene, and is expressed therein.

The expression of a gene can be increased by, for example, increasing the copy number of the gene.

The copy number of a gene can be increased by introducing the gene into the chromosome of a host. A gene can be introduced into a chromosome by, for example, using homologous recombination (Miller, J. H., Experiments in Molecular Genetics, 1972, Cold Spring Harbor Laboratory). Examples of the gene transfer method utilizing homologous recombination can include, for example, a method of using a linear DNA such as Red-driven integration (Datsenko, K. A., and Wanner, B. L., Proc. Natl. Acad. Sci. USA, 97:6640-6645 (2000)), a method of using a plasmid containing a temperature sensitive replication origin, a method of using a plasmid capable of conjugative transfer, a method of using a suicide vector not having a replication origin that functions in a host, and a transduction method using a phage. Only one copy, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome can include repetitive DNAs, and inverted repeats located at the both ends of a transposon. Alternatively, homologous recombination may be performed by using an appropriate sequence on a chromosome such as a gene unnecessary for the production of an objective substance as a target. Furthermore, a gene can also be randomly introduced into a chromosome by using a transposon or Mini-Mu (Japanese Patent Laid-open (Kokai) No. 2-109985, U.S. Pat. No. 5,882,888, EP 805867 B1).

Introduction of a target gene into a chromosome can be confirmed by Southern hybridization using a probe having a sequence complementary to the whole gene or a part thereof, PCR using primers prepared on the basis of the sequence of the gene, or the like.

Furthermore, the copy number of a gene can also be increased by introducing a vector containing the gene into a host. For example, the copy number of a target gene can be increased by ligating a DNA fragment containing the target gene with a vector that functions in a host to construct an expression vector of the gene, and transforming the host with the expression vector. The DNA fragment containing the target gene can be obtained by, for example, PCR using the genomic DNA of a microorganism having the target gene as the template. As the vector, a vector autonomously replicable in the cell of the host can be used. The vector can be a multi-copy vector. Furthermore, the vector preferably has a marker such as an antibiotic resistance gene for selection of transformant. Furthermore, the vector may have a promoter and/or terminator for expressing the introduced gene. The vector may be, for example, a vector derived from a bacterial plasmid, a vector derived from a yeast plasmid, a vector derived from a bacteriophage, cosmid, phagemid, or the like. Specific examples of vector autonomously replicable in *Enterobacteriaceae* bacteria such as *Escherichia coli* can include, for example, pUC19, pUC18, pHSG299, pHSG399, pHSG398, pBR322, pSTV29 (all of these are available from Takara Bio), pACYC184, pMW219 (NIPPON GENE), pTrc99A (Pharmacia), pPROK series vectors (Clontech), pKK233-2 (Clontech), pET series vectors (Novagen), pQE series vectors (QIAGEN), pCold TF DNA (Takara Bio), pACYC series vectors, and the broad host spectrum vector RSF1010. Specific examples of vector autonomously replicable in coryneform bacteria can include, for example, pHM1519 (Agric. Biol. Chem., 48, 2901-2903 (1984)); pAM330 (Agric. Biol. Chem., 48, 2901-2903 (1984)); plasmids obtained by improving these and having a drug resistance gene; plasmid pCRY30 described in Japanese Patent Laid-open (Kokai) No. 3-210184; plasmids pCRY21, pCRY2KE, pCRY2KX, pCRY31, pCRY3KE, and pCRY3KX described in Japanese Patent Laid-open (Kokai) No. 2-72876 and U.S. Pat. No. 5,185,262; plasmids pCRY2 and pCRY3 described in Japanese Patent Laid-open (Kokai) No. 1-191686; pAJ655, pAJ611, and pAJ1844 described in Japanese Patent Laid-open (Kokai) No. 58-192900; pCG1 described in Japanese Patent Laid-open (Kokai) No. 57-134500; pCG2 described in Japanese Patent Laid-open (Kokai) No. 58-35197; pCG4 and pCG11 described in Japanese Patent Laid-open (Kokai) No. 57-183799; pVK7 described in Japanese Patent Laid-open (Kokai) No. 10-215883; pVK9 described in WO2007/046389; pVS7 described in WO2013/069634; and pVC7 described in Japanese Patent Laid-open (Kokai) No. 9-070291.

When a gene is introduced, it is sufficient that the gene is expressibly harbored by a host. Specifically, it is sufficient that the gene is harbored by a host so that it is expressed under control of a promoter that functions in the host. The term "a promoter that functions in a host" can refer to a promoter that shows a promoter activity in the host. The promoter may be a promoter derived from the host, or a heterogenous promoter. The promoter may be the native promoter of the gene to be introduced, or a promoter of another gene. As the promoter, for example, such a stronger promoter as mentioned later may also be used.

A terminator for termination of gene transcription may be located downstream of the gene. The terminator is not particularly limited so long as it functions in a host. The terminator may be a terminator derived from the host, or a heterogenous terminator. The terminator may be the native terminator of the gene to be introduced, or a terminator of another gene. Specific examples of the terminator can include, for example, T7 terminator, T4 terminator, fd phage terminator, tet terminator, and trpA terminator.

Vectors, promoters, and terminators available in various microorganisms are disclosed in detail in "Fundamental Microbiology Vol. 8, Genetic Engineering, KYORITSU SHUPPAN CO., LTD, 1987", and those can be used.

Furthermore, when two or more of genes are introduced, it is sufficient that the genes each are operably harbored by a host. For example, all the genes may be carried by a single expression vector or a chromosome. Furthermore, the genes may be separately carried by two or more expression vectors, or separately carried by a single or two or more expression vectors and a chromosome. An operon made up of two or more genes may also be introduced. The case of "introducing two or more genes" can include, for example, cases of introducing respective genes encoding two or more kinds of proteins (such as enzymes), introducing respective genes encoding two or more subunits making up a single protein complex (such as enzyme complex), and a combination of the foregoing cases.

The gene to be introduced is not particularly limited so long as it encodes a protein that is able to function in the host. The gene to be introduced may be a gene derived from the host, or may be a heterogenous gene. The gene to be introduced can be obtained by, for example, PCR using primers designed on the basis of the nucleotide sequence of the gene, and using the genomic DNA of an organism having the gene, a plasmid carrying the gene, or the like as a template. The gene to be introduced may also be totally synthesized, for example, on the basis of the nucleotide sequence of the gene (Gene, 60(1), 115-127 (1987)). The obtained gene can be used as it is, or after being modified as required. That is, a variant of a gene may be obtained by modifying the gene. A gene can be modified by a known technique. For example, an objective mutation can be introduced into an objective site of DNA by the site-specific mutation method. That is, the coding region of a gene can be modified by the site-specific mutation method so that a specific site of the encoded protein includes substitution, deletion, insertion, and/or addition of amino acid residues. Examples of the site-specific mutation method can include the method utilizing PCR (Higuchi, R., 61, in PCR Technology, Erlich, H. A. Eds., Stockton Press (1989); Carter, P., Meth. in Enzymol., 154, 382 (1987)), and the method utilizing phage (Kramer, W. and Frits, H. J., Meth. in Enzymol., 154, 350 (1987); Kunkel, T. A. et al., Meth. in Enzymol., 154, 367 (1987)). Alternatively, a variant of a gene may be totally synthesized.

In addition, when a protein functions as a complex having a plurality of subunits, a part or all of the plurality of subunits may be modified, so long as the activity of the protein is eventually increased. That is, for example, when the activity of a protein is increased by increasing the expression of a gene, the expression of a part or all of the plurality of genes that encode the subunits may be enhanced. It is usually preferable to enhance the expression of all of the plurality of genes encoding the subunits. Furthermore, the subunits making up the complex may be derived from a single kind of organism or two or more kinds of organisms, so long as the complex has a function of the objective protein. That is, for example, genes of the same organism encoding a plurality of subunits may be introduced into a host, or genes of different organisms encoding a plurality of subunits may be introduced into a host.

Furthermore, the expression of a gene can be increased by improving the transcription efficiency of the gene. In addition, the expression of a gene can also be increased by improving the translation efficiency of the gene. The transcription efficiency of the gene and the translation efficiency of the gene can be improved by, for example, modifying an expression control sequence of the gene. The term "expression control sequence" collectively can refer to sites that affect the expression of a gene. Examples of the expression control sequence can include, for example, promoter, Shine-Dalgarno (SD) sequence (also referred to as ribosome binding site (RBS)), and spacer region between RBS and the start codon. Expression control sequences can be identified by using a promoter search vector or gene analysis software such as GENETYX. These expression control sequences can be modified by, for example, a method of using a temperature sensitive vector, or the Red driven integration method (WO2005/010175).

The transcription efficiency of a gene can be improved by, for example, replacing the promoter of the gene on a chromosome with a stronger promoter. The term "stronger promoter" can mean a promoter providing an improved transcription of a gene compared with an inherently existing wild-type promoter of the gene. Examples of stronger promoters can include, for example, the known high expression promoters such as T7 promoter, trp promoter, lac promoter, thr promoter, tac promoter, trc promoter, tet promoter, araBAD promoter, rpoH promoter, msrA promoter, Pm1 promoter (derived from the genus *Bifidobacterium*), PR promoter, and PL promoter. Examples of stronger promoters that function in coryneform bacteria can include, for example, the artificially modified P54-6 promoter (Appl. Microbiol. Biotechnol., 53, 674-679 (2000)), pta, aceA, aceB, adh, and amyE promoters inducible in coryneform bacteria with acetic acid, ethanol, pyruvic acid, or the like, and cspB, SOD, and tuf (EF-Tu) promoters, which are potent promoters capable of providing a large expression amount in coryneform bacteria (Journal of Biotechnology, 104 (2003) 311-323; Appl. Environ. Microbiol., 2005 December; 71 (12): 8587-96), as well as lac promoter, tac promoter, and trc promoter. Furthermore, as the stronger promoter, a highly-active type of an inherent promoter may also be obtained by using various reporter genes. For example, by making the −35 and −10 regions in a promoter region closer to the consensus sequence, the activity of the promoter can be enhanced (WO00/18935). Examples of highly active-type promoter can include various tac-like promoters (Katashkina J I et al., Russian Federation Patent Application No. 2006134574). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

The translation efficiency of a gene can be improved by, for example, replacing the Shine-Dalgarno (SD) sequence (also referred to as ribosome binding site (RBS)) for the gene on a chromosome with a stronger SD sequence. The "stronger SD sequence" can mean a SD sequence that provides an improved translation of mRNA compared with the inherent wild-type SD sequence of the gene. Examples of stronger SD sequences can include, for example, RBS of the gene 10 derived from phage T7 (Olins P. O. et al, Gene, 1988, 73, 227-235). Furthermore, it is known that substitution, insertion, or deletion of several nucleotides in a spacer region between RBS and the start codon, especially in a sequence immediately upstream of the start codon (5'-UTR), significantly affects the stability and translation efficiency of mRNA, and hence, the translation efficiency of a gene can also be improved by modifying them.

The translation efficiency of a gene can also be improved by, for example, modifying codons. For example, the translation efficiency of the gene can be improved by replacing a rare codon present in the gene with a synonymous codon that is more frequently used. That is, the gene to be introduced may be modified, for example, so as to contain optimal codons according to the frequencies of codons observed in a host to be used. Codons can be replaced by, for example, the site-specific mutation method. Alternatively, a gene fragment in which objective codons are replaced may be totally synthesized. Frequencies of codons in various organisms are disclosed in the "Codon Usage Database" (kazusa.or.jp/codon; Nakamura, Y. et al, Nucl. Acids Res., 28, 292 (2000)).

Furthermore, the expression of a gene can also be increased by amplifying a regulator that increases the expression of the gene, or deleting or attenuating a regulator that reduces the expression of the gene.

Such methods for increasing the gene expression as mentioned above may be used independently or in an arbitrary combination.

Furthermore, the modification that increases the activity of a protein can also be attained by, for example, enhancing the specific activity of the enzyme. Enhancement of the specific activity can also include desensitization to feedback inhibition. That is, when a protein is subject to feedback inhibition by a metabolite, the activity of the protein can be increased by making a host harbor a gene encoding a mutant protein that has been desensitized to the feedback inhibition. The expression "desensitization to feedback inhibition" can include complete elimination of the feedback inhibition, and attenuation of the feedback inhibition, unless otherwise stated. Also, the state of "being desensitized to feedback inhibition", i.e. the state that feedback inhibition is eliminated or attenuated, can also be referred to as "tolerant to feedback inhibition". A protein showing an enhanced specific activity can be obtained by, for example, searching various organisms. Furthermore, a highly-active type of an inherent protein may also be obtained by introducing a mutation into the existing protein. The mutation to be introduced may be, for example, substitution, deletion, insertion, or addition of one or several amino acid residues at one or several positions in the protein. The mutation can be introduced by, for example, such a site-specific mutation method as mentioned above. The mutation may also be introduced by, for example, a mutagenesis treatment. Examples of the mutagenesis treatment can include irradiation of X-ray, irradiation of ultraviolet, and a treatment with a mutation agent such as N-methyl-N'-nitro-N-nitrosoguanidine (MNNG), ethyl methanesulfonate (EMS), and methyl methanesulfonate (MMS). Furthermore, a random mutation may be induced by directly treating DNA in vitro with hydroxylamine. Enhancement of the specific activity may be independently used, or may be used in an arbitrary combination with such methods for enhancing gene expression as mentioned above.

The method for the transformation is not particularly limited, and conventionally known methods can be used. There can be used, for example, a method of treating recipient cells with calcium chloride so as to increase the permeability thereof for DNA, which has been reported for the *Escherichia coli* K-12 strain (Mandel, M. and Higa, A., J. Mol. Biol., 1970, 53, 159-162), and a method of preparing competent cells from cells which are in the growth phase, followed by transformation with DNA, which has been reported for *Bacillus subtilis* (Duncan, C. H., Wilson, G. A. and Young, F. E., Gene, 1977, 1:153-167). Alternatively, there can also be used a method of making DNA-recipient cells into protoplasts or spheroplasts, which can easily take up recombinant DNA, followed by introducing a recombinant DNA into the DNA-recipient cells, which is known to be applicable to *Bacillus subtilis*, actinomycetes, and yeasts (Chang, S. and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Acad. Sci. USA, 75:1929-1933). Furthermore, the electric pulse method reported for coryneform bacteria (Japanese Patent Laid-open (Kokai) No. 2-207791) can also be used.

An increase in the activity of a protein can be confirmed by measuring the activity of the protein.

An increase in the activity of a protein can also be confirmed by confirming an increase in the expression of a gene encoding the protein. An increase in the expression of a gene can be confirmed by confirming an increase in the transcription amount of the gene, or by confirming an increase in the amount of a protein expressed from the gene.

An increase of the transcription amount of a gene can be confirmed by comparing the amount of mRNA transcribed from the gene with that of a non-modified strain such as a wild-type strain or parent strain. Examples of the method for evaluating the amount of mRNA can include Northern hybridization, RT-PCR, and so forth (Sambrook, J., et al., Molecular Cloning A Laboratory Manual/Third Edition, Cold Spring Harbor Laboratory Press, Cold Spring Harbor (USA), 2001). The amount of mRNA may increase to, for example, 1.2 times or more, 1.5 times or more, 2 times or more, or 3 times or more of that of a non-modified strain.

An increase in the amount of a protein can be confirmed by Western blotting using antibodies (Molecular Cloning, Cold Spring Harbor Laboratory Press, Cold Spring Harbor (USA), 2001). The amount of the protein (such as the number of molecules of the protein per cell) may increase to, for example, 1.2 times or more, 1.5 times or more, 2 times or more, or 3 times or more of that of a non-modified strain.

The aforementioned methods for increasing the activity of a protein can be applied to enhancement of the activities of arbitrary proteins such as an objective substance biosynthesis enzyme, phosphopantetheinylation enzyme, and uptake system of a substance, and enhancement of the expression of arbitrary genes such as genes encoding those arbitrary proteins, besides introduction of a specific CAR gene.

<1-3> Method for Reducing Activity of Protein

Hereafter, the methods for reducing the activity of a protein will be described.

The expression "the activity of a protein is reduced" can mean that the activity of the protein is reduced as compared with a non-modified strain. Specifically, the expression "the activity of a protein is reduced" may mean that the activity of the protein per cell is reduced as compared with that of a non-modified strain. The term "non-modified strain" used herein can refer to a control strain that has not been modified so that the activity of an objective protein is reduced. Examples of the non-modified strain can include a wild-type strain and parent strain. Specific examples of the non-modified strain can include the respective type strains of the species of microorganisms. Specific examples of the non-modified strain can also include strains exemplified above in relation to the description of microorganisms. That is, in an embodiment, the activity of a protein may be reduced as compared with a type strain, i.e. the type strain of the species to which a microorganism belongs. In another embodiment, the activity of a protein may also be reduced as compared with the *C. glutamicum* ATCC 13869 strain. In another embodiment, the activity of a protein may also be reduced as compared with the *C. glutamicum* ATCC 13032 strain. In another embodiment, the activity of a protein may also be reduced as compared with the *E. coli* K-12 MG1655 strain. The state that "the activity of a protein is reduced" can also include a state that the activity of the protein has completely disappeared. More specifically, the expression "the activity of a protein is reduced" may mean that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may also mean the transcription amount of a gene (i.e. the amount of mRNA) encoding the protein or the translation amount of the protein (i.e. the amount of the protein).

The state that "the number of molecules of the protein per cell is reduced" can also include a state that the protein does not exist at all. The state that "the function of each molecule of the protein is reduced" can also include a state that the function of each protein molecule has completely disappeared. The degree of the reduction in the activity of a protein is not particularly limited, so long as the activity is reduced as compared with that of a non-modified strain. The activity of a protein may be reduced to, for example, 50% or less, 20% or less, 10% or less, 5% or less, or 0% of that of a non-modified strain.

The modification for reducing the activity of a protein can be attained by, for example, reducing the expression of a gene encoding the protein. The expression "the expression of a gene is reduced" can mean that the expression of the gene is reduced as compared with a non-modified strain such as a wild-type strain and parent strain. Specifically, the expression "the expression of a gene is reduced" may mean that the expression of the gene per cell is reduced as compared with that of a non-modified strain. More specifically, the expression "the expression of a gene is reduced" may mean that the transcription amount of the gene (i.e. the amount of mRNA) is reduced, and/or the translation amount of the gene (i.e. the amount of the protein expressed from the gene) is reduced. The state that "the expression of a gene is reduced" can also include a state that the gene is not expressed at all. The state that "the expression of a gene is reduced" can also be referred to as "the expression of a gene is attenuated". The expression of a gene may be reduced to, for example, 50% or less, 20% or less, 10% or less, 5% or less, or 0% of that of a non-modified strain.

The reduction in gene expression may be due to, for example, a reduction in the transcription efficiency, a reduction in the translation efficiency, or a combination of them. The expression of a gene can be reduced by modifying an expression control sequence of the gene such as a promoter, the Shine-Dalgarno (SD) sequence (also referred to as ribosome-binding site (RBS)), and a spacer region between RBS and the start codon of the gene. When an expression control sequence is modified, one or more nucleotides, two or more nucleotides, or three or more nucleotides, of the expression control sequence are modified. For example, the transcription efficiency of a gene can be reduced by, for example, replacing the promoter of the gene on a chromosome with a weaker promoter. The term "weaker promoter" can mean a promoter providing an attenuated transcription of a gene compared with an inherent wild-type promoter of the gene. Examples of weaker promoters can include, for example, inducible promoters. That is, an inducible promoter may function as a weaker promoter under a non-induced condition, such as in the absence of the corresponding inducer. Furthermore, a part of or the entire expression control sequence may be deleted. The expression of a gene can also be reduced by, for example, manipulating a factor responsible for expression control. Examples of the factor responsible for expression control can include low molecules responsible for transcription or translation control (inducers, inhibitors, etc.), proteins responsible for transcription or translation control (transcription factors etc.), nucleic acids responsible for transcription or translation control (siRNA etc.), and so forth. Furthermore, the expression of a gene can also be reduced by, for example, introducing a mutation that reduces the expression of the gene into the coding region of the gene. For example, the expression of a gene can be reduced by replacing a codon in the coding region of the gene with a synonymous codon used less frequently in a host. Furthermore, for example, the gene expression may be reduced due to disruption of a gene as described later.

The modification for reducing the activity of a protein can also be attained by, for example, disrupting a gene encoding the protein. The expression "a gene is disrupted" can mean that a gene is modified so that a protein that can normally function is not produced. The state that "a protein that normally functions is not produced" can include a state that the protein is not produced at all from the gene, and a state that the protein of which the function (such as activity or property) per molecule is reduced or eliminated is produced from the gene.

Disruption of a gene can be attained by, for example, deleting the gene on a chromosome. The term "deletion of a gene" can refer to deletion of a partial or entire region of the coding region of the gene. Furthermore, the entire gene including sequences upstream and downstream from the coding region of the gene on a chromosome may be deleted. The region to be deleted may be any region such as an N-terminal region (region encoding an N-terminal region of a protein), an internal region, or a C-terminal region (region encoding a C-terminal region of a protein), so long as the activity of the protein can be reduced. Deletion of a longer region can usually more surely inactivate the gene. The region to be deleted may be, for example, a region having a length of 10% or more, 20% or more, 30% or more, 40% or more, 50% or more, 60% or more, 70% or more, 80% or more, 90% or more, or 95% or more of the total length of the coding region of the gene. Furthermore, it is preferred that reading frames of the sequences upstream and downstream from the region to be deleted are not the same. Inconsistency of reading frames may cause a frameshift downstream of the region to be deleted.

Disruption of a gene can also be attained by, for example, introducing a mutation for an amino acid substitution (missense mutation), a stop codon (nonsense mutation), addition or deletion of one or two nucleotide residues (frame shift mutation), or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another nucleotide sequence into a coding region of the gene on a chromosome. Site of the insertion may be in any region of the gene, and insertion of a longer nucleotide sequence can usually more surely inactivate the gene. It is preferred that reading frames of the sequences upstream and downstream from the insertion site are not the same. Inconsistency of reading frames may cause a frameshift downstream of the region to be deleted. The other nucleotide sequence is not particularly limited so long as a sequence that reduces or eliminates the activity of the encoded protein is chosen, and examples thereof can include, for example, a marker gene such as antibiotic resistance genes, and a gene useful for production of an objective substance.

Particularly, disruption of a gene may be carried out so that the amino acid sequence of the encoded protein is deleted. In other words, the modification for reducing the activity of a protein can be attained by, for example, deleting the amino acid sequence of the protein, specifically, modifying a gene so as to encode a protein of which the amino acid sequence is deleted. The term "deletion of the amino acid sequence of a protein" can refer to deletion of a partial or entire region of the amino acid sequence of the protein. In addition, the term "deletion of the amino acid sequence of a protein" means that the original amino acid sequence disappears in the protein, and can also include cases where the original amino acid sequence is changed to another amino acid sequence. That is, for example, a region that was changed to another amino acid sequence by frameshift may be regarded as a deleted region. When the amino acid sequence of a protein is deleted, the total length of the protein is typically shortened, but there can also be cases where the total length of the protein is not changed or is extended. For example, by deletion of a partial or entire region of the coding region of a gene, a region encoded by the deleted region can be deleted in the encoded protein. In addition, for example, by introduction of a stop codon into the coding region of a gene, a region encoded by the downstream region of the introduction site can be deleted in the encoded protein. In addition, for example, by frameshift in the coding region of a gene, a region encoded by the frameshift region can be deleted in the encoded protein. The aforementioned descriptions concerning the position and length of the region to be deleted in deletion of a gene can be applied mutatis mutandis to the position and length of the region to be deleted in deletion of the amino acid sequence of a protein.

Such modification of a gene on a chromosome as described above can be attained by, for example, preparing a disruption-type gene modified so that it is unable to produce a protein that functions normally, and transforming a host with a recombinant DNA containing the disruption-type gene to cause homologous recombination between the disruption-type gene and the wild-type gene on a chromosome and thereby substitute the disruption-type gene for the wild-type gene on the chromosome. In this procedure, if a marker gene selected according to the characteristics of the host such as auxotrophy is included in the recombinant DNA, the operation becomes easier. Examples of the disruption-type gene can include a gene of which a partial or entire region of the coding region is deleted, gene including a missense mutation, gene including a nonsense mutation, gene including a frame shift mutation, and gene including insertion of a transposon or marker gene. The protein encoded by the disruption-type gene has a conformation different from that of the wild-type protein, even if it is produced, and thus the function thereof is reduced or eliminated. Such gene disruption based on gene substitution utilizing homologous recombination has already been established, and there are methods of using a linear DNA such as a method called "Red driven integration" (Datsenko, K. A, and Wanner, B. L., Proc. Natl. Acad. Sci. USA, 97:6640-6645 (2000)), and a method utilizing the Red driven integration in combination with an excision system derived from λ, phage (Cho, E. H., Gumport, R I., Gardner, J. F., J. Bacteriol., 184:5200-5203 (2002)) (refer to WO2005/010175), a method of using a plasmid having a temperature sensitive replication origin, a method of using a plasmid capable of conjugative transfer, a method of utilizing a suicide vector not having a replication origin that functions in a host (U.S. Pat. No. 6,303,383, Japanese Patent Laid-open (Kokai) No. 05-007491), and so forth.

The modification for reducing activity of a protein can also be attained by, for example, a mutagenesis treatment. Examples of the mutagenesis treatment can include irradiation of X-ray or ultraviolet and treatment with a mutation agent such as N-methyl-N'-nitro-N-nitrosoguanidine (MNNG), ethyl methanesulfonate (EMS), and methyl methanesulfonate (MMS).

Such methods for reducing the activity of a protein as mentioned above may be used independently or in an arbitrary combination.

When a protein functions as a complex having a plurality of subunits, a part or all of the plurality of subunits may be modified, so long as the activity of the protein is eventually reduced. That is, for example, a part or all of a plurality of genes that encode the respective subunits may be disrupted or the like. Furthermore, when there is a plurality of isozymes of a protein, a part or all of the activities of the plurality of isozymes may be reduced, so long as the activity of the protein is eventually reduced. That is, for example, a part or all of a plurality of genes that encode the respective isozymes may be disrupted or the like.

A reduction in the activity of a protein can be confirmed by measuring the activity of the protein.

A reduction in the activity of a protein can also be confirmed by confirming a reduction in the expression of a gene encoding the protein. A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that observed in a non-modified strain. Examples of the method for evaluating the amount of mRNA can include Northern hybridization, RT-PCR, and so forth (Molecular Cloning, Cold Spring Harbor Laboratory Press, Cold Spring Harbor (USA), 2001). The amount of mRNA can be reduced to, for example, 50% or less, 20% or less, 10% or less, 5% or less, or 0%, of that observed in a non-modified strain.

A reduction in the amount of a protein can be confirmed by Western blotting using antibodies (Molecular Cloning, Cold Spring Harbor Laboratory Press, Cold Spring Harbor (USA) 2001). The amount of the protein (such as the number of molecules of the protein per cell) can be reduced to, for example, 50% or less, 20% or less, 10% or less, 5% or less, or 0%, of that observed in a non-modified strain.

Disruption of a gene can be confirmed by determining nucleotide sequence of a part or the whole of the gene, restriction enzyme map, full length, or the like of the gene depending on the means used for the disruption.

Such methods for reducing the activity of a protein as mentioned above can be applied to reduction in the activities of arbitrary proteins such as a byproduct generation enzyme, and reduction in the expression of arbitrary genes such as genes encoding those arbitrary proteins.

<2> Method of the Present Invention

The method as described herein is a method for producing an objective substance by using the microorganism as described herein.

<2-1> Fermentation Method

An objective substance can be produced by, for example, fermentation of the microorganism as described herein. That is, an embodiment of the method as described herein may be a method for producing an objective substance by fermentation of the microorganism. This embodiment can also be referred to as "fermentation method". Also, the step of producing an objective substance by fermentation of the microorganism can also be referred to as "fermentation step".

The fermentation step can be performed by cultivating the microorganism as described herein. Specifically, in the fermentation method, an objective substance can be produced from a carbon source. That is, the fermentation step may be, for example, a step of cultivating the microorganism in a culture medium, such as a culture medium containing a carbon source, to produce and accumulate the objective substance in the culture medium. That is, the fermentation method may be a method for producing an objective substance by cultivating the microorganism in a culture medium, such as a culture medium containing a carbon source, to produce and accumulate the objective substance in the culture medium. Also, in other words, the fermentation step may be, for example, a step of producing the objective substance from a carbon source by using the microorganism.

The culture medium is not particularly limited, so long as the microorganism can proliferate in it and produce an objective substance. As the culture medium, for example, a culture medium that is typically used for culture of microorganisms such as bacteria and yeast can be used. The culture medium may contain a carbon source, nitrogen source, phosphate source, and sulfur source, as well as other medium components such as various organic components and inorganic components as required. The types and concentrations of the medium components can be appropriately determined according to various conditions such as the type of the microorganism to be used.

The carbon source is not particularly limited, so long as the microorganism can utilize it and produce an objective substance. Specific examples of the carbon source can include, for example, saccharides such as glucose, fructose, sucrose, lactose, galactose, xylose, arabinose, blackstrap molasses, hydrolysates of starches, and hydrolysates of biomass; organic acids such as acetic acid, citric acid, succinic acid, and gluconic acid; alcohols such as ethanol, glycerol, and crude glycerol; and fatty acids. As the carbon source, in particular, plant-derived materials can be used. Examples of the plant can include, for example, corn, rice, wheat, soybean, sugarcane, beet, and cotton. Examples of the plant-derived materials can include, for example, organs such as root, stem, trunk, branch, leaf, flower, and seed, plant bodies including them, and decomposition products of these plant organs. The forms of the plant-derived materials at the time of use thereof are not particularly limited, and they can be in any form such as an unprocessed product, juice, ground product, and purified product. Pentoses such as xylose, hexoses such as glucose, or mixtures of them can be obtained from, for example, plant biomass. Specifically, these saccharides can be obtained by subjecting a plant biomass to such a treatment as steam treatment, hydrolysis with concentrated acid, hydrolysis with diluted acid, hydrolysis with an enzyme such as cellulase, and alkaline treatment. Since hemicellulose is generally more easily hydrolyzed compared with cellulose, hemicellulose in a plant biomass may be hydrolyzed beforehand to liberate pentoses, and then cellulose may be hydrolyzed to generate hexoses. Furthermore, xylose may be supplied by conversion from hexoses by, for example, imparting a pathway for converting hexose such as glucose to xylose to the microorganism. As the carbon source, one kind of carbon source may be used, or two or more kinds of carbon sources may be used in combination.

The concentration of the carbon source in the culture medium is not particularly limited, so long as the microorganism can proliferate and produce an objective substance. The concentration of the carbon source in the culture medium may be as high as possible within such a range that production of the objective substance is not inhibited. Initial concentration of the carbon source in the culture medium may be, for example, usually 5 to 30% (w/v), or 10 to 20% (w/v). Furthermore, the carbon source may be additionally supplied to the culture medium as required. For example, the carbon source may be additionally supplied to the culture medium in proportion to decrease or depletion of the carbon source accompanying progress of the fermentation. While the carbon source may be temporarily depleted so long as an objective substance can be eventually produced, it may be preferable to perform the culture so that the carbon source is not depleted or the carbon source does not continue to be depleted.

Specific examples of the nitrogen source can include, for example, ammonium salts such as ammonium sulfate, ammonium chloride, and ammonium phosphate, organic nitrogen sources such as peptone, yeast extract, meat extract, and soybean protein decomposition products, ammonia, and urea. Ammonia gas and aqueous ammonia used for pH adjustment may also be used as a nitrogen source. As the nitrogen source, one kind of nitrogen source may be used, or two or more kinds of nitrogen sources may be used in combination.

Specific examples of the phosphate source can include, for example, phosphate salts such as potassium dihydrogenphosphate and dipotassium hydrogenphosphate, and phosphoric acid polymers such as pyrophosphoric acid. As the phosphate source, one kind of phosphate source may be used, or two or more kinds of phosphate sources may be used in combination.

Specific examples of the sulfur source can include, for example, inorganic sulfur compounds such as sulfates, thiosulfates, and sulfites, and sulfur-containing amino acids such as cysteine, cystine, and glutathione. As the sulfur source, one kind of sulfur source may be used, or two or more kinds of sulfur sources may be used in combination.

Specific examples of other various organic and inorganic components can include, for example, inorganic salts such as sodium chloride and potassium chloride; trace metals such as iron, manganese, magnesium, and calcium; vitamins such as vitamin B1, vitamin B2, vitamin B6, nicotinic acid, nicotinamide, and vitamin B12; amino acids; nucleic acids; and organic components containing these such as peptone, casamino acid, yeast extract, and soybean protein decomposition product. As the other various organic and inorganic components, one kind of component may be used, or two or more kinds of components may be used in combination.

Furthermore, when an auxotrophic mutant strain that requires a nutrient such as amino acids for growth thereof is used, it is preferable to supplement such a required nutrient to the culture medium. Furthermore, a component used for production of an objective substance may be supplemented to the culture medium. Specific examples of such a component can include, for example, methyl group donors such as SAM and precursors thereof such as methionine.

Culture conditions are not particularly limited, so long as the microorganism can proliferate, and an objective substance is produced. The culture can be performed with, for example, conditions typically used for the culture of microorganisms such as bacteria and yeast. The culture conditions may be appropriately determined according to various conditions such as the type of chosen microorganism.

The culture can be performed by using a liquid medium. At the time of the culture, for example, the microorganism cultured on a solid medium such as agar medium may be directly inoculated into a liquid medium, or the microorganism cultured in a liquid medium as seed culture may be inoculated into a liquid medium for main culture. That is, the culture may be performed separately as seed culture and main culture. In such a case, the culture conditions of the seed culture and the main culture may be or may not be the same. It is sufficient that an objective substance is produced at least during the main culture. The amount of the microorganism contained in the culture medium at the time of the start of the culture is not particularly limited. For example, a seed culture broth having an OD660 of 4 to 100 may be added to a culture medium for main culture in an amount of 0.1 to 100 mass %, or 1 to 50 mass %, at the time of the start of the culture.

The culture can be performed as batch culture, fed-batch culture, continuous culture, or a combination of these. The culture medium used at the start of the culture can also be referred to as "starting medium". The culture medium supplied to the culture system (e.g. fermentation tank) in the fed-batch culture or the continuous culture can also be referred to as "feed medium". To supply a feed medium to the culture system in the fed-batch culture or the continuous culture can also be referred to as "feed". Furthermore, when the culture is performed separately as seed culture and main culture, the culture schemes of the seed culture and the main culture may be or may not be the same. For example, both the seed culture and the main culture may be performed as batch culture. Alternatively, for example, the seed culture may be performed as batch culture, and the main culture may be performed as fed-batch culture or continuous culture.

The various components such as the carbon source may be present in the starting medium, feed medium, or both. That is, the various components such as the carbon source may be additionally supplied to the culture medium independently or in an arbitrary combination during the culture. These components may be supplied once or a plurality of times, or may be continuously supplied. The types of the components present in the starting medium may be or may not be the same as those of the components present in the feed medium. Furthermore, the concentrations of the components present in the starting medium may be or may not be the same as the concentrations of the components present in the feed medium. Furthermore, two or more kinds of feed media having components of different types and/or different concentrations may be used. For example, when feeding is intermittently performed two or more times, the types and/or concentrations of components contained in the feed medium may be or may not be the same for each feeding.

The culture can be performed, for example, under an aerobic condition. The term "aerobic condition" may refer to a condition where the dissolved oxygen concentration in the culture medium is 0.33 ppm or higher, or 1.5 ppm or higher. The oxygen concentration can be controlled to be, for example, 1 to 50%, or about 5%, of the saturated oxygen concentration. The culture can be performed, for example, with aeration or shaking. The pH of the culture medium may be, for example, 3 to 10, or 4.0 to 9.5. The pH of the culture medium can be adjusted during the culture as required. The pH of the culture medium can be adjusted by using various alkaline and acidic substances such as ammonia gas, aqueous ammonia, sodium carbonate, sodium bicarbonate, potassium carbonate, potassium bicarbonate, magnesium carbonate, sodium hydroxide, calcium hydroxide, and magnesium hydroxide. The culture temperature may be, for example, 20 to 45° C., or 25 to 37° C. The culture time may be, for example, 10 to 120 hours. The culture may be continued, for example, until the carbon source present in the culture medium is consumed, or until the activity of the microorganism is lost.

By cultivating the microorganism under such conditions as described above, an objective substance is accumulated in the culture medium.

Production of an objective substance can be confirmed by known methods used for detection or identification of compounds. Examples of such methods can include, for example, HPLC, UPLC, LC/MS, GC/MS, and NMR. These methods may be independently used, or may be used in an appropriate combination. These methods can also be used for determining the concentrations of various components present in the culture medium.

The produced objective substance can be appropriately collected. That is, the fermentation method may further comprise a step of collecting the objective substance. This step can also be referred to as "collection step". The collection step may be a step of collecting the objective substance from the culture broth, specifically from the culture medium. The objective substance can be collected by known methods used for separation and purification of compounds. Examples of such methods can include, for example, ion-exchange resin method, membrane treatment, precipitation, extraction, distillation, and crystallization. The objective substance can be collected specifically by extraction with an organic solvent such as ethyl acetate or by steam distillation. These methods may be independently used, or may be used in an appropriate combination.

Furthermore, when an objective substance deposits in the culture medium, it can be collected by, for example, centrifugation or filtration. The objective substance deposited in the culture medium and the objective substance dissolving in the culture medium may be isolated together after the objective substance dissolving in the culture medium is crystallized.

The collected objective substance may contain, for example, microbial cells, medium components, moisture, and by-product metabolites of the microorganism, in addition to the objective substance. The purity of the collected objective substance may be, for example, 30% (w/w) or higher, 50% (w/w) or higher, 70% (w/w) or higher, 80% (w/w) or higher, 90% (w/w) or higher, or 95% (w/w) or higher.

<2-2> Bioconversion Method

An objective substance can also be produced by, for example, bioconversion using the microorganism as described herein. That is, another embodiment of the method as described herein may be a method for producing an objective substance by bioconversion using the microorganism. This embodiment can also be referred to as "bioconversion method". Also, the step of producing an objective substance by bioconversion using the microorganism can also be referred to as "bioconversion step".

Specifically, in the bioconversion method, an objective substance can be produced from a precursor of the objective substance. More specifically, in the bioconversion method, an objective substance can be produced by converting a precursor of the objective substance into the objective substance by using the microorganism. That is, the bioconversion step may be a step of converting a precursor of an objective substance into the objective substance by using the microorganism.

A precursor of an objective substance can also be referred simply as "precursor". Examples of the precursor can include substances of which conversion into an object substance includes a step catalyzed by the specific CAR. Specific examples of the precursor can include intermediates of the biosynthesis pathway of an object substance, such as those recited in relation to descriptions of the objective substance biosynthesis enzymes, provided that conversion of the intermediates into the object substance includes a step catalyzed by the specific CAR. More specific examples of the precursor can include, for example, protocatechuic acid, vanillic acid, benzoic acid, L-phenylalanine, and cinnamic acid. Protocatechuic acid and vanillic acid each may be used as a precursor for producing, for example, vanillin. Benzoic acid may be used as a precursor for producing, for example, benzaldehyde. L-phenylalanine and cinnamic acid each may be used as a precursor for producing, for example, cinnamaldehyde. As the precursor, one kind of precursor may be used, or two or more kinds of precursors may be used in combination. In cases where the precursor is a compound that can form a salt, the precursor may be used as a free compound, a salt thereof, or a mixture thereof. That is, the term "precursor" can refer to a precursor in a free form, a salt thereof, or a mixture thereof, unless otherwise stated. Examples of the salt can include, for example, sulfate salt, hydrochloride salt, carbonate salt, ammonium salt, sodium salt, and potassium salt. As the salt of the precursor, one kind of salt may be employed, or two or more kinds of salts may be employed in combination.

As the precursor, a commercial product may be used, or one appropriately prepared and obtained may be used. That is, the bioconversion method may further comprise a step of producing a precursor. The method for producing a precursor is not particularly limited, and for example, known methods can be used. A precursor can be produced by, for example, a chemical synthesis method, enzymatic method, bioconversion method, fermentation method, extraction method, or a combination of these. That is, for example, a precursor of an objective substance can be produced from a further precursor thereof using an enzyme that catalyzes the conversion of such a further precursor into the precursor of an objective substance (also referred to as "precursor biosynthesis enzyme"). Furthermore, for example, a precursor of an objective substance can be produced from a carbon source or such a further precursor by using a microorganism having a precursor-producing ability. The term "microorganism having a precursor-producing ability" can refer to a microorganism that is able to generate a precursor of an objective substance from a carbon source or a further precursor thereof. For example, examples of the method for producing protocatechuic acid according to an enzymatic method or bioconversion method can include the method of converting para-cresol into protocatechuic acid using *Pseudomonas putida* KS-0180 (Japanese Patent Laid-open (Kokai) No. 7-75589), the method of converting para-hydroxybenzoic acid into protocatechuic acid using an NADH-dependent para-hydroxybenzoic acid hydroxylase (Japanese Patent Laid-open (Kokai) No. 5-244941), the method of producing protocatechuic acid by cultivating a transformant harboring a gene that is involved in the reaction of generating protocatechuic acid from terephthalic acid in a culture medium containing terephthalic acid (Japanese Patent Laid-open (Kokai) No. 2007-104942), and the method of producing protocatechuic acid from a precursor thereof by using a microorganism having protocatechuic acid-producing ability and having a reduced activity of protocatechuic acid 5-oxidase or being deficient in that activity (Japanese Patent Laid-open (Kokai) No. 2010-207094). Furthermore, examples of the method for producing protocatechuic acid by fermentation can include the method of producing protocatechuic acid by using a bacterium of the genus *Brevibacterium* and acetic acid as a carbon source (Japanese Patent Laid-open (Kokai) No. 50-89592), the method of producing protocatechuic acid by using a bacterium of the genus *Escherichia* or *Klebsiella* introduced with a gene encoding 3-dihydroshikimate dehydrogenase and glucose as a carbon source (U.S. Pat. No. 5,272,073). Furthermore, vanillic acid can be produced by using protocatechuic acid as a precursor according to an enzymatic method using OMT or a bioconversion method using a microorganism having OMT (J. Am. CHm. Soc., 1998, Vol. 120), or by using ferulic acid as a precursor according to a bioconversion method using *Pseudomonas* sp. AV10 (J. App. Microbiol., 2013, Vol. 116, p 903-910). The produced precursor can be used for the bioconversion method as it is, or after being subjected to an appropriate treatment such as concentration, dilution, drying, dissolution, fractionation, extraction, and purification, as required. That is, as the precursor, for example, a purified product purified to a desired extent may be used, or a material containing a precursor may be used. The material containing a precursor is not particularly limited so long as the microorganism can use the precursor. Specific examples of the material containing a precursor can include a culture broth obtained by cultivating a microorganism having a precursor-producing ability, a culture supernatant separated from the culture broth, and processed products thereof such as concentrated products (such as concentrated liquid) thereof and dried products thereof.

In an embodiment, the bioconversion step can be performed by, for example, cultivating the microorganism as described herein. This embodiment can also be referred to as "first embodiment of the bioconversion method". That is, the bioconversion step may be, for example, a step of cultivating the microorganism in a culture medium containing a precursor of an objective substance to convert the precursor into the objective substance. The bioconversion step may be, specifically, a step of cultivating the microorganism in a culture medium containing a precursor of an objective substance to produce and accumulate the objective substance in the culture medium.

The culture medium to be used is not particularly limited, so long as the culture medium contains a precursor of an objective substance, and the microorganism can proliferate in it and produce the objective substance. Culture conditions are not particularly limited, so long as the microorganism can proliferate, and an objective substance is produced. The descriptions concerning the culture mentioned for the fermentation method, such as those concerning the culture medium and culture conditions, can be applied mutatis mutandis to the culture in the first embodiment of the bioconversion method, except that the culture medium contains the precursor in the first embodiment.

The precursor may be present in the culture medium over the whole period of the culture, or may be present in the culture medium during only a partial period of the culture. That is, the phrase "cultivating a microorganism in a culture medium containing a precursor" does not necessarily mean that the precursor is present in the culture medium over the whole period of the culture. For example, the precursor may be or may not be present in the culture medium from the start of the culture. When the precursor is not present in the culture medium at the time of the start of the culture, the precursor is added to the culture medium after the start of the culture. Timing of the addition can be appropriately determined according to various conditions such as the length of the culture period. For example, after the microorganism sufficiently grows, the precursor may be added to the culture medium. Furthermore, in any case, the precursor may be added to the culture medium as required. For example, the precursor may be added to the culture medium in proportion to decrease or depletion of the precursor that occurs when objective substance is generated. Methods for supplying the precursor to the culture medium are not particularly limited.

For example, the precursor can be supplied to the culture medium by feeding a feed medium containing the precursor to the culture medium. Furthermore, for example, the microorganism as described herein and a microorganism having a precursor-producing ability can be co-cultured to allow the microorganism having a precursor-producing ability to produce the precursor in the culture medium, and thereby supply the precursor to the culture medium. These supply means may be independently used, or may be used in an appropriate combination. The concentration of the precursor in the culture medium is not particularly limited so long as the microorganism can use the precursor as a raw material of an objective substance. The concentration of the precursor in the culture medium, for example, may be 0.1 g/L or higher, 1 g/L or higher, 2 g/L or higher, 5 g/L or higher, 10 g/L or higher, or 15 g/L or higher, or may be 200 g/L or lower, 100 g/L or lower, 50 g/L or lower, or 20 g/L or lower, or may be within a range defined with a combination thereof, in terms of the weight of the free compound. The precursor may be or may not be present in the culture medium at a concentration within the range exemplified above over the whole period of the culture. For example, the precursor may be present in the culture medium at a concentration within the range exemplified above at the time of the start of the culture, or it may be added to the culture medium so that a concentration within the range exemplified above is attained after the start of the culture. In cases where the culture is performed separately as seed culture and main culture, it is sufficient that an objective substance is produced at least during the main culture. Hence, it is sufficient that the precursor is present in the culture medium at least during the main culture, i.e. over the whole period of the main culture or during a partial period of the main culture, and that is, the precursor may be or may not be present in the culture medium during the seed culture. In such cases, terms regarding the culture, such as "culture period (period of culture)" and "start of culture", can be read as those regarding the main culture.

In another embodiment, the bioconversion step can also be performed by, for example, using cells of the microorganism as described herein. This embodiment can also be referred to as "second embodiment of the bioconversion method". That is, the bioconversion step may be, for example, a step of converting a precursor of an objective substance in a reaction mixture into the objective substance by using cells of the microorganism. The bioconversion step may be, specifically, a step of allowing cells of the microorganism to act on a precursor of an objective substance in a reaction mixture to generate and accumulate the objective substance in the reaction mixture. The bioconversion step performed by using such cells can also be referred to as "conversion reaction".

Cells of the microorganism can be obtained by cultivating the microorganism. The culture method for obtaining the cells is not particularly limited so long as the microorganism can proliferate. At the time of the culture for obtaining the cells, the precursor may be or may not be present in the culture medium. Also, at the time of the culture for obtaining the cells, an objective substance may be or may not be produced in the culture medium. The descriptions concerning the culture described for the fermentation method, such as those concerning the culture medium and culture conditions, can be applied mutatis mutandis to the culture for obtaining the cells used for the second embodiment of the bioconversion method.

The cells may be used for the conversion reaction while being present in the culture broth (specifically, culture medium), or after being collected from the culture broth (specifically, culture medium). The cells may also be used for the conversion reaction after being subjected to a treatment as required. That is, examples of the cells can include a culture broth containing the cells, the cells collected from the culture broth, or a processed product thereof. In other words, examples of the cells can include cells present in a culture broth of the microorganism, cells collected from the culture broth, and cells present in a processed product thereof. Examples of the processed product can include products obtained by subjecting the cells, such as a culture broth containing the cells, or the cells collected from the culture broth, to a treatment. Cells in these forms may be independently used, or may be used in an appropriate combination.

The method for collecting the cells from the culture medium is not particularly limited, and for example, known methods can be used. Examples of such methods can include, for example, spontaneous precipitation, centrifugation, and filtration. A flocculant may also be used. These methods may be independently used, or may be used in an appropriate combination. The collected cells can be washed as required by using an appropriate medium. The collected cells can be re-suspended as required by using an appropriate medium. Examples of the medium that can be used for washing or suspending the cells can include, for example, aqueous media (aqueous solvents) such as water and aqueous buffer.

Examples of the treatment of the cells can include, for example, dilution, condensation, immobilization on a carrier such as acrylamide and carrageenan, freezing and thawing treatment, and treatment for increasing permeability of cell membranes. Permeability of cell membranes can be increased by, for example, using a surfactant or organic solvent. These treatments may be independently used, or may be used in an appropriate combination.

The cells used for the conversion reaction are not particularly limited so long as the cells have the ability to produce the objective substance. It is preferred that the cells maintain the metabolic activities thereof. The expression "the cells maintain the metabolic activities thereof" may mean that the cells have an ability to utilize a carbon source to generate or regenerate a substance required for producing an objective substance. Examples of such a substance can include, for example, ATP, electron donors such as NADH and NADPH, and methyl group donors such as SAM. The cells may have or may not have proliferation ability.

The conversion reaction can be carried out in an appropriate reaction mixture. Specifically, the conversion reaction can be carried out by allowing the cells and the precursor to coexist in an appropriate reaction mixture. The conversion reaction may be carried out by the batch method or may be carried out by the column method. In the case of the batch method, the conversion reaction can be carried out by, for example, mixing the cells of the microorganism and the precursor in a reaction mixture contained in a reaction vessel. The conversion reaction may be carried out statically, or may be carried out with stirring or shaking the reaction mixture. In the case of the column method, the conversion reaction can be carried out by, for example, passing a reaction mixture containing the precursor through a column filled with immobilized cells. Examples of the reaction mixture can include those based on an aqueous medium (aqueous solvent) such as water and aqueous buffer.

The reaction mixture may contain components other than the precursor as required, in addition to the precursor. Examples of the components other than the precursor can include ATP, electron donors such as NADH and NADPH, methyl group donors such as SAM, metal ions, buffering agents, surfactants, organic solvents, carbon sources, phosphate sources, and other various medium components. That is, for example, a culture medium containing the precursor may also be used as a reaction mixture. That is, the descriptions concerning the culture medium mentioned for the first embodiment of the bioconversion method may also be applied mutatis mutandis to the reaction mixture in the second embodiment of the bioconversion method. The types and concentrations of the components contained in the reaction mixture may be determined according to various conditions such as the type of the precursor and the form of the cells.

Conditions of the conversion reaction, such as dissolved oxygen concentration, pH of the reaction mixture, reaction temperature, reaction time, concentrations of various components, etc., are not particularly limited so long as an objective substance is generated. The conversion reaction can be performed with, for example, conditions typically used for substance conversion using microbial cells such as resting cells. The conditions of the conversion reaction may be determined according to various conditions such as the type of microorganism. The conversion reaction can be performed, for example, under an aerobic condition. The term "aerobic condition" may refer to a condition where the dissolved oxygen concentration in the reaction mixture is 0.33 ppm or higher, or 1.5 ppm or higher. The oxygen concentration can be controlled to be, for example, 1 to 50%, or about 5%, of the saturated oxygen concentration. The pH of the reaction mixture may be, for example, usually 6.0 to 10.0, or 6.5 to 9.0. The reaction temperature may be, for example, usually 15 to 50° C., 15 to 45° C., or 20 to 40° C. The reaction time may be, for example, 5 minutes to 200 hours. In the case of the column method, the loading rate of the reaction mixture may be, for example, such a rate that the reaction time falls within the range of the reaction time exemplified above. Furthermore, the conversion reaction can also be performed with, for example, a culture condition, such as conditions typically used for culture of microorganisms such as bacteria and yeast. During the conversion reaction, the cells may or may not proliferate. That is, the descriptions concerning the culture conditions described for the first embodiment of the bioconversion method may also be applied mutatis mutandis to the conditions of the conversion reaction in the second embodiment of the bioconversion method, except that the cells may or may not proliferate in the second embodiment. In such a case, the culture conditions for obtaining the cells and the conditions of the conversion reaction may be the same or different. The concentration of the precursor in the reaction mixture, for example, may be 0.1 g/L or higher, 1 g/L or higher, 2 g/L or higher, 5 g/L or higher, 10 g/L or higher, or 15 g/L or higher, or may be 200 g/L or lower, 100 g/L or lower, 50 g/L or lower, or 20 g/L or lower, or may be within a range defined with a combination thereof, in terms of the weight of the free compound. The density of the cells in the reaction mixture, for example, may be 1 or higher, or may be 300 or lower, or may be within a range defined with a combination thereof, in terms of the optical density (OD) at 600 nm.

During the conversion reaction, the cells, the precursor, and the other components may be additionally supplied to the reaction mixture independently or in any arbitrary combination thereof. For example, the precursor may be additionally supplied to the reaction mixture in proportion to decrease or depletion of the precursor accompanying generation of an objective substance. These components may be supplied once or a plurality of times, or may be continuously supplied.

Methods for supplying the various components such as the precursor to the reaction mixture are not particularly limited. These components each can be supplied to the reaction mixture by, for example, directly adding them to the reaction mixture. Furthermore, for example, the microorganism as described herein and a microorganism having a precursor-producing ability can be co-cultured to allow the microorganism having a precursor-producing ability to produce the precursor in the reaction mixture, and thereby supply the precursor to the reaction mixture. Furthermore, for example, components such as ATP, electron donors, and methyl group donors each may be generated or regenerated in the reaction mixture, may be generated or regenerated in the cells of the microorganism, or may be generated or regenerated by a coupling reaction between different cells. For example, when cells of the microorganism maintain the metabolic activities thereof, they can generate or regenerate components such as ATP, electron donors, and methyl group donors within them by using a carbon source. In addition, examples of the method for generating or regenerating ATP can include, for example, the method of supplying ATP from a carbon source by using a *Corynebacterium* bacterium (Hori, H. et al., Appl. Microbiol. Biotechnol., 48(6):693-698 (1997)), the method of regenerating ATP by using yeast cells and glucose (Yamamoto, S et al., Biosci. Biotechnol. Biochem., 69(4):784-789 (2005)), the method of regenerating ATP using phosphoenolpyruvic acid and pyruvate kinase (C. Aug'e and Ch. Gautheron, Tetrahedron Lett., 29:789-790 (1988)), and the method of regenerating ATP by using polyphosphoric acid and polyphosphate kinase (Murata, K. et al., Agric. Biol. Chem., 52(6):1471-1477 (1988)).

Furthermore, the reaction conditions may be constant from the start to the end of the conversion reaction, or they may change during the conversion reaction. The expression "the reaction conditions change during the conversion reaction" can include not only cases where the reaction conditions temporally change, but can also include cases where the reaction conditions spatially change. The expression "the reaction conditions spatially change" can mean that, for example, when the conversion reaction is performed by the column method, the reaction conditions such as reaction temperature and cell density differ depending on position in the flow.

A culture broth (or culture medium) or reaction mixture containing an objective substance is obtained by carrying out the bioconversion step as described above. Confirmation of the production of the objective substance and collection of the objective substance can be carried out in the same manners as those for the fermentation method described above. That is, the bioconversion method may further comprise the collection step, e.g. a step of collecting the objective substance from the culture broth (or culture medium) or reaction mixture. The collected objective substance may contain, for example, microbial cells, medium components, reaction mixture components, moisture, and by-product metabolites of the microorganism, in addition to the objective substance. Purity of the collected objective substance may be, for example, 30% (w/w) or higher, 50% (w/w) or higher, 70% (w/w) or higher, 80% (w/w) or higher, 90% (w/w) or higher, or 95% (w/w) or higher.

EXAMPLES

Hereafter, the present invention will be more specifically explained with reference to the following non-limiting examples.

In this example, strains harboring various CAR genes were constructed from the *Corynebacterium glutamicum* 2256 strain (ATCC 13869) as a parent strain, and vanillin is produced using these constructed strains.

<1> Construction of a Strain Deficient in the Vanillate Demethylase Genes (FKS0165 Strain)

It has been reported that, in coryneform bacteria, vanillin is metabolized in the order of vanillin → vanillic acid → protocatechuic acid, and utilized (Current Microbiology, 2005, Vol. 51, pp. 59-65). The conversion reaction from vanillic acid to protocatechuic acid is catalyzed by vanillate demethylase. The vanA gene and vanB gene encode the subunit A and subunit B of vanillate demethylase, respectively. The vanK gene encodes the vanillic acid uptake system, and constitutes the vanABK operon together with the vanAB genes (M. T. Chaudhry, et al., Microbiology, 2007, 153:857-865). Therefore, a strain that is unable to utilize an objective substance such as vanillin and vanillic acid (FKS0165 strain) was first constructed from *C. glutamicum* 2256 strain by deleting the vanABK operon. The procedure is shown below.

<1-1> Construction of Plasmid pBS4SΔvanABK56 for deletion of vanABK Genes

PCR was performed by using the genomic DNA of the *C. glutamicum* 2256 strain as the template, and the synthetic DNAs of SEQ ID NOS: 51 and 52 as the primers to obtain a PCR product containing an N-terminus side coding region of the vanA gene. Separately, PCR was also performed by using the genomic DNA of the *C. glutamicum* 2256 strain as the template, and the synthetic DNAs of SEQ ID NOS: 53 and 54 as the primers to obtain a PCR product containing a C-terminus side coding region of the vanK gene. The sequences of SEQ ID NOS: 52 and 53 are partially complementary to each other. Then, the PCR product containing the N-terminus side coding region of the vanA gene and the PCR product containing the C-terminus side coding region of the vanK gene were mixed in approximately equimolar amounts, and inserted into the pBS4S vector (WO2007/046389) that had been treated with BamHI and PstI by using In Fusion HD Cloning Kit (Clontech). With this DNA, competent cells of *Escherichia coli* JM109 (Takara Bio) were transformed, and the cells were applied to the LB medium containing 100 μM IPTG, 40 μg/mL of X-Gal, and 40 μg/mL of kanamycin, and cultured overnight. Then, white colonies that appeared were picked up, and separated into single colonies to obtain transformants. Plasmids were extracted from the obtained transformants, and one into which the target PCR product was inserted was designated as pBS4SΔvanABK56.

<1-2> Construction of FKS0165 Strain pBS4SΔvanABK56 obtained above does not contain the region enabling autonomous replication of the plasmid in cells of coryneform bacteria. Therefore, if coryneform bacteria are transformed with this plasmid, a strain in which this plasmid is incorporated into the genome by homologous recombination appears as a transformant, although it occurs at an extremely low frequency. Therefore, pBS4SΔvanABK56 was introduced into the *C. glutamicum* 2256 strain by the electric pulse method. The cells were applied to the CM-Dex agar medium (5 g/L of glucose, 10 g/L of polypeptone, 10 g/L of yeast extract, 1 g/L of $KH_2PO_4$, 0.4 g/L of $MgSO_4$-$7H_2O$, 0.01 g/L of $FeSO_4$-$7H_2O$, 0.01 g/L of $MnSO_4$-$7H_2O$, 3 g/L of urea, 1.2 g/L of soybean hydrolysate, 10 μg/L of biotin, 15 g/L of agar, adjusted to pH 7.5 with NaOH) containing 25 μg/mL of kanamycin, and cultured at 31.5° C. It was confirmed by PCR that the grown strain was a once-recombinant strain in which pBS4SΔvanABK56 was incorporated into the genome by homologous recombination. This once-recombinant strain had both the wild-type vanABK genes, and the deficient-type vanABK genes.

The once-recombinant strain was cultured overnight in the CM-Dex liquid medium (having the same composition as that of the CM-Dex agar medium except that it does not contain agar), and the culture broth was applied to the S10 agar medium (100 g/L of sucrose, 10 g/L of polypeptone, 10 g/L of yeast extract, 1 g/L of $KH_2PO_4$, 0.4 g/L of $MgSO_4$-$7H_2O$, 0.01 g/L of $FeSO_4$-$7H_2O$, 0.01 g/L of $MnSO_4$-$4$-$5H_2O$, 3 g/L of urea, 1.2 g/L of soybean protein hydrolysate solution, 10 μg/L of biotin, 20 g/L of agar, adjusted to pH 7.5 with NaOH, and autoclaved at 120° C. for 20 minutes), and cultured at 31.5° C. Among the colonies that appeared, a strain that showed kanamycin susceptibility was purified on the CM-Dex agar medium. By preparing genomic DNA from the purified strain, and using it to perform PCR with the synthetic DNAs of SEQ ID NOS: 55 and 56 as the primers, deletion of the vanABK genes was confirmed, and the strain was designated as FKS0165 strain.

<2> Construction of a Strain Deficient in Alcohol Dehydrogenase Homologue Genes (FKFC14 Strain)

Subsequently, by using the *Corynebacterium glutamicum* FKS0165 strain as a parent strain, a strain FKFC14 was constructed, which is deficient in alcohol dehydrogenase homologue genes, that is, NCgl0324 gene (adhC), NCgl0313 gene (adhE), and NCgl2709 gene (adhA), via the following procedure.

<2-1> Construction of FKFC5 Strain (FKS0165ΔNCgl0324 Strain)

<2-1-1> Construction of Plasmid pBS4SΔ2256adhC for Deletion of NCgl0324 gene

PCR was performed by using the genomic DNA of the *C. glutamicum* 2256 strain as the template, and the synthetic DNAs of SEQ ID NOS: 57 and 58 as the primers to obtain a PCR product containing an N-terminus side coding region of the NCgl0324 gene. Separately, PCR was performed by using the genomic DNA of the *C. glutamicum* 2256 strain as the template, and the synthetic DNAs of SEQ ID NOS: 59 and 60 as the primers to obtain a PCR product containing a C-terminus side coding region of the NCgl0324 gene. The sequences of SEQ ID NOS: 58 and 59 are partially complementary to each other. Then, approximately equimolar amounts of the PCR product containing the N-terminus side coding region of the NCgl0324 gene and the PCR product containing the C-terminus side coding region of the NCgl0324 gene were mixed, and inserted into the pBS4S vector (WO2007/046389) that had been treated with BamHI and PstI by using In Fusion HD Cloning Kit (Clontech). With this DNA, competent cells of *Escherichia coli* JM109 (Takara Bio) were transformed, and the cells were applied to the LB medium containing 100 μM IPTG, 40 μg/mL of X-Gal, and 40 μg/mL of kanamycin, and cultured overnight. Then, white colonies that appeared were picked up, and separated into single colonies to obtain transformants. Plasmids were extracted from the obtained transformants, and one in which the target PCR product was inserted was designated as pBS4SΔ2256adhC.

<2-1-2> Construction of FKFC5 strain (FKS0165ΔNCgl0324 strain)

Since pBS4SΔ2256adhC obtained above does not contain the region enabling autonomous replication of the plasmid in cells of coryneform bacteria, if coryneform bacteria are transformed with this plasmid, a strain in which this plasmid is incorporated into the genome by homologous recombination appears as a transformant, although it occurs at an extremely low frequency. Therefore, pBS4S42256adhC was introduced into the *C. glutamicum* FKS0165 strain by the electric pulse method. The cells were applied to the CM-Dex agar medium containing 25 μg/mL of kanamycin, and cultured at 31.5° C. It was confirmed by PCR that the grown strain was a once-recombinant strain in which pBS4SΔ2256adhC was incorporated into the genome by homologous recombination. This once-recombinant strain had both the wild-type NCgl0324 gene, and the deficient-type NCgl0324 gene. [000290] The once-recombinant strain was cultured overnight in the CM-Dex liquid medium, the culture medium was applied to the S10 agar medium, and culture was performed at 31.5° C. Among the colonies that appeared, a strain that showed kanamycin susceptibility was purified on the CM-Dex agar medium. Genomic DNA was prepared from the purified strain, and used to perform PCR with the synthetic DNAs of SEQ ID NOS: 61 and 62 as the primers to confirm deletion of the NCgl0324 gene, and the strain was designated as FKFC5 strain.

<2-2> Construction of FKFC11 strain (2256ΔvanABKΔNCgl0324ΔNCgl0313 strain)

<2-2-1> Construction of plasmid pBS4SΔ2256adhE for deletion of NCgl0313 gene

PCR was performed by using the genomic DNA of the *C. glutamicum* 2256 strain as the template, and the synthetic DNAs of SEQ ID NOS: 63 and 64 as the primers to obtain a PCR product containing an N-terminus side coding region of the NCgl0313 gene. Separately, PCR was performed by using the genomic DNA of the *C. glutamicum* 2256 strain as the template, and the synthetic DNAs of SEQ ID NOS: 65 and 66 as the primers to obtain a PCR product containing a C-terminus side coding region of the NCgl0313 gene. The sequences of SEQ ID NOS: 64 and 65 are partially complementary to each other. Then, approximately equimolar amounts of the PCR product containing the N-terminus side coding region of the NCgl0313 gene and the PCR product containing the C-terminus side coding region of the NCgl0313 gene were mixed, and inserted into the pBS4S vector (WO2007/046389) treated with BamHI and PstI by using In Fusion HD Cloning Kit (Clontech). With this DNA, competent cells of *Escherichia coli* JM109 (Takara Bio) were transformed, and the cells were applied to the LB medium containing 100 μM IPTG, 40 μg/mL of X-Gal, and 40 μg/mL of kanamycin, and cultured overnight. Then, white colonies that appeared were picked up, and separated into single colonies to obtain transformants. Plasmids were extracted from the obtained transformants, and one in which the target PCR product was inserted was designated as pBS4SΔ2256adhE.

<2-2-2> Construction of FKFC11 strain (2256ΔvanABKΔNCgl0324ΔNCgl0313 strain)

Since pBS4SΔ2256adhE obtained above does not contain the region enabling autonomous replication of the plasmid in cells of coryneform bacteria, if coryneform bacteria are transformed with this plasmid, a strain in which this plasmid is incorporated into the genome by homologous recombination appears as a transformant, although it occurs at an extremely low frequency. Therefore, pBS4SΔ2256adhE was introduced into the *C. glutamicum* FKFC5 strain by the electric pulse method. The cells were applied to the CM-Dex agar medium containing 25 μg/mL of kanamycin, and cultured at 31.5° C. It was confirmed by PCR that the grown strain was a once-recombinant strain in which pBS4SΔ2256adhE was incorporated into the genome by homologous recombination. This once-recombinant strain had both the wild-type NCgl0313 gene, and the deficient-type NCgl0313 gene.

The once-recombinant strain was cultured overnight in the CM-Dex liquid medium, the culture medium was applied to the S10 agar medium, and culture was performed at 31.5° C. Among the colonies that appeared, a strain that showed kanamycin susceptibility was purified on the CM-Dex agar medium. Genomic DNA was prepared from the purified strain, and used to perform PCR with the synthetic DNAs of SEQ ID NOS: 67 and 68 as the primers to confirm deletion of the NCgl0313 gene, and the strain was designated as FKFC11 strain.

<2-3> Construction of FKFC14 strain (2256ΔvanABKΔNCgl0324ΔNCgl0313ΔNCgl2709 strain)

<2-3-1> Construction of plasmid pBS4SΔ2256adhA for deletion of NCgl2709 gene

PCR was performed by using the genomic DNA of the *C. glutamicum* 2256 strain as the template, and the synthetic DNAs of SEQ ID NOS: 69 and 70 as the primers to obtain a PCR product containing an N-terminus side coding region of the NCgl2709 gene. Separately, PCR was performed by using the genomic DNA of the *C. glutamicum* 2256 strain as the template, and the synthetic DNAs of SEQ ID NOS: 71 and 72 as the primers to obtain a PCR product containing a C-terminus side coding region of the NCgl2709 gene. The sequences of SEQ ID NOS: 70 and 71 are partially complementary to each other. Then, approximately equimolar amounts of the PCR product containing the N-terminus side coding region of the NCgl2709 gene and the PCR product containing the C-terminus side coding region of the NCgl2709 gene were mixed, and inserted into the pBS4S vector treated with BamHI and PstI by using In Fusion HD Cloning Kit (Clontech). With this DNA, competent cells of *Escherichia coli* JM109 (Takara Bio) were transformed, and the cells were applied to the LB medium containing 100 μM IPTG, 40 μg/mL of X-Gal, and 40 μg/mL of kanamycin, and cultured overnight. Then, white colonies that appeared were picked up, and separated into single colonies to obtain transformants. Plasmids were extracted from the obtained transformants, and one in which the target PCR product was inserted was designated as pBS4SΔ2256adhA.

<2-3-2> Construction of FKFC14 strain (2256ΔvanABKΔNCgl0324ΔNCgl0313ΔNCgl2709 strain)

Since pBS4SΔ2256adhA obtained above does not contain the region enabling autonomous replication of the plasmid in cells of coryneform bacteria, if coryneform bacteria are transformed with this plasmid, a strain in which this plasmid is incorporated into the genome by homologous recombination appears as a transformant, although it occurs at an extremely low frequency. Therefore, pBS4SΔ2256adhA was introduced into the *C. glutamicum* FKFC11 strain by the electric pulse method. The cells were applied to the CM-Dex agar medium containing 25 μg/mL of kanamycin, and cultured at 31.5° C. It was confirmed by PCR that the grown strain was a once-recombinant strain in which pBS4SΔ2256adhA was incorporated into the genome by homologous recombination. This once-recombinant strain had both the wild-type NCgl2709 gene, and the deficient-type NCgl2709 gene.

The once-recombinant strain was cultured overnight in the CM-Dex liquid medium, the culture medium was applied to the S10 agar medium, and culture was performed at 31.5° C. Among the colonies that appeared, a strain that showed kanamycin susceptibility was purified on the CM-Dex agar medium. Genomic DNA was prepared from the purified strain, and used to perform PCR with the synthetic DNAs of SEQ ID NOS: 73 and 74 as the primers to confirm deletion of the NCgl2709 gene, and the strain was designated as FKFC14 strain.

<3> Construction of vanillin-producing strains

<3-1> Construction of plasmids for co-expression of CAR and PPT genes

A plasmid pVK9::Ptuf*-Nb_ACAR-entD for co-expression of CAR gene of *Nocardia brasiliensis* (Nb_ACAR) and PPT gene (entD) of *E. coli*, a plasmid pVK9::Ptuf*-Ge_ACAR-entD for co-expression of CAR gene of *Gordonia effusa* (Ge_ACAR) and PPT gene (entD) of *E. coli*, a plasmid pVK9::Ptuf*-Nm_ACAR-entD for co-expression of CAR gene of *Novosphingobium malaysiense* (Nm_ACAR) and PPT gene (entD) of *E. coli*, and a plasmid pVK9::Ptuf*-Cs2_ACAR-entD for co-expression of CAR gene of *Coccomyxa subelhpsoidea* C-169 (Cs2_ACAR) and PPT gene (entD) of *E. coli* were constructed via the following procedure. PPT catalyzes the addition of a phosphopantetheinyl group into CAR to thereby activate CAR. The CAR genes were codon-optimized for the codon usage of *E. coli* and used. These genes were cloned into the pVK9 vector (WO2007/046389). The pVK9 vector is a shuttle-vector for coryneform bacteria and *Escherichia coli*.

The pVK9 vector was treated with BamHI and PstI, and inserted with a DNA fragment comprising an artificial operon consisting of Tuf* promoter, SD sequence, Nb_ACAR (codon-optimized), SD sequence, and *E. coli* entD gene in this order, to obtain the plasmid pVK9::Ptuf*-Nb_ACAR-entD. The nucleotide sequence of the portion containing the inserted DNA fragment of this plasmid is shown as SEQ ID NO: 19, wherein the inserted DNA fragment corresponds to position 16-4621.

The pVK9 vector was treated with BamHI and PstI, and inserted with a DNA fragment comprising an artificial operon consisting of Tuf* promoter, SD sequence, Ge_ACAR (codon-optimized), SD sequence, and *E. coli* entD gene in this order, to obtain the plasmid pVK9::Ptuf*-Ge_ACAR-entD. The nucleotide sequence of the portion containing the inserted DNA fragment of this plasmid is shown as SEQ ID NO: 20, wherein the inserted DNA fragment corresponds to position 16-4517. Also, the nucleotide sequence of Ge_ACAR (codon-optimized) is shown as SEQ ID NO: 77.

The pVK9 vector was treated with BamHI and PstI, and inserted with a DNA fragment comprising an artificial operon consisting of Tuf* promoter, SD sequence, Nm_ACAR (codon-optimized), SD sequence, and *E. coli* entD gene in this order, to obtain the plasmid pVK9::Ptuf*-Nm_ACAR-entD. The nucleotide sequence of the portion containing the inserted DNA fragment of this plasmid is shown as SEQ ID NO: 80, wherein the inserted DNA fragment corresponds to position 16-4528. Also, the nucleotide sequence of Nm_ACAR (codon-optimized) is shown as SEQ ID NO: 81.

The pVK9 vector was treated with BamHI and PstI, and inserted with a DNA fragment comprising an artificial operon consisting of the Tuf* promoter, SD sequence, Cs2_ACAR (codon-optimized), SD sequence, and *E. coli* entD gene in this order, to obtain the plasmid pVK9::Ptuf*-Cs2_ACAR-entD. The nucleotide sequence of the portion containing the inserted DNA fragment of this plasmid is shown as SEQ ID NO: 84, wherein the inserted DNA fragment corresponds to position 16-4702. Also, the nucleotide sequence of Cs2_ACAR (codon-optimized) is shown as SEQ ID NO: 85.

<3-2> Construction of plasmid pVS7::Plac-vanK for expression of vanK gene vanK gene encodes a vanillic acid uptake system. Thus, in order to improve the uptake of vanillic acid, a plasmid pVS7::Plac-vanK for expression of vanK gene of the *C. glutamicum* 2256 strain was constructed via the following procedure.

PCR was performed by using the genomic DNA of the *C. glutamicum* 2256 strain as the template, and the synthetic DNAs of SEQ ID NOS: 75 and 76 as the primers to obtain a PCR product containing an ORF and SD sequence of vanK gene. Then, the PCR product was inserted into the pVS7 vector (WO2013/069634) treated with BamHI and PstI by using In Fusion HD Cloning Kit (Clontech). The pVS7 vector is a shuttle-vector for coryneform bacteria and *Escherichia coli*. With this DNA, competent cells of *Escherichia coli* JM109 (Takara Bio) were transformed, and the cells were applied to the LB medium containing 100 μM IPTG, 40 μg/mL of X-Gal, and 50 μg/mL of spectinomycin, and cultured overnight. Then, white colonies that appeared were picked up, and separated into single colonies to obtain transformants. Plasmids were extracted from the obtained transformants, and one into which the target PCR product was inserted was designated as pVS7::Plac-vanK. In this plasmid, the cloned vanK gene is expressed from lac promoter derived from the pVS7 vector.

<3-3> Construction of vanillin-producing strains

The plasmid pVK9::Ptuf*-Nb_ACAR-entD, pVK9::Ptuf*-Ge_ACAR-entD, pVK9::Ptuf*-Nm_ACAR-entD, or pVK9::Ptuf*-Cs2_ACAR-entD, as well as the plasmid pVS7::Plac-vanK, was introduced into the *C. glutamicum* FKFC14 strain by the electric pulse method. The cells were applied to the CM-Dex SGFC agar medium (2.5 g/L of glucose, 2.5 g/L of fructose, 10 g/L of polypeptone, 10 g/L of yeast extract, 1 g/L of $KH_2PO_4$, 0.4 g/L of $MgSO_4$-$7H_2O$, 0.01 g/L of $FeSO_4$-$7H_2O$, 0.01 g/L of $MnSO_4$-$7H_2O$, 2 g/L of disodium succinate hexahydrate, 4 g/L of sodium gluconate, 3 g/L of urea, 1.2 g/L of soybean hydrolysate, 10 μg/L of biotin, 15 g/L of agar, adjusted to pH 7.5 with NaOH) containing 25 μg/mL of kanamycin and 50 μg/mL of spectinomycin, and cultured at 31.5° C. The grown strains were purified on the same agar medium, and designated as FKFC14/pVK9::Ptuf*-Nb_ACAR-entD pVS7-vanK, FKFC14/pVK9::Ptuf*-Ge_ACAR-entD pVS7-vanK, FKFC14/pVK9::Ptuf*-Nm_ACAR-entD pVS7-vanK, and FKFC14/pVK9::Ptuf*-Cs2_ACAR-entD pVS7-vanK, respectively. These strains were each inoculated into 4 mL of the CM-Dex SGFC medium (having the same composition as that of the CM-Dex SGFC agar medium except that it does not contain agar) contained in a test tube, and cultured at 31.5° C. with shaking for about 16 hr. A 0.9 mL aliquot of the obtained culture broth was mixed with 0.6 mL of 50% glycerol aqueous solution to obtain a glycerol stock, and stored at −80° C.

<4> Comparison of vanillin production and protocatechualdehyde production by *C. glutamicum* vanillin-producing strains A 20 μL aliquot of each of the glycerol stocks of the constructed vanillin-producing strains was applied to the CM-Dex SGFC agar medium, and cultured at 31.5° C. for 20 hr as preculture. The obtained cells were suspended in sterilized physiological saline. The optical density (OD) of the cell suspension was measured, and the cell suspension was diluted with physiological saline to obtain an OD at 600 nm of 83. A 1.5 mL aliquot of the diluted cell suspension was inoculated into 3.5 mL of a vanillin production medium (42.9 g/L of vanillic acid, 85.7 g/L of glucose, 10 g/L of polypeptone, 10 g/L of yeast extract, 1 g/L of $KH_2PO_4$, 0.4 g/L of $MgSO_4\text{-}7H_2O$, 0.01 g/L of $FeSO_4\text{-}7H_2O$, 0.01 g/L of $MnSO_4\text{-}7H_2O$, 3 g/L of urea, 1.2 g/L of soybean hydrolysate, 10 µg/L of biotin, adjusted to pH 7.4 with KOH, and then mixed with 8.6 g/L of $CaCO_3$ (sterilized with hot air at 180° C. for 3 hours)) containing 25 µg/mL of kanamycin and 50 µg/mL of spectinomycin, or a protocatechualdehyde production medium (42.9 g/L of protocatechuic acid, 85.7 g/L of glucose, 10 g/L of polypeptone, 10 g/L of yeast extract, 1 g/L of $KH_2PO_4$, 0.4 g/L of $MgSO_4\text{-}7H_2O$, 0.01 g/L of $FeSO_4\text{-}7H_2O$, 0.01 g/L of $MnSO_4\text{-}7H_2O$, 3 g/L of urea, 1.2 g/L of soybean hydrolysate, 10 µg/L of biotin, adjusted to pH 7.4 with KOH, and then mixed with 8.6 g/L of $CaCO_3$ (sterilized with hot air at 180° C. for 3 hours)) containing 25 µg/mL of kanamycin and 50 µg/mL of spectinomycin, contained in a test tube, and cultured at 30° C. with shaking for 21 hr.

At the start and completion of the culture, the concentration of glucose in the medium was analyzed with Biotech Analyzer AS-310 (Sakura SI). The concentrations of vanillic acid, vanillin, protocatechuic acid, and protocatechualdehyde in the medium were also analyzed by using Ultra Performance Liquid Chromatography NEXERA X2 System (SHIMADZU) with the following conditions.

Conditions of UPLC analysis

Column: KINETEX 2.6 µm XB-C18, 150×30 mm (Phenomenex)

Oven temperature: 40° C.

Mobile phase (A): 0.1% Trifluoroacetic acid

Mobile phase (B): 0.1% Trifluoroacetic acid/80% acetonitrile

Gradient program (time, A (%), B (%)): (0, 90, 10) → (3, 80, 20)

Flow rate: 1.5 ml/min

The results are shown in Tables 1-3.

V/P ratio, that is, the ratio of the production amount of vanillin with respect to the production amount of protocatechualdehyde, observed for the FKFC14/pVK9::Ptuf*-Ge_ACAR-entD pVS7-vanK strain was about 1.4 times as high as that observed for the FKFC14/pVK9::Ptuf*-Nb_ACAR-entD pVS7-vanK strain (Table 1). Therefore, it was concluded that Ge_ACAR is useful for production of vanillin.

FKFC14/pVK9::Ptuf*-Nb_ACAR-entD pVS7-vanK strain produced protocatechualdehyde at a concentration of 9.6 g/L, while FKFC14/pVK9::Ptuf*-Nm_ACAR-entD pVS7-vanK strain did not produce protocatechualdehyde (Table 2). Therefore, it was concluded that Nm_ACAR is useful for production of vanillin.

V/P ratio, that is, the ratio of the production amount of vanillin with respect to the production amount of protocatechualdehyde, observed for the FKFC14/pVK9::Ptuf*-Cs2_ACAR-entD pVS7-vanK strain was about 1.6 times as high as that observed for the FKFC14/pVK9::Ptuf*-Nb_ACAR-entD pVS7-vanK strain (Table 3). Therefore, it was concluded that Cs2_ACAR is useful for production of vanillin.

TABLE 1

Vanillin and protocatechualdehyde production by *C. glutamicum* vanillin-producing strains (average ± S.E.)

| | Substrate: V. acid | | | | |
|---|---|---|---|---|---|
| | At the start of culture | | At the completion of culture | | |
| Strain | Glc concn. (g/L) | V. acid concn. (g/L) | Glc concn. (g/L) | V. acid concn. (g/L) | Vanillin concn. (g/L) |
| FKFC14/pVK9::Ptuf*-Nb_ACAR-entD pVS7-vanK | 59.2 ± 0.0 | 29.7 ± 0.2 | 36.9 ± 0.7 | 1.5 ± 0.1 | 23.0 ± 0.1 |
| FKFC14/pVK9::Ptuf*-Ge_ACAR-entD pVS7-vanK | 59.9 ± 0.0 | 29.7 ± 0.0 | 26.3 ± 0.5 | 7.3 ± 0.0 | 18.5 ± 0.1 |

| | Substrate: P. acid | | | | | |
|---|---|---|---|---|---|---|
| | At the start of culture | | At the completion of culture | | | |
| Strain | Glc concn. (g/L) | P. acid concn. (g/L) | Glc concn. (g/L) | P. acid concn. (g/L) | P. ald. concn. (g/L) | V/P ratio (g/g) |
| FKFC14/pVK9::Ptuf*-Nb_ACAR-entD pVS7-vanK | 62.1 ± 0.7 | 33.4 ± 0.2 | 26.1 ± 0.2 | 15.9 ± 0.2 | 9.6 ± 0.1 | 2.4 |
| FKFC14/pVK9::Ptuf*-Ge_ACAR-entD pVS7-vanK | 62.5 ± 0.2 | 31.2 ± 0.8 | 19.1 ± 0.2 | 22.6 ± 0.0 | 5.5 ± 0.1 | 3.4 |

Abbreviations:

Glc, glucose;

V. acid, vanillic acid;

P. acid, protocatechuic acid;

P. ald., protocatechualdehyde;

concn., concentration;

V/P ratio, the ratio of the production amount of vanillin with respect to the production amount of protocatechualdehyde.

TABLE 2

Vanillin and protocatechualdehyde production by *C. glutamicum* vanillin-producing strains (average ± S.E.)

| | Substrate: V. acid | | | | |
|---|---|---|---|---|---|
| | At the start of culture | | At the completion of culture | | |
| Strain | Glc concn. (g/L) | V. acid concn. (g/L) | Glc concn. (g/L) | V. acid concn. (g/L) | Vanillin concn. (g/L) |
| FKFC14/pVK9::Ptuf*-Nb_ACAR-entD pVS7-vanK | 59.2 ± 0.0 | 29.7 ± 0.2 | 36.9 ± 0.7 | 1.5 ± 0.1 | 23.0 ± 0.1 |
| FKFC14/pVK9::Ptuf*-Nm_ACAR-entD pVS7-vanK | 60.6 ± 0.5 | 30.9 ± 0.7 | 20.3 ± 1 | 28.3 ± 0.4 | 3.7 ± 0.2 |

| | Substrate: P. acid | | | | | |
|---|---|---|---|---|---|---|
| | At the start of culture | | At the completion of culture | | | |
| Strain | Glc concn. (g/L) | P. acid concn. (g/L) | Glc concn. (g/L) | P. acid concn. (g/L) | P. ald. concn. (g/L) | V/P ratio (g/g) |
| FKFC14/pVK9::Ptuf*-Nb_ACAR-entD pVS7-vanK | 62.1 ± 0.7 | 33.4 ± 0.2 | 26.1 ± 0.2 | 15.9 ± 0.2 | 9.6 ± 0.1 | 2.4 |
| FKFC14/pVK9::Ptuf*-Nm_ACAR-entD pVS7-vanK | 62.5 ± 0.7 | 31.0 ± 0.4 | 24.7 ± 0.2 | 24.5 ± 0.1 | N.D. | — |

Abbreviations:
Glc, glucose;
V. acid, vanillic acid;
P. acid, protocatechuic acid;
P. ald., protocatechualdehyde;
concn., concentration;
N.D., Not Detected;
V/P ratio, the ratio of the production amount of vanillin with respect to the production amount of protocatechualdehyde.

TABLE 3

Vanillin and protocatechualdehyde production by *C. glutamicum* vanillin-producing strains (average ± S.E.)

| | Substrate: V. acid | | | | |
|---|---|---|---|---|---|
| | At the start of culture | | At the completion of culture | | |
| Strain | Glc concn. (g/L) | V. acid concn. (g/L) | Glc concn. (g/L) | V. acid concn. (g/L) | Vanillin concn. (g/L) |
| FKFC14/pVK9::Ptuf*-Nb_ACAR-entD pVS7-vanK | 59.2 ± 0.0 | 29.7 ± 0.2 | 36.9 ± 0.7 | 1.5 ± 0.1 | 23.0 ± 0.1 |
| FKFC14/pVK9::Ptuf*-Cs2_ACAR-entD pVS7-vanK | 60.6 ± 0.0 | 29.9 ± 0.0 | 25.2 ± 0.5 | 14.4 ± 0.1 | 13.6 ± 0.3 |

| | Substrate: P. acid | | | | | |
|---|---|---|---|---|---|---|
| | At the start of culture | | At the completion of culture | | | |
| Strain | Glc concn. (g/L) | P. acid concn. (g/L) | Glc concn. (g/L) | P. acid concn. (g/L) | P. ald. concn. (g/L) | V/P ratio (g/g) |
| FKFC14/pVK9::Ptuf*-Nb_ACAR-entD pVS7-vanK | 62.1 ± 0.7 | 33.4 ± 0.2 | 26.1 ± 0.2 | 15.9 ± 0.2 | 9.6 ± 0.1 | 2.4 |

TABLE 3-continued

Vanillin and protocatechualdehyde production by *C. glutamicum*
vanillin-producing strains (average ± S.E.)

| | | | | | | |
|---|---|---|---|---|---|---|
| FKFC14/pVK9::Ptuf*-Cs2_ACAR-entD pVS7-vanK | 62.8 ± 0.2 | 30.3 ± 0.3 | 18.7 ± 0.7 | 23.3 ± 0.1 | 3.7 ± 0.0 | 3.7 |

Abbreviations:
Glc, glucose;
V. acid, vanillic acid;
P. acid, protocatechuic acid;
P. ald., protocatechualdehyde;
concn., concentration;
V/P ratio, the ratio of the production amount of vanillin with respect to the production amount of protocatechualdehyde.

<5> Comparison of vanillin production and isovanillin production by *C. glutamicum* vanillin-producing strains A 20 μL aliquot of each of the glycerol stocks of the constructed vanillin-producing strains was applied to the CM-Dex SGFC agar medium, and cultured at 31.5° C. for 20 hr as preculture. The obtained cells were suspended in sterilized physiological saline. The optical density (OD) of the cell suspension was measured, and the cell suspension was diluted with physiological saline to obtain an OD at 600 nm of 83. A 1.5 mL aliquot of the diluted cell suspension was inoculated into 3.5 mL of a vanillin production medium (42.9 g/L of vanillic acid, 85.7 g/L of glucose, 10 g/L of polypeptone, 10 g/L of yeast extract, 1 g/L of $KH_2PO_4$, 0.4 g/L of $MgSO_4$-$7H_2O$, 0.01 g/L of $FeSO_4$-$7H_2O$, 0.01 g/L of $MnSO_4$-$7H_2O$, 3 g/L of urea, 1.2 g/L of soybean hydrolysate, 10 μg/L of biotin, adjusted to pH 7.4 with KOH, and then mixed with 8.6 g/L of $CaCO_3$ (sterilized with hot air at 180° C. for 3 hours)) containing 25 μg/mL of kanamycin and 50 μg/mL of spectinomycin, or a isovanillin production medium (42.9 g/L of isovanillic acid, 85.7 g/L of glucose, 10 g/L of polypeptone, 10 g/L of yeast extract, 1 g/L of $KH_2PO_4$, 0.4 g/L of $MgSO_4$-$7H_2O$, 0.01 g/L of $FeSO_4$-$7H_2O$, 0.01 g/L of $MnSO_4$-$7H_2O$, 3 g/L of urea, 1.2 g/L of soybean hydrolysate, 10 μg/L of biotin, adjusted to pH 7.4 with KOH, and then mixed with 8.6 g/L of $CaCO_3$ (sterilized with hot air at 180° C. for 3 hours)) containing 25 μg/mL of kanamycin and 50 μg/mL of spectinomycin, contained in a test tube, and cultured at 30° C. with shaking for 21 hr.

At the start and completion of the culture, the concentration of glucose in the medium was analyzed with Biotech Analyzer AS-310 (Sakura SI). The concentrations of vanillic acid, vanillin, isovanillic acid, and isovanillin in the medium were also analyzed by using Ultra Performance Liquid Chromatography NEXERA X2 System (SHIMADZU) with the following conditions.

Conditions of UPLC analysis
Column: KINETEX 2.6 μm XB-C18, 150×30 mm (Phenomenex)
Oven temperature: 40° C.
Mobile phase (A): 0.1% Trifluoroacetic acid
Mobile phase (B): 0.1% Trifluoroacetic acid/80% acetonitrile
Gradient program (time, A (%), B (%)): (0, 90, 10) → (3, 80, 20)
Flow rate: 1.5 ml/min
The results are shown in Tables 4-5.

Isovanillin production was not observed for the FKFC14/pVK9::Ptuf*-Nm_ACAR-entD pVS7-vanK strain, while the FKFC14/pVK9::Ptuf*-Nb_ACAR-entD pVS7-vanK strain produced isovanillin at a concentration of 9.3 g/L (Table 4). Therefore, it was concluded that Nm_ACAR is useful for production of vanillin.

V/iV ratio, that is, the ratio of the production amount of vanillin with respect to the production amount of isovanillin, observed for the FKFC14/pVK9::Ptuf*-Cs2_ACAR-entD pVS7-vanK strain was approximately 1.2 times as high as that observed for the FKFC14/pVK9::Ptuf*-Nb_ACAR-entD pVS7-vanK strain (Table 5). Therefore, it was concluded that Cs2_ACAR is useful for production of vanillin.

TABLE 4

Vanillin and isovanillin production by *C. glutamicum*
vanillin-producing strains (average ± S.E.)

| | Substrate: V. acid | | | | |
|---|---|---|---|---|---|
| | At the start of culture | | At the completion of culture | | |
| Strain | Glc concn. (g/L) | V. acid concn. (g/L) | Glc concn. (g/L) | V. acid concn. (g/L) | Vanillin concn. (g/L) |
| FKFC14/pVK9::Ptuf*-Nb_ACAR-entD pVS7-vanK | 59.9 ± 0.5 | 31.9 ± 1.4 | 40.8 ± 0.2 | 1.8 ± 0.3 | 26.5 ± 0.3 |
| FKFC14/pVK9::Ptuf*-Nm_ACAR-entD pVS7-vanK | 60.7 ± 0.2 | 32.8 ± 0.1 | 16.5 ± 0.5 | 29.8 ± 0.5 | 2.7 ± 0.2 |

TABLE 4-continued

Vanillin and isovanillin production by *C. glutamicum* vanillin-producing strains (average ± S.E.)

| | Substrate: iV. acid | | | | | |
|---|---|---|---|---|---|---|
| | At the start of culture | | At the completion of culture | | | |
| Strain | Glc concn. (g/L) | iV. acid concn. (g/L) | Glc concn. (g/L) | iV. acid concn. (g/L) | Iso-vanillin concn. (g/L) | V/iV ratio (g/g) |
| FKFC14/pVK9::Ptuf*-Nb_ACAR-entD pVS7-vanK | 60.9 ± 0.5 | 29.3 ± 0.0 | 43.2 ± 0.7 | 19.0 ± 0.6 | 9.3 ± 0.8 | 2.9 |
| FKFC14/pVK9::Ptuf*-Nm_ACAR-entD pVS7-vanK | 60.2 ± 0.0 | 30.4 ± 0.2 | 13.3 ± 0.0 | 29.5 ± 0.5 | N.D. | — |

Abbreviations:
Glc, glucose;
V. acid, vanillic acid;
iV. acid, isovanillic acid;
concn., concentration;
N.D., Not Detected;
V/iV ratio, the ratio of the production amount of vanillin with respect to the production amount of isovanillin.

TABLE 5

Vanillin and isovanillin production by *C. glutamicum* vanillin-producing strains (average ± S.E.)

| | Substrate: V. acid | | | | |
|---|---|---|---|---|---|
| | At the start of culture | | At the completion of culture | | |
| Strain | Glc concn. (g/L) | V. acid concn. (g/L) | Glc concn. (g/L) | V. acid concn. (g/L) | Vanillin concn. (g/L) |
| FKFC14/pVK9::Ptuf*-Nb_ACAR-entD pVS7-vanK | 59.9 ± 0.5 | 31.9 ± 1.4 | 40.8 ± 0.2 | 1.8 ± 0.3 | 26.5 ± 0.3 |
| FKFC14/pVK9::Ptuf*-Cs2_ACAR-entD pVS7-vanK | 60.9 ± 0.0 | 34.1 ± 0.2 | 18.0 ± 1.2 | 17.8 ± 0.1 | 13.5 ± 0.6 |

| | Substrate: iV. acid | | | | | |
|---|---|---|---|---|---|---|
| | At the start of culture | | At the completion of culture | | | |
| Strain | Glc concn. (g/L) | iV. acid concn. (g/L) | Glc concn. (g/L) | iV. acid concn. (g/L) | Iso-vanillin concn. (g/L) | V/iV ratio (g/g) |
| FKFC14/pVK9::Ptuf*-Nb_ACAR-entD pVS7-vanK | 60.9 ± 0.5 | 29.3 ± 0.0 | 43.2 ± 0.7 | 19.0 ± 0.6 | 9.3 ± 0.8 | 2.9 |
| FKFC14/pVK9::Ptuf*-Cs2_ACAR-entD pVS7-vanK | 60.4 ± 0.2 | 30.2 ± 0.2 | 3.9 ± 0.0 | 26.8 ± 0.0 | 4.0 ± 0.0 | 3.4 |

Abbreviations:
Glc, glucose;
V. acid, vanillic acid;
iV. acid, isovanillic acid;
concn., concentration;
N.D., Not Detected;
V/iV ratio, the ratio of the production amount of vanillin with respect to the production amount of isovanillin.

INDUSTRIAL APPLICABILITY

According to the present invention, an ability of a microorganism for producing an objective substance, i.e. an aldehyde such as vanillin, can be improved, and the objective substance can be efficiently produced.

EXPLANATION OF SEQUENCE LISTING

SEQ ID NOS:

1: Nucleotide sequence of aroG gene of *Escherichia coli* MG1655
2: Amino acid sequence of AroG protein of *Escherichia coli* MG1655
3: Nucleotide sequence of aroB gene of *Escherichia coli* MG1655
4: Amino acid sequence of AroB protein of *Escherichia coli* MG1655
5: Nucleotide sequence of aroD gene of *Escherichia coli* MG1655
6: Amino acid sequence of AroD protein of *Escherichia coli* MG1655
7: Nucleotide sequence of asbF gene of *Bacillus thuringiensis* BMB171
8: Amino acid sequence of AsbF protein of *Bacillus thuringiensis* BMB171
9: Nucleotide sequence of tyrR gene of *Escherichia coli* MG1655
10: Amino acid sequence of TyrR protein of *Escherichia coli* MG1655
11-14: Nucleotide sequences of transcript variants 1 to 4 of OMT gene of *Homo sapiens*
15: Amino acid sequence of OMT isoform (MB-COMT) of *Homo sapiens*
16: Amino acid sequence of OMT isoform (S-COMT) of *Homo sapiens*
17: Nucleotide sequence of CAR gene of *Gordonia effusa*
18: Amino acid sequence of CAR protein of *Gordonia effusa*
19: Nucleotide sequence of DNA fragment containing CAR gene of *Nocardia brasiliensis* (codon-optimized) and entD gene of *Escherichia coli*
20: Nucleotide sequence of DNA fragment containing CAR gene of *Gordonia effusa* (codon-optimized) and entD gene of *Escherichia coli*
21: Nucleotide sequence of entD gene of *Escherichia coli* MG1655
22: Amino acid sequence of EntD protein of *Escherichia coli* MG1655
23: Nucleotide sequence of PPT gene of *Corynebacterium glutamicum* ATCC 13032
24: Amino acid sequence of PPT protein of *Corynebacterium glutamicum* ATCC 13032
25: Nucleotide sequence of vanK gene of *Corynebacterium glutamicum* 2256 (ATCC 13869)
26: Amino acid sequence of VanK protein of *Corynebacterium glutamicum* 2256 (ATCC 13869)
27: Nucleotide sequence of pcaK gene of *Corynebacterium glutamicum* 2256 (ATCC 13869)
28: Amino acid sequence of PcaK protein of *Corynebacterium glutamicum* 2256 (ATCC 13869)
29: Nucleotide sequence of vanA gene of *Corynebacterium glutamicum* 2256 (ATCC 13869)
30: Amino acid sequence of VanA protein of *Corynebacterium glutamicum* 2256 (ATCC 13869)
31: Nucleotide sequence of vanB gene of *Corynebacterium glutamicum* 2256 (ATCC 13869)
32: Amino acid sequence of VanB protein of *Corynebacterium glutamicum* 2256 (ATCC 13869)
33: Nucleotide sequence of pcaG gene of *Corynebacterium glutamicum* ATCC 13032
34: Amino acid sequence of PcaG protein of *Corynebacterium glutamicum* ATCC 13032
35: Nucleotide sequence of pcaH gene of *Corynebacterium glutamicum* ATCC 13032
36: Amino acid sequence of PcaH protein of *Corynebacterium glutamicum* ATCC 13032
37: Nucleotide sequence of yqhD gene of *Escherichia coli* MG1655
38: Amino acid sequence of YqhD protein of *Escherichia coli* MG1655
39: Nucleotide sequence of NCgl0324 gene of *Corynebacterium glutamicum* 2256 (ATCC 13869)
40: Amino acid sequence of NCgl0324 protein of *Corynebacterium glutamicum* 2256 (ATCC 13869)
41: Nucleotide sequence of NCgl0313 gene of *Corynebacterium glutamicum* 2256 (ATCC 13869)
42: Amino acid sequence of NCgl0313 protein of *Corynebacterium glutamicum* 2256 (ATCC 13869)
43: Nucleotide sequence of NCgl2709 gene of *Corynebacterium glutamicum* 2256 (ATCC 13869)
44: Amino acid sequence of NCgl2709 protein of *Corynebacterium glutamicum* 2256 (ATCC 13869)
45: Nucleotide sequence of NCgl0219 gene of *Corynebacterium glutamicum* ATCC 13032
46: Amino acid sequence of NCgl0219 protein of *Corynebacterium glutamicum* ATCC 13032
47: Nucleotide sequence of NCgl2382 gene of *Corynebacterium glutamicum* ATCC 13032
48: Amino acid sequence of NCgl2382 protein of *Corynebacterium glutamicum* ATCC 13032
49: Nucleotide sequence of aroE gene of *Escherichia coli* MG1655
50: Amino acid sequence of AroE protein of *Escherichia coli* MG1655
51-76: Primers
77: Nucleotide sequence of CAR gene of *Gordonia effusa* codon-optimized for codon usage of *E. coli*
78: Nucleotide sequence of CAR gene of *Novosphingobium malaysiense*
79: Amino acid sequence of CAR protein of *Novosphingobium malaysiense*
80: Nucleotide sequence of DNA fragment containing CAR gene of *Novosphingobium malaysiense* (codon-optimized) and entD gene of *Escherichia coli*
81: Nucleotide sequence of CAR gene of *Novosphingobium malaysiense* codon-optimized for codon usage of *E. coli*
82: Nucleotide sequence of CAR gene (cDNA) of *Coccomyxa subellpsoidea* C-169
83: Amino acid sequence of CAR protein of *Coccomyxa subelhpsoidea* C-169
84: Nucleotide sequence of DNA fragment containing CAR gene of *Coccomyxa subelhpsoidea* (codon-optimized) and entD gene of *Escherichia coli*
85: Nucleotide sequence of CAR gene of *Coccomyxa subelhpsoidea* codon-optimized for codon usage of *E. coli*

The invention claimed is:

1. A method for producing an objective substance, the method comprising:
producing the objective substance by using a microorganism having an ability to produce the objective substance,
wherein said producing comprises:
(A) cultivating cells of the microorganism in a culture broth or medium containing a carbon source to produce and accumulate the objective substance in the culture broth or medium;
(B) cultivating cells of the microorganism in a culture broth or medium containing a precursor of the objective substance to produce and accumulate the objective substance in the culture broth or medium; or
(C) allowing cells of the microorganism to act on a precursor of the objective substance in a reaction mixture to produce and accumulate the objective substance in the reaction mixture,
wherein the objective substance is an aldehyde,
wherein the precursor is a substance selected from the group consisting of protocatechuic acid, vanillic acid, benzoic acid, L-phenylalanine, cinnamic acid, and combinations thereof,
wherein the cells of the microorganism is a bacterium or yeast,
wherein the cells of the microorganism have been modified to have an aldehyde oxidoreductase gene, and
wherein the aldehyde oxidoreductase gene encodes a protein selected from the group consisting of:
(a) a protein comprising the amino acid sequence of SEQ ID NO: 18, 79, or 83;
(b) a protein comprising the amino acid sequence of SEQ ID NO: 18, 79, or 83 but which includes substitution, deletion, insertion, and/or addition of 1 to 10 amino acid residues, and wherein said protein has aldehyde oxidoreductase activity;
(c) a protein comprising an amino acid sequence having an identity of 90% or higher to the amino acid sequence of SEQ ID NO: 18, 79, or 83, and wherein said protein has aldehyde oxidoreductase activity.

2. The method according to claim 1, the method further comprising collecting the objective substance from the culture medium or reaction mixture.

3. The method according to claim 1, wherein the microorganism is a bacterium belonging to the family *Enterobacteriaceae*, a coryneform bacterium, or yeast.

4. The method according to claim 3, wherein the microorganism is a bacterium belonging to the genus *Corynebacterium*.

5. The method according to claim 4, wherein the microorganism is *Corynebacterium glutamicum*.

6. The method according to claim 3, wherein the microorganism is a bacterium belonging to the genus *Escherichia*.

7. The method according to claim 6, wherein the microorganism is *Escherichia coli*.

8. The method according to claim 1, wherein the objective substance is an aromatic aldehyde.

9. The method according to claim 1, wherein the objective substance is an aromatic aldehyde selected from the group consisting of vanillin, benzaldehyde, cinnamaldehyde, and combinations thereof.

10. The method according to claim 1, wherein the cells of the microorganism have been further modified so that the activity of an enzyme that is involved in the biosynthesis of the objective substance is increased as compared with non-modified cells of the microorganism,
wherein the enzyme that is involved in the biosynthesis of the objective substance is selected from the group consisting of 3-deoxy-D-arabino-heptulosonic acid 7-phosphate synthase, 3-dehydroquinate synthase, 3-dehydroquinate dehydratase, 3-dehydroshikimate dehydratase, O-methyltransferase, phenylalanine ammonia lyase, and combinations thereof.

11. The method according to claim 1, wherein the cells of the microorganism have been further modified so that the activity of phosphopantetheinyl transferase is increased as compared with non-modified cells of the microorganism.

12. The method according to claim 1, wherein the cells of the microorganism have been further modified so that the activity of an uptake system of a substance other than the objective substance is increased as compared with non-modified cells of the microorganism,
wherein the uptake system is selected from the group consisting of a vanillic acid uptake system, a protocatechuic acid uptake system, and combinations thereof.

13. The method according to claim 1, wherein the cells of the microorganism have been further modified so that the activity of an enzyme that is involved in the production of a byproduct during the production of the objective substance is reduced as compared with non-modified cells of the microorganism,
wherein the enzyme that is involved in the production of a byproduct during the production of the objective substance is selected from the group consisting of vanillate demethylase, protocatechuate 3,4-dioxygenase, alcohol dehydrogenase, shikimate dehydrogenase, and combinations thereof.

* * * * *